United States Patent
Pinchman et al.

(10) Patent No.: US 11,813,259 B2
(45) Date of Patent: Nov. 14, 2023

(54) BENZAMIDE COMPOUNDS

(71) Applicant: Recurium IP Holdings, LLC, San Diego, CA (US)

(72) Inventors: Joseph Robert Pinchman, San Diego, CA (US); Peter Qinhua Huang, San Diego, CA (US); Kevin Duane Bunker, Escondido, CA (US); Rakesh Kumar Sit, San Diego, CA (US); Ahmed Abdi Samatar, San Diego, CA (US)

(73) Assignee: RECURIUM IP HOLDINGS, LLC, San Diego, CA (US)

( * ) Notice: Subject to any disclaimer, the term of this patent is extended or adjusted under 35 U.S.C. 154(b) by 0 days.

(21) Appl. No.: 17/656,726

(22) Filed: Mar. 28, 2022

(65) Prior Publication Data

US 2022/0226314 A1    Jul. 21, 2022

Related U.S. Application Data

(62) Division of application No. 16/957,861, filed as application No. PCT/US2019/012695 on Jan. 8, 2019, now Pat. No. 11,318,134.

(60) Provisional application No. 62/615,857, filed on Jan. 10, 2018.

(51) Int. Cl.
| | |
|---|---|
| C07D 413/12 | (2006.01) |
| C07D 471/04 | (2006.01) |
| A61K 31/5355 | (2006.01) |
| A61K 31/496 | (2006.01) |
| A61K 45/06 | (2006.01) |
| C07D 519/00 | (2006.01) |
| C07D 241/04 | (2006.01) |
| C07D 205/04 | (2006.01) |
| C07D 207/12 | (2006.01) |
| C07D 211/46 | (2006.01) |
| C07D 211/58 | (2006.01) |
| C07D 295/112 | (2006.01) |
| C07D 295/13 | (2006.01) |

(52) U.S. Cl.
CPC ........ *A61K 31/496* (2013.01); *A61K 31/5355* (2013.01); *A61K 45/06* (2013.01); *C07D 205/04* (2013.01); *C07D 207/12* (2013.01); *C07D 211/46* (2013.01); *C07D 211/58* (2013.01); *C07D 241/04* (2013.01); *C07D 295/112* (2013.01); *C07D 295/13* (2013.01); *C07D 413/12* (2013.01); *C07D 471/04* (2013.01); *C07D 519/00* (2013.01)

(58) Field of Classification Search
CPC .. C07D 241/04; C07D 205/04; C07D 207/12; A61K 31/496
USPC .................................................. 514/210.16
See application file for complete search history.

(56) References Cited

U.S. PATENT DOCUMENTS

| | | | |
|---|---|---|---|
| 8,557,983 B2 | 10/2013 | Bruncko et al. | |
| 8,952,157 B2 | 2/2015 | Bruncko et al. | |
| 9,029,404 B2 | 5/2015 | Bruncko et al. | |
| 9,034,875 B2 | 5/2015 | Bruncko et al. | |
| 11,053,239 B2 | 7/2021 | Zhao et al. | |
| 2006/0128706 A1 | 6/2006 | Bruncko et al. | |
| 2006/0258657 A1 | 11/2006 | Bruncko et al. | |
| 2007/0015787 A1 | 1/2007 | Bruncko et al. | |
| 2007/0027135 A1 | 2/2007 | Bruncko et al. | |
| 2008/0199873 A1* | 8/2008 | Anderson | A61P 35/00 435/6.16 |
| 2010/0160322 A1 | 6/2010 | Bruncko et al. | |
| 2010/0227838 A1 | 9/2010 | Shah et al. | |
| 2010/0298323 A1 | 11/2010 | Bruncko et al. | |
| 2010/0305122 A1 | 12/2010 | Bruncko et al. | |
| 2010/0311751 A1 | 12/2010 | Schmitt et al. | |
| 2010/0323020 A1 | 12/2010 | Gokhale et al. | |
| 2011/0124628 A1 | 5/2011 | Bruncko et al. | |
| 2012/0108590 A1 | 5/2012 | Birtalan et al. | |
| 2012/0129853 A1 | 5/2012 | Elmore et al. | |
| 2012/0189539 A1 | 7/2012 | Wang et al. | |
| 2014/0199234 A1 | 7/2014 | Wang et al. | |
| 2014/0275082 A1 | 9/2014 | Tao et al. | |
| 2015/0336994 A1 | 11/2015 | Wang et al. | |
| 2016/0220573 A1 | 8/2016 | DiPaolo et al. | |
| 2016/0243247 A1 | 8/2016 | Bradner et al. | |
| 2017/0087162 A1 | 3/2017 | Starczynowski et al. | |
| 2017/0158666 A1 | 6/2017 | Bruncko et al. | |
| 2020/0338071 A1 | 10/2020 | Pinchman et al. | |
| 2020/0339605 A1 | 10/2020 | Pinchman et al. | |
| 2021/0009543 A1 | 1/2021 | Pinchman et al. | |

FOREIGN PATENT DOCUMENTS

| | | |
|---|---|---|
| CN | 101798292 | 8/2010 |
| CN | 104131034 | 11/2014 |
| CN | 106565706 | 4/2017 |
| CN | 106608895 | 5/2017 |
| CN | 106749233 | 5/2017 |
| CN | 106957315 | 7/2017 |
| CN | 107089981 | 8/2017 |
| JP | 2003/096461 | 4/2003 |
| RU | 2542994 C2 | 1/2014 |
| RU | 2554346 C2 | 6/2015 |
| WO | WO 2003/089441 | 10/2003 |
| WO | WO 2005/049593 | 6/2005 |
| WO | WO 2005/049594 | 6/2005 |

(Continued)

OTHER PUBLICATIONS

Belikov V.G., Pharmaceutical chemistry, educational allowance, 2007, Moscow, MEDpress-inform, pp. 27-29.

(Continued)

*Primary Examiner* — Niloofar Rahmani
(74) *Attorney, Agent, or Firm* — Knobbe, Martens, Olson & Bear, LLP

(57) ABSTRACT

Compounds of Formula (I) are provided herein. Such compounds, as well as pharmaceutically acceptable salts and compositions thereof, are useful for treating diseases or conditions, including conditions characterized by excessive cellular proliferation, such as cancer and tumors, as well as viral infections such as HIV.

17 Claims, 33 Drawing Sheets

(56) References Cited

FOREIGN PATENT DOCUMENTS

| | | |
|---|---|---|
| WO | WO 2005/079803 | 9/2005 |
| WO | WO 2006/093346 | 9/2006 |
| WO | WO 2008/008374 | 1/2008 |
| WO | WO 2008/030836 | 3/2008 |
| WO | WO 2008/033747 | 3/2008 |
| WO | WO 2008/064116 | 5/2008 |
| WO | WO 2009/036051 | 3/2009 |
| WO | WO 2010/065824 | 6/2010 |
| WO | WO 2010/065865 | 6/2010 |
| WO | WO 2010/083442 | 7/2010 |
| WO | WO 2010/138588 | 12/2010 |
| WO | WO 2010/148422 | 12/2010 |
| WO | WO 2011/021038 | 2/2011 |
| WO | WO 2011/068561 | 6/2011 |
| WO | WO 2011/149492 | 12/2011 |
| WO | WO 2011/150016 | 12/2011 |
| WO | WO 2012/058392 | 5/2012 |
| WO | WO 2012/063085 | 5/2012 |
| WO | WO 2013/185202 | 12/2013 |
| WO | WO 2014/113413 | 7/2014 |
| WO | WO 2014/165044 | 10/2014 |
| WO | WO 2014/189393 | 11/2014 |
| WO | WO 2015/003816 | 1/2015 |
| WO | WO 2015/085238 | 6/2015 |
| WO | WO 2015/158299 | 10/2015 |
| WO | WO 2016/025652 | 2/2016 |
| WO | WO 2016/127135 | 8/2016 |
| WO | WO 2016/131100 | 8/2016 |
| WO | WO 2016/172194 | 10/2016 |
| WO | WO 2016/188935 | 12/2016 |
| WO | WO 2017/017469 | 2/2017 |
| WO | WO 2017/044720 | 3/2017 |
| WO | WO 2017/101851 | 6/2017 |
| WO | WO 2017/123616 | 7/2017 |
| WO | WO 2017/132474 | 8/2017 |
| WO | WO 2017/184995 | 10/2017 |
| WO | WO 2017/214491 | 12/2017 |
| WO | WO 2018/026646 | 2/2018 |
| WO | WO 2018/127130 | 7/2018 |
| WO | WO 2018/146506 | 8/2018 |
| WO | WO 2019/139899 | 7/2019 |
| WO | WO 2019/139902 | 7/2019 |
| WO | WO 2019/139907 | 7/2019 |
| WO | WO 2019/210828 | 11/2019 |
| WO | WO 2020/061216 | 3/2020 |

OTHER PUBLICATIONS

Durnov L.A. et al., Pediatric oncology, Second edition, Moscow: Medicine Publishing House, 2002, p. 139.
Dyson G. et al., Chemistry of Synthetic Drugs substances, ed. Mir, Moscow, 1964, pp. 12-19.
Kummerer, K., Pharmaceuticals in the environment, Annual Review of Environment and Resources, 2010, v. 35, p. 57-75, doi:10.1146/annurev-environ-052809-161223 (abstract, p. 60).
Mashkovsky M.D., "Medicinal funds", Moscow, "Medicine", 1993, part I, p. 8.
Office Action issued in Mexican Patent Application No. MX/a/2020/007388, dated Apr. 21, 2022.
Office Action issued in Mexican Patent Application No. MX/a/2020/007388, dated Aug. 31, 2022.
Office Action issued in Russian Patent Application No. 2020120933, dated Oct. 21, 2022.
Office Action issued in Japanese Patent Application No. 2020-53869, dated Feb. 2, 2023.
Office Action issued in New Zealand Patent Application No. 765825, dated Feb. 7, 2023.
Office Action issued in Mexican Patent Application No. MX/a/2020/00738, dated Feb. 15, 2023.
Office Action issued in Taiwan Patent Application No. 108101048, dated Jan. 4, 2023.
Chinese Office Action dated Aug. 26, 2022 for Chinese Patent Application No. 201980015882.X.
Auberson, Y. et al, "Improving Nonspecific Binding and Solubility: Bicycloalkyl Groups and Cubanes as para-Phenyl Bioisosteres" ChemMedChem (2017), 12, 590-598.
Aguilar, A. et al, "A Potent and Highly Efficacious Bcl-2/Bcl-xL Inhibitor" Journal of Medicinal Chemistry (2013), 56(7), 3048-3067.
Almerico, A. et al, "3D-QSAR pharmacophore modeling and in silico screening of new Bcl-xl inhibitors" European Journal of Medicinal Chemistry, (2010),(11), 4774-4782.
Bai, L. et al, "BM-1197: a novel and specific Bcl-2/Bcl-xL inhibitor inducing complete and long-lasting tumor regression in vivo" PLoS One (2014), 9(6), e99404/1-e99404/13, 13 pp.
Bernardo P. et al, "Structure-Activity Relationship Studies of Phenanthridine-Based Bcl-XL Inhibitors" J Med Chem, (2008), 51(21), 6699-6710.
Bruncko, M. et al., "Studies Leading to Potent, Dual Inhibitors of Bcl-2 and Bcl-Xl" Journal of Medicinal Chemistry 2007 50 (4), 641-662.
Chen, J. et al, "Structure-Based Discovery of BM-957 as a Potent Small-Molecule Inhibitor of Bcl-2 and Bcl-xL Capable of Achieving Complete Tumor Regression" Journal of Medicinal Chemistry (2012), 55(19), 8502-8514.
Giedt R. et al, "Imaging Cellular Distribution of Bcl Inhibitors Using Small Molecule Drug Conjugates" Bioconjugate Chemistry (2014), 25(11), 2081-2085.
Hou, X. et al, "3D-QSAR study on a series of Bcl-2 protein inhibitors using comparative molecular field analysis" Protein & Peptide Letters (2011), 18(5), 440-449.
Kastritis, P. et al, "A Biophysical Model for Predicting the Binding Affinity of Protein-Protein Interaction Inhibitors" Journal of Chemical Information and Modeling (2014), 54(3), 826-836.
Lee, E. et al, "Conformational Changes in Bcl-2 Pro-survival Proteins Determine their Capacity to Bind Ligands" Journal of Biological Chemistry (2009), 284(44), 30508-30517.
Mabrouk, M. "Discovering best candidates for hepatocellular carcinoma(HCC) by in-silico techniques and tools" Int. J. Bioinfo. Res. and Appl.,(2012), 8(1/2), 141-152.
Magee, Thomas V., "Progress in discovery of small-molecule modulators of protein-protein interactions via fragment screeing" Bioorganic & Medicinal Chemistry Letters, 2015, 25(12), 2461.
Park, C-M. et al, "Discovery of an Orally Bioavailable Small Molecule Inhibitor of Prosurvival B-Cell Lymphoma 2 Proteins" J Med Chem, (2008), 51(21), 6902-6915.
Shipra, G. et al., "Identification of Novel Potent Inhibitors Against Bcl-xL Anti-apoptotic Protein Using Docking Studies" Protein & Peptide Letters 19(12), 2012, pp. 1302-1317.
Varnes, J. et al, "Towards the next generation of dual Bcl-2/Bcl-xL inhibitors" Bioorganic & Medicinal Chemistry Letters (2014), 24(14), 3026-3033.
Ye, L. et al, "The small-molecule compound BM-1197 inhibits the antiapoptotic regulators Bcl-2/Bcl-xL and triggers apoptotic cell death in human colorectal cancer cells" Tumor Biology (2015), 36(5), 3447-3455.
Zhou, H. et al, "Correction to Design of Bcl-2 and Bcl-xL Inhibitors with Subnanomolar Binding Affinities Based upon a New Scaffold" Journal of Medicinal Chemistry (2012), 55(12), 5987.
Zhou, H. et al, "Structure-Based Design of Potent Bcl-2/Bcl-xL Inhibitors with Strong in Vivo Antitumor Activity" Journal of Medicinal Chemistry (2012), 55(13), 6149-6161.
Zhou, H. et al, "Design of Bcl-2 and Bcl-xL Inhibitors with Subnanomolar Binding Affinities Based upon a New Scaffold" Journal of Medicinal Chemistry (2012), 55(10), 4664-4682.
International Search Report dated Apr. 4, 2019 for PCT/US2019/012704, filed Jan. 8, 2019.
International Search Report dated Apr. 1, 2019 for PCT/US2019/012719, filed Jan. 8, 2019.
International Search Report dated Apr. 10, 2019 for PCT/US2019/012695, filed Jan. 8, 2019.
International Preliminary Report on Patentability dated Jul. 23, 2020 for PCT/US2019/012704, filed Jan. 8, 2019.

(56) References Cited

OTHER PUBLICATIONS

International Preliminary Report on Patentability dated Jul. 23, 2020 for PCT/US2019/012719, filed Jan. 8, 2019.
International Preliminary Report on Patentability dated Jul. 23, 2020 for PCT/US2019/012695, filed Jan. 8, 2019.
Office Action issued in U.S. Appl. No. 16/957,861 dated Jul. 29, 2021.
Extended European search report dated Aug. 12, 2021 for EP 19 738 922.4, filed Jul. 23, 2020.
Extended European Search Report for EP 19 738 922.4, dated Oct. 8, 2021.
Written Opinion and Search Report for Singapore Application No. 11202005785X, dated Jan. 6, 2022.
Written Opinion and Search Report for Singapore Application No. 11202005784Y, dated Jan. 6, 2022.
Written Opinion and Search Report for Singapore Application No. 11202005985P, dated Jan. 6, 2022.
First Examination Report for Indian Application No. 202017026070, dated Jan. 27, 2022.
Mexican Office Action dated Apr. 21, 2022 in Mexican Patent Application No. MX/a/2020/007388.
Mexican Office Action dated Aug. 30, 2022 in Mexican Patent Application No. MX/a/2020/007388.
Office Action issued in Japanese Patent Application No. 2020-538691, dated May 16, 2023.
Office Action issued in Australian Patent Application No. 2019207608, dated Jun. 8, 2023.
Office Action issued in Brazilian Patent Application No. BR 11 2020 014169 0, dated Jun. 5, 2023.

\* cited by examiner

FIGURE 1

| Common Name / Compound No. | Structure | Chemical Name |
|---|---|---|
| prostratin | 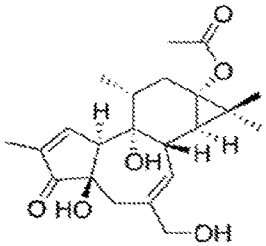 | (1aR,1bS,4aR,7aS,7bR,8R,9aS)-4a,7b-dihydroxy-3-(hydroxymethyl)-1,1,6,8-tetramethyl-5-oxo-1,1a,1b,4,4a,5,7a,7b,8,9-decahydro-9aH-cyclopropa[3,4]benzo[1,2-e]azulen-9a-yl acetate |
| bryostatin-1 | 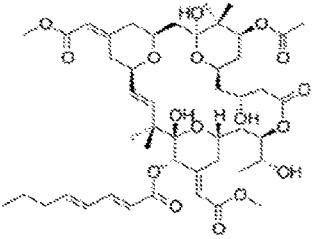 | (1S,3S,5Z,7R,8E,11S,12S,13E,15S,17R,20R,23R,25S)-25-Acetoxy-1,11,20-trihydroxy-17-[(1R)-1-hydroxyethyl]-5,13-bis(2-methoxy-2-oxoethylidene)-10,10,26,26-tetramethyl-19-oxo-18,27,28,29-tetraoxatetracyclo[21.3.1.1$^{3,7}$.1$^{11,15}$]nonacos-8-en-12-yl (2E,4E)-2,4-octadienoate |
| ingenol | 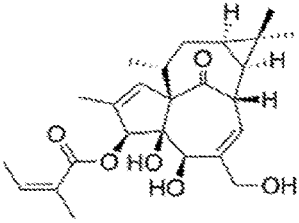 | (1aR,2S,5R,5aS,6S,8aS,9R,10aR)-5,5a-Dihydroxy-4-(hydroxymethyl)-1,1,7,9-tetramethyl-11-oxo-1a,2,5,5a,6,9,10,10a-octahydro-1H-2,8a-methanocyclopenta[a]cyclopropa[e][10]annulen-6-yl (2Z)-2-methylbut-2-enoate |
| nivolumab | Anti-PD-1 Antibody | -- |
| pembrolizumab | Anti-PD-1 Antibody | -- |
| BGB-A317 | Anti-PD-1 Antibody | -- |
| pidilizumab | Anti-PD-1 Antibody | -- |
| AMP-224 | Anti-PD-1 Antibody | -- |
| AMP-514 | Anti-PD-1 Antibody | -- |
| PDR001 | Anti-PD-1 Antibody | -- |
| REGN2810 | Anti-PD-1 Antibody | -- |
| MEDI0680 | Anti-PD-1 Antibody | -- |
| atezolizumab | Anti-PD-L1 Antibody | -- |
| durvalumab | Anti-PD-L1 Antibody | -- |
| avelumab | Anti-PD-L1 Antibody | -- |
| BMS-936559 | Anti-PD-L1 Antibody | -- |
| vorinostat | 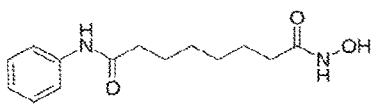 | N-Hydroxy-N'-phenyloctanediamide |

FIGURE 1 (cont.)

| Common Name / Compound No. | Structure | Chemical Name |
|---|---|---|
| panobinostat | 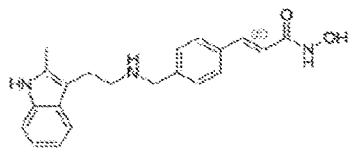 | (2E)-N-hydroxy-3-[4-({[2-(2-methyl-1H-indol-3-yl)ethyl]amino}methyl)phenyl]acrylamide |
| romidepsin | 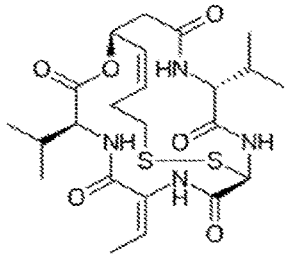 | (1S,4S,7Z,10S,16E,21R)-7-ethylidene-4,21-diisopropyl-2-oxa-12,13-dithia-5,8,20,23-tetrazabicyclo[8.7.6]tricos-16-ene-3,6,9,19,22-pentone |
| valproic acid | 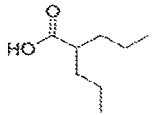 | 2-propylpentanoic acid |
| phorbol 12-myristate-13-acetate | 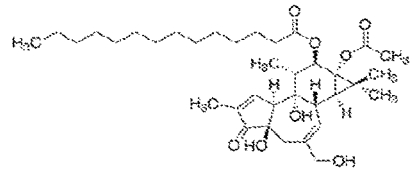 | (1aR,1bS,4aR,7aS,7bS,8R,9R,9aS)-9a-(acetyloxy)-4a,7b-dihydroxy-3-(hydroxymethyl)-1,1,6,8-tetramethyl-5-oxo-1a,1b,4,4a,5,7a,7b,8,9,9a-decahydro-H-cyclopropa[3,4]benzo[1,2-e]azulen-9-yl myristate |
| JQ1 | 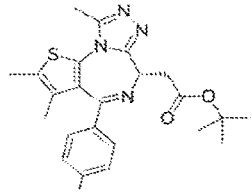 | (S)-tert-butyl-2-(4-(4-chlorophenyl)-2,3,9-trimethyl-6H-thieno[3,2-f][1,2,4]triazolo[4,3-a][1,4]diazepin-6-yl)acetate) |

FIGURE 1 (cont.)

| Common Name / Compound No. | Structure | Chemical Name |
|---|---|---|
| I-BET762 | 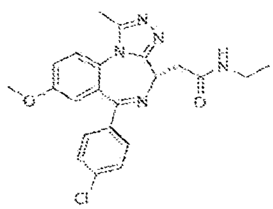 | (4S)-6-(4-chlorophenyl)-N-ethyl-8-methoxy-1-methyl-4H-[1,2,4]triazolo[4,3-a][1,4]benzodiazepine-4-acetamide |
| OTX015 | 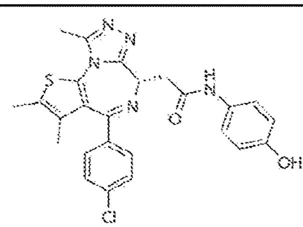 | (6S)-4-(4-chlorophenyl)-N-(4-hydroxyphenyl)-2,3,9-trimethyl-6H-thieno[3,2-f][1,2,4]triazolo[4,3-a][1,4]diazepine-6-acetamide |
| I-BET151 | 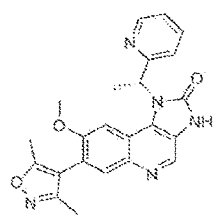 | 7-(3,5-dimethylisoxazol-4-yl)-8-methoxy-1-((R)-1-(pyridin-2-yl)ethyl)-1H-imidazo[4,5-c]quinolin-2(3H)-one |
| CPI203 (TEN-010) | 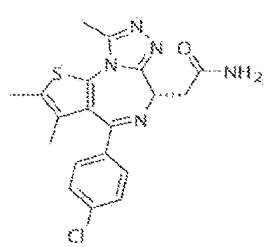 | (6S)-4-(4-chlorophenyl)-2,3,9-trimethyl-6H-Thieno[3,2-f][1,2,4]triazolo[4,3-a][1,4]diazepine-6-acetic amide |
| PFI-1 | 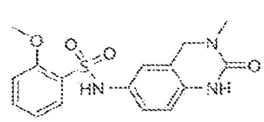 | 2-methoxy-N-(1,2,3,4-tetrahydro-3-methyl-2-oxo-6-quinazolinyl)- benzenesulfonamide, |

FIGURE 1 (cont.)

| Common Name / Compound No. | Structure | Chemical Name |
|---|---|---|
| MS436 | 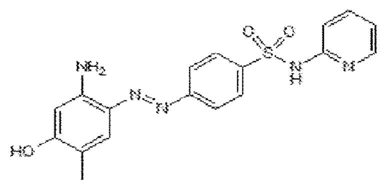 | (E)-4-[2-(2-Amino-4-hydroxy-5-methylphenyl)diazenyl]-N-2-pyridinylbenzenesulfonamide |
| CPI-0610 | 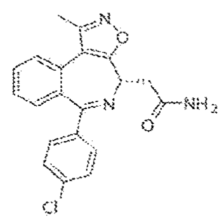 | (4S)-6-(4-chlorophenyl)-1-methyl-4H-isoxazolo[5,4-d][2]benzazepine-4-acetamide |
| RVX2135 | 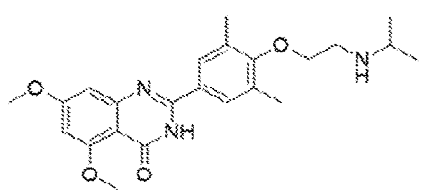 | 2-(4-(2-(isopropylamino)ethoxy)-3,5-dimethylphenyl)-5,7-dimethoxyquinazolin-4(3H)-one |
| BAY1238097 | 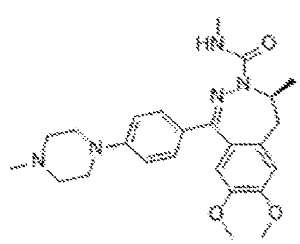 | (S)-7,8-dimethoxy-N,4-dimethyl-1-(4-(4-methylpiperazin-1-yl)phenyl)-4,5-dihydro-3H-benzo[d][1,2]diazepine-3-carboxamide |
| BAY-299 | 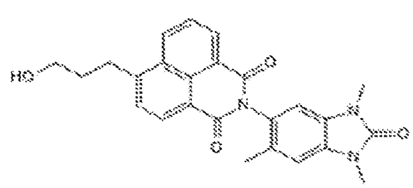 | 6-(3-Hydroxypropyl)-2-(1,3,6-trimethyl-2-oxo-2,3-dihydro-1H-benzimidazol-5-yl)-1H-benzo[de]isoquinoline-1,3(2H)-dione |

| Common Name / Compound No. | Structure | Chemical Name |
|---|---|---|
| BMS-986158 | 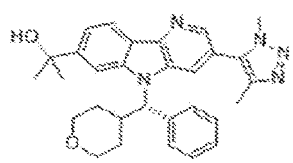 | (S)-2-(3-(1,4-dimethyl-1H-1,2,3-triazol-5-yl)-5-(phenyl(tetrahydro-2H-pyran-4-yl)methyl)-5H-pyrido[3,2-b]indol-7-yl)propan-2-ol |
| ABBV-075 | 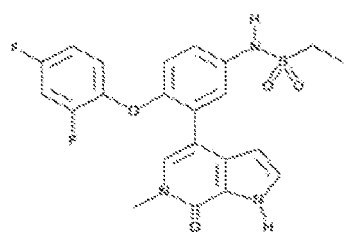 | N-[4-(2,4-difluorophenoxy)-3-(6,7-dihydro-6-methyl-7-oxo-1H-pyrrolo[2,3-c]pyridin-4-yl)phenyl]-ethanesulfonamide |
| FT-1101 | | |
| INCB054329 | | |
| GSK2820151 | | |
| ZEN003694 | | |
| GS-5829 | | |

FIGURE 2

| Common Name / Compound No. | Structure | Chemical Name |
|---|---|---|
| venetoclax | 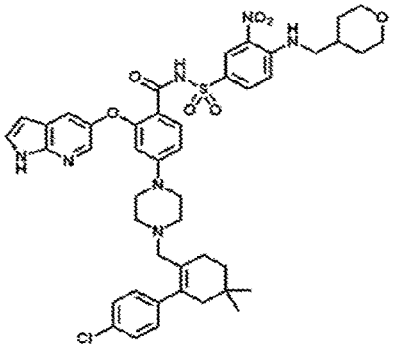 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide |
| navitoclax | 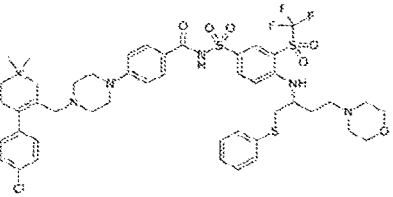 | 4-(4-{[2-(4-Chlorophenyl)-5,5-dimethyl-1-cyclohexen-1-yl]methyl}-1-piperazinyl)-N-[(4-{[(2R)-4-(4-morpholinyl)-1-(phenylsulfanyl)-2-butanyl]amino}-3-[(trifluoromethyl)sulfonyl]phenyl)sulfonyl]benzamide |
| obatoclax | 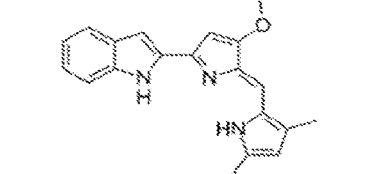 | 2-(2-((3,5-Dimethyl-1H-pyrrol-2-yl)methylene)-3-methoxy-2H-pyrrol-5-yl)-1H-indole |

FIGURE 2 (cont.)

| Common Name / Compound No. | Structure | Chemical Name |
|---|---|---|
| ABT-737 | 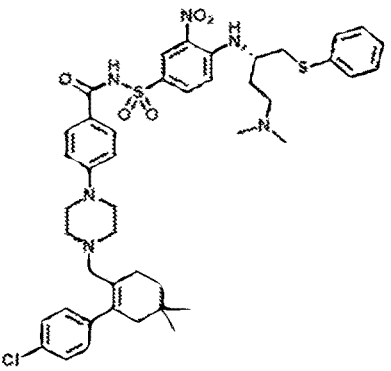 | (S)-4-(4-((4'-chloro-5,5-dimethyl-3,4,5,6-tetrahydro-[1,1'-biphenyl]-2-yl)methyl)piperazin-1-yl)-N-((4-((4-(dimethylamino)-1-(phenylthio)butan-2-yl)amino)-3-nitrophenyl)sulfonyl)benzamide |
| S55746 | | N-(4-hydroxyphenyl)-3-{6-[((3S)-3-(4-morpholinylmethyl)-3,4-dihydro-2(1H)-isoquinolinyl)carbonyl]-1,3-benzodioxol-5-yl}-N-phenyl-5,6,7,8-tetrahydro-1-indolizine carboxamide |
| AT-101 | | R-(−)-gossypol acetic acid |
| APG-1252 | | |
| APG-2575 | | |

| Common Name / Compound No. | Structure | Chemical Name |
|---|---|---|
| AZD5991 | 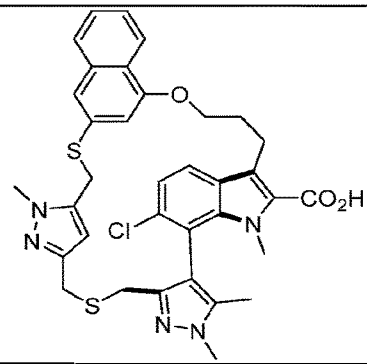 | (Z)-$1^6$-chloro-$1^1,2^1,2^5,6^1$-tetramethyl-$1^1$H,$2^1$H,$6^1$H-10-oxa-4,8-dithia-1(7,3)-indola-2(4,3),6(3,5)-dipyrazola-9(3,1)-naphthalenacyclotridecaphane-$1^2$-carboxylic acid |
| AMG176 | 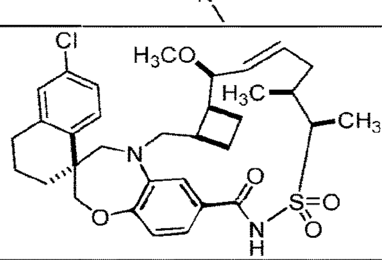 | -- |

FIGURE 3

| Example No. | Structure | Name |
|---|---|---|
| 45 | 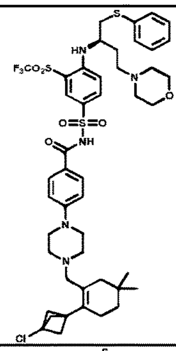 | (R)-4-(4-((2-(3-chlorobicyclo[1.1.1]pentan-1-yl)-5,5-dimethylcyclohex-1-en-1-yl)methyl)piperazin-1-yl)-N-((4-((4-morpholino-1-(phenylthio)butan-2-yl)amino)-3-((trifluoromethyl)sulfonyl)phenyl)sulfonyl)benzamide |
| 46 | 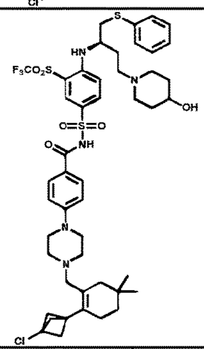 | (R)-4-(4-((2-(3-chlorobicyclo[1.1.1]pentan-1-yl)-5,5-dimethylcyclohex-1-en-1-yl)methyl)piperazin-1-yl)-N-((4-((4-(4-hydroxypiperidin-1-yl)-1-(phenylthio)butan-2-yl)amino)-3-((trifluoromethyl)sulfonyl)phenyl)sulfonyl)benzamide |
| 47 | 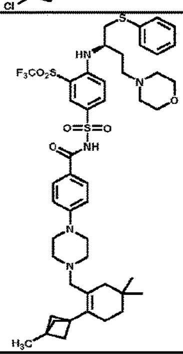 | (R)-4-(4-((5,5-dimethyl-2-(3-methylbicyclo[1.1.1]pentan-1-yl)cyclohex-1-en-1-yl)methyl)piperazin-1-yl)-N-((4-((4-morpholino-1-(phenylthio)butan-2-yl)amino)-3-((trifluoromethyl)sulfonyl)phenyl)sulfonyl)benzamide |
| 48 | 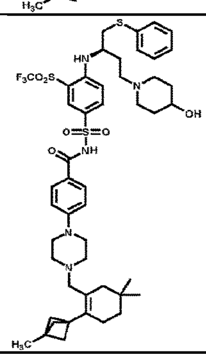 | (R)-4-(4-((5,5-dimethyl-2-(3-methylbicyclo[1.1.1]pentan-1-yl)cyclohex-1-en-1-yl)methyl)piperazin-1-yl)-N-((4-((4-(4-hydroxypiperidin-1-yl)-1-(phenylthio)butan-2-yl)amino)-3-((trifluoromethyl)sulfonyl)phenyl)sulfonyl)benzamide |

FIGURE 3 (cont.)

| Example No. | Structure | Name |
|---|---|---|
| 49 | 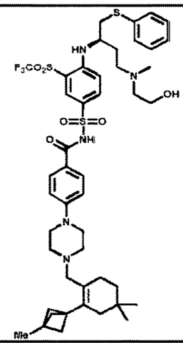 | (R)-4-(4-((4,4-dimethyl-2-(3-methylbicyclo[1.1.1]pentan-1-yl)cyclohex-1-en-1-yl)methyl)piperazin-1-yl)-N-((4-((4-((2-hydroxyethyl)(methyl)amino)-1-(phenylthio)butan-2-yl)amino)-3-((trifluoromethyl)sulfonyl)phenyl)sulfonyl)benzamide |
| 50 | 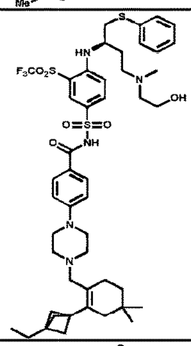 | (R)-4-(4-((2-(3-ethylbicyclo[1.1.1]pentan-1-yl)-4,4-dimethylcyclohex-1-en-1-yl)methyl)piperazin-1-yl)-N-((4-((4-((2-hydroxyethyl)(methyl)amino)-1-(phenylthio)butan-2-yl)amino)-3-((trifluoromethyl)sulfonyl)phenyl)sulfonyl)benzamide |
| 51 | 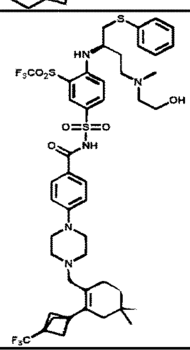 | (R)-4-(4-((4,4-dimethyl-2-(3-(trifluoromethyl)bicyclo[1.1.1]pentan-1-yl)cyclohex-1-en-1-yl)methyl)piperazin-1-yl)-N-((4-((4-((2-hydroxyethyl)(methyl)amino)-1-(phenylthio)butan-2-yl)amino)-3-((trifluoromethyl)sulfonyl)phenyl)sulfonyl)benzamide |
| 52 | 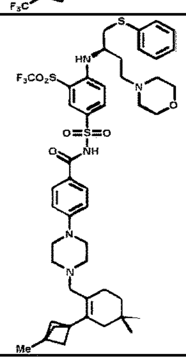 | (R)-4-(4-((4,4-dimethyl-2-(3-methylbicyclo[1.1.1]pentan-1-yl)cyclohex-1-en-1-yl)methyl)piperazin-1-yl)-N-((4-((4-morpholino-1-(phenylthio)butan-2-yl)amino)-3-((trifluoromethyl)sulfonyl)phenyl)sulfonyl)benzamide |

FIGURE 3 (cont.)

| Example No. | Structure | Name |
|---|---|---|
| 53 | 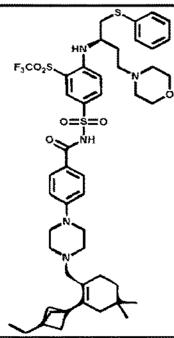 | (R)-4-(4-((2-(3-ethylbicyclo[1.1.1]pentan-1-yl)-4,4-dimethylcyclohex-1-en-1-yl)methyl)piperazin-1-yl)-N-((4-((4-morpholino-1-(phenylthio)butan-2-yl)amino)-3-((trifluoromethyl)sulfonyl)phenyl)sulfonyl)benzamide |
| 54 | 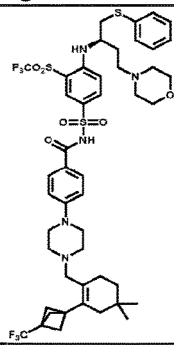 | (R)-4-(4-((4,4-dimethyl-2-(3-(trifluoromethyl)bicyclo[1.1.1]pentan-1-yl)cyclohex-1-en-1-yl)methyl)piperazin-1-yl)-N-((4-((4-morpholino-1-(phenylthio)butan-2-yl)amino)-3-((trifluoromethyl)sulfonyl)phenyl)sulfonyl)benzamide |
| 55 | 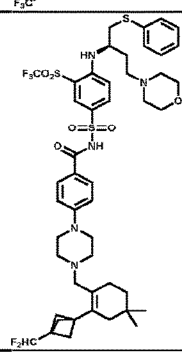 | (R)-4-(4-((2-(3-(difluoromethyl)bicyclo[1.1.1]pentan-1-yl)-4,4-dimethylcyclohex-1-en-1-yl)methyl)piperazin-1-yl)-N-((4-((4-morpholino-1-(phenylthio)butan-2-yl)amino)-3-((trifluoromethyl)sulfonyl)phenyl)sulfonyl)benzamide |
| 56 | 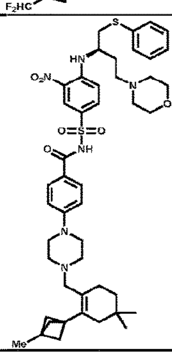 | (R)-4-(4-((4,4-dimethyl-2-(3-methylbicyclo[1.1.1]pentan-1-yl)cyclohex-1-en-1-yl)methyl)piperazin-1-yl)-N-((4-((4-morpholino-1-(phenylthio)butan-2-yl)amino)-3-nitrophenyl)sulfonyl)benzamide |

FIGURE 3 (cont.)

| Example No. | Structure | Name |
|---|---|---|
| 57 | 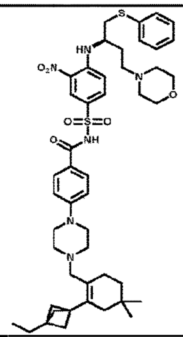 | (R)-4-(4-((2-(3-ethylbicyclo[1.1.1]pentan-1-yl)-4,4-dimethylcyclohex-1-en-1-yl)methyl)piperazin-1-yl)-N-((4-((4-morpholino-1-(phenylthio)butan-2-yl)amino)-3-nitrophenyl)sulfonyl)benzamide |
| 58 | 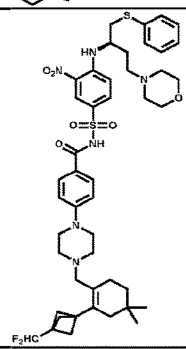 | (R)-4-(4-((2-(3-(difluoromethyl)bicyclo[1.1.1]pentan-1-yl)-4,4-dimethylcyclohex-1-en-1-yl)methyl)piperazin-1-yl)-N-((4-((4-morpholino-1-(phenylthio)butan-2-yl)amino)-3-nitrophenyl)sulfonyl)benzamide |
| 59 | 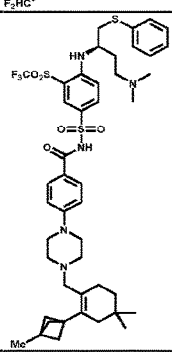 | (R)-4-(4-((4,4-dimethyl-2-(3-methylbicyclo[1.1.1]pentan-1-yl)cyclohex-1-en-1-yl)methyl)piperazin-1-yl)-N-((4-((4-(dimethylamino)-1-(phenylthio)butan-2-yl)amino)-3-((trifluoromethyl)sulfonyl)phenyl)sulfonyl)benzamide |
| 60 | 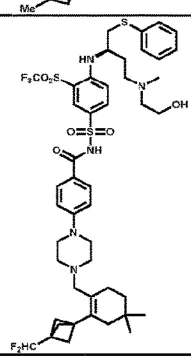 | (R)-4-(4-((2-(3-(difluoromethyl)bicyclo[1.1.1]pentan-1-yl)-4,4-dimethylcyclohex-1-en-1-yl)methyl)piperazin-1-yl)-N-((4-((4-((2-hydroxyethyl)(methyl)amino)-1-(phenylthio)butan-2-yl)amino)-3-((trifluoromethyl)sulfonyl)phenyl)sulfonyl)benzamide |

FIGURE 3 (cont.)

| Example No. | Structure | Name |
|---|---|---|
| 61 | 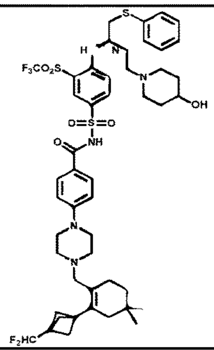 | (R)-4-(4-((2-(3-(difluoromethyl)bicyclo[1.1.1]pentan-1-yl)-4,4-dimethylcyclohex-1-en-1-yl)methyl)piperazin-1-yl)-N-((4-((4-(4-hydroxypiperidin-1-yl)-1-(phenylthio)butan-2-yl)amino)-3-((trifluoromethyl)sulfonyl)phenyl)sulfonyl)benzamide |
| 62 | 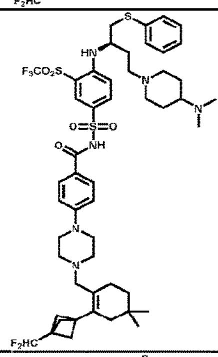 | (R)-4-(4-((2-(3-(difluoromethyl)bicyclo[1.1.1]pentan-1-yl)-4,4-dimethylcyclohex-1-en-1-yl)methyl)piperazin-1-yl)-N-((4-((4-(4-(dimethylamino)piperidin-1-yl)-1-(phenylthio)butan-2-yl)amino)-3-((trifluoromethyl)sulfonyl)phenyl)sulfonyl)benzamide |
| 63 | 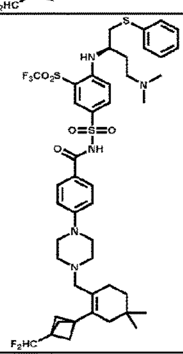 | (R)-4-(4-((2-(3-(difluoromethyl)bicyclo[1.1.1]pentan-1-yl)-4,4-dimethylcyclohex-1-en-1-yl)methyl)piperazin-1-yl)-N-((4-((4-(dimethylamino)-1-(phenylthio)butan-2-yl)amino)-3-((trifluoromethyl)sulfonyl)phenyl)sulfonyl)benzamide |
| 64 | 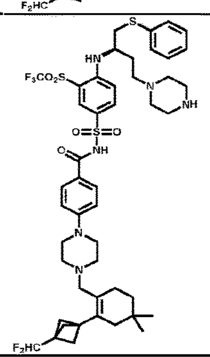 | (R)-4-(4-((2-(3-(difluoromethyl)bicyclo[1.1.1]pentan-1-yl)-4,4-dimethylcyclohex-1-en-1-yl)methyl)piperazin-1-yl)-N-((4-((1-(phenylthio)-4-(piperazin-1-yl)butan-2-yl)amino)-3-((trifluoromethyl)sulfonyl)phenyl)sulfonyl)benzamide |

FIGURE 3 (cont.)

| Example No. | Structure | Name |
|---|---|---|
| 65 | 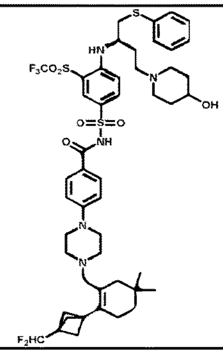 | (R)-4-(4-((2-(3-(difluoromethyl)bicyclo[1.1.1]pentan-1-yl)-5,5-dimethylcyclohex-1-en-1-yl)methyl)piperazin-1-yl)-N-((4-((4-(4-hydroxypiperidin-1-yl)-1-(phenylthio)butan-2-yl)amino)-3-((trifluoromethyl)sulfonyl)phenyl)sulfonyl)benzamide |
| 66 | 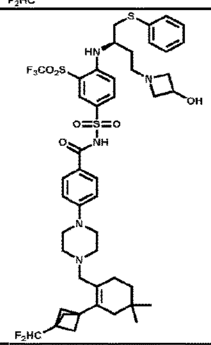 | (R)-4-(4-((2-(3-(difluoromethyl)bicyclo[1.1.1]pentan-1-yl)-4,4-dimethylcyclohex-1-en-1-yl)methyl)piperazin-1-yl)-N-((4-((4-(3-hydroxyazetidin-1-yl)-1-(phenylthio)butan-2-yl)amino)-3-((trifluoromethyl)sulfonyl)phenyl)sulfonyl)benzamide |
| 67 | 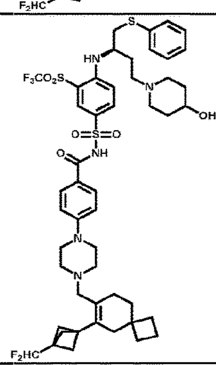 | (R)-4-(4-((6-(3-(difluoromethyl)bicyclo[1.1.1]pentan-1-yl)spiro[3.5]non-6-en-7-yl)methyl)piperazin-1-yl)-N-((4-((4-(4-hydroxypiperidin-1-yl)-1-(phenylthio)butan-2-yl)amino)-3-((trifluoromethyl)sulfonyl)phenyl)sulfonyl)benzamide |
| 68 | 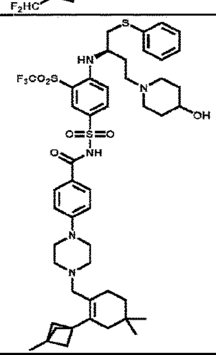 | (R)-4-(4-((4,4-dimethyl-2-(3-methylbicyclo[1.1.1]pentan-1-yl)cyclohex-1-en-1-yl)methyl)piperazin-1-yl)-N-((4-((4-(4-hydroxypiperidin-1-yl)-1-(phenylthio)butan-2-yl)amino)-3-((trifluoromethyl)sulfonyl)phenyl)sulfonyl)benzamide |

FIGURE 3 (cont.)

| Example No. | Structure | Name |
|---|---|---|
| 69 | 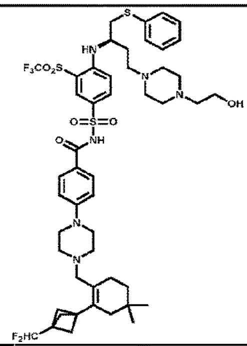 | (R)-4-(4-((2-(3-(difluoromethyl)bicyclo[1.1.1]pentan-1-yl)-4,4-dimethylcyclohex-1-en-1-yl)methyl)piperazin-1-yl)-N-((4-((4-(4-(2-hydroxyethyl)piperazin-1-yl)-1-(phenylthio)butan-2-yl)amino)-3-((trifluoromethyl)sulfonyl)phenyl)sulfonyl)benzamide |
| 70 | 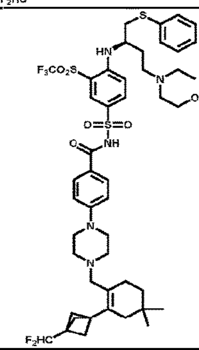 | (R)-4-(4-((2-(3-(difluoromethyl)bicyclo[1.1.1]pentan-1-yl)-4,4-dimethylcyclohex-1-en-1-yl)methyl)piperazin-1-yl)-N-((4-((4-(ethyl(2-hydroxyethyl)amino)-1-(phenylthio)butan-2-yl)amino)-3-((trifluoromethyl)sulfonyl)phenyl)sulfonyl)benzamide |
| 71 | 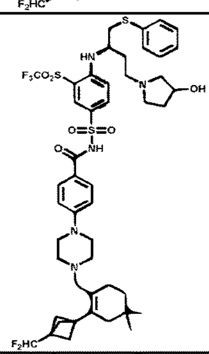 | 4-(4-((2-(3-(difluoromethyl)bicyclo[1.1.1]pentan-1-yl)-4,4-dimethylcyclohex-1-en-1-yl)methyl)piperazin-1-yl)-N-((4-(((2R)-4-(3-hydroxypyrrolidin-1-yl)-1-(phenylthio)butan-2-yl)amino)-3-((trifluoromethyl)sulfonyl)phenyl)sulfonyl)benzamide |
| 74 | 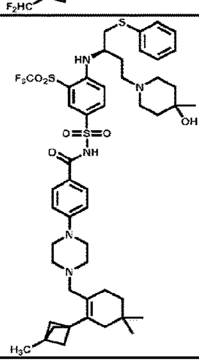 | (R)-4-(4-((4,4-dimethyl-2-(3-methylbicyclo[1.1.1]pentan-1-yl)cyclohex-1-en-1-yl)methyl)piperazin-1-yl)-N-((4-((4-(4-hydroxy-4-methylpiperidin-1-yl)-1-(phenylthio)butan-2-yl)amino)-3-((trifluoromethyl)sulfonyl)phenyl)sulfonyl)benzamide |

FIGURE 3 (cont.)

| Example No. | Structure | Name |
|---|---|---|
| 75 | 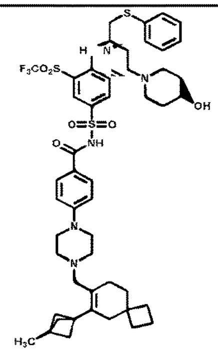 | (R)-N-((4-((4-(4-hydroxypiperidin-1-yl)-1-(phenylthio)butan-2-yl)amino)-3-((trifluoromethyl)sulfonyl)phenyl)sulfonyl)-4-(4-((6-(3-methylbicyclo[1.1.1]pentan-1-yl)spiro[3.5]non-6-en-7-yl)methyl)piperazin-1-yl)benzamide |
| 76 | 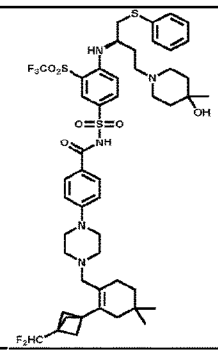 | (R)-4-(4-((2-(3-(difluoromethyl)bicyclo[1.1.1]pentan-1-yl)-4,4-dimethylcyclohex-1-en-1-yl)methyl)piperazin-1-yl)-N-((4-((4-(4-hydroxy-4-methylpiperidin-1-yl)-1-(phenylthio)butan-2-yl)amino)-3-((trifluoromethyl)sulfonyl)phenyl)sulfonyl)benzamide |
| 77 | 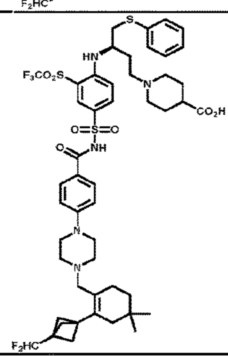 | (R)-1-(3-((4-(N-(4-(4-((2-(3-(difluoromethyl)bicyclo[1.1.1]pentan-1-yl)-4,4-dimethylcyclohex-1-en-1-yl)methyl)piperazin-1-yl)benzoyl)sulfamoyl)-2-((trifluoromethyl)sulfonyl)phenyl)amino)-4-(phenylthio)butyl)piperidine-4-carboxylic acid |

FIGURE 3 (cont.)

| Example No. | Structure | Name |
|---|---|---|
| 78 | 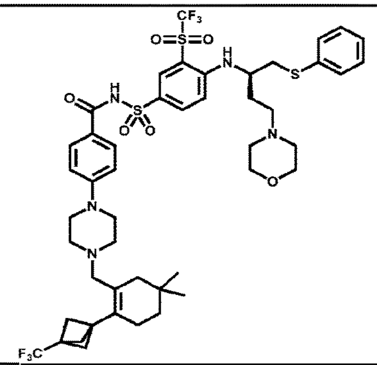 | (R)-4-(4-((5,5-dimethyl-2-(3-(trifluoromethyl)bicyclo[1.1.1]pentan-1-yl)cyclohex-1-en-1-yl)methyl)piperazin-1-yl)-N-((4-((4-morpholino-1-(phenylthio)butan-2-yl)amino)-3-((trifluoromethyl)sulfonyl)phenyl)sulfonyl)benzamide |
| 79 | 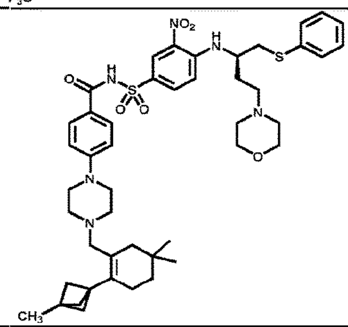 | (R)-4-(4-((5,5-dimethyl-2-(3-methylbicyclo[1.1.1]pentan-1-yl)cyclohex-1-en-1-yl)methyl)piperazin-1-yl)-N-((4-((4-morpholino-1-(phenylthio)butan-2-yl)amino)-3-nitrophenyl)sulfonyl)benzamide |
| 80 | 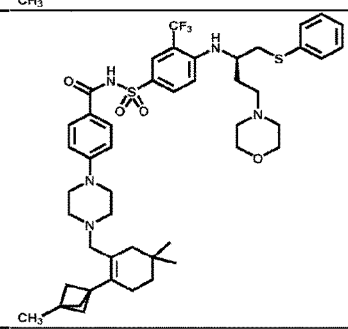 | (R)-4-(4-((5,5-dimethyl-2-(3-methylbicyclo[1.1.1]pentan-1-yl)cyclohex-1-en-1-yl)methyl)piperazin-1-yl)-N-((4-((4-morpholino-1-(phenylthio)butan-2-yl)amino)-3-(trifluoromethyl)phenyl)sulfonyl)benzamide |
| 81 | 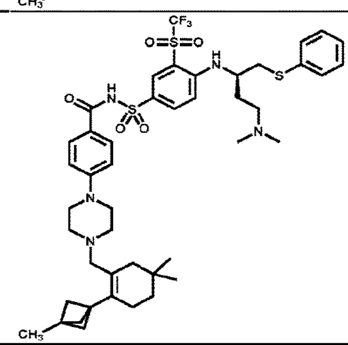 | (R)-4-(4-((5,5-dimethyl-2-(3-methylbicyclo[1.1.1]pentan-1-yl)cyclohex-1-en-1-yl)methyl)piperazin-1-yl)-N-((4-((4-(dimethylamino)-1-(phenylthio)butan-2-yl)amino)-3-((trifluoromethyl)sulfonyl)phenyl)sulfonyl)benzamide |

FIGURE 3 (cont.)

| Example No. | Structure | Name |
|---|---|---|
| 82 | 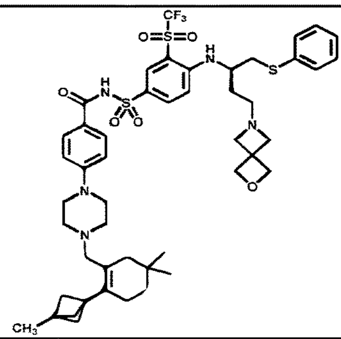 | (R)-4-(4-((5,5-dimethyl-2-(3-methylbicyclo[1.1.1]pentan-1-yl)cyclohex-1-en-1-yl)methyl)piperazin-1-yl)-N-((4-((1-(phenylthio)-4-(2-oxa-6-azaspiro[3.3]heptan-6-yl)butan-2-yl)amino)-3-((trifluoromethyl)sulfonyl)phenyl)sulfonyl)benzamide |

FIGURE 4A

| Example No. | Structure | Name |
|---|---|---|
| 1 | 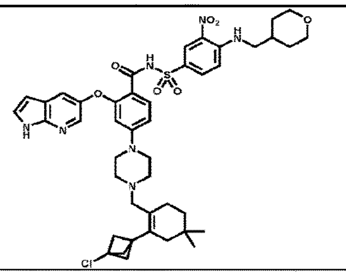 | 2-((1H-pyrrolo[2,3-b]pyridin-5-yl)oxy)-4-(4-((2-(3-chlorobicyclo[1.1.1]pentan-1-yl)-4,4-dimethylcyclohex-1-en-1-yl)methyl)piperazin-1-yl)-N-((3-nitro-4-((((tetrahydro-2H-pyran-4-yl)methyl)amino)phenyl)sulfonyl)benzamide |
| 2 | 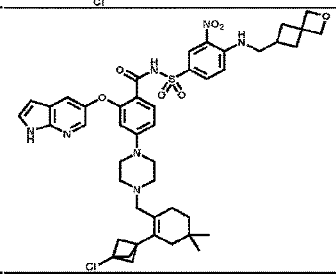 | 2-((1H-pyrrolo[2,3-b]pyridin-5-yl)oxy)-N-((4-(((2-oxaspiro[3.3]heptan-6-yl)methyl)amino)-3-nitrophenyl)sulfonyl)-4-(4-((2-(3-chlorobicyclo[1.1.1]pentan-1-yl)-4,4-dimethylcyclohex-1-en-1-yl)methyl)piperazin-1-yl)benzamide |
| 3 | 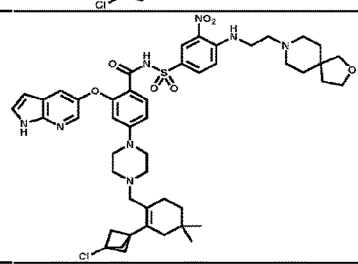 | 2-((1H-pyrrolo[2,3-b]pyridin-5-yl)oxy)-N-((4-((2-(2-oxa-8-azaspiro[4.5]decan-8-yl)ethyl)amino)-3-nitrophenyl)sulfonyl)-4-(4-((2-(3-chlorobicyclo[1.1.1]pentan-1-yl)-4,4-dimethylcyclohex-1-en-1-yl)methyl)piperazin-1-yl)benzamide |
| 4 | 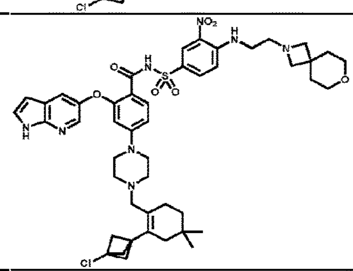 | 2-((1H-pyrrolo[2,3-b]pyridin-5-yl)oxy)-N-((4-((2-(7-oxa-2-azaspiro[3.5]nonan-2-yl)ethyl)amino)-3-nitrophenyl)sulfonyl)-4-(4-((2-(3-chlorobicyclo[1.1.1]pentan-1-yl)-4,4-dimethylcyclohex-1-en-1-yl)methyl)piperazin-1-yl)benzamide |
| 5 | 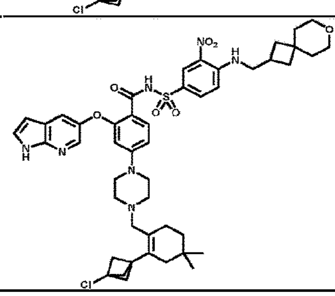 | 2-((1H-pyrrolo[2,3-b]pyridin-5-yl)oxy)-N-((4-(((7-oxaspiro[3.5]nonan-2-yl)methyl)amino)-3-nitrophenyl)sulfonyl)-4-(4-((2-(3-chlorobicyclo[1.1.1]pentan-1-yl)-4,4-dimethylcyclohex-1-en-1-yl)methyl)piperazin-1-yl)benzamide |

FIGURE 4A (cont.)

| Example No. | Structure | Name |
|---|---|---|
| 9 | 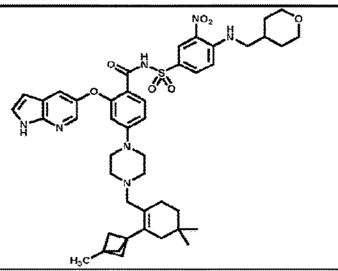 | 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((3-nitro-4-(((tetrahydro-2H-pyran-4-yl)methyl)amino)phenyl)sulfonyl)benzamide |
| 10 | 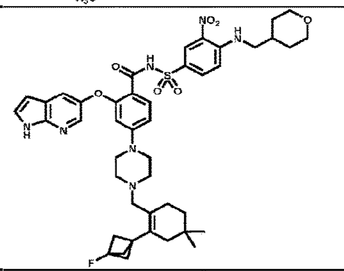 | 2-((1H-pyrrolo[2,3-b]pyridin-5-yl)oxy)-4-(4-((2-(3-fluorobicyclo[1.1.1]pentan-1-yl)-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide |
| 11 | 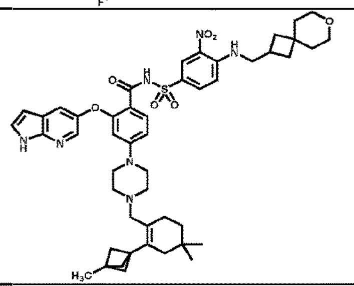 | 2-((1H-pyrrolo[2,3-b]pyridin-5-yl)oxy)-N-((4-(((7-oxaspiro[3.5]nonan-2-yl)methyl)amino)-3-nitrophenyl)sulfonyl)-4-(4-((4,4-dimethyl-2-(3-methylbicyclo[1.1.1]pentan-1-yl)cyclohex-1-en-1-yl)methyl)piperazin-1-yl)benzamide |
| 12 | 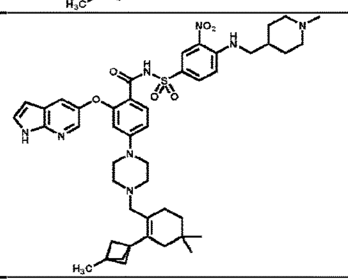 | 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-(((1-methylpiperidin-4-yl)methyl)amino)-3-nitrophenyl)sulfonyl)benzamide |
| 13 | 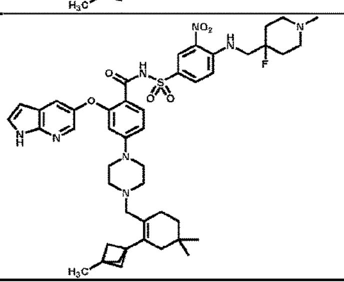 | 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-(((4-fluoro-1-methylpiperidin-4-yl)methyl)amino)-3-nitrophenyl)sulfonyl)benzamide |

FIGURE 4A (cont.)

| Example No. | Structure | Name |
|---|---|---|
| 14 | 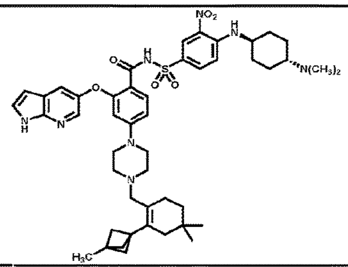 | 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-(((1r,4r)-4-(dimethylamino)cyclohexyl)amino)-3-nitrophenyl)sulfonyl)benzamide |
| 15 | 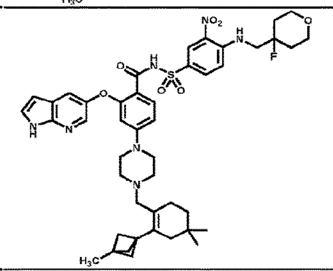 | 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-(((4-fluorotetrahydro-2H-pyran-4-yl)methyl)amino)-3-nitrophenyl)sulfonyl)benzamide |
| 17 | 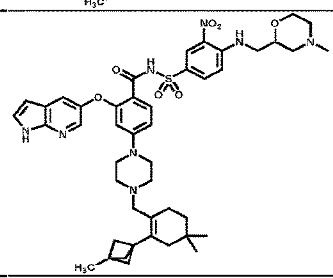 | 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-(((4-methylmorpholin-2-yl)methyl)amino)-3-nitrophenyl)sulfonyl)benzamide |
| 18 | 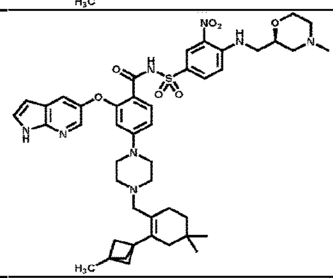 | (R)-2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-(((4-methylmorpholin-2-yl)methyl)amino)-3-nitrophenyl)sulfonyl)benzamide<br><br>*(stereochemistry arbitrarily assigned) |
| 19 | 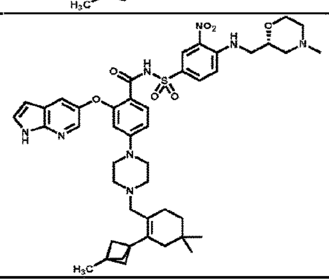 | (S)-2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-(((4-methylmorpholin-2-yl)methyl)amino)-3-nitrophenyl)sulfonyl)benzamide<br>*(stereochemistry arbitrarily assigned) |

FIGURE 4A (cont.)

| Example No. | Structure | Name |
|---|---|---|
| 20 | 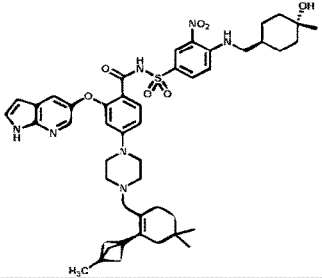 | 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide |
| 21 | 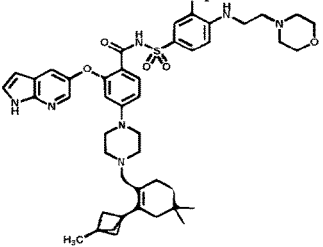 | 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-((2-morpholinoethyl)amino)-3-nitrophenyl)sulfonyl)benzamide |
| 23 | 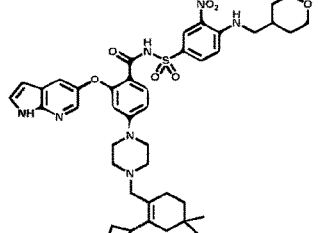 | 2-((1H-pyrrolo[2,3-b]pyridin-5-yl)oxy)-4-(4-((2-(3-ethylbicyclo[1.1.1]pentan-1-yl)-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide |
| 24 | 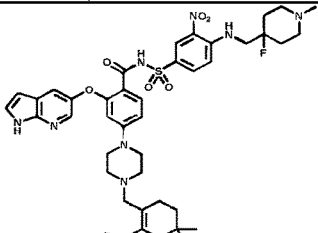 | 2-((1H-pyrrolo[2,3-b]pyridin-5-yl)oxy)-4-(4-((2-(3-ethylbicyclo[1.1.1]pentan-1-yl)-4,4-dimethylcyclohex-1-en-1-yl)methyl)piperazin-1-yl)-N-((4-(((4-fluoro-1-methylpiperidin-4-yl)methyl)amino)-3-nitrophenyl)sulfonyl)benzamide |
| 25 | 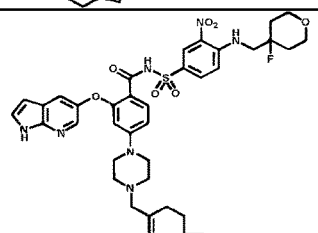 | 2-((1H-pyrrolo[2,3-b]pyridin-5-yl)oxy)-4-(4-((2-(3-ethylbicyclo[1.1.1]pentan-1-yl)-4,4-dimethylcyclohex-1-en-1-yl)methyl)piperazin-1-yl)-N-((4-(((4-fluorotetrahydro-2H-pyran-4-yl)methyl)amino)-3-nitrophenyl)sulfonyl)benzamide |

FIGURE 4A (cont.)

| Example No. | Structure | Name |
|---|---|---|
| 27 | 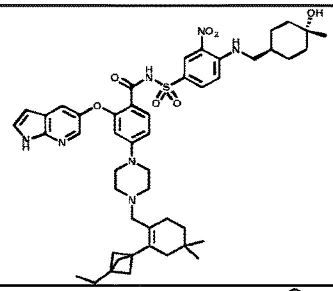 | 2-((1H-pyrrolo[2,3-b]pyridin-5-yl)oxy)-4-(4-((2-(3-ethylbicyclo[1.1.1]pentan-1-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide |
| 39 | 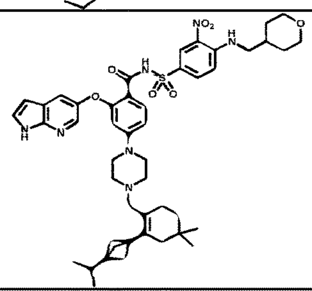 | 2-((1H-pyrrolo[2,3-b]pyridin-5-yl)oxy)-4-(4-((2-(3-isopropylbicyclo[1.1.1]pentan-1-yl)-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide |
| 40 | 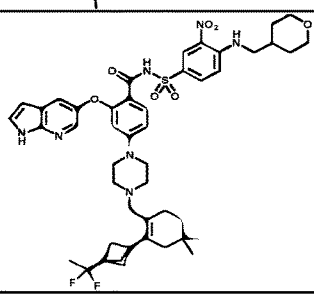 | 2-((1H-pyrrolo[2,3-b]pyridin-5-yl)oxy)-4-(4-((2-(3-(1,1-difluoroethyl)bicyclo[1.1.1]pentan-1-yl)-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide |
| 43 | 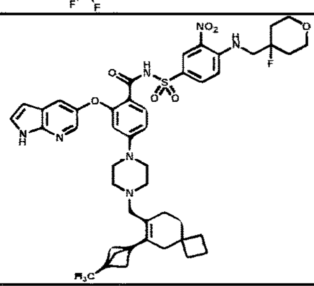 | 2-((1H-pyrrolo[2,3-b]pyridin-5-yl)oxy)-N-((4-(((4-fluorotetrahydro-2H-pyran-4-yl)methyl)amino)-3-nitrophenyl)sulfonyl)-4-(4-((6-(3-methylbicyclo[1.1.1]pentan-1-yl)spiro[3.5]non-6-en-7-yl)methyl)piperazin-1-yl)benzamide |

FIGURE 4A (cont.)

| Example No. | Structure | Name |
|---|---|---|
| 72 | 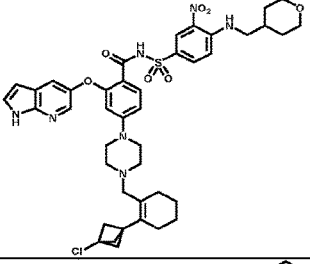 | 2-((1H-pyrrolo[2,3-b]pyridin-5-yl)oxy)-4-(4-((2-(3-chlorobicyclo[1.1.1]pentan-1-yl)cyclohex-1-en-1-yl)methyl)piperazin-1-yl)-N-((3-nitro-4-(((tetrahydro-2H-pyran-4-yl)methyl)amino)phenyl)sulfonyl)benzamide |
| 83 | 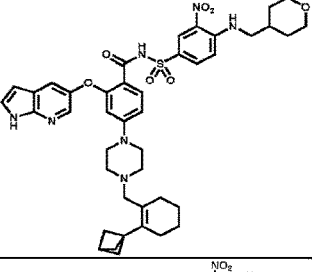 | 2-((1H-pyrrolo[2,3-b]pyridin-5-yl)oxy)-4-(4-((2-(bicyclo[1.1.1]pentan-1-yl)-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide |
| 84 | 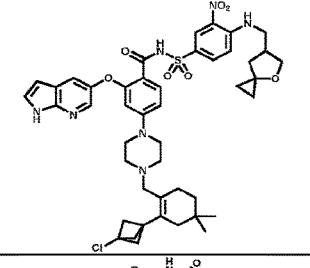 | 2-((1H-pyrrolo[2,3-b]pyridin-5-yl)oxy)-N-((4-(((4-oxaspiro[2.4]heptan-6-yl)methyl)amino)-3-nitrophenyl)sulfonyl)-4-(4-((2-(3-chlorobicyclo[1.1.1]pentan-1-yl)-4,4-dimethylcyclohex-1-en-1-yl)methyl)piperazin-1-yl)benzamide |
| 85 | 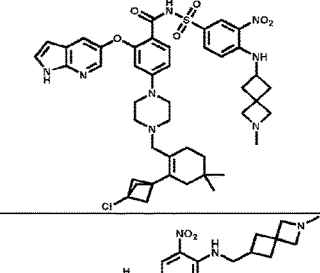 | 2-((1H-pyrrolo[2,3-b]pyridin-5-yl)oxy)-4-(4-((2-(3-chlorobicyclo[1.1.1]pentan-1-yl)-4,4-dimethylcyclohex-1-en-1-yl)methyl)piperazin-1-yl)-N-((4-((2-methyl-2-azaspiro[3.3]heptan-6-yl)amino)-3-nitrophenyl)sulfonyl)benzamide |
| 86 | 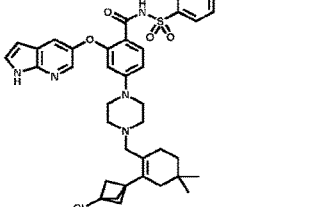 | 2-((1H-pyrrolo[2,3-b]pyridin-5-yl)oxy)-4-(4-((2-(3-chlorobicyclo[1.1.1]pentan-1-yl)-4,4-dimethylcyclohex-1-en-1-yl)methyl)piperazin-1-yl)-N-((4-(((2-methyl-2-azaspiro[3.3]heptan-6-yl)methyl)amino)-3-nitrophenyl)sulfonyl)benzamide |

FIGURE 4A (cont.)

| Example No. | Structure | Name |
|---|---|---|
| 87 | 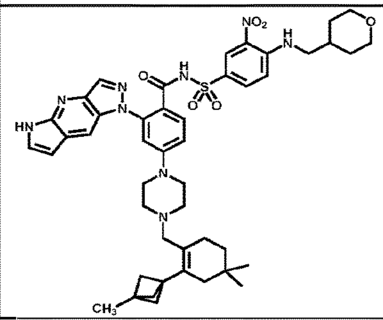 | 4-(4-((4,4-dimethyl-2-(3-methylbicyclo[1.1.1]pentan-1-yl)cyclohex-1-en-1-yl)methyl)piperazin-1-yl)-N-((3-nitro-4-(((tetrahydro-2H-pyran-4-yl)methyl)amino)phenyl)sulfonyl)-2-(pyrazolo[4,3-b]pyrrolo[3,2-e]pyridin-1(5H)-yl)benzamide |
| 88 | 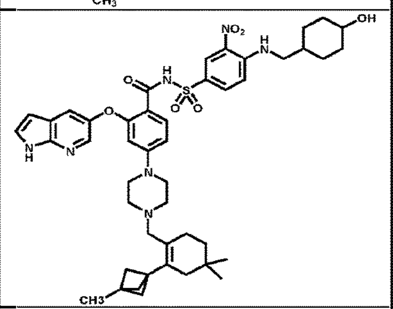 | 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-(((4-hydroxycyclohexyl)methyl)amino)-3-nitrophenyl)sulfonyl)benzamide |
| 89 | 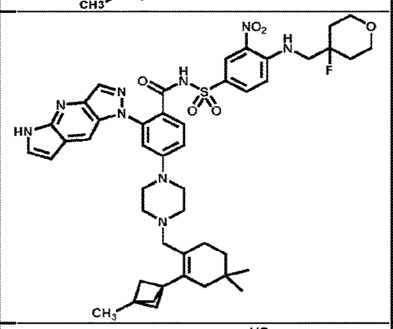 | 4-(4-((4,4-dimethyl-2-(3-methylbicyclo[1.1.1]pentan-1-yl)cyclohex-1-en-1-yl)methyl)piperazin-1-yl)-N-((4-(((4-fluorotetrahydro-2H-pyran-4-yl)methyl)amino)-3-nitrophenyl)sulfonyl)-2-(pyrazolo[4,3-b]pyrrolo[3,2-e]pyridin-1(5H)-yl)benzamide |
| 90 | 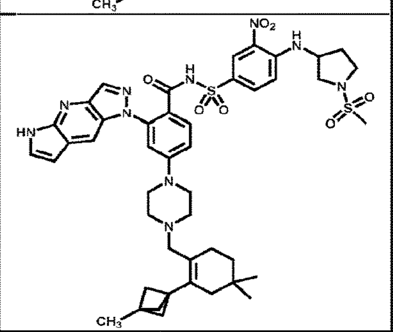 | 4-(4-((4,4-dimethyl-2-(3-methylbicyclo[1.1.1]pentan-1-yl)cyclohex-1-en-1-yl)methyl)piperazin-1-yl)-N-((4-((1-(methylsulfonyl)pyrrolidin-3-yl)amino)-3-nitrophenyl)sulfonyl)-2-(pyrazolo[4,3-b]pyrrolo[3,2-e]pyridin-1(5H)-yl)benzamide |

FIGURE 4A (cont.)

| Example No. | Structure | Name |
|---|---|---|
| 91 | 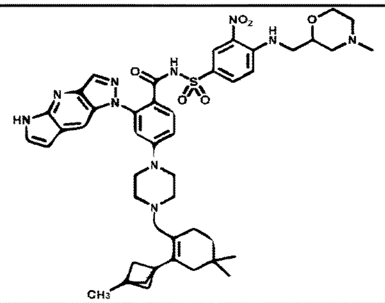 | 4-(4-((4,4-dimethyl-2-(3-methylbicyclo[1.1.1]pentan-1-yl)cyclohex-1-en-1-yl)methyl)piperazin-1-yl)-N-((4-(((4-methylmorpholin-2-yl)methyl)amino)-3-nitrophenyl)sulfonyl)-2-(pyrazolo[4,3-b]pyrrolo[3,2-e]pyridin-1(5H)-yl)benzamide |
| 92 | 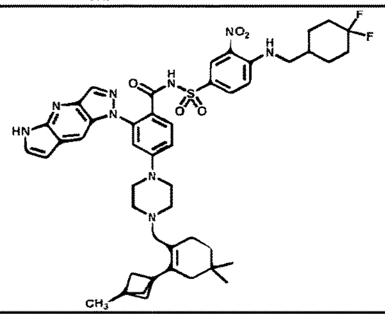 | N-((4-(((4,4-difluorocyclohexyl)methyl)amino)-3-nitrophenyl)sulfonyl)-4-(4-((4,4-dimethyl-2-(3-methylbicyclo[1.1.1]pentan-1-yl)cyclohex-1-en-1-yl)methyl)piperazin-1-yl)-2-(pyrazolo[4,3-b]pyrrolo[3,2-e]pyridin-1(5H)-yl)benzamide |
| 93 | 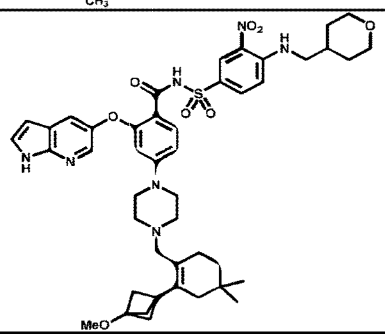 | 2-((1H-pyrrolo[2,3-b]pyridin-5-yl)oxy)-4-(4-((2-(3-methoxybicyclo[1.1.1]pentan-1-yl)-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide |
| 94 | 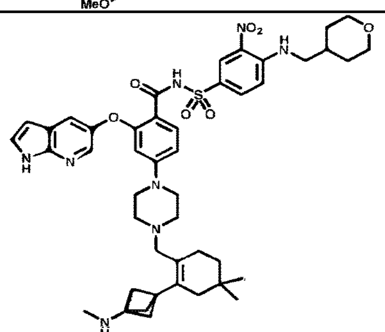 | 2-((1H-pyrrolo[2,3-b]pyridin-5-yl)oxy)-4-(4-((4,4-dimethyl-2-(3-(methylamino)bicyclo[1.1.1]pentan-1-yl)cyclohex-1-en-1-yl)methyl)piperazin-1-yl)-N-((3-nitro-4-(((tetrahydro-2H-pyran-4-yl)methyl)amino)phenyl)sulfonyl)benzamide |

| Example No. | Structure | Name |
|---|---|---|
| 95 | 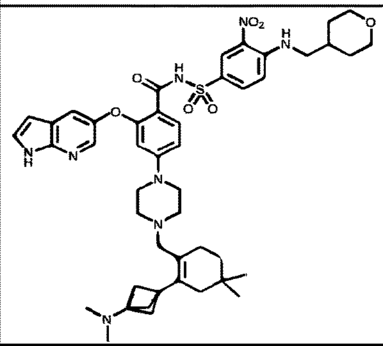 | 2-((1H-pyrrolo[2,3-b]pyridin-5-yl)oxy)-4-(4-((2-(3-(dimethylamino)bicyclo[1.1.1]pentan-1-yl)-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide |

FIGURE 4B

| Example No. | Structure | Name |
|---|---|---|
| 6 | 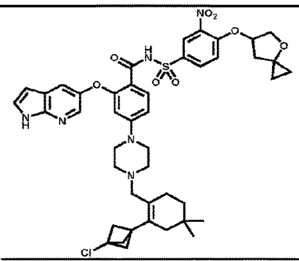 | 2-((1H-pyrrolo[2,3-b]pyridin-5-yl)oxy)-N-((4-((4-oxaspiro[2.4]heptan-6-yl)oxy)-3-nitrophenyl)sulfonyl)-4-(4-((2-(3-chlorobicyclo[1.1.1]pentan-1-yl)-4,4-dimethylcyclohex-1-en-1-yl)methyl)piperazin-1-yl)benzamide |
| 7 | 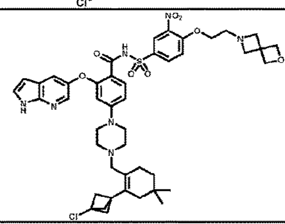 | 2-((1H-pyrrolo[2,3-b]pyridin-5-yl)oxy)-N-((4-(2-(2-oxa-6-azaspiro[3.3]heptan-6-yl)ethoxy)-3-nitrophenyl)sulfonyl)-4-(4-((2-(3-chlorobicyclo[1.1.1]pentan-1-yl)-4,4-dimethylcyclohex-1-en-1-yl)methyl)piperazin-1-yl)benzamide |
| 8 | 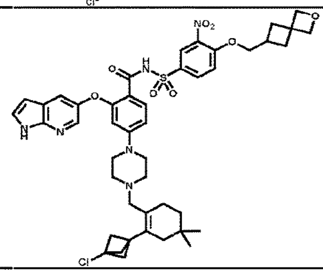 | 2-((1H-pyrrolo[2,3-b]pyridin-5-yl)oxy)-N-((4-((2-oxaspiro[3.3]heptan-6-yl)methoxy)-3-nitrophenyl)sulfonyl)-4-(4-((2-(3-chlorobicyclo[1.1.1]pentan-1-yl)-4,4-dimethylcyclohex-1-en-1-yl)methyl)piperazin-1-yl)benzamide |
| 16 | 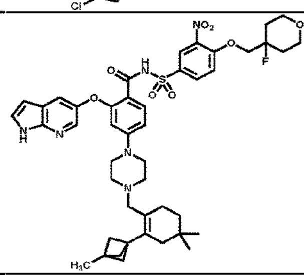 | 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-((4-fluorotetrahydro-2H-pyran-4-yl)methoxy)-3-nitrophenyl)sulfonyl)benzamide |
| 22 | 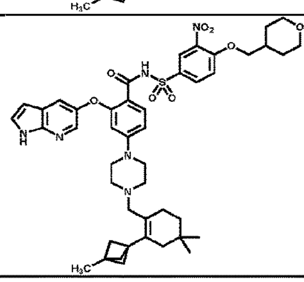 | 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((3-nitro-4-((tetrahydro-2H-pyran-4-yl)methoxy)phenyl)sulfonyl)benzamide |

FIGURE 4B (cont.)

| Example No. | Structure | Name |
|---|---|---|
| 26 | 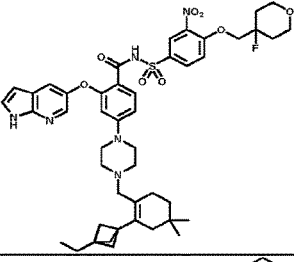 | 2-((1H-pyrrolo[2,3-b]pyridin-5-yl)oxy)-4-(4-((2-(3-ethylbicyclo[1.1.1]pentan-1-yl)-4,4-dimethylcyclohex-1-en-1-yl)methyl)piperazin-1-yl)-N-((4-((4-fluorotetrahydro-2H-pyran-4-yl)methoxy)-3-nitrophenyl)sulfonyl)benzamide |
| 31 | 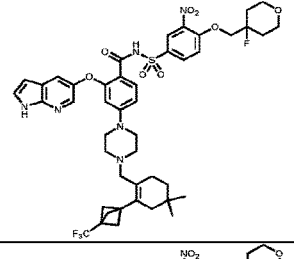 | 2-((1H-pyrrolo[2,3-b]pyridin-5-yl)oxy)-4-(4-((4,4-dimethyl-2-(3-(trifluoromethyl)bicyclo[1.1.1]pentan-1-yl)cyclohex-1-en-1-yl)methyl)piperazin-1-yl)-N-((4-((4-fluorotetrahydro-2H-pyran-4-yl)methoxy)-3-nitrophenyl)sulfonyl)benzamide |
| 36 | 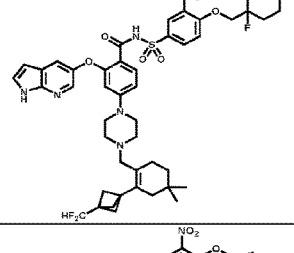 | 2-((1H-pyrrolo[2,3-b]pyridin-5-yl)oxy)-4-(4-((2-(3-(difluoromethyl)bicyclo[1.1.1]pentan-1-yl)-4,4-dimethylcyclohex-1-en-1-yl)methyl)piperazin-1-yl)-N-((4-((4-fluorotetrahydro-2H-pyran-4-yl)methoxy)-3-nitrophenyl)sulfonyl)benzamide |
| 96 | 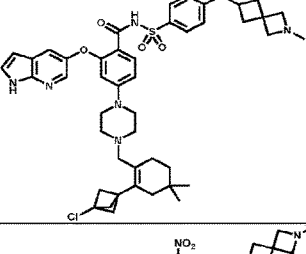 | 2-((1H-pyrrolo[2,3-b]pyridin-5-yl)oxy)-4-(4-((2-(3-chlorobicyclo[1.1.1]pentan-1-yl)-4,4-dimethylcyclohex-1-en-1-yl)methyl)piperazin-1-yl)-N-((4-((2-methyl-2-azaspiro[3.3]heptan-6-yl)oxy)-3-nitrophenyl)sulfonyl)benzamide |
| 97 | 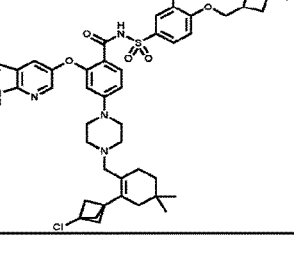 | 2-((1H-pyrrolo[2,3-b]pyridin-5-yl)oxy)-4-(4-((2-(3-chlorobicyclo[1.1.1]pentan-1-yl)-4,4-dimethylcyclohex-1-en-1-yl)methyl)piperazin-1-yl)-N-((4-((2-methyl-2-azaspiro[3.3]heptan-6-yl)methoxy)-3-nitrophenyl)sulfonyl)benzamide |

FIGURE 4C

| Example No. | Structure | Name |
|---|---|---|
| 28 | 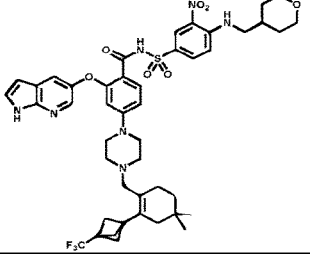 | 2-((1H-pyrrolo[2,3-b]pyridin-5-yl)oxy)-4-(4-((4,4-dimethyl-2-(3-(trifluoromethyl)bicyclo[1.1.1]pentan-1-yl)cyclohex-1-en-1-yl)methyl)piperazin-1-yl)-N-((3-nitro-4-(((tetrahydro-2H-pyran-4-yl)methyl)amino)phenyl)sulfonyl)benzamide |
| 29 | 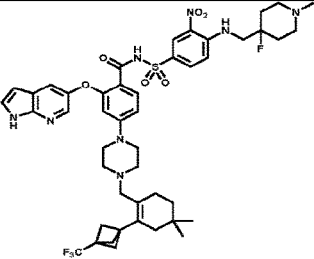 | 2-((1H-pyrrolo[2,3-b]pyridin-5-yl)oxy)-4-(4-((4,4-dimethyl-2-(3-(trifluoromethyl)bicyclo[1.1.1]pentan-1-yl)cyclohex-1-en-1-yl)methyl)piperazin-1-yl)-N-((4-(((4-fluoro-1-methylpiperidin-4-yl)methyl)amino)-3-nitrophenyl)sulfonyl)benzamide |
| 30 | 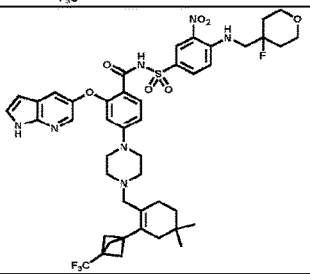 | 2-((1H-pyrrolo[2,3-b]pyridin-5-yl)oxy)-4-(4-((4,4-dimethyl-2-(3-(trifluoromethyl)bicyclo[1.1.1]pentan-1-yl)cyclohex-1-en-1-yl)methyl)piperazin-1-yl)-N-((4-(((4-fluorotetrahydro-2H-pyran-4-yl)methyl)amino)-3-nitrophenyl)sulfonyl)benzamide |
| 32 | 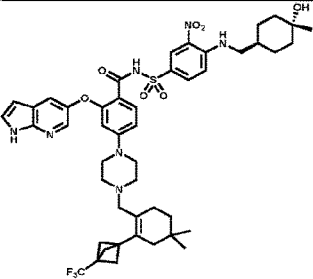 | 2-((1H-pyrrolo[2,3-b]pyridin-5-yl)oxy)-4-(4-((4,4-dimethyl-2-(3-(trifluoromethyl)bicyclo[1.1.1]pentan-1-yl)cyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide |
| 33 | 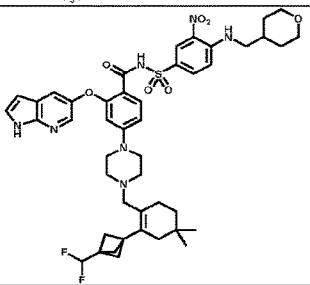 | 2-((1H-pyrrolo[2,3-b]pyridin-5-yl)oxy)-4-(4-((2-(3-(difluoromethyl)bicyclo[1.1.1]pentan-1-yl)-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide |

FIGURE 4C (cont.)

| Example No. | Structure | Name |
|---|---|---|
| 34 | 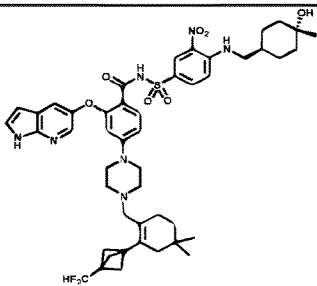 | 2-((1H-pyrrolo[2,3-b]pyridin-5-yl)oxy)-4-(4-((2-(3-(difluoromethyl)bicyclo[1.1.1]pentan-1-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide |
| 35 | 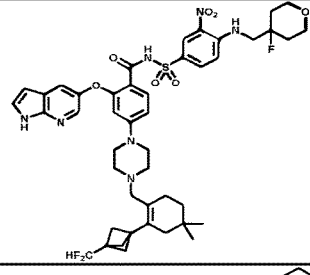 | 2-((1H-pyrrolo[2,3-b]pyridin-5-yl)oxy)-4-(4-((2-(3-(difluoromethyl)bicyclo[1.1.1]pentan-1-yl)-4,4-dimethylcyclohex-1-en-1-yl)methyl)piperazin-1-yl)-N-((4-(((4-fluorotetrahydro-2H-pyran-4-yl)methyl)amino)-3-nitrophenyl)sulfonyl)benzamide |
| 37 | 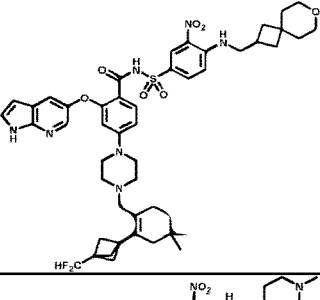 | 2-((1H-pyrrolo[2,3-b]pyridin-5-yl)oxy)-N-((4-(((7-oxaspiro[3.5]nonan-2-yl)methyl)amino)-3-nitrophenyl)sulfonyl)-4-(4-((2-(3-(difluoromethyl)bicyclo[1.1.1]pentan-1-yl)-4,4-dimethylcyclohex-1-en-1-yl)methyl)piperazin-1-yl)benzamide |
| 38 | 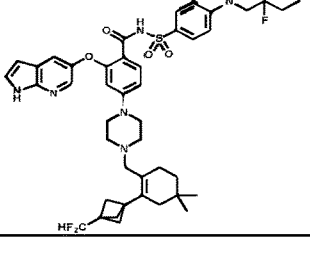 | 2-((1H-pyrrolo[2,3-b]pyridin-5-yl)oxy)-4-(4-((2-(3-(difluoromethyl)bicyclo[1.1.1]pentan-1-yl)-4,4-dimethylcyclohex-1-en-1-yl)methyl)piperazin-1-yl)-N-((4-(((4-fluoro-1-methylpiperidin-4-yl)methyl)amino)-3-nitrophenyl)sulfonyl)benzamide |

FIGURE 4C (cont.)

| Example No. | Structure | Name |
|---|---|---|
| 41 | 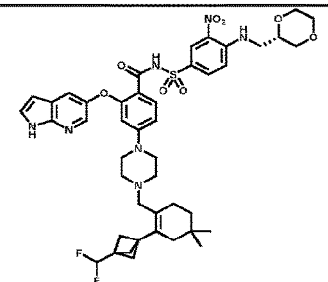 | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(3-(difluoromethyl)bicyclo[1.1.1]pentan-1-yl)-4,4-dimethylcyclohex-1-en-1-yl)methyl)piperazin-1-yl)benzamide |
| 42 | 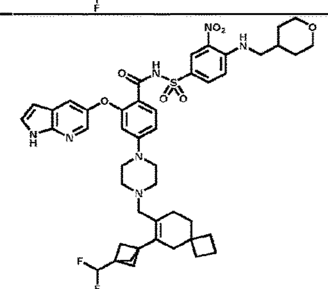 | 2-((1H-pyrrolo[2,3-b]pyridin-5-yl)oxy)-4-(4-((6-(3-(difluoromethyl)bicyclo[1.1.1]pentan-1-yl)spiro[3.5]non-6-en-7-yl)methyl)piperazin-1-yl)-N-((3-nitro-4-(((tetrahydro-2H-pyran-4-yl)methyl)amino)phenyl)sulfonyl)benzamide |
| 44 | 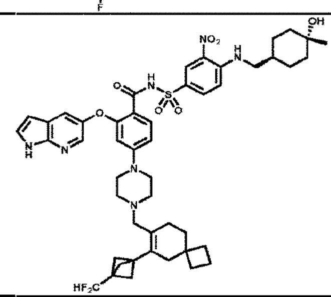 | 2-((1H-pyrrolo[2,3-b]pyridin-5-yl)oxy)-4-(4-((6-(3-(difluoromethyl)bicyclo[1.1.1]pentan-1-yl)spiro[3.5]non-6-en-7-yl)methyl)piperazin-1-yl)-N-((4-((((1r,4r)-4-hydroxy-4-methylcyclohexyl)methyl)amino)-3-nitrophenyl)sulfonyl)benzamide |
| 73 | 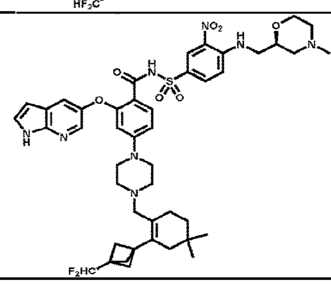 | (R)-2-((1H-pyrrolo[2,3-b]pyridin-5-yl)oxy)-4-(4-((2-(3-(difluoromethyl)bicyclo[1.1.1]pentan-1-yl)-4,4-dimethylcyclohex-1-en-1-yl)methyl)piperazin-1-yl)-N-((4-(((4-methylmorpholin-2-yl)methyl)amino)-3-nitrophenyl)sulfonyl)benzamide |

BENZAMIDE COMPOUNDS

RELATED APPLICATION INFORMATION

This application is a divisional of U.S. application Ser. No. 16/957,861, filed Jun. 25, 2020, which is a national stage filing under § 371 of PCT Application No. PCT/US2019/012695, filed Jan. 8, 2019, which claims priority to U.S. Provisional Application Ser. No. 62/615,857, filed Jan. 10, 2018. All of the foregoing are hereby incorporated herein by references in their entireties.

FIELD

The present application relates to compounds that are Bcl-2 inhibitors and methods of using them to treat conditions characterized by excessive cellular proliferation, such as cancer and tumors, and viral infections such as infection with the human immunodeficiency virus (HIV).

DESCRIPTION

Bcl-2 plays a role in cell death regulation, including apoptosis, necrosis and autophagy. Accordingly, alterations in Bcl-2 expression and function contribute to pathogenesis and progression of human cancers and tumors, and may facilitate certain viral infections such as HIV.

SUMMARY

Some embodiments provide a compound of Formula (I), or a pharmaceutically acceptable salt thereof.

Some embodiments disclosed herein relate to a pharmaceutical composition that can include an effective amount of one or more of compounds of Formula (I), or a pharmaceutically acceptable salt thereof, and a pharmaceutically acceptable carrier, diluent, excipient or combination thereof.

Some embodiments described herein relate to a method for treating a cancer or a tumor described herein that can include administering an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) in the manufacture of a medicament for treating a cancer or a tumor described herein. Still other embodiments described herein relate to an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) for treating a cancer or a tumor described herein.

Some embodiments described herein relate to a method for inhibiting replication of a malignant growth or a tumor described herein that can include contacting the growth or the tumor with an effective amount of a compound described herein (for example, a compound of Formula (I), or a pharmaceutically acceptable salt thereof). Other embodiments described herein relate to the use of an effective amount of a compound described herein (for example, a compound of Formula (I), or a pharmaceutically acceptable salt thereof) in the manufacture of a medicament for inhibiting replication of a malignant growth or a tumor described herein. Still other embodiments described herein relate to an effective amount of a compound described herein (for example, a compound of Formula (I), or a pharmaceutically acceptable salt thereof) for inhibiting replication of a malignant growth or a tumor described herein.

Some embodiments described herein relate to a method for treating a cancer described herein that can include contacting a malignant growth or a tumor described herein with an effective amount of a compound described herein (for example, a compound of Formula (I), or a pharmaceutically acceptable salt thereof). Other embodiments described herein relate to the use of an effective amount of a compound described herein (for example, a compound of Formula (I), or a pharmaceutically acceptable salt thereof) in the manufacture of a medicament for treating a cancer described herein, wherein the use comprises contacting a malignant growth or a tumor described herein with the medicament. Still other embodiments described herein relate to an effective amount of a compound described herein (for example, a compound of Formula (I), or a pharmaceutically acceptable salt thereof) for contacting a malignant growth or a tumor described herein, wherein the malignant growth or tumor is due to a cancer described herein.

Some embodiments described herein relate to a method for inhibiting the activity of Bcl-2 that can include administering an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) to a subject and can also include contacting a cell that expresses Bcl-2 with an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof). Other embodiments described herein relate to the use of an effective amount of a compound described herein (for example, a compound of Formula (I), or a pharmaceutically acceptable salt thereof) in the manufacture of a medicament for inhibiting the activity of Bcl-2 in a subject or, in the manufacture of a medicament for inhibiting the activity of Bcl-2, wherein the use comprises contacting a cell that expresses Bcl-2. Still other embodiments described herein relate to an effective amount of a compound described herein (for example, a compound of Formula (I), or a pharmaceutically acceptable salt thereof) for inhibiting the activity of Bcl-2 in a subject; or for inhibiting the activity of Bcl-2 by contacting a cell that expresses Bcl-2.

Some embodiments described herein relate to a method of ameliorating or treating a HIV infection that can include administering an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) and an effective amount of a HIV latency reversing agent, or a pharmaceutically acceptable salt thereof, to a subject suffering from the HIV infection; and can also include contacting a cell infected with HIV with a compound described herein (for example, a compound of Formula (I), or a pharmaceutically acceptable salt thereof), and an effective amount of a HIV latency reversing agent, or a pharmaceutically acceptable salt thereof. Other embodiments described herein relate to the use of an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) and an effective amount of a HIV latency reversing agent, or a pharmaceutically acceptable salt thereof, in the manufacture of a medicament for ameliorating or treating a HIV infection in a subject suffering from the HIV infection; or, in the manufacture of a medicament for ameliorating or treating a HIV infection, wherein the use comprises contacting a cell infected with HIV with the medicament. Still other embodiments described herein relate to an effective amount of a compound described herein (for example, a compound of Formula (I), or a pharmaceutically acceptable salt thereof) and an effective amount of a HIV latency reversing agent, or a pharmaceutically acceptable salt thereof, for ameliorating or treating a HIV infection in a subject suffering from the HIV infection; or for ameliorating or treating a HIV infection by contacting a cell infected with HIV.

Some embodiments described herein relate to a method of reducing the population of HIV infected cells that can include administering an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) and an effective amount of a HIV latency reversing agent, or a pharmaceutically acceptable salt thereof to a subject suffering from the HIV infection; and can also include contacting a cell infected with HIV with a compound described herein (for example, a compound of Formula (I), or a pharmaceutically acceptable salt thereof), and an effective amount of a HIV latency reversing agent, or a pharmaceutically acceptable salt thereof. Other embodiments described herein relate to the use of an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) and an effective amount of a HIV latency reversing agent, or a pharmaceutically acceptable salt thereof, in the manufacture of a medicament for reducing the population of HIV infected cells in a subject suffering from the HIV infection; or, for reducing the population of HIV infected cells, wherein the use comprises contacting a cell infected with HIV with the medicament. Still other embodiments described herein relate to an effective amount of a compound described herein (for example, a compound of Formula (I), or a pharmaceutically acceptable salt thereof) and an effective amount of a HIV latency reversing agent, or a pharmaceutically acceptable salt thereof, for reducing the population of HIV infected cells in a subject suffering from the HIV infection; or for reducing the population of HIV infected cells by contacting a cell infected with HIV.

Some embodiments described herein relate to a method of reducing the reoccurrence of a HIV infection in a subject that can include administering an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) and an effective amount of a HIV latency reversing agent, or a pharmaceutically acceptable salt thereof to a subject suffering from the HIV infection; and can also include contacting a cell infected with HIV with a compound described herein (for example, a compound of Formula (I), or a pharmaceutically acceptable salt thereof) and an effective amount of a HIV latency reversing agent, or a pharmaceutically acceptable salt thereof. Other embodiments described herein relate to the use of an effective amount of a compound described herein (for example, a compound of Formula (I), or a pharmaceutically acceptable salt thereof) and an effective amount of a HIV latency reversing agent, or a pharmaceutically acceptable salt thereof, in the manufacture of a medicament for reducing the reoccurrence of a HIV infection in a subject suffering from the HIV infection; or, for reducing the reoccurrence of a HIV infection, wherein the use comprises contacting a cell infected with HIV with the medicament. Still other embodiments described herein relate to an effective amount of a compound described herein (for example, a compound of Formula (I), or a pharmaceutically acceptable salt thereof) and an effective amount of a HIV latency reversing agent, or a pharmaceutically acceptable salt thereof, for reducing the reoccurrence of a HIV infection in a subject suffering from the HIV infection; or for reducing the reoccurrence of a HIV infection by contacting a cell infected with HIV.

Some embodiments described herein relate to a method of ameliorating or treating a HIV infection that can include administering an effective amount of a Bcl protein inhibitor, or a pharmaceutically acceptable salt thereof, and an effective amount of a HIV latency reversing agent, or a pharmaceutically acceptable salt thereof, to a subject suffering from the HIV infection; and can also include contacting a cell infected with HIV with a Bcl protein inhibitor, or a pharmaceutically acceptable salt thereof, and an effective amount of a HIV latency reversing agent, or a pharmaceutically acceptable salt thereof. Other embodiments described herein relate to the use of an effective amount of a Bcl protein inhibitor, or a pharmaceutically acceptable salt thereof, and an effective amount of a HIV latency reversing agent, or a pharmaceutically acceptable salt thereof, in the manufacture of a medicament for ameliorating or treating a HIV infection; or, in the manufacture of a medicament for ameliorating or treating a HIV infection, wherein the use comprises contacting a cell infected with HIV with the medicament. Still other embodiments described herein relate to an effective amount of a Bcl protein inhibitor, or a pharmaceutically acceptable salt thereof, and an effective amount of a HIV latency reversing agent, or a pharmaceutically acceptable salt thereof, for ameliorating or treating a HIV infection in a subject suffering from the HIV infection; or for ameliorating or treating a HIV infection by contacting a cell infected with HIV.

Some embodiments described herein relate to a method of reducing the population of HIV infected cells that can include administering an effective amount of a Bcl protein inhibitor, or a pharmaceutically acceptable salt thereof, and an effective amount of a HIV latency reversing agent, or a pharmaceutically acceptable salt thereof, to a subject suffering from the HIV infection; and can also include contacting a cell infected with HIV with a Bcl protein inhibitor, or a pharmaceutically acceptable salt thereof, and an effective amount of a HIV latency reversing agent, or a pharmaceutically acceptable salt thereof. Other embodiments described herein relate to the use of an effective amount of a Bcl protein inhibitor, or a pharmaceutically acceptable salt thereof, and an effective amount of a HIV latency reversing agent, or a pharmaceutically acceptable salt thereof, in the manufacture of a medicament for reducing the population of HIV infected cells; or, in the manufacture of a medicament for reducing the population of HIV infected cells, wherein the use comprises contacting a cell infected with HIV with the medicament. Still other embodiments described herein relate to an effective amount of a Bcl protein inhibitor, or a pharmaceutically acceptable salt thereof, and an effective amount of a HIV latency reversing agent, or a pharmaceutically acceptable salt thereof, for reducing the population of HIV infected cells in a subject suffering from the HIV infection; or for reducing the population of HIV infected cells by contacting a cell infected with HIV.

Some embodiments described herein relate to a method of reducing the reoccurrence of a HIV infection in a subject that can include administering an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) and an effective amount of a HIV latency reversing agent, or a pharmaceutically acceptable salt thereof to a subject suffering from the HIV infection; and can also include contacting a cell infected with HIV with an effective amount of a Bcl protein inhibitor, or a pharmaceutically acceptable salt thereof, and an effective amount of a HIV latency reversing agent, or a pharmaceutically acceptable salt thereof. Other embodiments described herein relate to the use of an effective amount of a Bcl protein inhibitor, or a pharmaceutically acceptable salt thereof, and an effective amount of a HIV latency reversing agent, or a pharmaceutically acceptable salt thereof, in the manufacture of a medicament for reducing the reoccurrence of a HIV infection in a subject suffering from the HIV infection; or, for reducing the reoccurrence of a HIV infection, wherein the use comprises contacting a cell infected with HIV with the medicament. Still other embodiments described herein relate to an effective amount of a Bcl protein inhibitor, or a pharmaceutically acceptable salt thereof, and an effective amount of a HIV latency reversing agent, or a pharmaceutically acceptable salt thereof, for reducing the reoccurrence of a HIV infection in a subject suffering from the HIV infection; or for reducing the reoccurrence of a HIV infection by contacting a cell infected with HIV.

These and other embodiments are described in greater detail below.

BRIEF DESCRIPTION OF THE DRAWINGS

FIG. 3 shows examples of compounds of the Formula (I).
FIGS. 4A, 4B and 4C show examples of compounds of the Formula (I).

DETAILED DESCRIPTION

Figure 1:
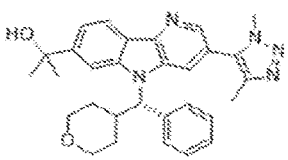
FIG. 1 shows example HIV latency reversing agents.
Figure 1:
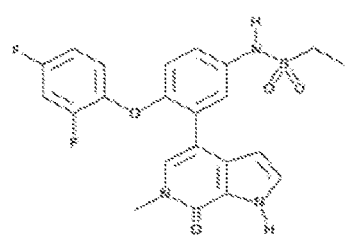
Figure 2:
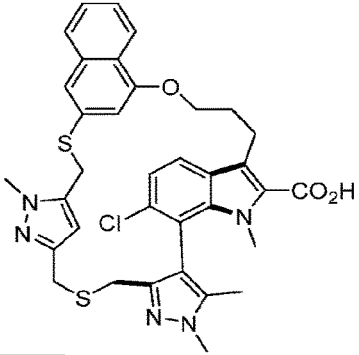
FIG. 2 shows example Bcl protein inhibitors.
Figure 2:
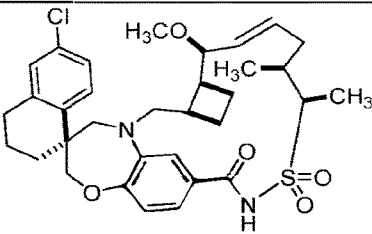

Bcl-2 is a critical regulator of programmed cell death (apoptosis). Bcl-2 belongs to the B cell lymphoma 2 (BCL-2) a family of proteins, which includes both pro-apoptotic proteins (such as Bak, Bax, Bim, Bid, tBid, Bad, Bik, PUMA, Bnip-1, Hrk, Bmf and Noxa) and anti-apoptotic proteins (such as Bcl-2, Bcl-$X_L$, Bcl-W, Mcl-1 and Bcl-2A1). For example, under normal conditions, Bcl-2 inhibits apoptosis in part by preventing activation of Bak and Bax. Activation of the intrinsic apoptosis pathway (e.g., by cellular stress) inhibits Bcl-2, thus activating Bak and Bax. These proteins facilitate mitochondrial outer membrane permeabilization, releasing cytochrome c and Smac. This initiates the caspase signaling pathway, ultimately resulting in cell death. Dysregulation of Bcl-2 leads to sequestration of cell-death-promoting proteins, leading to evasion of apoptosis. This process contributes to malignancy, and facilitates cell survival under other disadvantageous conditions, such as during viral infection. For example, transcriptionally active HIV can incidentally generate a caspase protein fragment. This fragment binds to and activates the pro-apoptotic Bak. However, this fragment also binds to, and is sequestered by, Bcl-2 reducing its effectiveness at inducing cell death. Inhibition of Bcl-2 disrupts sequestration of pro-apoptotic proteins, restoring apoptotic signaling, and promoting damaged cells to undergo programmed cell death. Therefore, Bcl-2 inhibition has the potential to ameliorate or treat cancers and tumors, as well as ameliorate or treat certain viral infections in combination with other agents.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), cycloalkyl(alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, nitro, sulfenyl, sulfinyl, sulfonyl, haloalkyl, haloalkoxy, an amino, a mono-substituted amine group, a di-substituted amine group, a mono-substituted amine(alkyl) and a di-substituted amine(alkyl).

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated, the broadest range described in these definitions is to be assumed.

If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

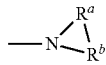

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkyl" where no numerical range is designated). The alkyl group may also be a medium size alkyl having 1 to 12 carbon atoms. The alkyl group could also be a lower alkyl having 1 to 6 carbon atoms. An alkyl group may be substituted or unsubstituted.

As used herein, the term "alkylene" refers to a bivalent fully saturated straight chain aliphatic hydrocarbon group. Examples of alkylene groups include, but are not limited to, methylene, ethylene, propylene, butylene, pentylene, hexylene, heptylene and octylene. An alkylene group may be represented by ～, followed by the number of carbon atoms, followed by a "*". For example,

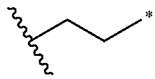

to represent ethylene. The alkylene group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkylene" where no numerical range is designated). The alkylene group may also be a medium size alkyl having 1 to 12 carbon atoms. The alkylene group could also be a lower alkyl having 1 to 4 carbon atoms. An alkylene group may be substituted or unsubstituted. For example, a lower alkylene group can be substituted by replacing one or more hydrogen of the lower alkylene group and/or by substituting both hydrogens on the same carbon with a $C_{3-6}$ monocyclic cycloalkyl group

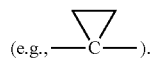

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic (such as bicyclic) hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Examples of mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl and norbornanyl; and examples of spiro cycloalkyl groups include spiro[3.3]heptane and spiro[4.5]decane.

As used herein, "cycloalkenyl" refers to a mono- or multi-cyclic (such as bicyclic) hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s), 3 to 8 atoms in the ring(s) or 3 to 6 atoms in the ring(s). When composed of two or more rings, the rings may be connected together in a fused, bridged or spiro fashion. A cycloalkenyl group may be unsubstituted or substituted.

As used herein, "aryl" refers to a carbocyclic (all carbon) monocyclic or multicyclic (such as bicyclic) aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic (such as bicyclic) aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" or "bridged heteroalicyclyl" refers to compounds wherein the heterocyclyl or heteroalicyclyl contains a linkage of one or more atoms connecting non-adjacent atoms. As used herein, the term "spiro" refers to two rings which have one atom in common and the two rings are not linked by a bridge. Heterocyclyl and heteroalicyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl and imidazolylalkyl and their benzo-fused analogs.

A "heteroalicyclyl(alkyl)" and "heterocyclyl(alkyl)" refer to a heterocyclic or a heteroalicyclic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl) and 1,3-thiazinan-4-yl(methyl).

As used herein, the term "hydroxy" refers to a —OH group.

As used herein, "alkoxy" refers to the Formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

A "cyano" group refers to a "—CN" group.

The term "halogen atom" or "halogen" as used herein, means any one of the radio-stable atoms of column 7 of the Periodic Table of the Elements, such as, fluorine, chlorine, bromine and iodine.

A "thiocarbonyl" group refers to a "—C(=S)R" group in which R can be the same as defined with respect to O-carboxy. A thiocarbonyl may be substituted or unsubstituted.

An "O-carbamyl" group refers to a "—OC(=O)N ($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N ($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N ($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

An "S-sulfonamido" group refers to a "—SO$_2$N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carboxy" group refers to a "RC(=O)O—" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "nitro" group refers to an "—NO$_2$" group.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

As used herein, "haloalkyl" refers to an alkyl group in which one or more of the hydrogen atoms are replaced by a halogen (e.g., mono-haloalkyl, di-haloalkyl, tri-haloalkyl and polyhaloalkyl). Such groups include but are not limited to, chloromethyl, fluoromethyl, difluoromethyl, trifluoromethyl, 1-chloro-2-fluoromethyl, 2-fluoroisobutyl and pentafluoroethyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

The terms "amino" and "unsubstituted amino" as used herein refer to a —NH$_2$ group.

A "mono-substituted amine" group refers to a "—NHR$_A$" group in which R$_A$ can be an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. The R$_A$ may be substituted or unsubstituted. A mono-substituted amine group can include, for example, a mono-alkylamine group, a mono-$C_1$-$C_6$ alkylamine group, a mono-arylamine group, a mono-$C_6$-$C_{10}$ arylamine group and the like. Examples of mono-substituted amine groups include, but are not limited to, —NH(methyl), —NH(phenyl) and the like.

A "di-substituted amine" group refers to a "—NR$_A$R$_B$" group in which R$_A$ and R$_B$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. R$_A$ and R$_B$ can independently be substituted or unsubstituted. A di-substituted amine group can include, for example, a di-alkylamine group, a di-$C_1$-$C_6$ alkylamine group, a di-arylamine group, a di-$C_6$-$C_{10}$ arylamine group and the like. Examples of di-substituted amine groups include, but are not limited to, —N(methyl)$_2$, —N(phenyl)(methyl), —N(ethyl)(methyl) and the like.

As used herein, "mono-substituted amine(alkyl)" group refers to a mono-substituted amine as provided herein connected, as a substituent, via a lower alkylene group. A mono-substituted amine(alkyl) may be substituted or unsubstituted. A mono-substituted amine(alkyl) group can include, for example, a mono-alkylamine(alkyl) group, a mono-$C_1$-$C_6$ alkylamine($C_1$-$C_6$ alkyl) group, a mono-arylamine(alkyl group), a mono-$C_6$-$C_{10}$ arylamine($C_1$-$C_6$ alkyl) group and the like. Examples of mono-substituted amine(alkyl) groups include, but are not limited to, —CH$_2$NH(methyl), —CH$_2$NH(phenyl), —CH$_2$CH$_2$NH(methyl), —CH$_2$CH$_2$NH(phenyl) and the like.

As used herein, "di-substituted amine(alkyl)" group refers to a di-substituted amine as provided herein connected, as a substituent, via a lower alkylene group. A di-substituted amine(alkyl) may be substituted or unsubstituted. A di-substituted amine(alkyl) group can include, for example, a dialkylamine(alkyl) group, a di-$C_1$-$C_6$ alkylamine($C_1$-$C_6$ alkyl) group, a di-arylamine(alkyl) group, a di-$C_6$-$C_{10}$ arylamine($C_1$-$C_6$ alkyl) group and the like. Examples of di-substituted amine(alkyl)groups include, but are not limited to, —CH$_2$N(methyl)$_2$, —CH$_2$N(phenyl)(methyl), —NCH$_2$(ethyl)(methyl), —CH$_2$CH$_2$N(methyl)$_2$, —CH$_2$CH$_2$N(phenyl)(methyl), —NCH$_2$CH$_2$(ethyl)(methyl) and the like.

Where the number of substituents is not specified (e.g. haloalkyl), there may be one or more substituents present. For example, "haloalkyl" may include one or more of the same or different halogens. As another example, "$C_1$-$C_3$ alkoxyphenyl" may include one or more of the same or different alkoxy groups containing one, two or three atoms.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), a sulfuric acid, a nitric acid and a phosphoric acid (such as 2,3-dihydroxypropyl dihydrogen phosphate). Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, trifluoroacetic, benzoic, salicylic, 2-oxopentanedioic or naphthalenesulfonic acid. Pharmaceutical salts can also be obtained by reacting a compound with a base to form a salt such as an ammonium salt, an alkali metal salt, such as a sodium, a potassium or a lithium salt, an alkaline earth metal salt, such as a calcium or a magnesium salt, a salt of a carbonate, a salt of a bicarbonate, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine and salts with amino acids such as arginine and lysine. For compounds of Formula (I), those skilled in the art understand that when a salt is formed by protonation of a nitrogen-based group (for example, $NH_2$), the nitrogen-based group can be associated with a positive charge (for example, $NH_2$ can become $NH_3^+$) and the positive charge can be balanced by a negatively charged counterion (such as $Cl^-$).

Latently infected HIV cells harbor transcriptionally silent virus that may still replicate to produce active HIV. The term "HIV latency reversing agent" refers to an agent (including small molecules and proteins) that stimulates HIV transcription, converting latently infected HIV cells into cells expressing replicating HIV. HIV latency reversing agents include, but are not limited to protein kinase C agonists (such as prostratin, bryostatin-1 and ingenol), PD-1 inhibitors (such as nivolumab, pembrolizumab, BGB-A317, pidilizumab, AMP-224, AMP-514, PDR001, REGN2810 and MEDI0680), PD-L1 inhibitors (such as atezolizumab, durvalumab, avelumab and BMS-936559), HDAC inhibitors (such as vorinostat, panobinostat, romidepsin and valproic acid), phorbol esters (such as phorbol 12-myristate-13-acetate and (S)-tert-butyl-2-(4-(4-chlorophenyl)-2,3,9-trimethyl-6H-thieno[3,2-f][1,2,4]triazolo[4,3-a][1,4]diazepin-6-yl)acetate) and bromodomain inhibitors (such as JQ1, I-BET762, OTX015, I-BET151, CPI203, PFI-1, MS436, CPI-0610, RVX2135, FT-1101, BAY1238097, INCB054329, TEN-010, GSK2820151, ZEN003694, BAY-299, BMS-986158, ABBV-075 and GS-5829).

The term "Bcl protein inhibitor" refers to an agent (including small molecules and proteins) that inhibit the binding of an anti-apoptic Bcl protein (such as Bcl-2, Bcl-$X_L$, Bcl-W, Mcl-1 and Bcl-2A1) to a pro-apoptotic Bcl protein (such as Bak, Bax, Bim, Bid, tBid, Bad, Bik, PUMA, Bnip-1, Hrk, Bmf and Noxa). Bcl protein inhibitors include, but are not limited to venetoclax, navitoclax, obatoclax, 555746, APG-2575, ABT-737, AMG176, AZD5991 and APG-1252. Additional Bcl protein inhibitors include, but are not limited to, compounds disclosed in PCT Application Publication Nos. WO2017/132474, WO 2014/113413 and WO 2013/110890, U.S. Patent Application Publication No. 2015/0051189 and Chinese Patent Application No. CN 106565607, which are each incorporated herein by reference for the limited purpose of disclosing additional Bcl protein inhibitors. As will be understood by those of skill in the art, there are numerous methods of evaluating protein binding interactions, including, but not limited to co-immunoprecipitation, fluorescence resonance energy transfer (FRET), surface plasmon resonance (SPR) and fluorescence polarization/anisotropy.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched or a stereoisomeric mixture. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates and hydrates. In some embodiments, the compounds described herein exist in solvated forms with pharmaceutically acceptable solvents such as water, ethanol or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol or the like. Hydrates are formed when the solvent is water or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a compound, composition or device, the term "comprising" means that the compound, composition or device includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Compounds

Some embodiments disclosed herein relate to a compound of Formula (I), or a pharmaceutically acceptable salt thereof, having the structure:

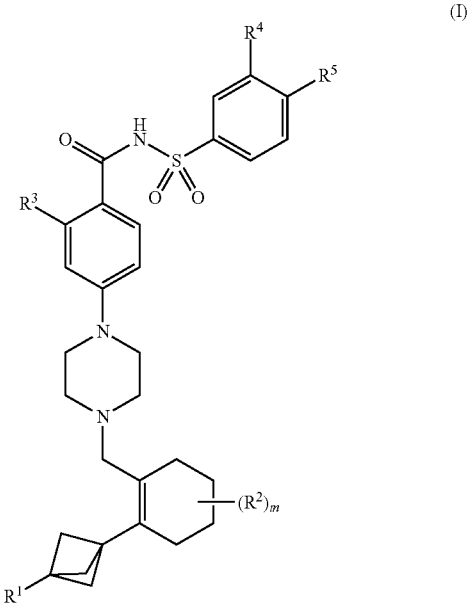

(I)

wherein: $R^1$ can be selected from hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine; each $R^2$ can be independently selected from halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl; $R^3$ can be selected from hydrogen, halogen, X—$R^{3A}$,

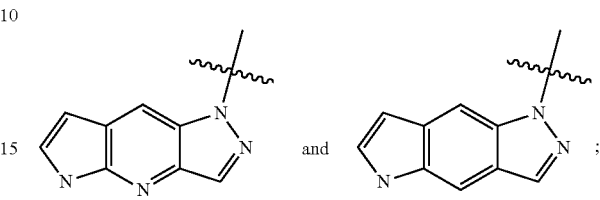

and $R^{3A}$ can be a substituted or unsubstituted 5 to 10 membered heteroaryl; $R^4$ can be selected from $NO_2$, $S(O)R^6$, $SO_2R^6$, halogen, cyano and an unsubstituted $C_1$-$C_6$ haloalkyl; $R^5$ can be selected from —$X^1$-(Alk$^1$)$_n$-$R^7$ and —$X^2$(CHR$^8$)-(Alk$^2$)$_p$-$X^3$—$R^9$; Alk$^1$ and Alk$^2$ can be independently selected from an unsubstituted $C_1$-$C_4$ alkylene and a $C_1$-$C_4$ alkylene substituted with 1, 2 or 3 substituents independently selected from fluoro, chloro, an unsubstituted $C_1$-$C_3$ alkyl and an unsubstituted $C_1$-$C_3$ haloalkyl; $R^6$ can be selected from a substituted or unsubstituted $C_1$-$C_6$ alkyl, a substituted or unsubstituted $C_1$-$C_6$ haloalkyl and a substituted or unsubstituted $C_3$-$C_6$ cycloalkyl; $R^7$ can be selected from a substituted or unsubstituted $C_1$-$C_6$ alkoxy, a substituted or unsubstituted $C_3$-$C_{10}$ cycloalkyl, a substituted or unsubstituted 3 to 10 membered heterocyclyl, hydroxy, an amino group, a substituted or unsubstituted mono-substituted amine group, a substituted or unsubstituted di-substituted amine group, a substituted or unsubstituted N-carbamyl, a substituted or unsubstituted C-amido and a substituted or unsubstituted N-amido; $R^8$ can be selected from a substituted or unsubstituted 3 to 10 membered heterocyclyl($C_1$-$C_6$ alkyl), a substituted or unsubstituted di-$C_1$-$C_6$ alkylamine($C_1$-$C_6$ alkyl) and a substituted or unsubstituted mono-$C_1$-$C_6$ alkylamine($C_1$-$C_6$ alkyl); $R^9$ can be selected from a substituted or unsubstituted 5 to 10 membered heteroaryl and a substituted or unsubstituted monocyclic or bicyclic $C_6$-$C_{10}$ aryl; m can be 0, 1, 2 and 3; n and p can be independently selected from 0 and 1; X, $X^1$, $X^2$ and $X^3$ can be independently selected from —O—, —S— and —NH—; and wherein when m is 2 or 3, two $R^2$ groups can be taken together with the atom(s) to which they are attached to form a substituted or unsubstituted $C_3$-$C_6$ cycloalkyl or a substituted or unsubstituted 3 to 6 membered heterocyclyl.

In some embodiments, $R^1$ can be halogen, for example, fluoro, chloro, bromo or iodo. In some embodiments, $R^1$ can be fluoro. In some embodiments, $R^1$ can be chloro. In some embodiments, $R^1$ can be hydrogen.

In some embodiments, $R^1$ can be a substituted or unsubstituted $C_1$-$C_6$ alkyl. For example, in some embodiments, $R^1$ can be a substituted $C_1$-$C_6$ alkyl. In other embodiments, $R^1$ can be an unsubstituted $C_1$-$C_6$ alkyl. Examples of suitable $C_1$-$C_6$ alkyl groups include, but are not limited to methyl, ethyl, n-propyl, isopropyl, n-butyl, isobutyl, tert-butyl, pentyl (branched and straight-chained) and hexyl (branched and straight-chained). In some embodiments, $R^1$ can be an unsubstituted methyl or an unsubstituted ethyl.

In some embodiments, $R^1$ can be a substituted or unsubstituted $C_1$-$C_6$ haloalkyl, for example, a substituted or unsubstituted mono-halo $C_1$-$C_6$ alkyl, a substituted or unsubstituted di-halo $C_1$-$C_6$ alkyl, a substituted or unsubstituted tri-halo $C_1$-$C_6$ alkyl, a substituted or unsubstituted tetra-halo $C_1$-$C_6$ alkyl or a substituted or unsubstituted penta-halo $C_1$-$C_6$ alkyl. In some embodiments, $R^1$ can be an unsubstituted —$CHF_2$, —$CF_3$, —$CH_2CF_3$ or —$CF_2CH_3$.

In some embodiments, $R^1$ can be a substituted or unsubstituted monocyclic or bicyclic $C_3$-$C_6$ cycloalkyl. For example, in some embodiments, $R^1$ can be a substituted monocyclic $C_3$-$C_6$ cycloalkyl. In other embodiments, $R^1$ can be an unsubstituted monocyclic $C_3$-$C_6$ cycloalkyl. Examples of suitable monocyclic or bicyclic $C_3$-$C_6$ cycloalkyl groups include, but are not limited to cyclopropyl, cyclobutyl, cyclopentyl, [1.1.1]bicyclopentyl and cyclohexyl.

In some embodiments, $R^1$ can be a substituted or unsubstituted $C_1$-$C_6$ alkoxy. For example, in some embodiments, $R^1$ can be a substituted $C_1$-$C_6$ alkoxy. In other embodiments, $R^1$ can be an unsubstituted $C_1$-$C_6$ alkoxy. Examples of suitable $C_1$-$C_6$ alkoxy groups include, but are not limited to methoxy, ethoxy, n-propoxy, isopropoxy, n-butoxy, isobutoxy, tert-butoxy, pentoxy (branched and straight-chained) and hexoxy (branched and straight-chained). In some embodiments, $R^1$ can be an unsubstituted methoxy or an unsubstituted ethoxy.

In some embodiments, $R^1$ can be an unsubstituted mono-$C_1$-$C_6$ alkylamine, for example, methylamine, ethylamine, n-propylamine, isopropylamine, n-butylamine, isobutylamine, tert-butylamine, pentylamine (branched and straight-chained) and hexylamine (branched and straight-chained). In some embodiments, $R^1$ can be methylamine or ethylamine.

In some embodiments, $R^1$ can be an unsubstituted di-$C_1$-$C_6$ alkylamine. In some embodiments, each $C_1$-$C_6$ alkyl in the di-$C_1$-$C_6$ alkylamine is the same. In other embodiments, each $C_1$-$C_6$ alkyl in the di-$C_1$-$C_6$ alkylamine is different. Examples of suitable di-$C_1$-$C_6$ alkylamine groups include, but are not limited to di-methylamine, di-ethylamine, (methyl)(ethyl)amine, (methyl)(isopropyl)amine and (ethyl)(isopropyl)amine.

In some embodiments, m can be 0. When m is 0, those skilled in the art understand that the ring to which $R^2$ is attached is unsubstituted. In some embodiments, m can be 1. In some embodiments, m can be 2. In some embodiments, m can be 3.

In some embodiments, one $R^2$ can be an unsubstituted $C_1$-$C_6$ alkyl (for example, methyl, ethyl, n-propyl, isopropyl, n-butyl, isobutyl, tert-butyl, pentyl (branched and straight-chained) and hexyl (branched and straight-chained)) and any other $R^2$, if present, can be independently selected from halogen (for example, fluoro or chloro), a substituted or unsubstituted $C_1$-$C_6$ alkyl (such as those described herein), a substituted or unsubstituted $C_1$-$C_6$ haloalkyl (such as those described herein) and a substituted or unsubstituted monocyclic or bicyclic $C_3$-$C_6$ cycloalkyl (such as those described herein). In some embodiments, each $R^2$ can be independently selected from an unsubstituted $C_1$-$C_6$ alkyl, such as those described herein.

In some embodiments, m can be 2; and each $R^2$ can be geminal. In some embodiments, m can be 2; and each $R^2$ can be vicinal. In some embodiments, m can be 2; and each $R^2$ can be an unsubstituted methyl. In some embodiments, m can be 2; and each $R^2$ can be a geminal unsubstituted methyl.

In some embodiments, two $R^2$ groups can be taken together with the atom(s) to which they are attached to form a substituted or unsubstituted monocyclic $C_3$-$C_6$ cycloalkyl. For example, in some embodiments, two $R^2$ groups can be taken together with the atom(s) to which they are attached to form a substituted monocyclic $C_3$-$C_6$ cycloalkyl, such as those described herein. In other embodiments, two $R^2$ groups can be taken together with the atom(s) to which they are attached to form an unsubstituted monocyclic $C_3$-$C_6$ cycloalkyl, such as those described herein. In some embodiments, two $R^2$ groups can be taken together with the atom to which they are attached to form an unsubstituted cyclopropyl.

In some embodiments, two $R^2$ groups can be taken together with the atom(s) to which they are attached to form a substituted or unsubstituted monocyclic 3 to 6 membered heterocyclyl. For example, in some embodiments, two $R^2$ groups can be taken together with the atom(s) to which they are attached to form a substituted monocyclic 3 to 6 membered heterocyclyl. In other embodiments, two $R^2$ groups can be taken together with the atom(s) to which they are attached to form an unsubstituted monocyclic 3 to 6 membered monocyclic heterocyclyl. In some embodiments, the substituted monocyclic 3 to 6 membered heterocyclyl can be substituted on one or more nitrogen atoms. Examples of suitable substituted or unsubstituted monocyclic 3 to 6 membered heterocyclyl groups include, but are not limited to azidirine, oxirane, azetidine, oxetane, pyrrolidine, tetrahydrofuran, imidazoline, pyrazolidine, piperidine, tetrahydropyran, piperazine, morpholine, thiomorpholine and dioxane.

In some embodiments, $R^3$ can be

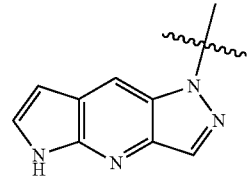

In some embodiments, $R^3$ can be

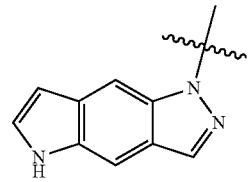

In some embodiments, $R^3$ can be X—$R^{3A}$. In some embodiments, X can be —O—. In some embodiments, X can be —S—. In some embodiments, X can be —NH—. In some embodiments, $R^{3A}$ can be

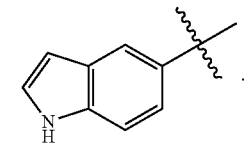 [SMILES: *c1ccc2[nH]ccc2c1]

In some embodiments, $R^{3A}$ can be

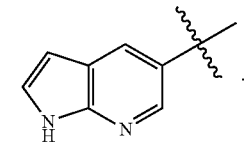 [SMILES: *c1cnc2[nH]ccc2c1]

In some embodiments, $R^{3A}$ can be a substituted or unsubstituted 5 to 10 membered heteroaryl. In some embodiments, $R^{3A}$ can be a substituted 5 to 10 membered monocyclic heteroaryl. In other embodiments, $R^{3A}$ can be a substituted 5 to 10 membered bicyclic heteroaryl. In some embodiments, $R^{3A}$ can be an unsubstituted 5 to 10 membered monocyclic heteroaryl. In other embodiments, $R^{3A}$ can be an unsubstituted 5 to 10 membered bicyclic heteroaryl. Examples of suitable substituted or unsubstituted monocyclic or bicyclic 5 to 10 membered heteroaryl groups include, but are not limited to pyrrole, furan, thiophene, imidazole, pyrazole, oxazole, isoxazole, thiazole, isothiazole, triazole, pyridine, pyridazine, pyrimidine, pyrazine, pyrrolo-pyrroles, pyrrolo-furans, pyrrolo-thiophenes, indole, isoindole, indolizine, indazole, benzimidazole, azaindoles, azaindazoles, purine, benzofuran, isobenzofuran, benzothiophene, isobenzothiophene, quinoline, isoquinoline, quinoxaline, phthalazine, quinazoline, cinnoline, 1,8-naphthyridine, pyrido-pyrimidines and pteridine.

In some embodiments, $R^3$ can be hydrogen. In some embodiments, $R^3$ can be halogen. In some embodiments, $R^3$ can be fluoro or chloro.

In some embodiments, $R^4$ can be $NO_2$. In some embodiments, $R^4$ can be cyano. In some embodiments, $R^4$ can be halogen.

In some embodiments, $R^4$ can be an unsubstituted $C_1$-$C_6$ haloalkyl, such as those described herein. In some embodiments, $R^4$ can be —$CF_3$.

In some embodiments, $R^4$ can be $S(O)R^6$. In some embodiments, $R^4$ can be $SO_2R^6$. In some embodiments, $R^4$ can be $SO_2CF_3$.

In some embodiments, $R^6$ can be a substituted or unsubstituted $C_1$-$C_6$ alkyl. For example, in some embodiments, $R^6$ can be a substituted $C_1$-$C_6$ alkyl, such as those described herein. In other embodiments, $R^6$ can be an unsubstituted $C_1$-$C_6$ alkyl, such as those described herein.

In some embodiments, $R^6$ can be a substituted or unsubstituted monocyclic or bicyclic $C_3$-$C_6$ cycloalkyl. For example, in some embodiments, $R^6$ can be a substituted monocyclic or bicyclic $C_3$-$C_6$ cycloalkyl. In other embodiments, $R^6$ can be an unsubstituted monocyclic or bicyclic $C_3$-$C_6$ cycloalkyl. Examples of suitable monocyclic or bicyclic $C_3$-$C_6$ cycloalkyl groups include, but are not limited to cyclopropyl, cyclobutyl, cyclopentyl, [1.1.1]bicyclopentyl and cyclohexyl.

In some embodiments, $R^6$ can be a substituted or unsubstituted $C_1$-$C_6$ haloalkyl, such as those described herein. In some embodiments, $R^6$ can be —$CF_3$.

In some embodiments, $R^5$ can be —$X^1$-$(Alk^1)_n$-$R^7$. In some embodiments, $X^1$ can be —O—. In some embodiments, $X^1$ can be —S—. In some embodiments, $X^1$ can be —NH—.

In some embodiments, $Alk^1$ can be unsubstituted —$(CH_2)_{1-4}$—* for which "*" represents the point of attachment to $R^7$. In some embodiments, $Alk^1$ can be

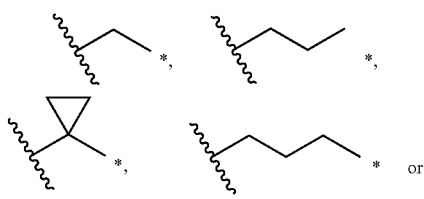

In some embodiments, $Alk^1$ can be a substituted

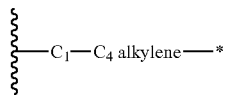

for which "*" represents the point of attachment to $R^7$. For example, in some embodiments, $Alk^1$ can be a substituted methylene, a substituted ethylene, a substituted propylene or a substituted butylene. In some embodiments, $Alk^1$ can be mono-substituted, di-substituted or tri-substituted. In some embodiments, $Alk^1$ can be mono-substituted with a halogen (such as fluoro or chloro) or unsubstituted $C_1$-$C_3$ alkyl, such as those described herein. In other embodiments, $Alk^1$ can be mono-substituted unsubstituted $C_1$-$C_3$ haloalkyl, such as those described herein. In some embodiments, $Alk^1$ can be mono-substituted with fluoro or unsubstituted methyl. In some embodiments, $Alk^1$ can be di-substituted with one fluoro and one unsubstituted $C_1$-$C_3$ alkyl, such as those described herein. In other embodiments, $Alk^1$ can be di-substituted with one unsubstituted $C_1$-$C_3$ haloalkyl, such as those described herein, and one unsubstituted $C_1$-$C_3$ alkyl, such as those described herein. In some embodiments, $Alk^1$ can be di-substituted with one fluoro and one unsubstituted methyl. In some embodiments, $Alk^1$ can be di-substituted with two independently selected unsubstituted $C_1$-$C_3$ alkyl groups, such as those described herein. In some embodiments, $Alk^1$ can be di-substituted with unsubstituted methyl.

In some embodiments, $Alk^1$ can be selected from:

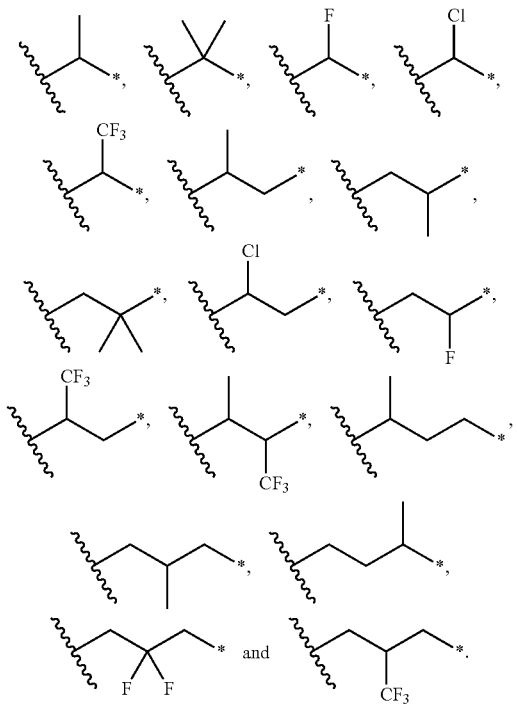

In some embodiments, n can be 0. When n is 0, those skilled in the art understand that $X^1$ is directly connected to $R^7$. In some embodiments, n can be 1.

In some embodiments, $R^7$ can be a substituted or unsubstituted mono-substituted amine group. For example, $R^7$ can be an amino group mono-substituted with a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted monocyclic or bicyclic $C_3$-$C_6$ cycloalkyl, a substituted or unsubstituted monocyclic or bicyclic $C_6$-$C_{10}$ aryl, a substituted or unsubstituted monocyclic or bicyclic 5 to 10 membered heteroaryl, a substituted or unsubstituted monocyclic or bicyclic 3 to 10 membered heterocyclyl, a substituted or unsubstituted monocyclic or bicyclic $C_3$-$C_6$ cycloalkyl(unsubstituted $C_1$-$C_6$ alkyl), a substituted or unsubstituted monocyclic or bicyclic $C_6$-$C_{10}$ aryl(unsubstituted $C_1$-$C_6$ alkyl), a substituted or unsubstituted monocyclic or bicyclic 5 to 10 membered heteroaryl (unsubstituted $C_1$-$C_6$ alkyl) or a substituted or unsubstituted monocyclic or bicyclic 3 to 10 membered heterocyclyl (unsubstituted $C_1$-$C_6$ alkyl). Examples of suitable mono-substituted amine groups include, but are not limited to —NH(methyl), —NH(isopropyl), —NH(cyclopropyl), —NH(phenyl), —NH(benzyl) and —NH(pyridine-3-yl).

In some embodiments, $R^7$ can be a substituted or unsubstituted di-substituted amine group. For example, $R^7$ can be an amino group substituted with two substituents independently selected from a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted monocyclic or bicyclic $C_3$-$C_6$ cycloalkyl, a substituted or unsubstituted monocyclic or bicyclic $C_6$-$C_{10}$ aryl, a substituted or unsubstituted monocyclic or bicyclic 5 to 10 membered heteroaryl, a substituted or unsubstituted monocyclic or bicyclic 3 to 10 membered heterocyclyl, a substituted or unsubstituted monocyclic or bicyclic $C_3$-$C_6$ cycloalkyl(unsubstituted $C_1$-$C_6$ alkyl), a substituted or unsubstituted monocyclic or bicyclic $C_6$-$C_{10}$ aryl(unsubstituted $C_1$-$C_6$ alkyl), a substituted or unsubstituted monocyclic or bicyclic 5 to 10 membered heteroaryl(unsubstituted $C_1$-$C_6$ alkyl) or a substituted or unsubstituted monocyclic or bicyclic 3 to 10 membered heterocyclyl(unsubstituted $C_1$-$C_6$ alkyl). In some embodiments the two substituents can be the same. In other embodiments the two substituents can be different. Examples of suitable di-substituted amine groups include, but are not limited to, —N(methyl)$_2$, —N(ethyl)$_2$, —N(isopropyl)$_2$, —N(benzyl)$_2$, —N(ethyl)(methyl), —N(isopropyl)(methyl), —N(ethyl)(isopropyl), —N(phenyl)(methyl) and —N(benzyl)(methyl).

In some embodiments, $R^7$ can be selected from a substituted or unsubstituted N-carbamyl, a substituted or unsubstituted C-amido and a substituted or unsubstituted N-amido.

In some embodiments, $R^7$ can be a substituted or unsubstituted $C_3$-$C_{10}$ cycloalkyl. In some embodiments, $R^7$ can be a substituted or unsubstituted monocyclic $C_3$-$C_{10}$ cycloalkyl. In other embodiments, $R^7$ can be a substituted or unsubstituted bicyclic $C_3$-$C_{10}$ cycloalkyl, for example, a bridged, fused or spiro $C_3$-$C_{10}$ cycloalkyl. Suitable substituted or unsubstituted monocyclic or bicyclic $C_3$-$C_{10}$ cycloalkyl groups include, but are not limited to, cyclopropyl, cyclobutyl, cyclopentyl, cyclohexyl, cycloheptyl, cyclooctyl, cyclononyl, cyclodecyl, spiro[3.3]heptyl, spiro[2.3]hexyl, spiro[3.4]octyl, spiro[3.5]nonyl, spiro[3.6]decyl, spiro[2.4]heptyl, spiro[4.4]nonyl, spiro[4.5]decyl, spiro[2.5]octyl, spiro[3.5]nonyl, bicyclo[1.1.1]pentyl, bicyclo[2.1.1]hexyl, bicyclo[2.2.1]heptyl, decahydronaphthalenyl, octahydro-1H-indenyl, octahydropentalenyl, bicyclo[4.2.0]octyl, bicyclo[2.1.0]pentyl and bicyclo[3.2.0]heptyl.

In some embodiments, $R^7$ can be a substituted or unsubstituted $C_6$-$C_{10}$ spirocycloalkyl. In some embodiments, $R^7$ can be a substituted $C_6$-$C_{10}$ spirocycloalkyl. In other embodiments, $R^7$ can be an unsubstituted $C_6$-$C_{10}$ spirocycloalkyl. In some embodiments, $R^7$ can be a substituted or unsubstituted -cyclopropyl-cyclobutyl spiroalkyl, -cyclopropyl-cyclopentyl spiroalkyl, -cyclopropyl-cyclohexyl spiroalkyl, -cyclopropyl-cycloheptyl spiroalkyl, -cyclopropyl-cyclooctyl spiroalkyl, -cyclobutyl-cyclopropyl spiroalkyl, -cyclobutyl-cyclobutyl spiroalkyl, -cyclobutyl-cyclopentyl spiroalkyl, -cyclobutyl-cyclohexyl spiroalkyl, -cyclobutyl-cycloheptyl spiroalkyl, -cyclopentyl-cyclopropyl spiroalkyl, -cyclopentyl-cyclobutyl spiroalkyl, -cyclopentyl-cyclopentyl spiroalkyl, cyclopentyl-cyclohexyl spiroalkyl, -cyclohexyl-cyclopropyl spiroalkyl, -cyclohexyl-cyclobutyl spiroalkyl, -cyclohexyl-cyclopentyl spiroalkyl, -cycloheptyl-cyclopropyl spiroalkyl, -cycloheptyl-cyclobutyl spiroalkyl or -cyclooctyl-cyclopropyl spiroalkyl.

In some embodiments, $R^7$ can be a substituted or unsubstituted 3 to 10 membered heterocyclyl. In some embodiments, $R^7$ can be a substituted 3 to 10 membered heterocyclyl. In other embodiments, $R^7$ can be an unsubstituted 3 to 10 membered heterocyclyl. In some embodiments, $R^7$ can be a substituted or unsubstituted monocyclic 3 to 10 membered heterocyclyl. In other embodiments, $R^7$ can be a substituted or unsubstituted bicyclic 5 to 10 membered heterocyclyl, for example, a fused, bridged or spiro 5 to 10 membered heterocyclyl. Suitable substituted or unsubstituted 3 to 10 membered heterocyclyl groups include, but are not limited to, azidirine, oxirane, azetidine, oxetane, pyrrolidine, tetrahydrofuran, imidazoline, pyrazolidine, piperidine, tetrahydropyran, piperazine, morpholine, thiomorpholine, dioxane, 2-azaspiro[3.3]heptane, 2-oxaspiro[3.3]heptane, 2,6-diazaspiro[3.3]heptane, 2-oxa-6-azaspiro[3.3]heptane, 2-azaspiro[3.4]octane, 6-oxaspiro[3.4]octane, 6-oxa-2-azaspiro[3.4]octane, 7-oxa-2-azaspiro[3.5]nonane, 7-oxaspiro[3.5]nonane and 2-oxa-8-azaspiro[4.5]decane. In some embodiments, the substituted or unsubstituted monocyclic or bicyclic 3 to 10 membered heterocyclyl can be connected to the rest of the molecule through a nitrogen atom. In other embodiments, the substituted or unsubstituted monocyclic or bicyclic 3 to 10 membered heterocyclyl can be connected to the rest of the molecule through a carbon atom. In some embodiments, the substituted monocyclic or bicyclic 3 to 10 membered heterocyclyl can be substituted on one or more nitrogen atoms.

In some embodiments, $R^7$ can be a substituted or unsubstituted 6 to 10 membered spiro heterocyclyl. In some embodiments, $R^7$ can be a substituted 6 to 10 membered spiro heterocyclyl. In other embodiments, $R^7$ can be an unsubstituted 6 to 10 membered spiro heterocyclyl. In some embodiments, $R^7$ can be a substituted or unsubstituted azaspirohexane, azaspiroheptane, azaspirooctane, oxaspirohexane, oxaspiroheptane, oxaspirooctane, diazaspirohexane, diazaspiroheptane, diazaspirooctane, dioxaspirohexane, dioxaspiroheptane, dioxaspirooctane, oxa-azaspirohexane, oxa-azaspiroheptane or oxa-azaspirooctane. Suitable substituted or unsubstituted 3 to 10 membered heterocyclyl groups include, but are not limited to, 2-azaspiro[3.3]heptane, 2-oxaspiro[3.3]heptane, 2,6-diazaspiro[3.3]heptane, 2-oxa-6-azaspiro[3.3]heptane, 2-azaspiro[3.4]octane, 6-oxaspiro[3.4]octane, 6-oxa-2-azaspiro[3.4]octane, 7-oxa-2-azaspiro[3.5]nonane, 7-oxaspiro[3.5]nonane and 2-oxa-8-azaspiro[4.5]decane. In some embodiments, the substituted or unsubstituted 6 to 10 membered spiro heterocyclyl can be connected to the rest of the molecule through a nitrogen atom. In other embodiments, the substituted or unsubstituted 6 to 10 membered spiro heterocyclyl can be connected to the rest of the molecule through a carbon atom. In some embodiments, the substituted 6 to 10 membered spiroheterocyclyl can be substituted on one or more nitrogen atoms.

In some embodiments, $R^7$ can be hydroxy or amino.

In some embodiments, $R^7$ can be unsubstituted. In other embodiments, $R^7$ can be substituted. In some embodiments, $R^7$ can be substituted with 1 or 2 substituents independently selected from an unsubstituted $C_1$-$C_6$ alkyl (such as those described herein), an unsubstituted $C_1$-$C_6$ alkoxy (such as those described herein), fluoro, chloro, hydroxy and —$SO_2$-(unsubstituted $C_1$-$C_6$ alkyl). For example, the $C_1$-$C_6$ alkoxy, $C_3$-$C_{10}$ cycloalkyl, 3 to 10 membered heterocyclyl, mono-substituted amine group, di-substituted amine group, N-carbamyl, C-amido and N-amido groups of $R^7$ can be substituted with 1 or 2 substituents independently selected from any of the aforementioned substituents.

In some embodiments, $R^7$ can be

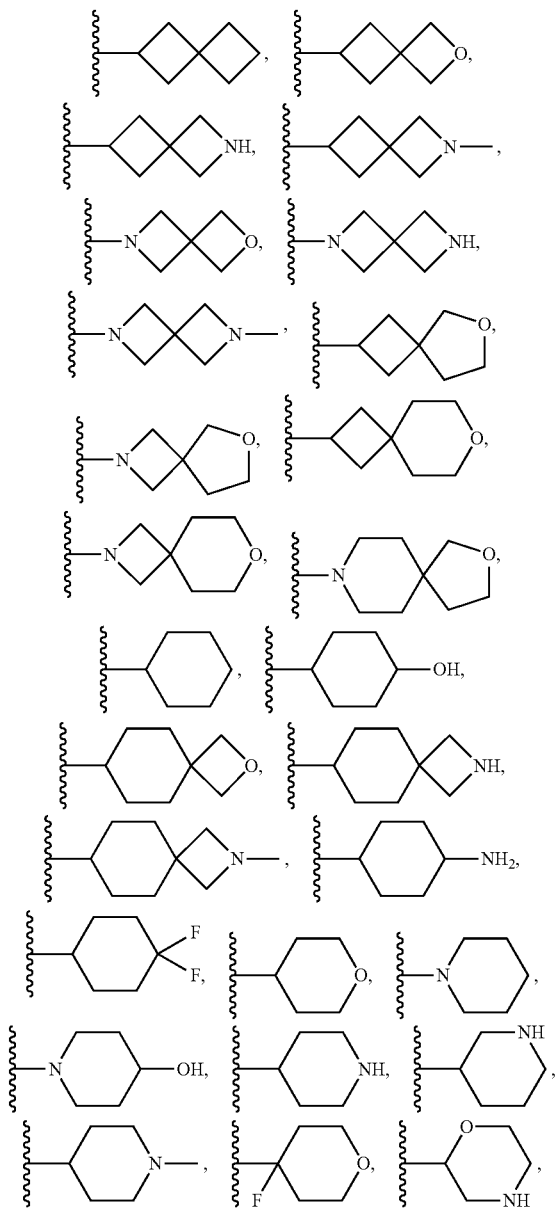

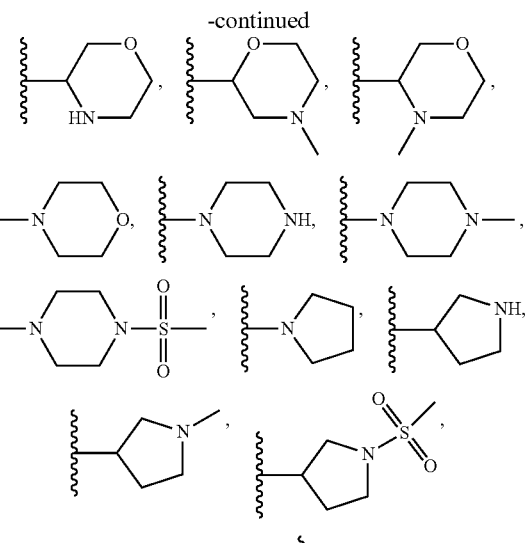

In some embodiments, $R^7$ can be

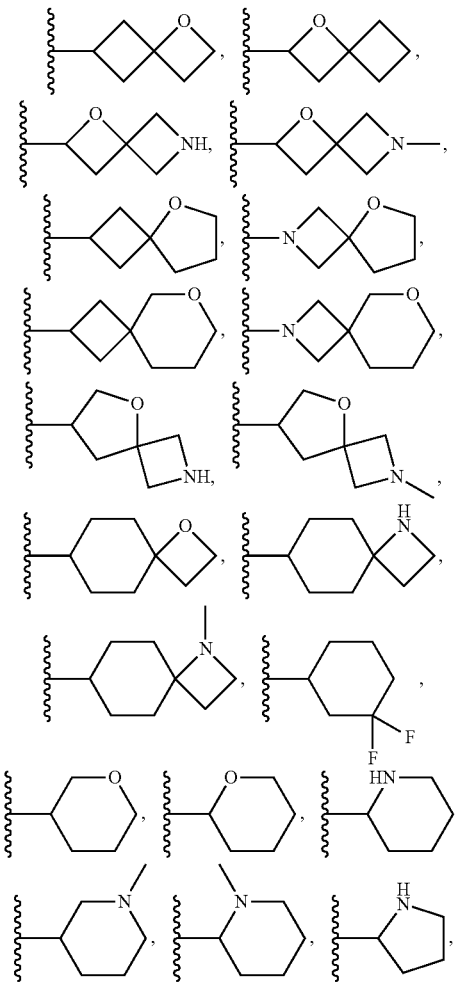

-continued

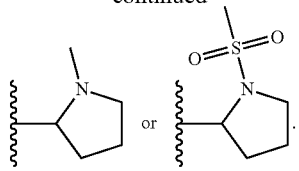

In some embodiments, R$^7$ can be

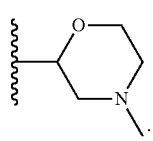

For example, in some embodiments R$^7$ can be

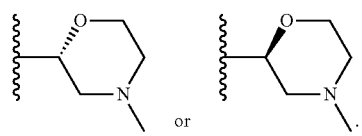

In some embodiments R$^7$ can be

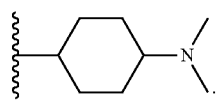

For example, in some embodiments R$^7$ can be

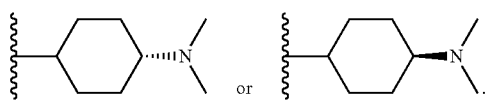

In some embodiments R$^7$ can be

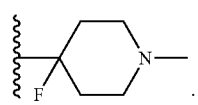

In some embodiments R$^7$ can be

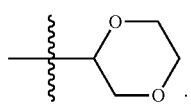

For example, in some embodiments R$^7$ can be

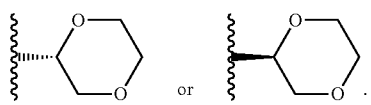

In some embodiments R$^7$ can be

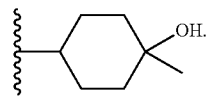

For example, in some embodiments R$^7$ can be

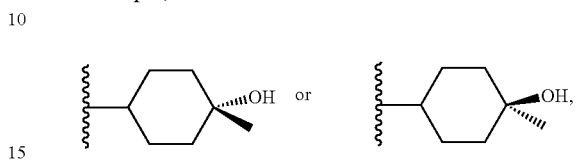

such as

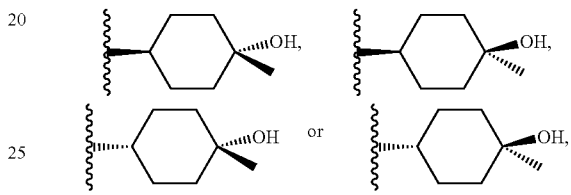

In some embodiments, R$^5$ can be —X$^2$—(CHR$^8$)-(Alk$^2$)$_p$-X$^3$—R$^9$. In some embodiments, X$^2$ can be —O—. In some embodiments, X$^2$ can be —S—. In some embodiments, X$^2$ can be —NH—. In some embodiments, X$^3$ can be —O—. In some embodiments, X$^3$ can be —S—. In some embodiments, X$^3$ can be —NH—. In some embodiments, X$^2$ can be —NH— and X$^3$ can be —S—. In some embodiments, X$^2$ can be —O— and X$^3$ can be —S—. In some embodiments, X$^2$ can be —NH— and X$^3$ can be —O—. In some embodiments, X$^2$ can be —O— and X$^3$ can be —O—.

In some embodiments, Alk$^2$ can be unsubstituted —(CH$_2$)$_{1-4}$—* for which "*" represents the point of attachment to X$^3$. In some embodiments, Alk$^2$ can be an unsubstituted methylene, an unsubstituted ethylene, an unsubstituted propylene or an unsubstituted butylene. In some embodiments, Alk$^2$ can be

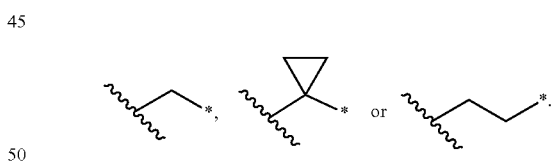

In some embodiments, Alk$^2$ can be a substituted

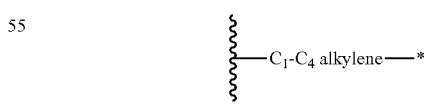

for which "*" represents the point of attachment to X$^3$. In some embodiments, Alk$^2$ can be a substituted methylene, a substituted ethylene, a substituted propylene or a substituted butylene. In some embodiments, Alk$^2$ can be mono-substituted, di-substituted or tri-substituted. In some embodiments, Alk$^2$ can be mono-substituted with fluoro or unsubstituted C$_1$-C$_3$ alkyl, such as those described herein. In some embodiments, Alk$^2$ can be mono-substituted with fluoro or unsubstituted methyl. In some embodiments, Alk² can be di-substituted with one fluoro and one unsubstituted $C_1$-$C_3$ alkyl, such as those described herein. In some embodiments, Alk² can be di-substituted with one fluoro and one unsubstituted methyl. In some embodiments, Alk² can be di-substituted with two independently selected unsubstituted $C_1$-$C_3$ alkyl, such as those described herein. In some embodiments, Alk² can be di-substituted with unsubstituted methyl.

In some embodiments, Alk² can be selected from:

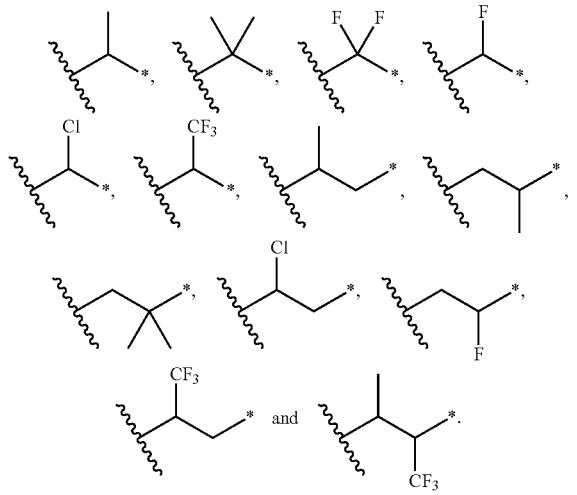

In some embodiments, p can be 0. When p is 0, those skilled in the art understand that the (CHR⁸) group is directly connected to X³. In some embodiments, p can be 1.

In some embodiments, the $C_1$-$C_6$ alkyl of the substituted or unsubstituted 3 to 10 membered heterocyclyl($C_1$-$C_6$ alkyl) of $R^8$ can be a substituted or unsubstituted $C_1$-$C_6$ alkyl such as those described herein. In some embodiments, the 3 to 10 membered heterocyclyl of the substituted or unsubstituted 3 to 10 membered heterocyclyl($C_1$-$C_6$ alkyl) of $R^8$ can be monocyclic. In some embodiments, the 3 to 10 membered heterocyclyl of the substituted or unsubstituted 3 to 10 membered heterocyclyl($C_1$-$C_6$ alkyl) can be bicyclic. In other embodiments, the 3 to 10 membered heterocyclyl of the substituted or unsubstituted 3 to 10 membered heterocyclyl($C_1$-$C_6$ alkyl) can be connected to the $C_1$-$C_6$ alkyl of the substituted or unsubstituted 3 to 10 membered heterocyclyl($C_1$-$C_6$ alkyl) through a carbon atom. In some embodiments, the 3 to 10 membered heterocyclyl of the substituted or unsubstituted 3 to 10 membered heterocyclyl($C_1$-$C_6$ alkyl) can be unsubstituted. In other embodiments, the 3 to 10 membered heterocyclyl of the substituted or unsubstituted 3 to 10 membered heterocyclyl($C_1$-$C_6$ alkyl) can be substituted. In some embodiments, the 3 to 10 membered heterocyclyl of the substituted or unsubstituted 3 to 10 membered heterocyclyl($C_1$-$C_6$ alkyl) can be substituted on one or more nitrogen atoms. Examples of suitable substituted or unsubstituted monocyclic or bicyclic 3 to 10 membered heterocyclyl groups of $R^8$ include, but are not limited to azidirine, oxirane, azetidine, oxetane, pyrrolidine, tetrahydrofuran, imidazoline, pyrazolidine, piperidine, tetrahydropyran, piperazine, morpholine, thiomorpholine, dioxane, 2-azaspiro[3.3]heptane, 2-oxaspiro[3.3]heptane, 2,6-diazaspiro[3.3]heptane, 2-oxa-6-azaspiro[3.3]heptane, 2-azaspiro[3.4]octane, 6-oxaspiro[3.4]octane, 6-oxa-2-azaspiro[3.4]octane, 7-oxa-2-azaspiro[3.5]nonane, 7-oxaspiro[3.5]nonane and 2-oxa-8-azaspiro[4.5]decane. In some embodiments, the $C_1$-$C_6$ alkyl of $R^8$ can be an unsubstituted methyl or an unsubstituted ethyl and the substituted or unsubstituted 3 to 10 membered heterocyclyl of $R^8$ can be a piperidine, tetrahydropyran, piperazine, morpholine, thiomorpholine, dioxane, 2-azaspiro[3.3]heptane, 2-oxaspiro[3.3]heptane, 2,6-diazaspiro[3.3]heptane, 2-oxa-6-azaspiro[3.3]heptane, 2-azaspiro[3.4]octane, 6-oxaspiro[3.4]octane, 6-oxa-2-azaspiro[3.4]octane, 7-oxa-2-azaspiro[3.5]nonane, 7-oxaspiro[3.5]nonane or 2-oxa-8-azaspiro[4.5]decane.

In some embodiments, $R^8$ can be a substituted or unsubstituted 6 to 10 membered spiro heterocyclyl($C_1$-$C_6$ alkyl). In some embodiments, the $C_1$-$C_6$ alkyl of the substituted or unsubstituted 6 to 10 membered spiro heterocyclyl($C_1$-$C_6$ alkyl) of $R^8$ can be a substituted or unsubstituted $C_1$-$C_6$ alkyl, such as those described herein. In some embodiments, the $C_1$-$C_6$ alkyl of the substituted or unsubstituted 6 to 10 membered spiro heterocyclyl($C_1$-$C_6$ alkyl) can be unsubstituted. In some embodiments, the 6 to 10 membered spiro heterocyclyl of the substituted or unsubstituted 6 to 10 membered spiro heterocyclyl($C_1$-$C_6$ alkyl) can be connected to the $C_1$-$C_6$ alkyl of $R^8$ through a nitrogen atom. In other embodiments, the 6 to 10 membered spiro heterocyclyl of the substituted or unsubstituted 6 to 10 membered spiro heterocyclyl($C_1$-$C_6$ alkyl) can be connected to the $C_1$-$C_6$alkyl of the substituted or unsubstituted 6 to 10 membered spiro heterocyclyl($C_1$-$C_6$ alkyl) through a carbon atom. In some embodiments, the substituted or unsubstituted 6 to 10 membered spiro heterocyclyl of the substituted or unsubstituted 6 to 10 membered spiro heterocyclyl($C_1$-$C_6$ alkyl) can be unsubstituted. In other embodiments, 6 to 10 membered spiro heterocyclyl of the substituted or unsubstituted 6 to 10 membered spiro heterocyclyl($C_1$-$C_6$ alkyl) can be substituted. In some embodiments, the 6 to 10 membered spiro heterocyclyl of the substituted or unsubstituted 6 to 10 membered spiro heterocyclyl($C_1$-$C_6$ alkyl) can be substituted on one or more nitrogen atoms. In some embodiments, the substituted or unsubstituted 6 to 10 membered spiro heterocyclyl of the substituted or unsubstituted 6 to 10 membered spiro heterocyclyl($C_1$-$C_6$ alkyl) can be an azaspirohexane, azaspiroheptane, azaspirooctane, oxaspirohexane, oxaspiroheptane, oxaspirooctane, diazaspirohexane, diazaspiroheptane, diazaspirooctane, dioxaspirohexane, dioxaspiroheptane, dioxaspirooctane, oxa-azaspirohexane, oxa-azaspiroheptane or oxa-azaspirooctane. Examples of suitable substituted or unsubstituted 6 to 10 membered spiro heterocyclyl of $R^5$ include, but are not limited to, 2-azaspiro[3.3]heptane, 2-oxaspiro[3.3]heptane, 2,6-diazaspiro[3.3]heptane, 2-oxa-6-azaspiro[3.3]heptane, 2-azaspiro[3.4]octane, 6-oxaspiro[3.4]octane, 6-oxa-2-azaspiro[3.4]octane, 7-oxa-2-azaspiro[3.5]nonane, 7-oxaspiro[3.5]nonane and 2-oxa-8-azaspiro[4.5]decane. In some embodiments, the $C_1$-$C_6$ alkyl of the substituted or unsubstituted 6 to 10 membered spiro heterocyclyl($C_1$-$C_6$ alkyl) can be an unsubstituted methyl or an unsubstituted ethyl and the 6 to 10 membered spiro heterocyclyl of $R^8$ can be an azaspirohexane, azaspiroheptane, azaspirooctane, oxaspirohexane, oxaspiroheptane, oxaspirooctane, diazaspirohexane, diazaspiroheptane, diazaspirooctane, dioxaspirohexane, dioxaspiroheptane, dioxaspirooctane, oxa-azaspirohexane, oxa-azaspiroheptane or oxa-azaspirooctane, for example, 2-azaspiro[3.3]heptane, 2-oxaspiro[3.3]heptane, 2,6-diazaspiro[3.3]heptane, 2-oxa-6-azaspiro[3.3]heptane, 2-azaspiro[3.4]octane, 6-oxaspiro[3.4]octane, 6-oxa-2-azaspiro[3.4]octane, 7-oxa-2-azaspiro[3.5]nonane, 7-oxaspiro[3.5]nonane or 2-oxa-8-azaspiro[4.5]decane.

In some embodiments, R⁸ can be a substituted or unsubstituted di-$C_1$-$C_6$ alkylamine($C_1$-$C_6$ alkyl), for example, a di-$C_1$-$C_6$ alkylamine(ethyl), di-$C_1$-$C_6$ alkylamine(propyl), di-$C_1$-$C_6$ alkylamine(butyl), di-$C_1$-$C_6$ alkylamine(pentyl) or di-$C_1$-$C_6$ alkylamine(hexyl). In some embodiments, each $C_1$-$C_6$ alkyl group in the di-$C_1$-$C_6$ alkylamine can be the same. In other embodiments, each $C_1$-$C_6$ alkyl group in the di-$C_1$-$C_6$ alkylamine can be different. Suitable substituted or unsubstituted di-$C_1$-$C_6$ alkylamine($C_1$-$C_6$ alkyl) include, but are not limited to, —N(methyl)$_2$, —N(ethyl)$_2$, —N(n-propyl)$_2$, —N(isopropyl)$_2$, —N(t-butyl)$_2$, —N(ethyl)(methyl), —N(isopropyl)(methyl), —N(t-butyl)(methyl) and —N(isopropyl)(ethyl); each connected to a substituted or unsubstituted $C_1$-$C_6$ alkyl group.

In some embodiments, R⁸ can be a substituted or unsubstituted di-methylamine($C_1$-$C_6$ alkyl), for example,

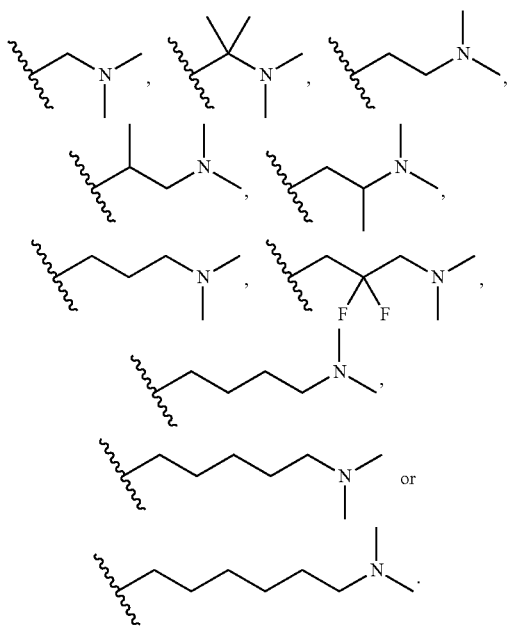

In some embodiments, R⁸ can be a substituted or unsubstituted mono-$C_1$-$C_6$ alkylamine($C_1$-$C_6$ alkyl), for example, a substituted or unsubstituted mono-$C_1$-$C_6$ alkylamine (ethyl), mono-$C_1$-$C_6$ alkylamine(propyl), mono-$C_1$-$C_6$ alkylamine(butyl), mono-$C_1$-$C_6$ alkylamine(pentyl) or mono-$C_1$-$C_6$ alkylamine(hexyl). In some embodiments, the $C_1$-$C_6$alkyl of the unsubstituted mono-$C_1$-$C_6$ alkylamine ($C_1$-$C_6$ alkyl) group can be an unsubstituted $C_1$-$C_6$ alkyl, such as those described herein.

In some embodiments, R⁸ can be unsubstituted. In other embodiments, R⁸ can be substituted. In some embodiments, R⁸ can be substituted with 1 or 2 substituents independently selected from an unsubstituted $C_1$-$C_6$ alkyl (such as those described herein), an unsubstituted $C_1$-$C_6$ alkoxy (such as those described herein), an unsubstituted di-$C_1$-$C_6$ alkylamine (such as those described herein), an unsubstituted acyl ($C_1$-$C_6$ alkyl) (for example, acetyl or benzoyl), an unsubstituted C-carboxy (for example, —$CO_2H$, —$CO_2$—$C_1$-$C_6$ alkyl, —$CO_2$—$C_3$-$C_6$ cycloalkyl or —$CO_2$—$C_6$-$C_{10}$ aryl), fluoro, chloro and hydroxy. For example, the 3 to 10 membered heterocyclyl($C_1$-$C_6$ alkyl), di-$C_1$-$C_6$ alkylamine ($C_1$-$C_6$ alkyl) and mono-$C_1$-$C_6$ alkylamine($C_1$-$C_6$ alkyl) groups of R⁸ can be substituted with 1 or 2 substituents independently selected from any of the aforementioned substituents.

In some embodiments, R⁸ can be:

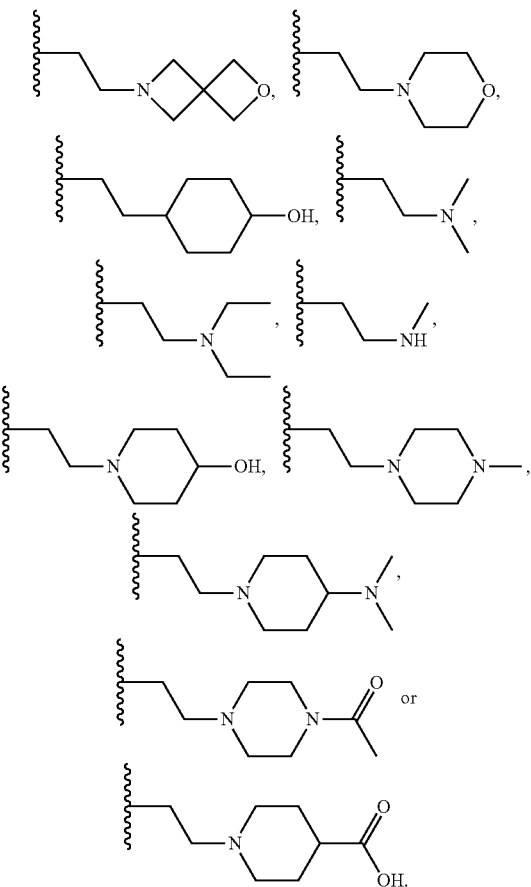

In some embodiments, R⁸ can be

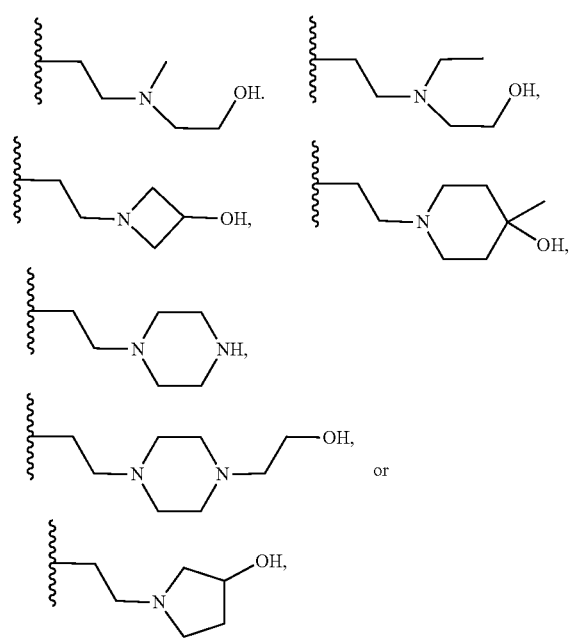

In some embodiments, R⁹ can be a substituted or unsubstituted monocyclic or bicyclic $C_6$-$C_{10}$ aryl. In some embodiments, $R^9$ can be a substituted monocyclic or bicyclic $C_6$-$C_{10}$ aryl. In other embodiments, $R^9$ can be an unsubstituted monocyclic or bicyclic $C_6$-$C_{10}$ aryl. In some embodiments, $R^9$ can be a substituted phenyl or a substituted naphthyl. In some embodiments, $R^9$ can be an unsubstituted phenyl or an unsubstituted naphthyl.

In some embodiments, $R^9$ can be a substituted or unsubstituted 5 to 10 membered heteroaryl. In some embodiments, $R^9$ can be a substituted 5 to 10 membered heteroaryl. In other embodiments, $R^9$ can be an unsubstituted 5 to 10 membered heteroaryl. In some embodiments, $R^9$ can be a monocyclic substituted or unsubstituted 5 to 10 membered heteroaryl. In other embodiments, $R^9$ can be a bicyclic substituted or unsubstituted 5 to 10 membered heteroaryl. Suitable substituted or unsubstituted monocyclic or bicyclic 5 to 10 membered heteroaryl include, but are not limited to, pyrrole, furan, thiophene, imidazole, pyrazole, oxazole, isoxazole, thiazole, isothiazole, triazole, pyridine, pyridazine, pyrimidine, pyrazine, pyrrolo-pyrroles, pyrrolo-furans, pyrrolo-thiophenes, indole, isoindole, indolizine, indazole, benzimidazole, azaindoles, purine, benzofuran, isobenzofuran, benzothiophene, isobenzothiophene, quinoline, isoquinoline, quinoxaline, phthalazine, quinazoline, cinnoline, 1,8-naphthyridine, pyrido-pyrimidines and pteridine.

In some embodiments, $R^3$ is hydrogen or halogen. For example, an embodiment provides a compound of Formula (I), or a pharmaceutically acceptable salt thereof, wherein:

$R^1$ is selected from the group consisting of hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine;

each $R^2$ is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl; or when m is 2 or 3, each $R^2$ is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl, or two $R^2$ groups taken together with the atom(s) to which they are attached form a substituted or unsubstituted $C_3$-$C_6$ cycloalkyl or a substituted or unsubstituted 3 to 6 membered heterocyclyl;

$R^3$ is hydrogen or halogen;

$R^4$ is selected from the group consisting of $NO_2$, $S(O)R^6$, $SO_2R^6$, halogen, cyano and an unsubstituted $C_1$-$C_6$ haloalkyl;

$R^5$ is selected from the group consisting of —$X^1$-(Alk$^1$)$_n$-$R^7$ and —$X^2$(CHR$^8$)-(Alk$^2$)$_p$-$X^3$—$R^9$;

Alk$^1$ and Alk$^2$ are independently selected from an unsubstituted $C_1$-$C_4$ alkylene and a $C_1$-$C_4$ alkylene substituted with 1, 2 or 3 substituents independently selected from fluoro, chloro, an unsubstituted $C_1$-$C_3$ alkyl and an unsubstituted $C_1$-$C_3$ haloalkyl;

$R^6$ is selected from the group consisting of a substituted or unsubstituted $C_1$-$C_6$ alkyl, a substituted or unsubstituted $C_1$-$C_6$ haloalkyl and a substituted or unsubstituted $C_3$-$C_6$ cycloalkyl;

$R^7$ is selected from a substituted or unsubstituted $C_1$-$C_6$ alkoxy, a substituted or unsubstituted $C_3$-$C_{10}$ cycloalkyl, a substituted or unsubstituted 3 to 10 membered heterocyclyl, hydroxy, amino, a substituted or unsubstituted mono-substituted amine group, a substituted or unsubstituted di-substituted amine group, a substituted or unsubstituted N-carbamyl, a substituted or unsubstituted C-amido and a substituted or unsubstituted N-amido;

$R^8$ is selected from a substituted or unsubstituted 3 to 10 membered heterocyclyl($C_1$-$C_6$ alkyl), a substituted or unsubstituted di-$C_1$-$C_6$ alkylamine($C_1$-$C_6$ alkyl) and a substituted or unsubstituted mono-$C_1$-$C_6$ alkylamine($C_1$-$C_6$ alkyl);

$R^9$ is selected from a substituted or unsubstituted 5 to 10 membered heteroaryl and a substituted or unsubstituted $C_6$-$C_{10}$ aryl;

m is 0, 1, 2 or 3;

n and p are independently selected from 0 and 1; and $X^1$, $X^2$ and $X^3$ are independently selected from the group consisting of —O—, —S— and —NH—.

In some embodiments, $R^3$ is selected from the group consisting of X—$R^{3A}$,

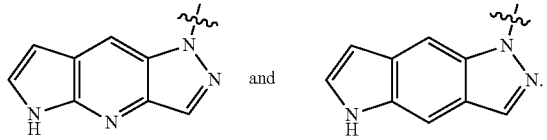

and

For example, an embodiment provides a compound of Formula (I), or a pharmaceutically acceptable salt thereof, wherein:

$R^1$ is selected from the group consisting of hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine;

each $R^2$ is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl; or when m is 2 or 3, each $R^2$ is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl, or two $R^2$ groups taken together with the atom(s) to which they are attached form a substituted or unsubstituted $C_3$-$C_6$ cycloalkyl or a substituted or unsubstituted 3 to 6 membered heterocyclyl;

$R^3$ is selected from the group consisting of X—$R^{3A}$,

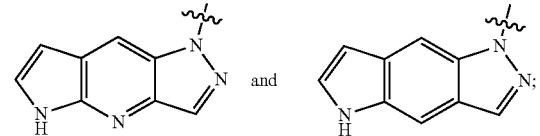

and $R^{3A}$ is a substituted or unsubstituted 5 to 10 membered heteroaryl;

$R^4$ is selected from the group consisting of $NO_2$, $S(O)R^6$, $SO_2R^6$, halogen, cyano and an unsubstituted $C_1$-$C_6$ haloalkyl;

$R^5$ is selected from the group consisting of —$X^1$-(Alk$^1$)$_n$-$R^7$ and —$X^2$(CHR$^8$)-(Alk$^2$)$_p$-$X^3$—$R^9$;

Alk$^1$ and Alk$^2$ are independently selected from an unsubstituted $C_1$-$C_4$ alkylene and a $C_1$-$C_4$ alkylene substituted with 1, 2 or 3 substituents independently selected from fluoro, chloro, an unsubstituted $C_1$-$C_3$ alkyl and an unsubstituted $C_1$-$C_3$ haloalkyl;

$R^6$ is selected from the group consisting of a substituted or unsubstituted $C_1$-$C_6$ alkyl, a substituted or unsubstituted $C_1$-$C_6$ haloalkyl and a substituted or unsubstituted $C_3$-$C_6$ cycloalkyl;

$R^7$ is selected from a substituted or unsubstituted $C_1$-$C_6$ alkoxy, a substituted or unsubstituted $C_3$-$C_{10}$ cycloalkyl, a substituted or unsubstituted 3 to 10 membered heterocyclyl, hydroxy, amino, a substituted or unsubstituted mono-substituted amine group, a substituted or unsubstituted di-substituted amine group, a substituted or unsubstituted N-carbamyl, a substituted or unsubstituted C-amido and a substituted or unsubstituted N-amido;

$R^8$ is selected from a substituted or unsubstituted 3 to 10 membered heterocyclyl($C_1$-$C_6$ alkyl), a substituted or unsubstituted di-$C_1$-$C_6$ alkylamine($C_1$-$C_6$ alkyl) and a substituted or unsubstituted mono-$C_1$-$C_6$ alkylamine($C_1$-$C_6$ alkyl);

$R^9$ is selected from a substituted or unsubstituted 5 to 10 membered heteroaryl and a substituted or unsubstituted $C_6$-$C_{10}$ aryl;

m is 0, 1, 2 or 3;

n and p are independently selected from 0 and 1;

X, $X^1$, $X^2$ and $X^3$ are independently selected from the group consisting of —O—, —S— and —NH—.

In some embodiments, $R^3$ is selected from the group consisting of X—$R^{3A}$,

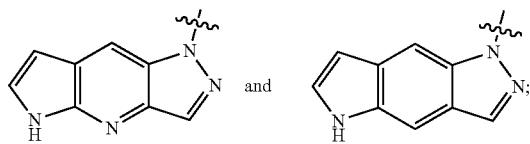

and $X^1$ and $X^2$ are —NH—. For example, an embodiment provides a compound of Formula (I), or a pharmaceutically acceptable salt thereof, wherein:

$R^1$ is selected from the group consisting of hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine;

each $R^2$ is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl; or when m is 2 or 3, each $R^2$ is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl, or two $R^2$ groups taken together with the atom(s) to which they are attached form a substituted or unsubstituted $C_3$-$C_6$ cycloalkyl or a substituted or unsubstituted 3 to 6 membered heterocyclyl;

$R^3$ is selected from the group consisting of X—$R^A$,

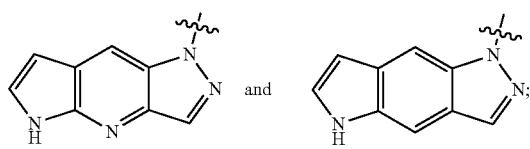

$R^{3A}$ is a substituted or unsubstituted 5 to 10 membered heteroaryl;

$R^4$ is selected from the group consisting of $NO_2$, S(O)$R^6$, $SO_2R^6$, halogen, cyano and an unsubstituted $C_1$-$C_6$ haloalkyl;

$R^5$ is selected from the group consisting of —$X^1$-(Alk$^1$)$_n$-$R^7$ and —$X^2$(CHR$^8$)-(Alk$^2$)$_p$-$X^3$—$R^9$;

Alk$^1$ and Alk$^2$ are independently selected from an unsubstituted $C_1$-$C_4$ alkylene and a $C_1$-$C_4$ alkylene substituted with 1, 2 or 3 substituents independently selected from fluoro, chloro, an unsubstituted $C_1$-$C_3$ alkyl and an unsubstituted $C_1$-$C_3$ haloalkyl;

$R^6$ is selected from the group consisting of a substituted or unsubstituted $C_1$-$C_6$ alkyl, a substituted or unsubstituted $C_1$-$C_6$ haloalkyl and a substituted or unsubstituted $C_3$-$C_6$ cycloalkyl;

$R^7$ is selected from a substituted or unsubstituted $C_1$-$C_6$ alkoxy, a substituted or unsubstituted $C_3$-$C_{10}$ cycloalkyl, a substituted or unsubstituted 3 to 10 membered heterocyclyl, hydroxy, amino, a substituted or unsubstituted mono-substituted amine group, a substituted or unsubstituted di-substituted amine group, a substituted or unsubstituted N-carbamyl, a substituted or unsubstituted C-amido and a substituted or unsubstituted N-amido;

$R^8$ is selected from a substituted or unsubstituted 3 to 10 membered heterocyclyl($C_1$-$C_6$ alkyl), a substituted or unsubstituted di-$C_1$-$C_6$ alkylamine($C_1$-$C_6$ alkyl) and a substituted or unsubstituted mono-$C_1$-$C_6$ alkylamine($C_1$-$C_6$ alkyl);

$R^9$ is selected from a substituted or unsubstituted 5 to 10 membered heteroaryl and a substituted or unsubstituted $C_6$-$C_{10}$ aryl;

m is 0, 1, 2 or 3;

n and p are independently selected from 0 and 1;

$X^1$ and $X^2$ are —NH—; and

X and $X^3$ are independently selected from the group consisting of —O—, —S— and —NH—.

In some embodiments, $R^1$ is as described above with the proviso that it is not —CH$_2$F, —CHF$_2$ or —CF$_3$; $R^3$ is selected from the group consisting of X—$R^{3A}$,

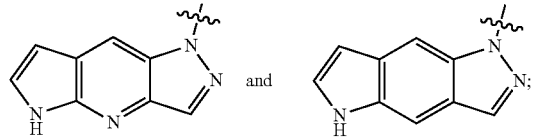

and $X^1$ and $X^2$ are —NH—. For example, an embodiment provides a compound of Formula (I), or a pharmaceutically acceptable salt thereof, wherein:

$R^1$ is selected from the group consisting of hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine, with the proviso that $R^1$ is not —CH$_2$F, —CHF$_2$ or —CF$_3$;

each $R^2$ is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl; or when m is 2 or 3, each $R^2$ is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl, or two $R^2$ groups taken together with the atom(s) to which they are attached form a substituted or unsubstituted C$_3$-C$_6$ cycloalkyl or a substituted or unsubstituted 3 to 6 membered heterocyclyl;

R$^3$ is selected from the group consisting of X—R$^{3A}$,

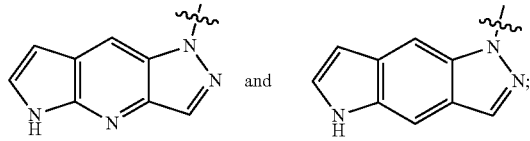

R$^{3A}$ is a substituted or unsubstituted 5 to 10 membered heteroaryl;

R$^4$ is selected from the group consisting of NO$_2$, S(O)R$^6$, SO$_2$R$^6$, halogen, cyano and an unsubstituted C$_1$-C$_6$ haloalkyl;

R$^5$ is selected from the group consisting of —X$^1$-(Alk$^1$)$_n$-R$^7$ and —X$^2$(CHR$^8$)-(Alk$^2$)$_p$-X$^3$—R$^9$;

Alk$^1$ and Alk$^2$ are independently selected from an unsubstituted C$_1$-C$_4$ alkylene and a C$_1$-C$_4$ alkylene substituted with 1, 2 or 3 substituents independently selected from fluoro, chloro, an unsubstituted C$_1$-C$_3$ alkyl and an unsubstituted C$_1$-C$_3$ haloalkyl;

R$^6$ is selected from the group consisting of a substituted or unsubstituted C$_1$-C$_6$ alkyl, a substituted or unsubstituted C$_1$-C$_6$ haloalkyl and a substituted or unsubstituted C$_3$-C$_6$ cycloalkyl;

R$^7$ is selected from a substituted or unsubstituted C$_1$-C$_6$ alkoxy, a substituted or unsubstituted C$_3$-C$_{10}$ cycloalkyl, a substituted or unsubstituted 3 to 10 membered heterocyclyl, hydroxy, amino, a substituted or unsubstituted mono-substituted amine group, a substituted or unsubstituted di-substituted amine group, a substituted or unsubstituted N-carbamyl, a substituted or unsubstituted C-amido and a substituted or unsubstituted N-amido;

R$^8$ is selected from a substituted or unsubstituted 3 to 10 membered heterocyclyl(C$_1$-C$_6$ alkyl), a substituted or unsubstituted di-C$_1$-C$_6$ alkylamine(C$_1$-C$_6$ alkyl) and a substituted or unsubstituted mono-C$_1$-C$_6$ alkylamine(C$_1$-C$_6$ alkyl);

R$^9$ is selected from a substituted or unsubstituted 5 to 10 membered heteroaryl and a substituted or unsubstituted C$_6$-C$_{10}$ aryl;

m is 0, 1, 2 or 3;

n and p are independently selected from 0 and 1;

X$^1$ and X$^2$ are —NH—; and

X and X$^3$ are independently selected from the group consisting of —O—, —S— and —NH—.

In some embodiments, R$^1$ is —CH$_2$F, —CHF$_2$ or —CF$_3$; R$^3$ is selected from the group consisting of X—R$^{3A}$,

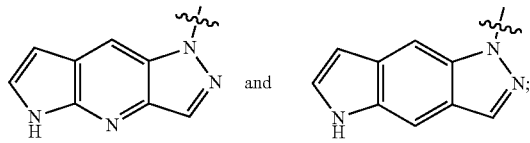

and X$^1$ and X$^2$ are —NH—. For example, an embodiment provides a compound of Formula (I), or a pharmaceutically acceptable salt thereof, wherein:

R$^1$ is —CH$_2$F, —CHF$_2$ or —CF$_3$;

each R$^2$ is independently selected from the group consisting of halogen, a substituted or unsubstituted C$_1$-C$_6$ alkyl, a substituted or unsubstituted C$_1$-C$_6$ haloalkyl and a substituted or unsubstituted C$_3$-C$_6$ cycloalkyl; or when m is 2 or 3, each R$^2$ is independently selected from the group consisting of halogen, a substituted or unsubstituted C$_1$-C$_6$ alkyl, a substituted or unsubstituted C$_1$-C$_6$ haloalkyl and a substituted or unsubstituted C$_3$-C$_6$ cycloalkyl, or two R$^2$ groups taken together with the atom(s) to which they are attached form a substituted or unsubstituted C$_3$-C$_6$ cycloalkyl or a substituted or unsubstituted 3 to 6 membered heterocyclyl;

R$^3$ is selected from the group consisting of X—R$^{3A}$,

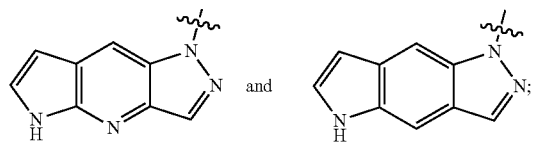

R$^{3A}$ is a substituted or unsubstituted 5 to 10 membered heteroaryl;

R$^4$ is selected from the group consisting of NO$_2$, S(O)R$^6$, SO$_2$R$^6$, halogen, cyano and an unsubstituted C$_1$-C$_6$ haloalkyl;

R$^5$ is selected from the group consisting of —X$^1$-(Alk$^1$)$_n$-R$^7$ and —X$^2$(CHR$^8$)-(Alk$^2$)$_p$-X$^3$—R$^9$;

Alk$^1$ and Alk$^2$ are independently selected from an unsubstituted C$_1$-C$_4$ alkylene and a C$_1$-C$_4$ alkylene substituted with 1, 2 or 3 substituents independently selected from fluoro, chloro, an unsubstituted C$_1$-C$_3$ alkyl and an unsubstituted C$_1$-C$_3$ haloalkyl;

R$^6$ is selected from the group consisting of a substituted or unsubstituted C$_1$-C$_6$ alkyl, a substituted or unsubstituted C$_1$-C$_6$ haloalkyl and a substituted or unsubstituted C$_3$-C$_6$ cycloalkyl;

R$^7$ is selected from a substituted or unsubstituted C$_1$-C$_6$ alkoxy, a substituted or unsubstituted C$_3$-C$_{10}$ cycloalkyl, a substituted or unsubstituted 3 to 10 membered heterocyclyl, hydroxy, amino, a substituted or unsubstituted mono-substituted amine group, a substituted or unsubstituted di-substituted amine group, a substituted or unsubstituted N-carbamyl, a substituted or unsubstituted C-amido and a substituted or unsubstituted N-amido;

R$^8$ is selected from a substituted or unsubstituted 3 to 10 membered heterocyclyl(C$_1$-C$_6$ alkyl), a substituted or unsubstituted di-C$_1$-C$_6$ alkylamine(C$_1$-C$_6$ alkyl) and a substituted or unsubstituted mono-C$_1$-C$_6$ alkylamine(C$_1$-C$_6$ alkyl);

R$^9$ is selected from a substituted or unsubstituted 5 to 10 membered heteroaryl and a substituted or unsubstituted C$_6$-C$_{10}$ aryl;

m is 0, 1, 2 or 3;

n and p are independently selected from 0 and 1;

X$^1$ and X$^2$ are —NH—; and

X and X$^3$ are independently selected from the group consisting of —O—, —S— and —NH—.

In some embodiments, R$^3$ is selected from the group consisting of X—R$^{3A}$,

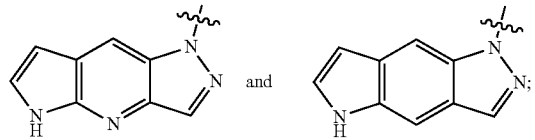

and X¹ and X² are —O—. For example, an embodiment provides a compound of Formula (I), or a pharmaceutically acceptable salt thereof, wherein:

R¹ is selected from the group consisting of hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine;

each R² is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl; or when m is 2 or 3, each R² is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl, or two R² groups taken together with the atom(s) to which they are attached form a substituted or unsubstituted $C_3$-$C_6$ cycloalkyl or a substituted or unsubstituted 3 to 6 membered heterocyclyl;

R³ is selected from the group consisting of X—$R^A$,

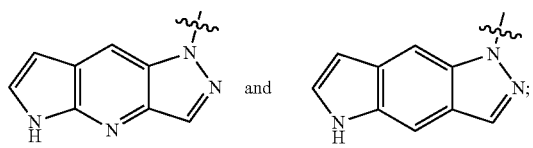

and $R^{3A}$ is a substituted or unsubstituted 5 to 10 membered heteroaryl;

R⁴ is selected from the group consisting of $NO_2$, $S(O)R^6$, $SO_2R^6$, halogen, cyano and an unsubstituted $C_1$-$C_6$ haloalkyl;

R⁵ is selected from the group consisting of —X¹-$(Alk^1)_n$-R⁷ and —X²(CHR⁸)-$(Alk^2)_p$-X³—R⁹;

Alk¹ and Alk² are independently selected from an unsubstituted $C_1$-$C_4$ alkylene and a $C_1$-$C_4$ alkylene substituted with 1, 2 or 3 substituents independently selected from fluoro, chloro, an unsubstituted $C_1$-$C_3$ alkyl and an unsubstituted $C_1$-$C_3$ haloalkyl;

R⁶ is selected from the group consisting of a substituted or unsubstituted $C_1$-$C_6$ alkyl, a substituted or unsubstituted $C_1$-$C_6$ haloalkyl and a substituted or unsubstituted $C_3$-$C_6$ cycloalkyl;

R⁷ is selected from a substituted or unsubstituted $C_1$-$C_6$ alkoxy, a substituted or unsubstituted $C_3$-$C_{10}$ cycloalkyl, a substituted or unsubstituted 3 to 10 membered heterocyclyl, hydroxy, amino, a substituted or unsubstituted mono-substituted amine group, a substituted or unsubstituted di-substituted amine group, a substituted or unsubstituted N-carbamyl, a substituted or unsubstituted C-amido and a substituted or unsubstituted N-amido;

R⁸ is selected from a substituted or unsubstituted 3 to 10 membered heterocyclyl($C_1$-$C_6$ alkyl), a substituted or unsubstituted di-$C_1$-$C_6$ alkylamine($C_1$-$C_6$ alkyl) and a substituted or unsubstituted mono-$C_1$-$C_6$ alkylamine($C_1$-$C_6$ alkyl);

R⁹ is selected from a substituted or unsubstituted 5 to 10 membered heteroaryl and a substituted or unsubstituted $C_6$-$C_{10}$ aryl;

m is 0, 1, 2 or 3;

n and p are independently selected from 0 and 1;

X¹ and X² are —O—; and

X and X³ are independently selected from the group consisting of —O—, —S— and —NH—.

In some embodiments, the compound of Formula (I), or a pharmaceutically acceptable salt thereof, can be selected from a compound of Formula (Ia), Formula (Ib), Formula (Ic) and Formula (Id):

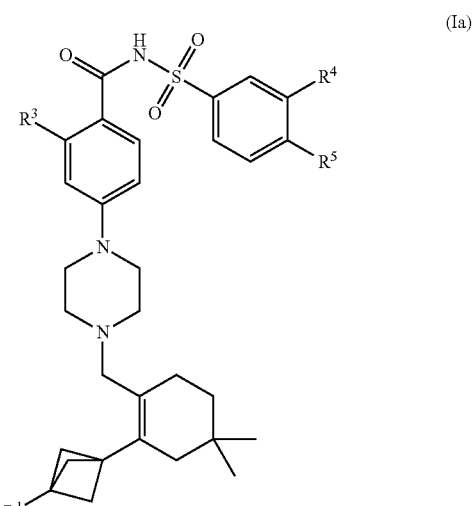

(Ia)

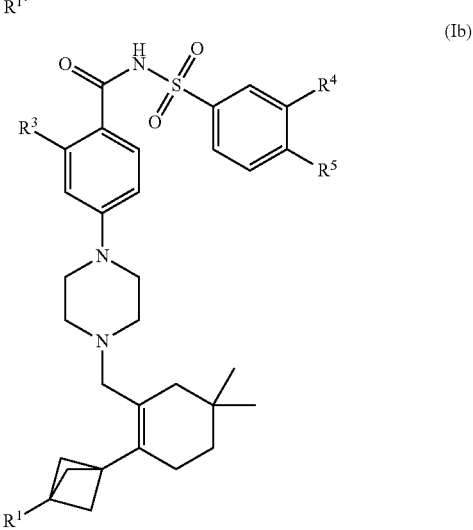

(Ib)

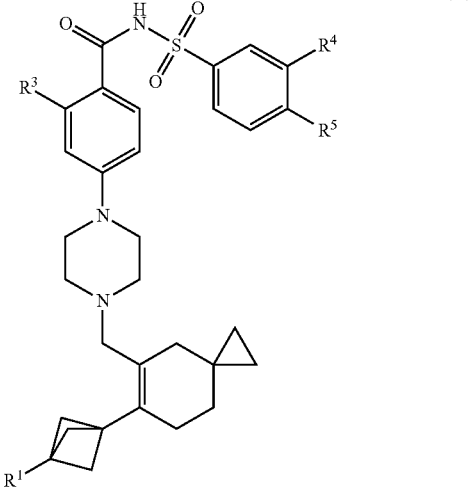

(Ic)

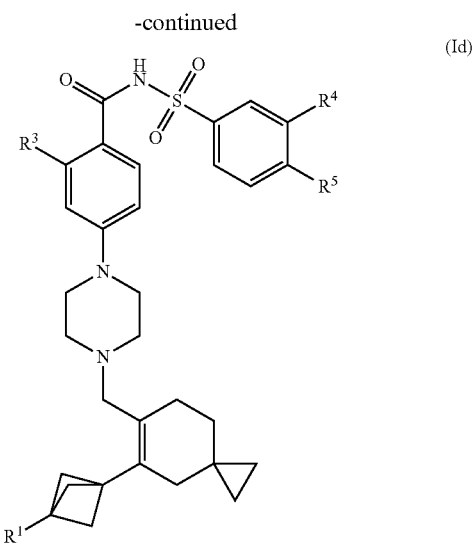

or pharmaceutically acceptable salts of any of the foregoing.

In some embodiments of Formulae (Ia), (Ib), (Ic) and/or (Id), $R^3$ can be hydrogen,

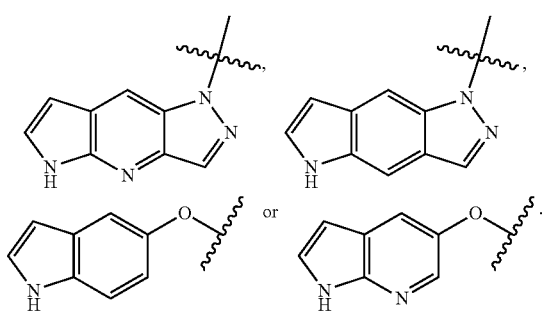

In some embodiments of Formulae (Ia), (Ib), (Ic) and/or (Id), $R^4$ can be nitro or $-SO_2CF_3$. In some embodiments of Formulae (Ia), (Ib), (Ic) and/or (Id), $R^1$ can be fluoro, chloro, $-CH_3$, $-CH_2CH_3$, $-CHF_2$, $-CF_3$, $-CH_2CF_3$, $-CF_2CH_3$, $-OCH_3$, $-OCH_2CH_3$, $-NHCH_3$, $-NHCH_2CH_3$, $-N(CH_3)_2$ or $-N(CH_2CH_3)_2$. In some embodiments of Formulae (Ia), (Ib), (Ic) and/or (Id), $R^5$ can be $-O-R^7$ or $-NH-R^7$. In some embodiments Formulae (Ia), (Ib), (Ic) and/or (Id), $R^5$ can be $-O-Alk^1-R^7$ or $-NH-Alk^1-R^7$. In some embodiments of Formulae (Ia), (Tb), (Ic) and/or (Id), $Alk^1$ can be an unsubstituted methylene, an unsubstituted ethylene, or an ethylene mono-substituted with $-CH_3$. In some embodiments of Formulae (Ia), (Tb), (Ic) and/or (Id), $R^7$ can be an unsubstituted cyclohexanyl or a cyclohexanyl substituted with one or two substituents independently selected from hydroxy, amino, fluoro and unsubstituted $C_1$-$C_3$ alkyl (such as those described herein). In some embodiments of this paragraph, $R^7$ can be a substituted or unsubstituted monocyclic 5 or 6 membered heterocyclyl, for example, pyrrolidine, piperidine, morpholine, piperazine or tetrahydropyran; wherein each of the aforementioned substituted groups can be substituted with 1 or 2 substituents independently selected from hydroxy, amino, fluoro, an unsubstituted $C_1$-$C_3$ alkyl (such as those described herein), an unsubstituted $C_1$-$C_3$ alkoxy (such as those described herein), or $-SO_2CH_3$. In some embodiments of Formulae (Ia), (Ib), (Ic) and/or (Id), $R^7$ can be connected to $Alk^1$ by a nitrogen atom. In some embodiments of Formulae (Ia), (Ib), (Ic) and/or (Id), $R^7$ can be connected to $Alk^1$ by a carbon atom. In some embodiments of Formulae (Ia), (Ib), (Ic) and/or (Id), $R^7$ can be substituted on one or more nitrogen atoms. In some embodiments of Formulae (Ia), (Ib), (Ic) and/or (Id), $R^5$ can be $-NH-(CHR^8)-Alk^2-S-R^9$, $-O-(CHR^8)-Alk^2-S-R^9$, $-NH-(CHR^8)-Alk^2-O-R^9$ or $-O-(CHR^8)-Alk^2-O-R^9$. In some embodiments of Formulae (Ia), (Ib), (Ic) and/or (Id), $Alk^2$ can be an unsubstituted methylene, an unsubstituted ethylene, a methylene mono-substituted with $-CH_3$ or a methylene di-substituted with $-CH_3$. In some embodiments of Formulae (Ia), (Ib), (Ic) and/or (Id), $R^8$ can be an unsubstituted di-$C_1$-$C_3$ alkylamine(methyl) or an unsubstituted di-$C_1$-$C_3$ alkylamine(ethyl). In some embodiments of Formulae (Ia), (Ib), (Ic) and/or (Id), $R^8$ can be a substituted or unsubstituted 5 to 7 membered heterocyclyl($C_1$-$C_6$ alkyl); wherein the $C_1$-$C_6$ alkyl can be am unsubstituted methyl, an unsubstituted ethyl or an unsubstituted n-propyl; the 5 to 7 membered heterocyclyl can (a) be monocyclic or spiro, (b) include 1 oxygen atom, 1 nitrogen atom, or 1 oxygen atom and one nitrogen atom, (c) be unsubstituted or substituted with 1 or 2 substituents independently selected from an unsubstituted $C_1$-$C_3$ alkyl (such as those described herein), $-N(CH_3)_2$, $-N(CH_2CH_3)_2$, an unsubstituted acetyl, $-CO_2H$, fluoro or hydroxy. In some embodiments of Formulae (Ia), (Ib), (Ic) and/or (Id), $R^9$ can be unsubstituted phenyl.

Examples of a compound of Formula (I) include:

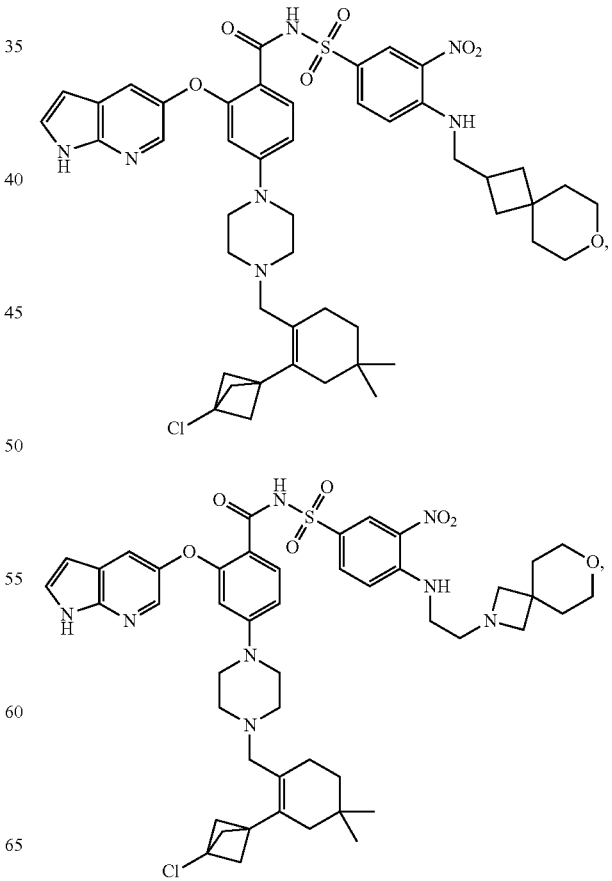

41
-continued
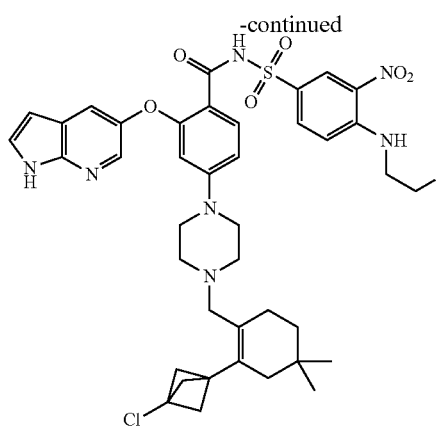
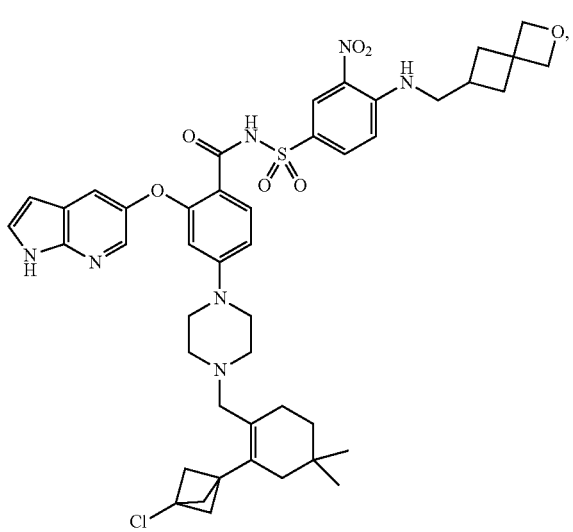
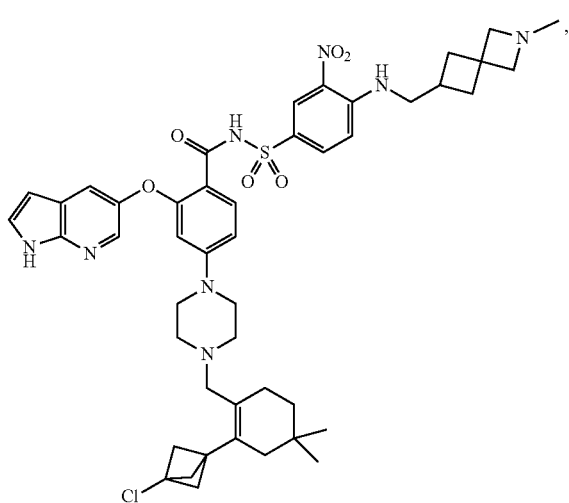
42
-continued
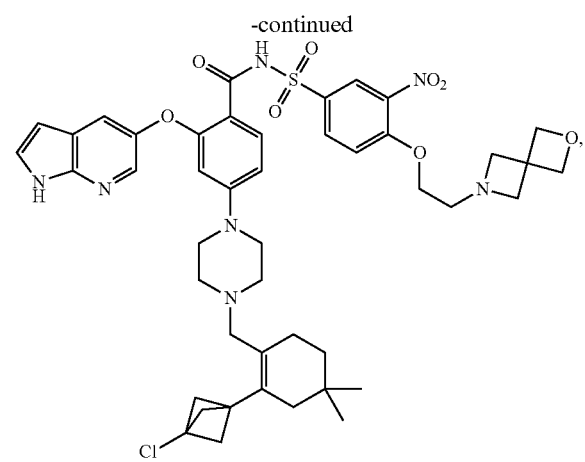
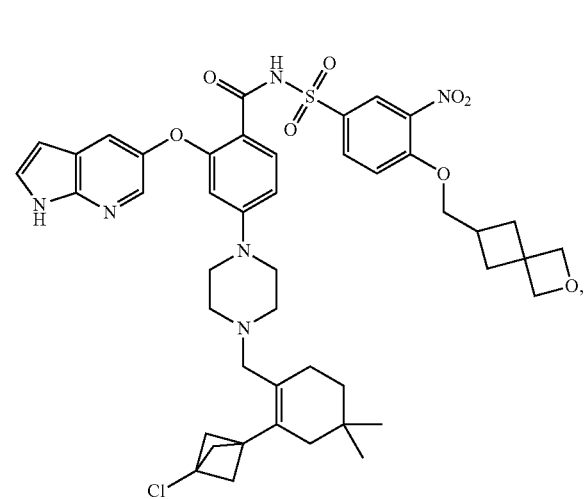
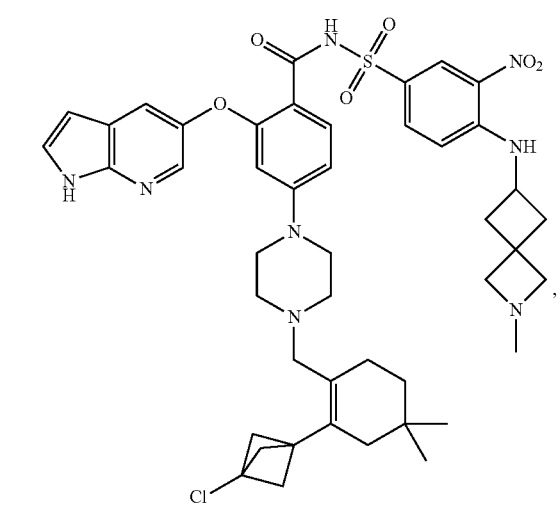

43
-continued
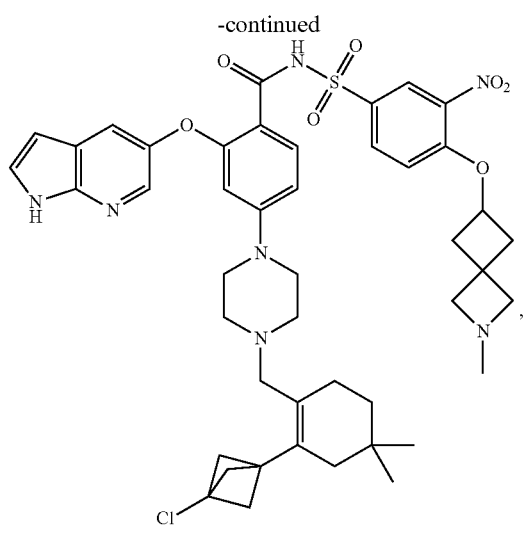
44
-continued
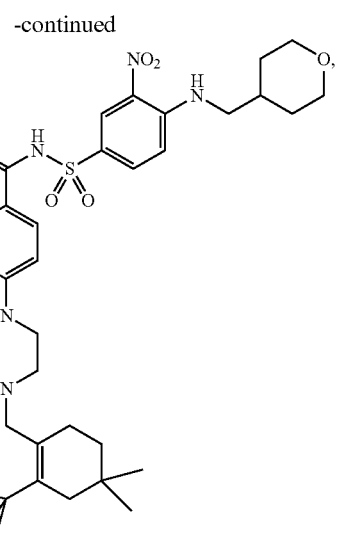
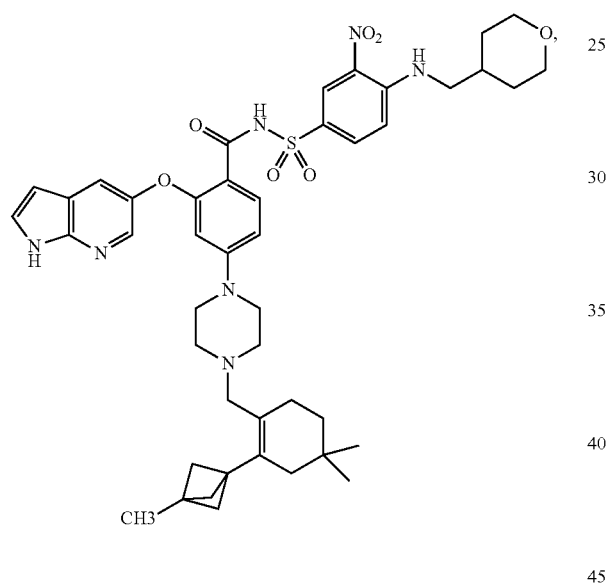
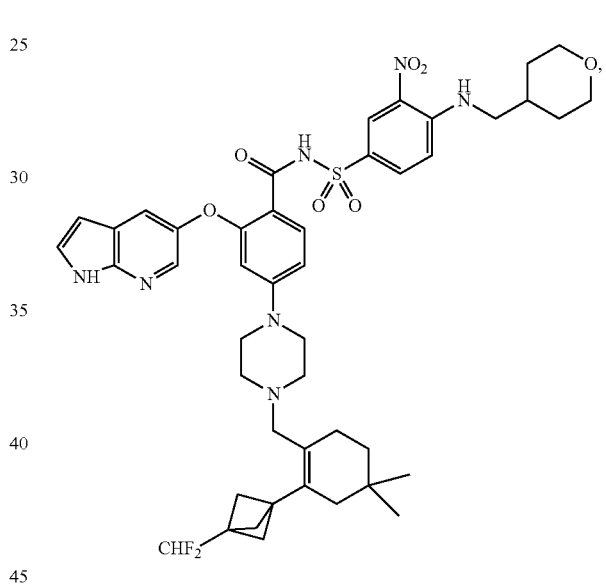
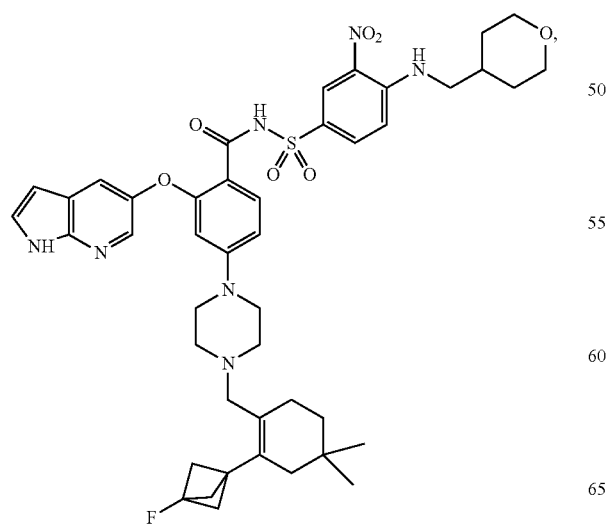
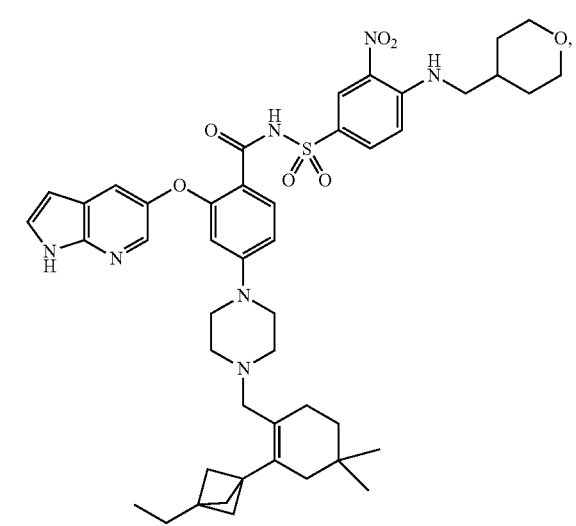

45
-continued
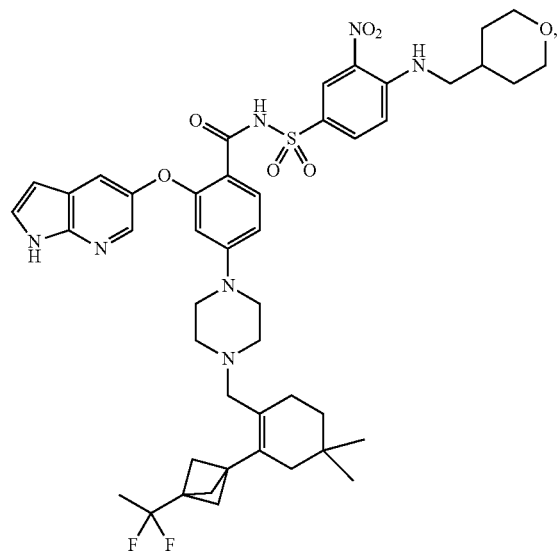
46
-continued
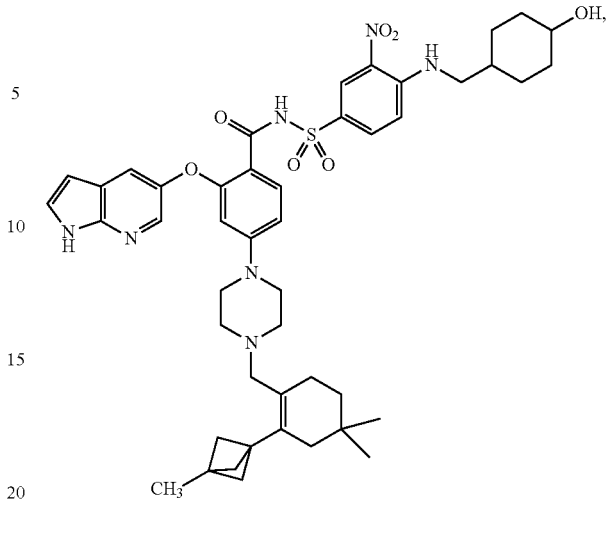
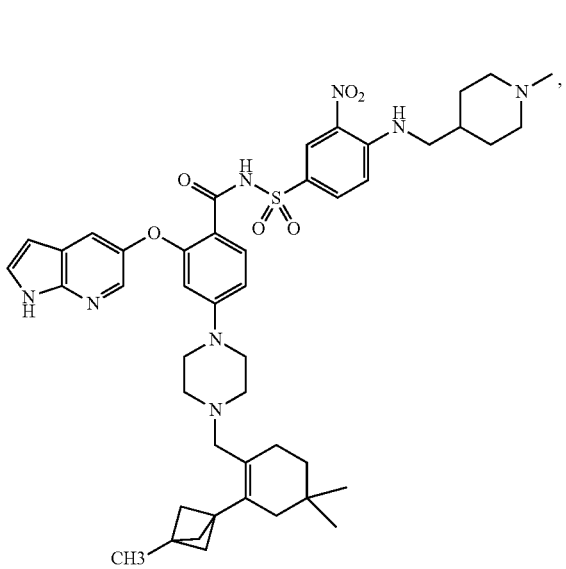
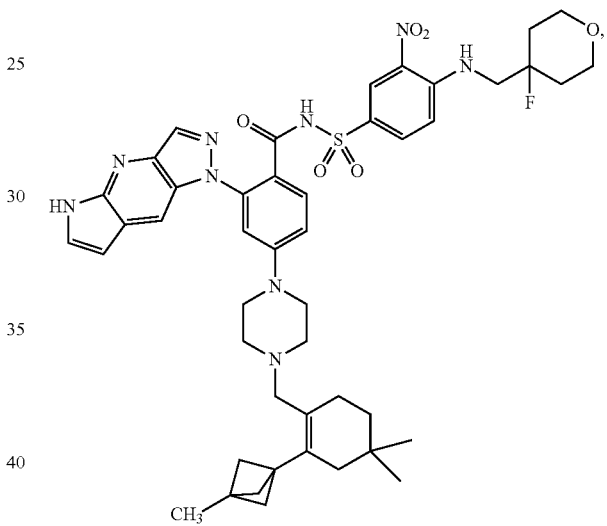
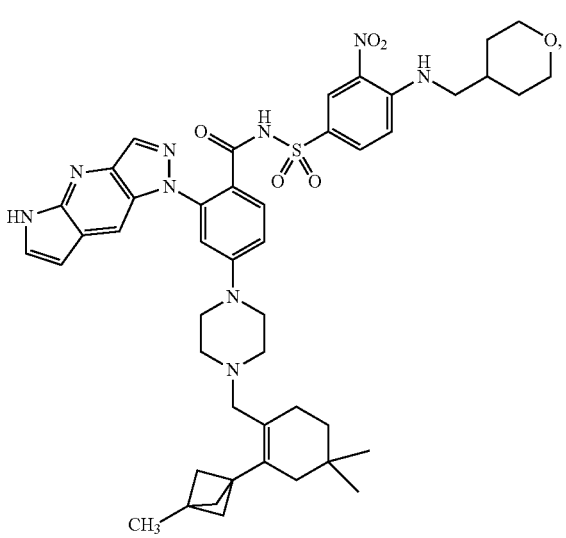
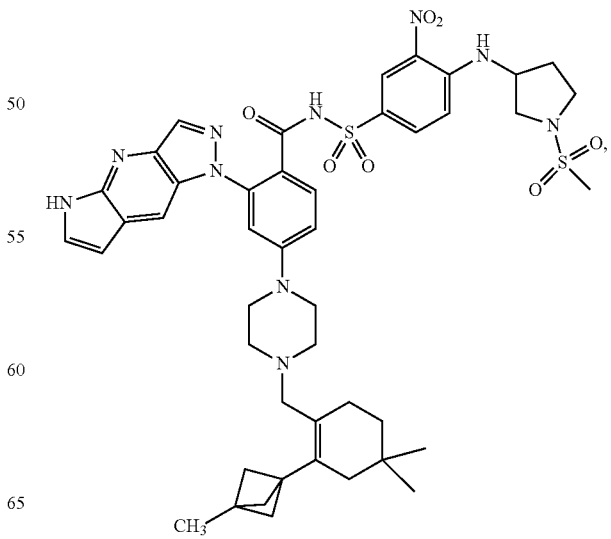

47
-continued
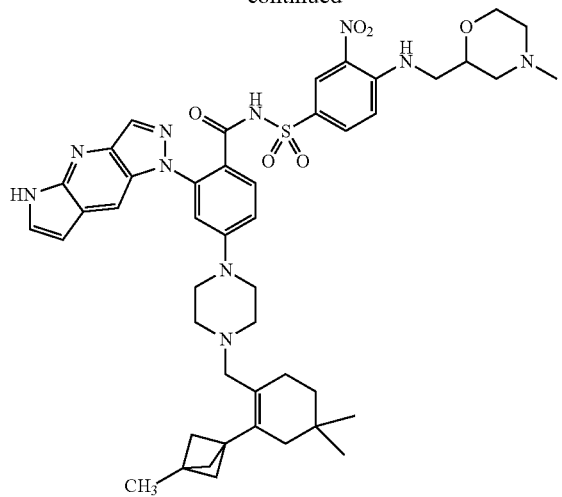
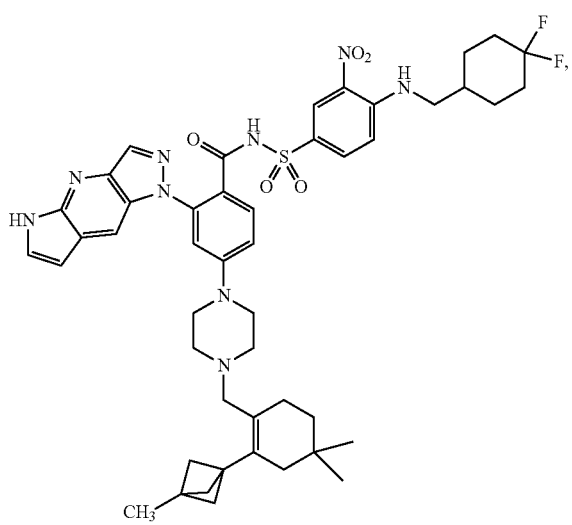
48
-continued
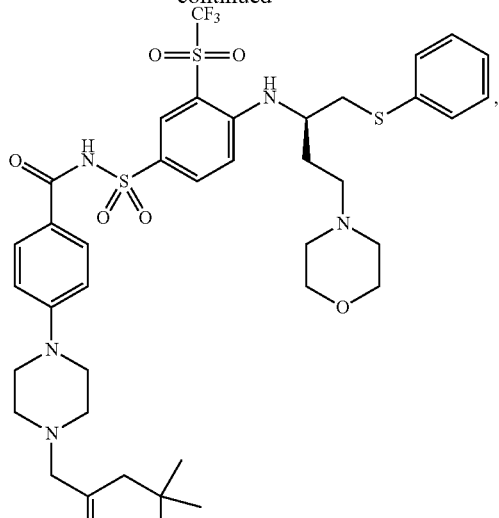
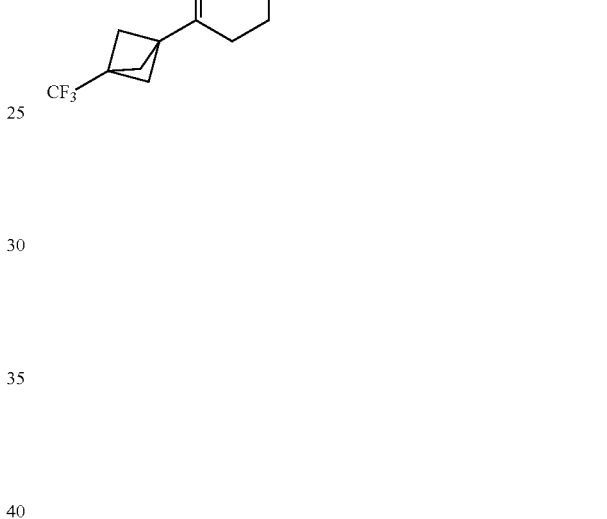
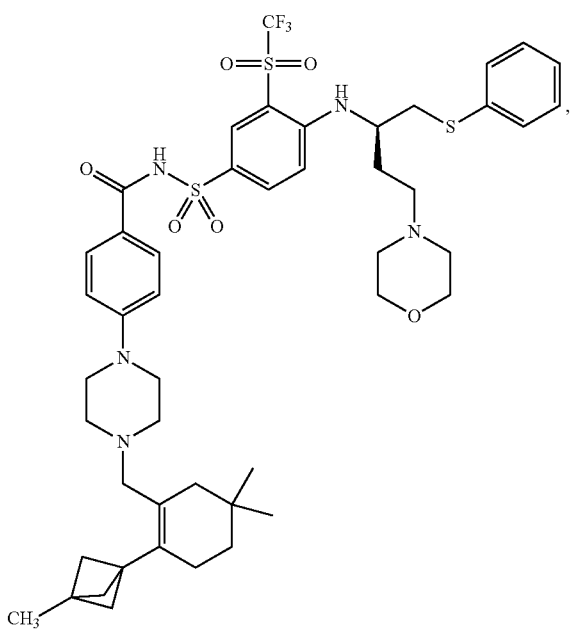
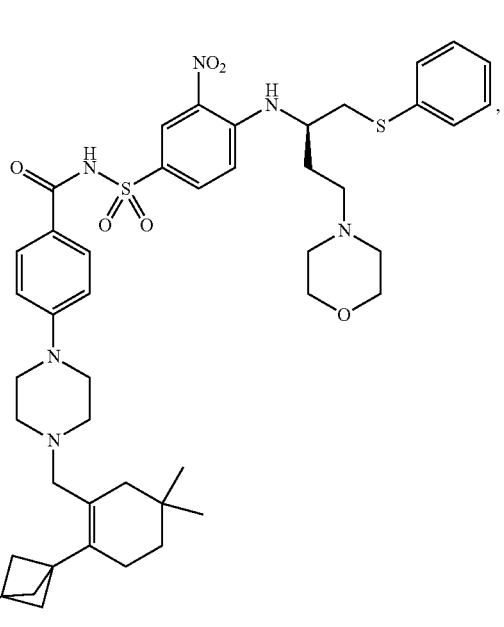

49
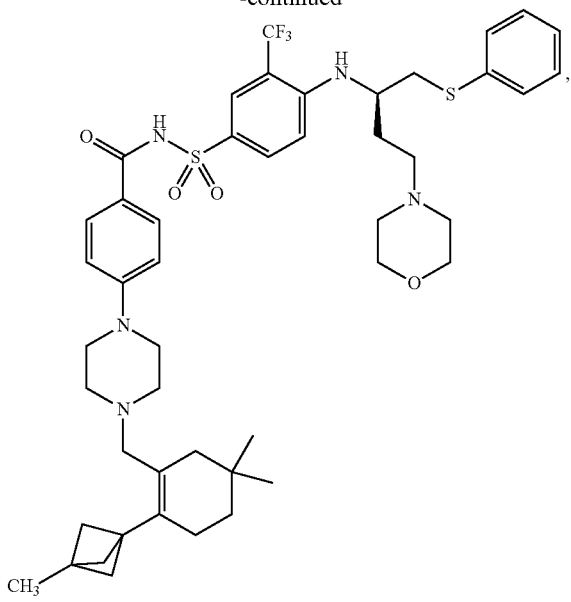
50
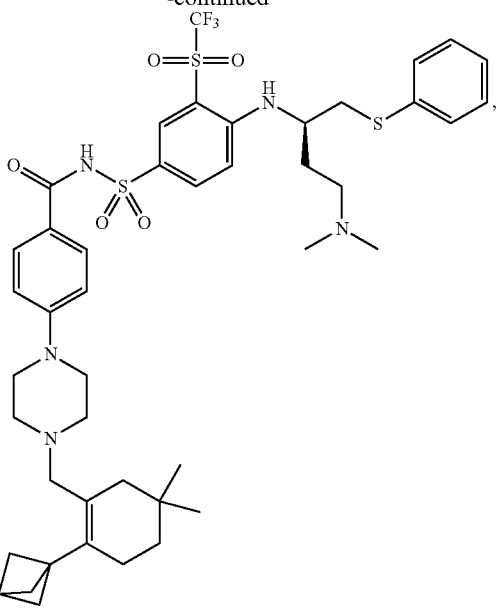
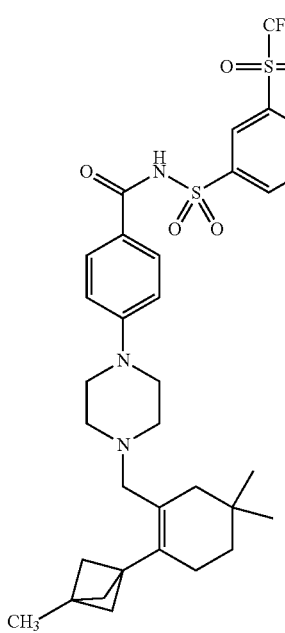
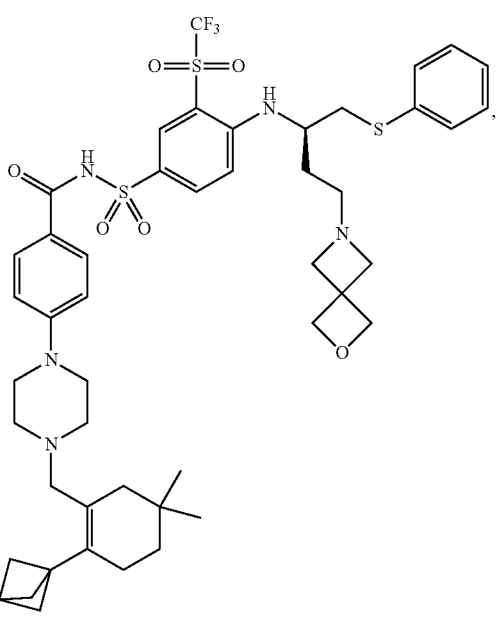

51
-continued

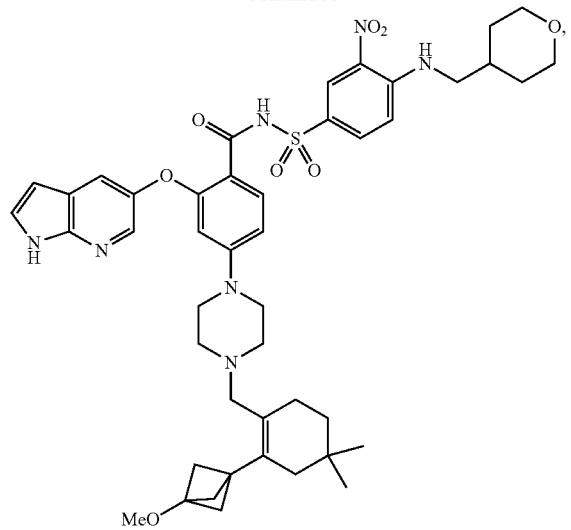

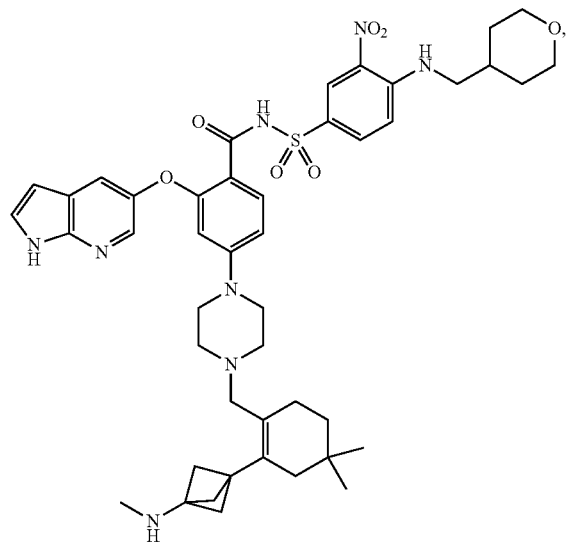

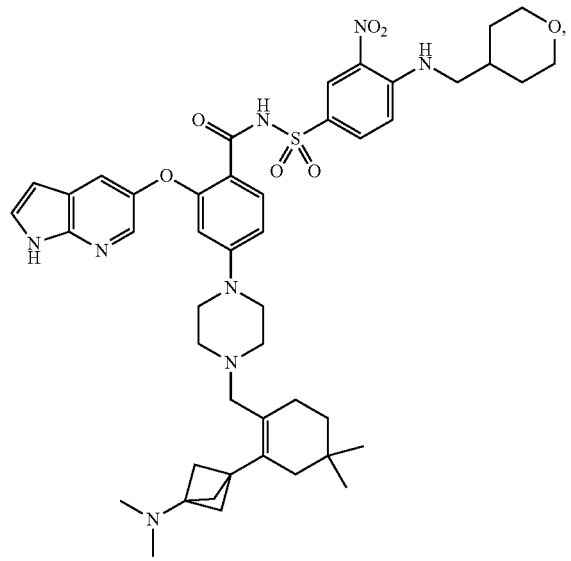

52
-continued

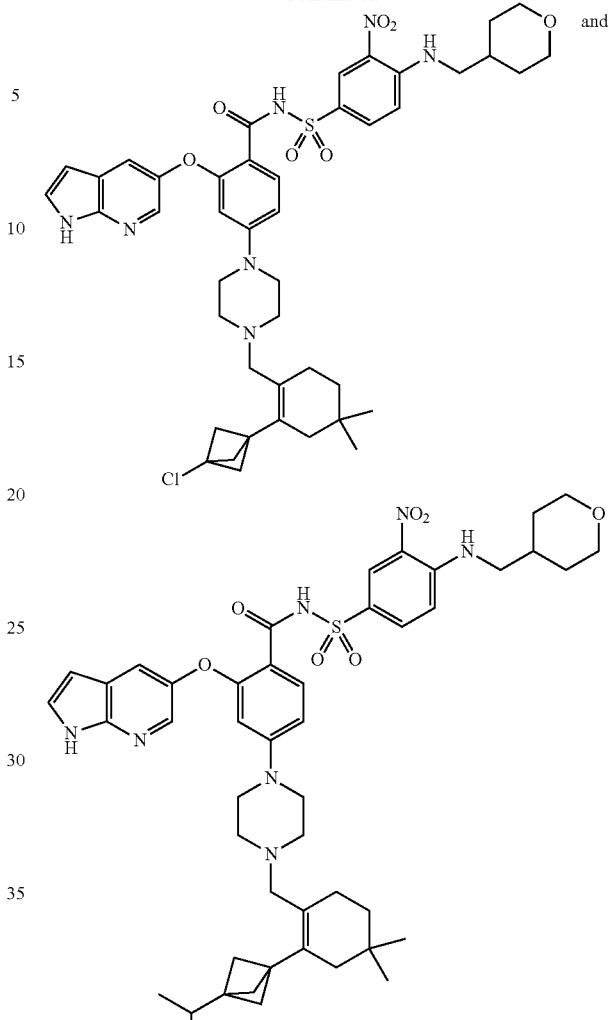

or a pharmaceutically acceptable salt of any of the foregoing.

Figure 4A:
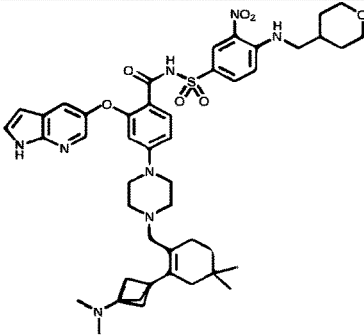

FIG. 3 provides the chemical names and structures for examples of the compounds of Formula (I) listed above in which $R^3$ is hydrogen or halogen, along with other examples of such compounds. In an embodiment, the compound of Formula (I) is a compound selected from FIG. 3, or a pharmaceutically acceptable salt of any of the compounds listed in FIG. 3. FIGS. 4A, 4B and 4C provide the chemical names and structures for examples of the compounds of Formula (I) listed above in which $R^3$ is X—$R^{3,4}$,

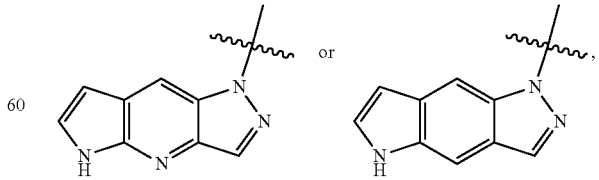

along with other examples of such compounds, including those in which $R^1$ is any of the aforementioned options for $R^1$ except that $R^1$ is not —$CH_2F$, —$CHF_2$ or —$CF_3$, and $X^1$ and $X^2$ are —NH— (FIG. 4A); those in which $R^1$ is any of the aforementioned options for $R^1$, and $X^1$ and $X^2$ are —O— (FIG. 4B); and those in which $R^1$ is —$CH_2F$, —$CHF_2$ or —$CF_3$, and $X^1$ and $X^2$ are —NH— (FIG. 4C). In an embodiment, the compound of Formula (I) is a compound selected from FIGS. 3, 4A, 4B, and/or 4C, or a pharmaceutically acceptable salt of any of the compounds listed in FIGS. 3, 4A, 4B and/or 4C. In an embodiment, the compound of Formula (I) is a compound selected from FIG. 3, or a pharmaceutically acceptable salt of any of the compounds listed in FIG. 3. In an embodiment, the compound of Formula (I) is a compound selected from FIG. 4A, or a pharmaceutically acceptable salt of any of the compounds listed in FIG. 4A. In an embodiment, the compound of Formula (I) is a compound selected from FIG. 4B, or a pharmaceutically acceptable salt of any of the compounds listed in FIG. 4B. In an embodiment, the compound of Formula (I) is a compound selected from FIG. 4C, or a pharmaceutically acceptable salt of any of the compounds listed in FIG. 4C.

In some embodiments, a compound of Formula (I), or a pharmaceutically acceptable salt thereof, can have increased metabolic and/or plasma stability. In some embodiments, a compound of Formula (I), or a pharmaceutically acceptable salt thereof, can be more resistant to hydrolysis and/or more resistant to enzymatic transformations. In some embodiments, a compound of Formula (I), or a pharmaceutically acceptable salt thereof, can have improved properties. A non-limiting list of example properties include, but are not limited to, increased biological half-life, increased bioavailability, increase potency, a sustained in vivo response, increased dosing intervals, decreased dosing amounts, decreased cytotoxicity, reduction in required amounts for treating disease conditions, a reduction of morbidity or mortality in clinical outcomes, decrease in or prevention of opportunistic infections, increased subject compliance and increased compatibility with other medications. In some embodiments, a compound of Formula (I), or a pharmaceutically acceptable salt thereof, can have more potent anti-cancer activity (for example, a lower $EC_{50}$ in a cell replication assay) as compared to the current standard of care (such as venetoclax). In some embodiments, a compound of Formula (I), or a pharmaceutically acceptable salt thereof, can have more potent antiviral activity (for example, a lower $EC_{50}$ in a HIV replicon assay) as compared to the current standard of care (such as dolutegravir).

Synthesis

Compounds of the Formula (I), or pharmaceutically acceptable salts thereof, can be made in various ways by those skilled using known techniques as guided by the detailed teachings provided herein. For example, in an embodiment, compounds of the Formula (I) are prepared in accordance with General Scheme 1 as shown herein.

In general, the coupling reactions between compounds of the general Formulae A and B to form compounds of the Formula (I) as illustrated in General Scheme 1 can be carried out in a manner similar to the reactions as described herein in the Examples, by appropriate adjustment of the reagents and conditions described in the Examples. Any preliminary reaction steps required to form starting compounds of the general Formula A and B, or other precursors, can be carried out by those skilled in the art. In General Scheme 1, $R^1$, $R^2$, $R^3$, $R^4$, $R^5$ and m can be as described herein.

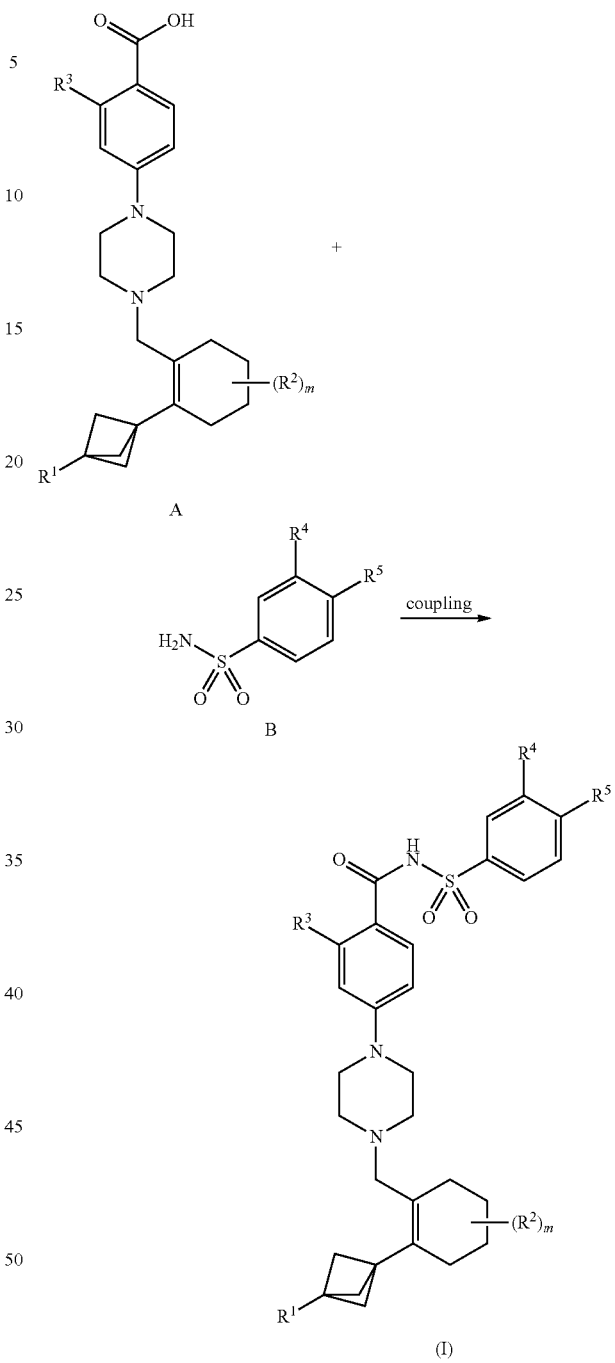

General Scheme 1

Pharmaceutical Compositions

Some embodiments described herein relate to a pharmaceutical composition, that can include an effective amount of one or more compounds described herein (for example, a compound of Formula (I), or a pharmaceutically acceptable salt thereof) and a pharmaceutically acceptable carrier, diluent, excipient or combination thereof.

The term "pharmaceutical composition" refers to a mixture of one or more compounds and/or salts disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration.

The term "physiologically acceptable" defines a carrier, diluent or excipient that does not abrogate the biological activity and properties of the compound nor cause appreciable damage or injury to an animal to which delivery of the composition is intended.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. For example, stabilizers such as antioxidants and metal-chelating agents are excipients. In an embodiment, the pharmaceutical composition comprises an anti-oxidant and/or a metal-chelating agent. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound, salt and/or composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections. In some embodiments, a compound of Formula (I), or a pharmaceutically acceptable salt thereof, can be administered orally.

One may also administer the compound, salt and/or composition in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory disease or condition may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or salt described herein formulated in a compatible pharmaceutical carrier may also be prepared, placed in an appropriate container and labeled for treatment of an indicated condition.

Uses and Methods of Treatment

Some embodiments described herein relate to a method for treating a cancer or a tumor described herein that can include administering an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) in the manufacture of a medicament for treating a cancer or a tumor described herein. Still other embodiments described herein relate to an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) for treating a cancer or a tumor described herein.

Some embodiments described herein relate to a method for inhibiting replication of a malignant growth or a tumor described herein that can include contacting the growth or the tumor with an effective amount of a compound described herein (for example, a compound of Formula (I), or a pharmaceutically acceptable salt thereof). Other embodiments described herein relate to the use of an effective amount of a compound described herein (for example, a compound of Formula (I), or a pharmaceutically acceptable salt thereof) in the manufacture of a medicament for inhibiting replication of a malignant growth or a tumor described herein. In some embodiments, the use can include contacting the growth or the tumor with the medicament. Still other embodiments described herein relate to an effective amount of a compound described herein (for example, a compound of Formula (I), or a pharmaceutically acceptable salt thereof) for inhibiting replication of a malignant growth or a tumor described herein.

Some embodiments described herein relate to a method for treating a cancer described herein that can include contacting a malignant growth or a tumor described herein with an effective amount of a compound described herein (for example, a compound of Formula (I), or a pharmaceutically acceptable salt thereof). Other embodiments described herein relate to the use of an effective amount of a compound described herein (for example, a compound of Formula (I), or a pharmaceutically acceptable salt thereof) in the manufacture of a medicament for treating a cancer described herein. In some embodiments, the use can include contacting the malignant growth or a tumor described herein with the medicament. Still other embodiments described herein relate to an effective amount of a compound described herein (for example, a compound of Formula (I), or a pharmaceutically acceptable salt thereof) for contacting a malignant growth or a tumor described herein, wherein the malignant growth or tumor is due to a cancer described herein.

Examples of suitable malignant growths, cancers and tumors include, but are not limited to: bladder cancers, brain cancers, breast cancers, bone marrow cancers, cervical cancers, colorectal cancers, esophageal cancers, hepatocellular cancers, lymphoblastic leukemias, follicular lymphomas, lymphoid malignancies of T-cell or B-cell origin, melanomas, myelogenous leukemias, Hodgkin's lymphoma, Non-Hodgkin's lymphoma, head and neck cancers (including oral cancers), ovarian cancers, non-small cell lung cancer, chronic lymphocytic leukemias, myelomas (including multiple myelomas), prostate cancer, small cell lung cancer, spleen cancers, polycythemia vera, thyroid cancers, endometrial cancer, stomach cancers, gallbladder cancer, bile duct cancers, testicular cancers, neuroblastomas, osteosarcomas, Ewings's tumor and Wilm's tumor.

As described herein, a malignant growth, cancer or tumor, can become resistant to one or more anti-proliferative agents. In some embodiments, a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) can be used to treat and/or ameliorate a malignant growth, cancer or tumor, that has become resistant to one or more anti-proliferative agents (such as one or more Bcl-2 inhibitors). Examples of anti-proliferative agents that a subject may have developed resistance to include, but are not limited to, Bcl-2 inhibitors (such as venetoclax, navitoclax, obatoclax, 555746, APG-1252, APG-2575 and ABT-737). In some embodiments, the malignant growth, cancer or tumor, that has become resistant to one or more anti-proliferative agents can be a malignant growth, cancer or tumor, described herein.

Some embodiments described herein relate to a method for inhibiting the activity of Bcl-2 that can include administering an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) to a subject and can also include contacting a cell that expresses Bcl-2 with an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof). Other embodiments described herein relate to the use of an effective amount of a compound described herein (for example, a compound of Formula (I), or a pharmaceutically acceptable salt thereof) in the manufacture of a medicament for inhibiting the activity of Bcl-2 in a subject or, in the manufacture of a medicament for inhibiting the activity of Bcl-2, wherein the use comprises contacting a cell that expresses Bcl-2. Still other embodiments described herein relate to an effective amount of a compound described herein (for example, a compound of Formula (I), or a pharmaceutically acceptable salt thereof) for inhibiting the activity of Bcl-2 in a subject; or for inhibiting the activity of Bcl-2 by contacting a cell that expresses Bcl-2.

Some embodiments described herein relate to a method of ameliorating or treating a HIV infection that can include administering an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) and an effective amount of a HIV latency reversing agent, or a pharmaceutically acceptable salt thereof, to a subject suffering from the HIV infection; and can also include contacting a cell infected with HIV with a compound described herein (for example, a compound of Formula (I), or a pharmaceutically acceptable salt thereof), and an effective amount of a HIV latency reversing agent, or a pharmaceutically acceptable salt thereof. Other embodiments described herein relate to the use of an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) and an effective amount of a HIV latency reversing agent, or a pharmaceutically acceptable salt thereof, in the manufacture of a medicament for ameliorating or treating a HIV infection in a subject suffering from the HIV infection; or, in the manufacture of a medicament for ameliorating or treating a HIV infection, wherein the use comprises contacting a cell infected with HIV with the medicament. Still other embodiments described herein relate to an effective amount of a compound described herein (for example, a compound of Formula (I), or a pharmaceutically acceptable salt thereof) and an effective amount of a HIV latency reversing agent, or a pharmaceutically acceptable salt thereof, for ameliorating or treating a HIV infection in a subject suffering from the HIV infection; or for ameliorating or treating a HIV infection by contacting a cell infected with HIV. In some embodiments, the cells can be in a subject. In some embodiments, the cells can be CD4+ T cells. In some embodiments, the CD4+ T cells can be in a subject.

Some embodiments described herein relate to a method of reducing the population of HIV infected cells that can include administering an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) and an effective amount of a HIV latency reversing agent, or a pharmaceutically acceptable salt thereof to a subject suffering from the HIV infection; and can also include contacting a cell infected with HIV with a compound described herein (for example, a compound of Formula (I), or a pharmaceutically acceptable salt thereof), and an effective amount of a HIV latency reversing agent, or a pharmaceutically acceptable salt thereof. Other embodiments described herein relate to the use of an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) and an effective amount of a HIV latency reversing agent, or a pharmaceutically acceptable salt thereof, in the manufacture of a medicament for reducing the population of HIV infected cells in a subject suffering from the HIV infection; or, for reducing the population of HIV infected cells, wherein the use comprises contacting a cell infected with HIV with the medicament. Still other embodiments described herein relate to an effective amount of a compound described herein (for example, a compound of Formula (I), or a pharmaceutically acceptable salt thereof) and an effective amount of a HIV latency reversing agent, or a pharmaceutically acceptable salt thereof, for reducing the population of HIV infected cells in a subject suffering from the HIV infection; or for reducing the population of HIV infected cells by contacting a cell infected with HIV. In some embodiments, the cells can be in a subject. In some embodiments, the cells can be CD4+ T cells. In some embodiments, the CD4+ T cells can be in a subject.

Some embodiments described herein relate to a method of reducing the reoccurrence of a HIV infection in a subject that can include administering an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) and an effective amount of a HIV latency reversing agent, or a pharmaceutically acceptable salt thereof to a subject suffering from the HIV infection; and can also include contacting a cell infected with HIV with a compound described herein (for example, a compound of Formula (I), or a pharmaceutically acceptable salt thereof) and an effective amount of a HIV latency reversing agent, or a pharmaceutically acceptable salt thereof. Other embodiments described herein relate to the use of an effective amount of a compound described herein (for example, a compound of Formula (I), or a pharmaceutically acceptable salt thereof) and an effective amount of a HIV latency reversing agent, or a pharmaceutically acceptable salt thereof, in the manufacture of a medicament for reducing the reoccurrence of a HIV infection in a subject suffering from the HIV infection; or, for reducing the reoccurrence of a HIV infection, wherein the use comprises contacting a cell infected with HIV with the medicament. Still other embodiments described herein relate to an effective amount of a compound described herein (for example, a compound of Formula (I), or a pharmaceutically acceptable salt thereof) and an effective amount of a HIV latency reversing agent, or a pharmaceutically acceptable salt thereof, for reducing the reoccurrence of a HIV infection in a subject suffering from the HIV infection; or for reducing the reoccurrence of a HIV infection by contacting a cell infected with HIV. In some embodiments, the cells can be in a subject. In some embodiments, the cells can be CD4+ T cells. In some embodiments, the CD4+ T cells can be in a subject.

Some embodiments described herein relate to a method of ameliorating or treating a HIV infection that can include administering an effective amount of a Bcl protein inhibitor, or a pharmaceutically acceptable salt thereof, and an effective amount of a HIV latency reversing agent, or a pharmaceutically acceptable salt thereof, to a subject suffering from the HIV infection; and can also include contacting a cell infected with HIV with a Bcl protein inhibitor, or a pharmaceutically acceptable salt thereof, and an effective amount of a HIV latency reversing agent, or a pharmaceutically acceptable salt thereof. Other embodiments described herein relate to the use of an effective amount of a Bcl protein inhibitor, or a pharmaceutically acceptable salt thereof, and an effective amount of a HIV latency reversing agent, or a pharmaceutically acceptable salt thereof, in the manufacture of a medicament for ameliorating or treating a HIV infection; or, in the manufacture of a medicament for ameliorating or treating a HIV infection, wherein the use comprises contacting a cell infected with HIV with the medicament. Still other embodiments described herein relate to an effective amount of a Bcl protein inhibitor, or a pharmaceutically acceptable salt thereof, and an effective amount of a HIV latency reversing agent, or a pharmaceutically acceptable salt thereof, for ameliorating or treating a HIV infection in a subject suffering from the HIV infection; or for ameliorating or treating a HIV infection by contacting a cell infected with HIV. In some embodiments, the cells can be in a subject. In some embodiments, the cells can be CD4+ T cells. In some embodiments, the CD4+ T cells can be in a subject.

Some embodiments described herein relate to a method of reducing the population of HIV infected cells that can include administering an effective amount of a Bcl protein inhibitor, or a pharmaceutically acceptable salt thereof, and an effective amount of a HIV latency reversing agent, or a pharmaceutically acceptable salt thereof, to a subject suffering from the HIV infection; and can also include contacting a cell infected with HIV with a Bcl protein inhibitor, or a pharmaceutically acceptable salt thereof, and an effective amount of a HIV latency reversing agent, or a pharmaceutically acceptable salt thereof. Other embodiments described herein relate to the use of an effective amount of a Bcl protein inhibitor, or a pharmaceutically acceptable salt thereof, and an effective amount of a HIV latency reversing agent, or a pharmaceutically acceptable salt thereof, in the manufacture of a medicament for reducing the population of HIV infected cells; or, in the manufacture of a medicament for reducing the population of HIV infected cells, wherein the use comprises contacting a cell infected with HIV with the medicament. Still other embodiments described herein relate to an effective amount of a Bcl protein inhibitor, or a pharmaceutically acceptable salt thereof, and an effective amount of a HIV latency reversing agent, or a pharmaceutically acceptable salt thereof, for reducing the population of HIV infected cells in a subject suffering from the HIV infection; or for reducing the population of HIV infected cells by contacting a cell infected with HIV. In some embodiments, the cells can be in a subject. In some embodiments, the cells can be CD4+ T cells. In some embodiments, the CD4+ T cells can be in a subject.

Some embodiments described herein relate to a method of reducing the reoccurrence of a HIV infection in a subject that can include administering an effective amount of a compound described herein (for example, a compound of Formula (I), or a pharmaceutically acceptable salt thereof) or a pharmaceutical composition that includes a compound described herein (for example, a compound of Formula (I), or a pharmaceutically acceptable salt thereof) and an effective amount of a HIV latency reversing agent, or a pharmaceutically acceptable salt thereof to a subject suffering from the HIV infection; and can also include contacting a cell infected with HIV with an effective amount of a Bcl protein inhibitor, or a pharmaceutically acceptable salt thereof, and an effective amount of a HIV latency reversing agent, or a pharmaceutically acceptable salt thereof. Other embodiments described herein relate to the use of an effective amount of a Bcl protein inhibitor, or a pharmaceutically acceptable salt thereof, and an effective amount of a HIV latency reversing agent, or a pharmaceutically acceptable salt thereof, in the manufacture of a medicament for reducing the reoccurrence of a HIV infection in a subject suffering from the HIV infection; or, for reducing the reoccurrence of a HIV infection, wherein the use comprises contacting a cell infected with HIV with the medicament. Still other embodiments described herein relate to an effective amount of a Bcl protein inhibitor, or a pharmaceutically acceptable salt thereof, and an effective amount of a HIV latency reversing agent, or a pharmaceutically acceptable salt thereof, for reducing the reoccurrence of a HIV infection in a subject suffering from the HIV infection; or for reducing the reoccurrence of a HIV infection by contacting a cell infected with HIV. In some embodiments, the cells can be in a subject. In some embodiments, the cells can be CD4+ T cells. In some embodiments, the CD4+ T cells can be in a subject.

In some embodiments, the HIV latency reversing agent can be a protein kinase C agonist, a PD-1 inhibitor, a PD-L1 inhibitor, an HDAC inhibitor, a phorbol ester or a bromodomain inhibitor. In some embodiments, the HIV latency reversing agent can be a protein kinase C agonist, which includes, but is not limited to prostratin, bryostatin-1 and ingenol. In some embodiments, the HIV latency reversing agent can be a PD-1 inhibitor, which includes, but is not limited to nivolumab, pembrolizumab, BGB-A317, pidilizumab, AMP-224, AMP-514, PDR001, REGN2810 and MEDI0680. In some embodiments, the HIV latency reversing agent can be a PD-L1 inhibitor, which includes, but is not limited to atezolizumab, durvalumab, avelumab and BMS-936559. In some embodiments, the HIV latency reversing agent can be a HDAC inhibitor, which includes, but is not limited to vorinostat, panobinostat, romidepsin and valproic acid. In some embodiments, the HIV latency reversing agent can be a phorbol ester, which includes, but is not limited to phorbol 12-myristate-13-acetate and (S)-tert-butyl-2-(4-(4-chlorophenyl)-2,3,9-trimethyl-6H-thieno[3,2-f][1,2,4]triazolo[4,3-a][1,4]diazepin-6-yl)acetate. In some embodiments, the HIV latency reversing agent can be a bromodomain inhibitor, which includes, but is not limited to JQ1, I-BET762, OTX015, I-BET151, CPI203, PFI-1, MS436, CPI-0610, RVX2135, FT-1101, BAY1238097, INCB054329, TEN-010, GSK2820151, ZEN003694, BAY-299, BMS-986158, ABBV-075 and GS-5829. In some embodiments, a combination of two or more HIV latency reversing agents may be used.

In some embodiments, the Bcl protein inhibitor of Formula (I) can be a selective Bcl-2 inhibitor, a selective Bcl-$X_L$ inhibitor, a selective Bcl-W inhibitor, a selective Mcl-1 inhibitor or a selective Bcl-2A1 inhibitor. In some embodiments, the Bcl protein inhibitor of Formula (I) can inhibit more than one Bcl protein. In some embodiments, the Bcl protein inhibitor can be an inhibitor of the activity of Bcl-2 and one of Bcl-$X_L$, Bcl-W, Mcl-1 and Bcl-2A1. In some embodiments, the Bcl protein inhibitor can be an inhibitor of the activity of Bcl-$X_L$ and one of Bcl-W, Mcl-1 and Bcl-2A1. In some embodiments, the Bcl protein inhibitor of Formula (I) can inhibit both Bcl-2 and Bcl-$X_L$. In some embodiments, the Bcl protein inhibitor can be venetoclax, navitoclax, obatoclax, ABT-737, 555746, AT-101, APG-1252, APG-2575, AMG176 or AZD5991, or a combination of any of the foregoing.

In some embodiments, the methods of ameliorating or treating a HIV infection can also include the use of one or more agents selected from a non-nucleoside reverse transcriptase inhibitor (NNRTI), a nucleoside reverse transcriptase inhibitor (NRTI), a protease inhibitor (PI), a fusion/entry inhibitor, an integrase strand transfer inhibitor (INSTI), a HIV vaccine, a HIV other antiretroviral therapy compound and combinations thereof, or a pharmaceutically acceptable salt of any of the aforementioned. In some embodiments, the subject suffering from the HIV infection is not using an agent selected from a non-nucleoside reverse transcriptase inhibitor (NNRTI), a nucleoside reverse transcriptase inhibitor (NRTI), a protease inhibitor (PI), a fusion/entry inhibitor, an integrase strand transfer inhibitor (INSTI), a HIV vaccine, a HIV other antiretroviral therapy compound and combinations thereof, or a pharmaceutically acceptable salt of any of the aforementioned.

Examples of suitable NNRTIs include, but are not limited to, delavirdine (Rescriptor®), efavirenz (Sustiva®), etravirine (Intelence@), nevirapine (Viramune®), rilpivirine (Edurant®), doravirine, and pharmaceutically acceptable salts of any of the foregoing, and/or a combination thereof. Examples of suitable NRTIs include, but are not limited to, abacavir (Ziagen®), adefovir (Hepsera@), amdoxovir, apricitabine, censavudine, didanosine (Videx®), elvucitabine, emtricitabine (Emtriva®), entecavir (Baraclude®), lamivudine (Epivir®), racivir, stampidine, stavudine (Zerit®), tenofovir disoproxil (including Viread®), tenofovir alafenamide, zalcitabine (Hivid®), zidovudine (Retrovir®), and pharmaceutically acceptable salts of any of the foregoing, and/or a combination thereof. Examples of vaccines include, but are not limited to Heplislav®, ABX-203, INO-1800, and pharmaceutically acceptable salts of any of the foregoing, and/or combinations thereof. Examples of suitable protease inhibitors include, but are not limited to, atazanavir (Reyataz®), darunavir (Prezista®), fosamprenavir (Lexiva®), indinavir (Crixivan®), lopinavir/ritonavir (Kaletra®), nelfinavir (Viracept®), ritonavir (Norvir®) and saquinavir (Invirase®). Examples of suitable fusion/entry inhibitors include, but are not limited to, enfuvirtide (Fuzeon®), maraviroc (Selzentry®), vicriviroc, apliviroc, ibalizumab, fostemsavir and PRO-140. Examples of suitable INSTIs include, but are not limited to, raltegravir (Isentress®), dolutegravir (Tivicay®) and elvitegravir (Viteka®).

Two types of HIV have been characterized, HIV-1 and HIV-2. HIV-1 is more virulent and more infective strain, and has a global prevalence. HIV-2 is considered to be less virulent and is geographically confined. In some embodiments, an effective amount of a compound of Formula (I), or a pharmaceutically acceptable salt thereof, or a pharmaceutical composition that includes an effective amount of a compound of Formula (I), or a pharmaceutically acceptable salt thereof, can be effective to treat HIV-1. In some embodiments, an effective amount of a compound of Formula (I), or a pharmaceutically acceptable salt thereof, or a pharmaceutical composition that includes an effective amount of a compound of Formula (I), or a pharmaceutically acceptable salt thereof, can be effective to treat HIV-2. In some embodiments, a compound described herein (for example, a compound of Formula (I), or a pharmaceutically acceptable salt thereof) can be effective to treat both genotypes of HIV (HIV-1 and HIV-2).

Various indicators for determining the effectiveness of a method for treating a HIV infection are known to those skilled in the art. Examples of suitable indicators include, but are not limited to, a reduction in viral load, a reduction in plasma viral load, a reduction in viral replication, a reduction in time to seroconversion (virus undetectable in patient serum), an increase CD4+ T lymphocyte counts, a reduction in the population of HIV infected cells, a reduction of morbidity or mortality in clinical outcomes and/or a reduction in the rate of opportunistic infections. Similarly, successful therapy with an effective amount of a compound or a pharmaceutical composition described herein (for example, a compound of Formula (I), or a pharmaceutically acceptable salt thereof) and an effective amount of a HIV latency reversing agent, or a pharmaceutically acceptable salt thereof, can reduce the incidence of opportunistic infections in HIV infected subjects.

In some embodiments, an effective amount of a compound of Formula (I), or a pharmaceutically acceptable salt thereof, is an amount that is effective to reduce the population of CD4+ T lymphocyte cells harboring HIV to undetectable levels.

In some embodiments, an effective amount of a compound of Formula (I), or a pharmaceutically acceptable salt thereof, is an amount that is effective to increase CD4+ T lymphocyte counts from less than about 200 cells/mL to greater than about 1,200 cells/mL. In some embodiments, an effective amount of a compound of Formula (I), or a pharmaceutically acceptable salt thereof, is an amount that is effective to increase CD4+ T lymphocyte counts from less than about 200 cells/mL to greater than about 500 cells/mL.

After a period of time, infectious agents can develop resistance to one or more therapeutic agents. The term "resistance" as used herein refers to a viral strain displaying a delayed, lessened and/or null response to a therapeutic agent(s). In some instances, the virus sometimes mutates or produces variations that are resistant or partially resistant to certain drugs. For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formula (I), or a pharmaceutically acceptable salt thereof, can be provided to a subject infected with a HIV strain that is resistant to one or more different anti-HIV agents (for example, an agent used in a conventional standard of care). Examples of anti-HIV agents include, but are not limited to, non-nucleoside reverse transcriptase inhibitors (NNRTIs), nucleoside reverse transcriptase inhibitors (NRTIs), protease inhibitors (PIs), fusion/entry inhibitors, integrase strand transfer inhibitors (INSTIs), HIV vaccines, and combinations thereof, or pharmaceutically acceptable salts of any of the aforementioned.

Several known Bcl-2 inhibitors can cause one or more undesirable side effects in the subject being treated. Examples of undesirable side effects include, but are not limited to, thrombocytopenia, neutropenia, anemia, diarrhea, nausea and upper respiratory tract infection. In some embodiments, a compound described herein (for example, a compound of Formula (I), or a pharmaceutically acceptable salt thereof) can decrease the number and/or severity of one or more side effects associated with a known Bcl-2 inhibitors. In some embodiments, a compound of Formula (I), or a pharmaceutically acceptable salt thereof, can result in a severity of a side effect (such as one of those described herein) that is 25% less than compared to the severity of the same side effect experienced by a subject receiving a known Bcl-2 inhibitors (such as venetoclax, navitoclax, obatoclax, ABT-737, 555746, AT-101, APG-1252 and APG-2575). In some embodiments, a compound of Formula (I), or a pharmaceutically acceptable salt thereof, results in a number of side effects that is 25% less than compared to the number of side effects experienced by a subject receiving a known Bcl-2 inhibitors (for example, venetoclax, navitoclax, obatoclax, ABT-737, 555746, AT-101, APG-1252 and APG-2575). In some embodiments, a compound of Formula (I), or a pharmaceutically acceptable salt thereof, results in a severity of a side effect (such as one of those described herein) that is less in the range of about 10% to about 30% compared to the severity of the same side effect experienced by a subject receiving a known Bcl-2 inhibitors (for example, venetoclax, navitoclax, obatoclax, ABT-737, S55746, AT-101, APG-1252 and APG-2575). In some embodiments, a compound of Formula (I), or a pharmaceutically acceptable salt thereof, results in a number of side effects that is in the range of about 10% to about 30% less than compared to the number of side effects experienced by a subject receiving a known Bcl-2 inhibitors (for example, venetoclax, navitoclax, obatoclax, ABT-737, S55746, APG-1252 and APG-2575).

The one or more compounds of Formula (I), or a pharmaceutically acceptable salt thereof, that can be used to treat, ameliorate and/or inhibit the replication of a cancer, malignant growth, or tumor wherein inhibiting the activity of Bcl-2 is beneficial is provided in any of the embodiments described above under the heading titled "Compounds." For example, in various embodiments, the methods and uses described above in the Uses and Methods of Treatment section of this disclosure are carried out in the described manner (generally involving cancer, malignant growth, and/or tumor) using a compound of Formula (I) in which $R^3$ is hydrogen or halogen, or a pharmaceutically acceptable salt thereof.

In other embodiments, the methods and uses described above in the Uses and Methods of Treatment section are carried out in the described manner (generally involving cancer, malignant growth, and/or tumor) using a compound of Formula (I) in which $R^3$ is X—$R^{3A}$,

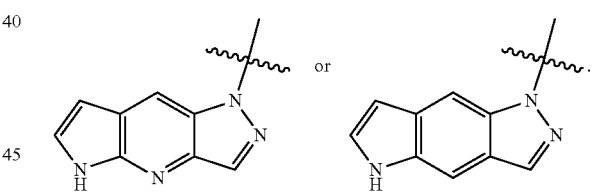

In other embodiments, the methods and uses described above in the Uses and Methods of Treatment section of this disclosure are carried out in the described manner (generally involving cancer, malignant growth, and/or tumor) using a compound of Formula (I) in which $R^3$ is X—$R^{3A}$,

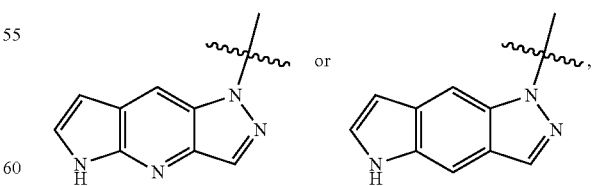

and in which $X^1$ and $X^2$ are —NH—.

In other embodiments, the methods and uses described above in the Uses and Methods of Treatment section are carried out in the described manner (generally involving cancer, malignant growth, and/or tumor) using a compound of Formula (I) in which $R^1$ is selected from the group consisting of hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine, with the proviso that $R^1$ is not —CH$_2$F, —CHF$_2$ or —CF$_3$; $R^3$ is X—$R^{3A}$,

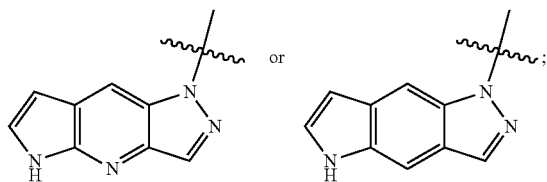 [SMILES: *n1ncc2nc3[nH]ccc3cc21 ; *n1ncc2cc3[nH]ccc3cc21]

and $X^1$ and $X^2$ are —NH—.

In other embodiments, the methods and uses described above in the Uses and Methods of Treatment section are carried out in the described manner (generally involving cancer, malignant growth, and/or tumor) using a compound of Formula (I) in which $R^1$ is selected from the group consisting of hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine; $R^3$ is X—$R^{3A}$,

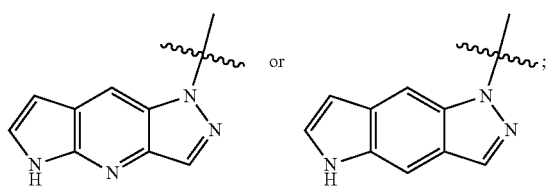 [SMILES: *n1ncc2nc3[nH]ccc3cc21 ; *n1ncc2cc3[nH]ccc3cc21]

and $X^1$ and $X^2$ are —O—.

In other embodiments, the methods and uses described above in the Uses and Methods of Treatment section are carried out in the described manner (generally involving cancer, malignant growth, and/or tumor) using a compound of Formula (I) in which $R^1$ is —CH$_2$F, —CHF$_2$ or —CF$_3$; $R^3$ is X—$R^{3A}$,

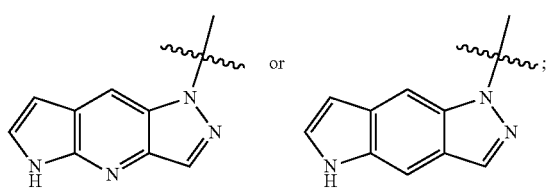 [SMILES: *n1ncc2nc3[nH]ccc3cc21 ; *n1ncc2cc3[nH]ccc3cc21]

and $X^1$ and $X^2$ are —NH—.

The one or more compounds of Formula (I), or a pharmaceutically acceptable salt thereof, that can be used to treat and/or ameliorate a HIV infection and/or reducing the reoccurrence of a HIV infection and/or reducing the population of HIV infected cells, wherein inhibiting the activity of Bcl-2 is beneficial is provided in any of the embodiments described above under the heading titled "Compounds." For example, in various embodiments, the methods and uses described above in the Uses and Methods of Treatment section of this disclosure are carried out in the described manner (generally involving HIV) using a compound of Formula (I) in which $R^3$ is hydrogen or halogen, or a pharmaceutically acceptable salt thereof.

In other embodiments, the methods and uses described above in the Uses and Methods of Treatment section are carried out in the described manner (generally involving HIV) using a compound of Formula (I) in which $R^3$ is X—$R^{3A}$,

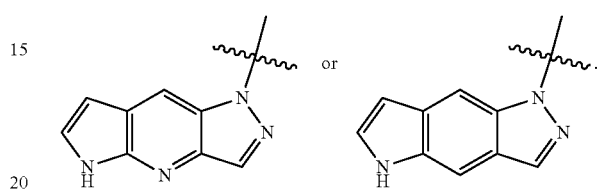

In other embodiments, the methods and uses described above in the Uses and Methods of Treatment section of this disclosure are carried out in the described manner (generally involving HIV) using a compound of Formula (I) in which $R^3$ is X—$R^{3A}$,

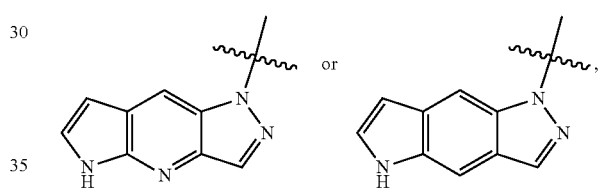

and in which $X^1$ and $X^2$ are —NH—.

In other embodiments, the methods and uses described above in the Uses and Methods of Treatment section are carried out in the described manner (generally involving HIV) using a compound of Formula (I) in which $R^1$ is selected from the group consisting of hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine, with the proviso that $R^1$ is not —CH$_2$F, —CHF$_2$ or —CF$_3$; $R^3$ is X—$R^{3A}$,

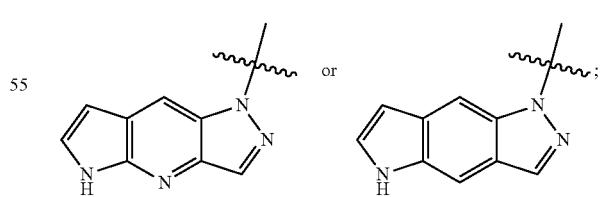

and $X^1$ and $X^2$ are —NH—.

In other embodiments, the methods and uses described above in the Uses and Methods of Treatment section are carried out in the described manner (generally involving HIV) using a compound of Formula (I) in which $R^3$ is X—$R^{3A}$,

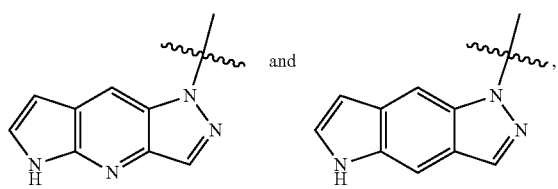 [SMILES: *n1ncc2nc3[nH]ccc3cc21 ; *n1ncc2cc3[nH]ccc3cc21]

and in which $X^1$ and $X^2$ are —O—.

In other embodiments, the methods and uses described above in the Uses and Methods of Treatment section are carried out in the described manner (generally involving HIV) using a compound of Formula (I) in which $R^1$ is —CH$_2$F, —CHF$_2$ or —CF$_3$; $R^3$ is X—$R^{3A}$,

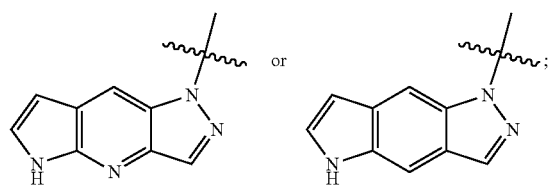 [SMILES: *n1ncc2nc3[nH]ccc3cc21 ; *n1ncc2cc3[nH]ccc3cc21]

and $X^1$ and $X^2$ are —NH—.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject can be human. In some embodiments, the subject can be a child and/or an infant, for example, a child or infant with a fever. In other embodiments, the subject can be an adult.

As used herein, the terms "treat," "treating," "treatment," "therapeutic," and "therapy" do not necessarily mean total cure or abolition of the disease or condition. Any alleviation of any undesired signs or symptoms of the disease or condition, to any extent can be considered treatment and/or therapy. Furthermore, treatment may include acts that may worsen the subject's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound, salt or composition can be the amount needed to prevent, alleviate or ameliorate symptoms of the disease or condition, or prolong the survival of the subject being treated. This response may occur in a tissue, system, animal or human and includes alleviation of the signs or symptoms of the disease or condition being treated. Determination of an effective amount is well within the capability of those skilled in the art, in view of the disclosure provided herein. The therapeutically effective amount of the compounds disclosed herein required as a dose will depend on the route of administration, the type of animal, including human, being treated and the physical characteristics of the specific animal under consideration. The dose can be tailored to achieve a desired effect, but will depend on such factors as weight, diet, concurrent medication and other factors which those skilled in the medical arts will recognize.

For example, an effective amount of a compound is the amount that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. In the treatment of lung cancer (such as non-small cell lung cancer), a therapeutically effective amount is that amount that alleviates or eliminates cough, shortness of breath and/or pain. As another example, an effective amount, or a therapeutically effective amount of a Bcl-2 inhibitor is the amount which results in the reduction in Bcl-2 activity and/or an increase in apoptosis. The reduction in Bcl-2 activity is known to those skilled in the art and can be determined by the analysis of Bcl-2 binding and relatives levels of cells undergoing apoptosis.

The amount of the compound of Formula (I), or a pharmaceutically acceptable salt thereof, required for use in treatment will vary not only with the particular compound or salt selected but also with the route of administration, the nature and/or symptoms of the disease or condition being treated and the age and condition of the patient and will be ultimately at the discretion of the attendant physician or clinician. In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the dosage ranges described herein in order to effectively and aggressively treat particularly aggressive diseases or conditions.

In general, however, a suitable dose will often be in the range of from about 0.05 mg/kg to about 10 mg/kg. For example, a suitable dose may be in the range from about 0.10 mg/kg to about 7.5 mg/kg of body weight per day, such as about 0.15 mg/kg to about 5.0 mg/kg of body weight of the recipient per day, about 0.2 mg/kg to about 4.0 mg/kg of body weight of the recipient per day, or any amount in between. The compound may be administered in unit dosage form; for example, containing 1 to 500 mg, 10 to 100 mg, 5 to 50 mg or any amount in between, of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, the mammalian species treated, the particular compounds employed and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies. For example, useful dosages of a compound of Formula (I), or pharmaceutically acceptable salts thereof, can be determined by comparing their in vitro activity and in vivo activity in animal models. Such comparison can be done by comparison against an established drug, such as cisplatin and/or gemcitabine)

Dosage amount and interval may be adjusted individually to provide plasma levels of the active moiety which are sufficient to maintain the modulating effects, or minimal effective concentration (MEC). The MEC will vary for each compound but can be estimated from in vivo and/or in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the disease or condition to be treated and to the route of administration. The severity of the disease or condition may, for example, be evaluated, in part, by standard prognostic evaluation methods. Further, the dose and perhaps dose frequency, will also vary according to the age, body weight and response of the individual patient. A program comparable to that discussed above may be used in veterinary medicine.

Compounds, salts and compositions disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

Additional embodiments are disclosed in further detail in the following examples, which are not in any way intended to limit the scope of the claims.

Intermediate 1

3-Chloro-N-methoxy-N-methylbicyclo[1.1.1]pentane-1-carboxamide

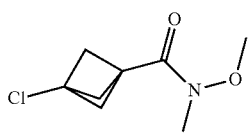

To a stirred solution of 3-chlorobicyclo[1.1.1]pentane-1-carboxylate (10.0 g, 62.3 mmol) and N,O-dimethylhydroxylamine hydrochloride (12.15 g, 124.5 mmol) in anhydrous THF (200 mL) at −78° C. was added i-PrMgCl (2 M in THF, 124.5 mL, 249 mmol). The temperature was then raised to −50° C. and stirred for 2 h. The reaction was quenched with sat. aq. NH$_4$Cl and extracted with EtOAc (3×150 mL). The combined organic layers were washed with water, brine, dried over Na$_2$SO$_4$, filtered, and concentrated. The crude product was purified by column chromatography (SiO$_2$, EtOAc/pet. ether) to provide Intermediate 1 (7.30 g, 62%) as an oil. $^1$H NMR (300 MHz, CDCl$_3$) δ 3.67 (s, 3H), 3.18 (s, 3H), 2.47 (s, 6H).

Intermediate 2

Tert-Butyl 2-(1H-pyrrolo[2,3-b]pyridin-5-yloxy)-4-(piperazin-1-yl)benzoate

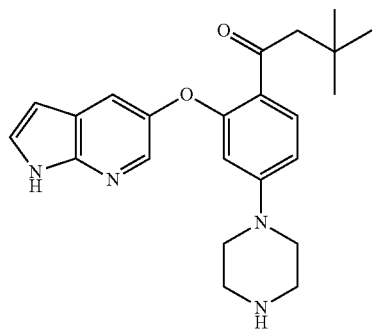 [SMILES: CC(C)(C)CC(=O)c1ccc(N2CCNCC2)cc1Oc1cnc2[nH]ccc2c1]

A solution of tert-butyl 2-(1H-pyrrolo[2,3-b]pyridin-5-yloxy)-4-fluorobenzoate (3.5 g, 10.67 mmol) in DMSO (35 mL) was treated with piperazine (2.33 ml, 32.0 mmol) at rt and stirred at 100° C. for 4 h. The reaction was cooled to rt and water (50 mL) was added. The mixture was extracted with EtOAc (3×50 ml) and the organic layers were concentrated and triturated with n-pentane to provide Intermediate 2 (3.0 g, 71%) as a white solid. LC/MS (ESI) m/z 395.5 [M+H]$^+$.

Intermediate 3

4-(2-oxaspiro[3.3]heptan-6-ylmethylamino)-3-nitrobenzenesulfonamide

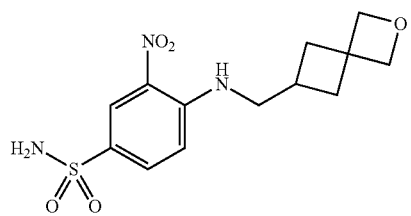 [SMILES: NS(=O)(=O)c1ccc(NCC2CC3(COC3)C2)c([N+](=O)[O-])c1]

A solution of 4-chloro-3-nitrobenzenesulfonamide (200 mg, 0.85 mmol) in CH$_3$CN (8 mL) was treated with (2-oxaspiro[3.3]heptan-6-yl)methanamine (129 mg, 1.01 mmol) and DIPEA (0.5 mL 2.95 mmol). The mixture was heated to 90° C. and stirred for 16 h. The reaction was cooled to rt, diluted with EtOAc, and washed with water and brine. The organic layer was dried over Na$_2$SO$_4$, filtered and concentrated. The crude product was purified by column chromatography (SiO$_2$, EtOAc/hexanes) to afford Intermediate 3 (120 mg, 43%) as a yellow solid. $^1$H NMR (400 MHz, DMSO-d$_6$) δ 8.47-8.43 (m, 2H), 7.83-7.80 (m, 1H), 7.30 (br s, 2H), 7.22 (d, J=9.6 Hz, 1H), 4.56 (s, 2H), 4.49 (s, 2H), 3.42-3.38 (m, 2H), 2.45-2.39 (m, 1H), 2.33-2.27 (m, 2H), 1.99-1.94 (m, 2H).

Intermediate 4

4-(2-(2-oxa-8-azaspiro[4.5]decan-8-yl)ethylamino)-3-nitrobenzenesulfonamide

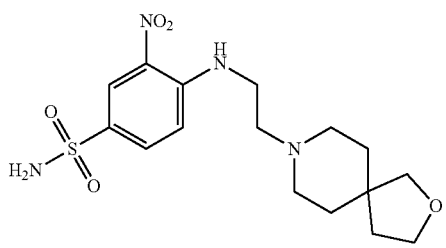 [SMILES: NS(=O)(=O)c1ccc(NCCN2CCC3(CCOC3)CC2)c([N+](=O)[O-])c1]

Step 1: A solution of 2-oxa-8-azaspiro[4.5] decane hydrochloride (500 mg, 2.81 mmol) in CH$_3$CN (20 mL) was treated with tert-butyl-2-bromoethylcarbamate (700 mg, 3.12 mmol) and K$_2$CO$_3$ (1.55 g, 11.24 mmol) and heated to 80° C. for 16 h. The reaction was concentrated, diluted with water (20 mL), and extracted with EtOAc (3×20 mL). The combined organic layers were dried over Na$_2$SO$_4$, filtered and concentrated. The residue was purified by column chromatography (SiO$_2$, EtOAc/pet. ether) to afford tert-butyl-2-(2-oxa-8-azaspiro[4.5]decan-8-yl)ethylcarbamate (Intermediate 4-1) (500 mg, 62%) as an oil. $^1$H NMR (300 MHz, DMSO-d$_6$) δ 6.62 (br s, 1H), 3.70 (t, J=6.9 Hz, 2H), 3.40 (s, 2H), 3.04-2.98 (m, 2H), 2.40-2.25 (m, 4H), 1.64 (t, J=7.5 Hz, 2H), 1.56-1.40 (m, 4H), 1.37 (s, 9H), 1.24 (s, 2H).

Step 2: To a stirred solution of Intermediate 4-1 (500 mg, 1.76 mmol) in DCM (20 mL) was added HCl (4 M in dioxane, 10 mL) at 0° C. The reaction was warmed to rt, stirred for 2 h, concentrated and triturated with Et$_2$O to afford 2-(2-oxa-8-azaspiro[4.5]decan-8-yl)ethanamine dihydrochloride (Intermediate 4-2) (300 mg, 66%) as an off white solid which was used for the next step without further purification. $^1$H NMR (300 MHz, DMSO-d$_6$) δ 10.84 (br s, 1H), 8.38 (br s, 3H), 3.85-3.70 (m, 2H), 3.59-3.40 (m, 8H), 3.12-2.90 (m, 2H), 2.05-1.60 (m, 6H).

Step 3: A solution of Intermediate 4-2 (300 mg, 1.17 mmol) in CH$_3$CN (15 mL) was treated with 4-chloro-3-nitrobenzenesulfonamide (276 mg, 1.17 mmol) followed by DIPEA (0.82 mL, 4.68 mmol) and then heated to 80° C. After 16 h, the reaction was cooled to rt and concentrated. The crude product was purified by column chromatography (SiO$_2$, MeOH(0.1% triethylamine)/DCM) to afford Intermediate 4 (300 mg, 66%) as a yellow solid. LC/MS (ESI) m/z 385.3 [M+H]$^+$.

Intermediate 5

2-(7-oxa-2-azaspiro[3.5]nonan-2-yl)ethanamine dihydrochloride

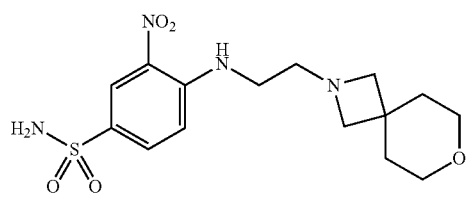 [SMILES: NS(=O)(=O)c1ccc(NCCN2CC3(CCOCC3)C2)c([N+](=O)[O-])c1]

Step 1: tert-butyl 2-(7-oxa-2-azaspiro[3.5]nonan-2-yl)ethylcarbamate (Intermediate 5-1) was prepared following the procedure described in Step 1 for Intermediate 4 using 7-oxa-2-azaspiro[3.5] nonane hemioxalic acid in place of 2-oxa-8-azaspiro[4.5] decane hydrochloride $^1$H NMR (300 MHz, DMSO-d$_6$) δ 6.94 (br s, 1H), 3.74 (br s, 4H), 3.51-3.42 (m, 4H), 3.10 (br s, 4H), 1.76 (br s, 4H), 1.39 (s, 9H).

Step 2: 2-(7-oxa-2-azaspiro[3.5]nonan-2-yl)ethanamine dihydrochloride (Intermediate 5-2) was prepared following the procedure described in Step 2 for Intermediate 4 using Intermediate 5-1 in place of Intermediate 4-1. $^1$H NMR (300 MHz, DMSO-d$_6$) δ 11.42 (br s, 1H), 8.3 (br s, 3H), 4.05-3.99 (m, 2H), 3.92-3.86 (m, 2H), 3.57-3.54 (m, 4H), 3.49-3.40 (m, 4H), 3.10-3.05 (m, 2H), 1.88 (br s, 2H), 1.72 (br s, 2H).

Step 3: A solution of Intermediate 5-2 (250 mg, 1.03 mmol) in CH$_3$CN (13 mL) was treated with 4-fluoro-3-nitrobenzenesulfonamide (226.8 mg, 1.03 mmol) followed by triethylamine (0.58 mL, 4.12 mmol) at rt. After 16 h, the reaction was concentrated to afford the crude product, which was purified by column chromatography (SiO$_2$, MeOH (containing 7N NH$_3$)/DCM) to obtain Intermediate 5 (200 mg, 52%) as a yellow solid. LC/MS (ESI) m/z 371.3 [M+H]$^+$.

Intermediate 6

4-(7-Oxaspiro[3.5]nonan-2-yl-methylamino)-3-nitrobenzenesulfonamide

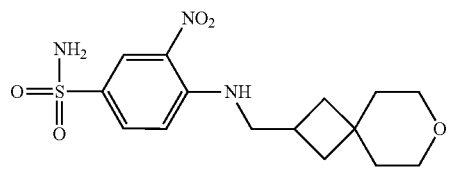 [SMILES: NS(=O)(=O)c1ccc(NCC2CC3(CCOCC3)C2)c([N+](=O)[O-])c1]

A solution of 7-oxaspiro[3.5]nonan-2-yl-methanamine (100 mg, 0.64 mmol) in THF (2 mL) was treated with 4-fluoro-3-nitrobenzenesulfonamide (157.6 mg, 0.72 mmol) and Et$_3$N (0.18 mL, 1.29 mmol) and the mixture was stirred at rt. After 16 h, the reaction was concentrated, and the residue was purified by column chromatography (SiO$_2$, MeOH/DCM) to provide Intermediate 6 (126 mg, 55%) as a yellow solid. LC/MS (ESI) m/z 356.1 [M+H]$^+$.

Intermediate 7

4-((4-oxaspiro[2.4]heptan-6-yl)oxy)-3-nitrobenzenesulfonamide

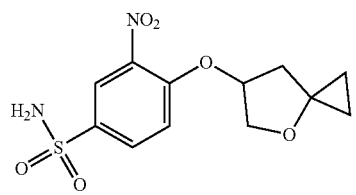 [SMILES: NS(=O)(=O)c1ccc(OC2COC3(CC3)C2)c([N+](=O)[O-])c1]

Step 1: To a stirred solution of 1-(3-hydroxy-2-(tetrahydro-2H-pyran-2-yloxy)propyl)cyclopropanol (prepared according to CN106565706) and triphenyl phosphine (9.10 g, 34.7 mmol) in THF (50 mL), was added diethyl azodicarboxylate (DEAD) (5.44 mL, 34.7 mmol) dropwise at rt. After 16 h, the reaction mixture was quenched with H$_2$O (50 mL) and extracted with EtOAc (3×50 mL). The combined organic layers were washed with water (50 mL), dried over Na$_2$SO$_4$ and concentrated. The crude product was purified by column chromatography (SiO$_2$, EtOAc/pet. ether) to obtain 6-(tetrahydro-2H-pyran-2-yloxy)-4-oxaspiro[2.4]heptane (Intermediate 7-1) (3.2 g, 69% yield) as a clear yellow oil. ¹H NMR (400 MHz, CDCl₃) δ 4.65-4.63 (m, 1H), 4.59-4.56 (m, 1H), 4.02-3.85 (m, 3H), 3.53-3.48 (m, 1H), 2.25-1.95 (m, 2H), 1.89-1.76 (m, 1H), 1.72-1.68 (m, 1H), 1.62-1.49 (m, 4H), 0.92-0.89 (m, 1H), 0.81-0.75 (m, 1H), 0.65-0.53 (m, 1H), 0.48-0.39 (m, 1H).

Step 2: To a stirred solution of Intermediate 7-1 (3.2 g, 16.1 mmol) in MeOH (32 mL) was added pyridinium p-toluenesulfonate (811 mg, 3.23 mmol) and stirred at 40° C. for 5 h. The reaction mixture was concentrated, and the residue was purified by column chromatography (SiO₂, EtOAc/pet. ether) to obtain 4-oxaspiro[2.4]heptan-6-ol (Intermediate 7-2) (1.0 g, 54% yield) as colorless oil. GC/MS m/z 114.1 [M]⁺.

Step 3: To a stirred solution of Intermediate 7-2 was added sodium hydride (63% dispersion in oil, 1.05 g, 26.3 mmol) at 0° C. After 30 min, a solution of 4-fluoro-3-nitrobenzenesulfonamide (1.92 g, 8.76 mmol) in THF (5 mL) was added dropwise at 0° C. The reaction was warmed to rt and stirred for 6 h. The reaction was cooled to 0° C. and quenched with sat. aq. NH₄Cl and extracted with EtOAc (3×50 mL). The combined organic layers were dried over Na₂SO₄ and concentrated. The residue was triturated with Et₂O and n-pentane to afford Intermediate 7 (700 mg, 25% yield) as a white solid. LC/MS (ESI) m/z 313.0 [M−H]⁻.

Intermediate 8

4-(2-(2-Oxa-6-azaspiro[3.3]heptan-6-yl)ethoxy)-3-nitrobenzenesulfonamide

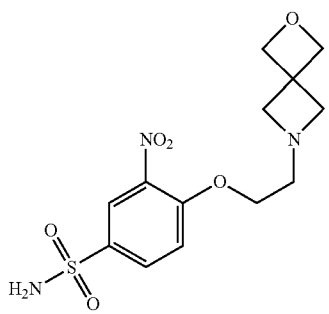 [SMILES: NS(=O)(=O)c1ccc(OCCN2CC3(COC3)C2)c([N+](=O)[O-])c1]

Intermediate 8 was prepared following the procedure described in Step 3 for Intermediate 7 by using 2-(2-oxa-6-azaspiro[3.3]heptan-6-yl)ethanol in place of Intermediate 7-2. LC/MS (ESI) m/z 344.2 [M+H]⁺.

Intermediate 9

4-(2-oxaspiro[3.3]heptan-6-ylmethoxy)-3-nitrobenzenesulfonamide

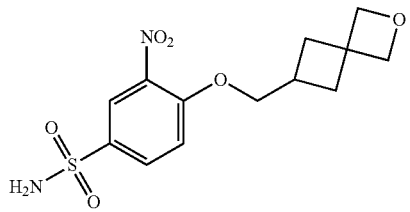 [SMILES: NS(=O)(=O)c1ccc(OCC2CC3(COC3)C2)c([N+](=O)[O-])c1]

Intermediate 9 was prepared following the procedure described in Step 3 for the synthesis of Intermediate 7 by using 2-oxaspiro[3.3]heptan-6-ylmethanol in place of Intermediate 7-2. LC/MS (ESI) m/z 327.4 [M−H]⁻.

Intermediate 10

N-methoxy-N,3-dimethylbicyclo[1.1.1]pentane-1-carboxamide

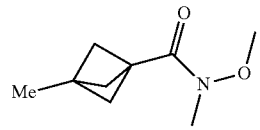

To a stirred solution of 3-methylbicyclo[1.1.1]pentane-1-carboxylic acid (3 g, 23.8 mmol) in DCM (100 mL) was added N,O-dimethylhydroxylamine hydrochloride (3.48 g, 35.7 mmol) and Et₃N (11.6 ml, 83.2 mmol) at rt. The mixture was then cooled to 0° C. and T₃P (50 wt. % in EtOAc, 6.43 g, 40.4 mmol) was added dropwise and reaction was warmed to rt. After 16 h, the reaction was quenched with water (100 mL) and extracted with DCM (3×100 mL). The combined organic layers were dried over Na₂SO₄, filtered and concentrated. The residue was purified by chromatography (SiO2, EtOAc/pet. ether) to provide Intermediate 10 as an oil (2.5 g, 62% yield). ¹H NMR (300 MHz, CDCl₃) δ 3.65 (s, 3H), 3.17 (s, 3H), 1.98 (s, 6H), 1.18 (s, 3H).

Intermediate 11

3-Fluoro-N-methoxy-N-methylbicyclo[1.1.1]pentane-1-carboxamide

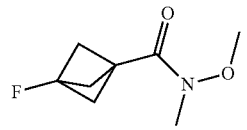

Intermediate 11 was prepared following the procedure described for the synthesis of Intermediate 10 by using 3-fluorobicyclo[1.1.1]pentane-1-carboxylic acid in place of 3-methylbicyclo[1.1.1]pentane-1-carboxylic acid. LC/MS (ESI) m/z 174.3 [M+H]⁺.

Intermediate 12

3-isopropyl-N-methoxy-N-methylbicyclo[1.1.1]pentane-1-carboxamide

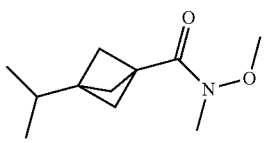

Intermediate 12 was prepared following the procedure described for the synthesis of Intermediate 10 by using 3-isopropylbicyclo[1.1.1]pentane-1-carboxylic acid in place of 3-methylbicyclo[1.1.1]pentane-1-carboxylic acid. LC/MS (ESI) m/z 198.4 [M+H]+.

Intermediate 13

3-(1,1-Difluoroethyl)-N-methoxy-N-methylbicyclo[1.1.1]pentane-1-carboxamide

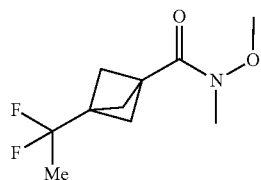

Step 1: To a stirred solution of 3-(methoxycarbonyl)bicyclo[1.1.1]pentane-1-carboxylic acid (10 g, 58.8 mmol), N,O-dimethylhydroxylamine hydrochloride (6.88 g, 42.4 mmol) and triethylamine (12.3 mL, 176.4 mmol) in DCM (200 mL) at 0° C. was added T3P (50% solution in EtOAc, 18.8 g, 58.8 mmol). The resulting reaction mixture warmed to rt and stirred for 16 h. The reaction mixture was quenched with water (250 mL) and extracted with DCM (3×250 mL). The combined organic layers were dried over Na2SO4 and concentrated. The crude product was purified by column chromatography (SiO2, EtOAc/pet. ether) to provide methyl-3-(methoxy(methyl)carbamoyl)bicyclo[1.1.1]pentane-1-carboxylate (Intermediate 13-1) (9.5 g, 76% yield) as a colorless oil. $^1$H NMR (400 MHz, CDCl3) δ 3.69 (s, 3H), 3.68 (s, 3H), 3.19 (s, 3H), 2.38 (s, 6H).

Step 2: To a stirred solution of Intermediate 13-1 (5 g, 23.5 mmol) in THF (100 mL) at −78° C. was added MeMgBr (3M in Et2O, 31.3 mL, 93.8 mmol). After stirring for 2 h at −78° C., the reaction was quenched with sat. aq. NH4Cl (100 mL) and extracted with EtOAc (3×100 mL). The combined organic layers were dried over Na2SO4, filtered and concentrated. The crude product was purified by column chromatography (SiO2, EtOAc/pet. ether) to provide methyl-3-acetylbicyclo[1.1.1]pentane-1-carboxylate (Intermediate 13-2) (2 g, 51% yield) as a white solid. $^1$H NMR (400 MHz, CDCl3) δ 3.70 (s, 3H), 2.29 (s, 6H), 2.14 (s, 3H).

Step 3: A solution of the Intermediate 13-2 (2.3 g, 13.6 mmol) in DCM (50 mL) at −78° C. was treated dropwise with DAST (6.62 g, 41.0 mmol). After the addition, the temperature was raised to rt. After 16 h, the reaction mixture was cooled to −78° C. and carefully quenched with sat. aq. NaHCO3 (100 mL). The mixture was extracted with DCM (3×100 mL) and the combined organic layers were dried over Na2SO4, filtered and concentrated. The crude product was purified by chromatography (SiO2, EtOAc/pet. ether) to provide methyl-3-(1,1-difluoroethyl)bicyclo[1.1.1]pentane-1-carboxylate (Intermediate 13-3) (1.8 g, 69% yield) as a clear oil. $^1$H NMR (400 MHz, CDCl3) δ 3.70 (s, 3H), 2.12 (s, 6H), 1.55 (t, J=18.0 Hz, 3H).

Step 4: To a stirred solution of Intermediate 13-3 (1.8 g, 9.46 mmol) and N,O-dimethylhydroxylamine hydrochloride (0.923 g, 9.46 mmol) in anhydrous THF (40 mL) at −78° C. was added i-PrMgCl (2M in THF, 18.9 mL, 37.8 mmol). The reaction mixture was warmed −50° C. and stirred for 2 h. The reaction was quenched with sat. aq. NH4Cl (50 mL) and extracted with EtOAc (3×75 mL). The combined organic layers were dried over Na2SO4, filtered and concentrated. The crude product was purified by column chromatography (SiO2, EtOAc/pet. ether) to provide Intermediate 13 (1.7 g, 82% yield) as a clear oil. LC/MS (ESI) m/z 220.4 [M+H]+.

Intermediate 14

4-[[(1-Methyl-4-piperidinyl)methyl]amino]-3-nitrobenzenesulfonamide

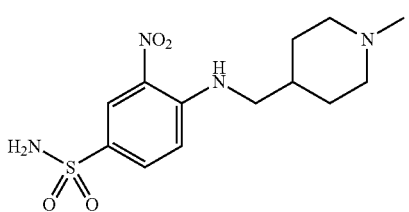 [SMILES: CN1CCC(CNc2ccc(S(N)(=O)=O)cc2[N+](=O)[O-])CC1]

To a solution of (1-methylpiperidin-4-yl)methanamine (1 g, 7.80 mmol) in THF (75 mL), was added 4-fluoro-3-nitrobenzenesulfonamide (1.71 g, 7.80 mmol) followed by triethylamine (3.15 g, 31.2 mmol) and the reaction was stirred at rt. After 16 h, the reaction was concentrated, diluted with water (50 mL) and extracted with 10% MeOH in DCM (3×50 mL). The combined organic layers were dried over Na2SO4, filtered and concentrated. The crude product was purified by column chromatography (C18, 0.1% HCO2H(aq)/MeCN) to obtain 650 mg of 4-((1-methylpiperidin-4-yl)methylamino)-3-nitrobenzenesulfonamide as the formate salt. The compound was dissolved in 10% MeOH in DCM (50 mL) and washed with sat. aq. NaHCO3. The organic layer was dried over Na2SO4, filtered and concentrated to afford Intermediate 14 as a yellow solid (510 mg, 20% yield). LC/MS (ESI) m/z 329.2 [M+H]+.

Intermediate 15

4-(((4-fluoro-1-methylpiperidin-4-yl)methyl)amino)-3-nitrobenzenesulfonamide

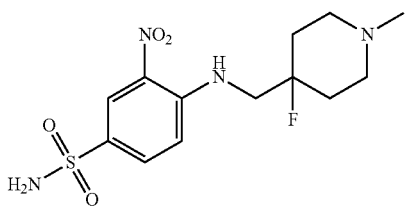 [SMILES: CN1CCC(F)(CNc2ccc(S(N)(=O)=O)cc2[N+](=O)[O-])CC1]

Step 1: To a stirred solution of tert-butyl 4-(aminomethyl)-4-fluoropiperidine-1-carboxylate (2.00 g, 8.61 mmol) in THF (30 mL), was added 4-fluoro-3-nitrobenzenesulfonamide (2.08 g, 9.47 mmol) followed by triethylamine (4.8 mL, 34.45 mmol). The resulting reaction mixture was stirred at rt for 16 h. The reaction was then concentrated, and the resulting residue was diluted with 10% MeOH-DCM (50 mL) and washed with ice-cold water (5×50 mL). The organic layer was dried over Na2SO4, filtered and concentrated. The crude product was purified by trituration with Et2O to afford tert-butyl 4-fluoro-4-((((2-nitro-4-sulfamoylphenyl)amino)methyl)piperidine-1-carboxylate (Intermediate 15-1) (1.6 g, 43% yield). LC/MS (ESI) m/z 333.10 [M-C5H9O2+H]+.

Step 2: To a stirred solution of Intermediate 15-1 (1.6 g, 3.70 mmol) in 1,4-dioxane (10 mL) at 0° C. was added HCl (4M HCl in 1,4-dioxane, 20 mL). The reaction was warmed to rt and stirred for 6 h. The reaction was concentrated and triturated with Et$_2$O to afford 4-(((4-fluoropiperidin-4-yl)methyl)amino)-3-nitrobenzenesulfonamide hydrochloride (Intermediate 15-2) (1.3 g, 96%) as a yellow solid. LC/MS (ESI) m/z 333.1 [C$_{12}$H$_{17}$FN$_4$O$_4$S+H]$^+$.

Step 3: To a stirred solution of Intermediate 15-2 (430 mg, 1.35 mmol) in MeOH (15 mL) was added paraformaldehyde (81 mg, 2.71 mmol) at 0° C. After 15 min, NaCNBH$_3$ (128 mg, 2.03 mmol) was added and the reaction was warmed to rt. After 18 h, the reaction was quenched sat. aq. NaHCO$_3$ (15 mL) and the reaction was extracted with DCM (3×100 mL). The combined organic layers were dried over Na$_2$SO$_4$, filtered and concentrated. The crude product was triturated with Et$_2$O followed by 1:1 EtOAc/Hexane to afford Intermediate 15 (340 mg, 25% yield) as a yellow solid. LC/MS (ESI) m/z 347.1 [M+H]$^+$.

Intermediate 16

4-(((1r,4r)-4-(dimethylamino)cyclohexyl)amino)-3-nitrobenzenesulfonamide

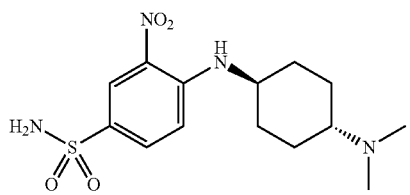 [SMILES: CN(C)[C@H]1CC[C@H](Nc2ccc(S(N)(=O)=O)cc2[N+](=O)[O-])CC1]

To a stirred solution of trans-N$^1$,N$^1$-dimethylcyclohexane-1,4-diamine dihydrochloride (350 mg, 1.39 mmol) in THF (10 mL) was added 4-fluoro-3-nitrobenzenesulfonamide (322 mg, 1.39 mmol) followed by triethylamine (844 mg, 8.34 mmol). After stirring for 16 h at rt, the reaction was concentrated and triturated with EtOAc and Et$_2$O to provide the crude product. The product was further purified by HPLC (75:25 to 1:99 10 mM NH$_4$OAc(aq): CH$_3$CN) to provide Intermediate 16 as a yellow solid. LC/MS (ESI) m/z 343.1 [M+H]$^+$.

Intermediate 17

4-((4-Methylmorpholin-2-yl)methylamino)-3-nitrobenzenesulfonamide

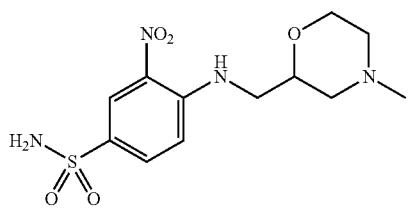 [SMILES: CN1CCOC(CNc2ccc(S(N)(=O)=O)cc2[N+](=O)[O-])C1]

To a stirred solution of (4-methylmorpholin-2-yl)methanamine (400 mg, 3.07 mmol) in THF (25 mL) was added 4-fluoro-3-nitrobenzenesulfonamide (609 mg, 2.76 mmol) followed by triethylamine (1.24 g, 12.28 mmol). After stirring at rt for 16 h, the reaction was concentrated and the resulting crude was diluted with 10% MeOH-DCM (50 mL), and washed with ice-cold water (3×50 mL). The organic layer was dried over Na$_2$SO$_4$, filtered and concentrated. The crude product was triturated with Et$_2$O/pentane to afford Intermediate 17 (600 mg, 65% yield) as a yellow solid. LC/MS (ESI) m/z 331.2 [M+H]$^+$.

Intermediate 17A (R)-4-(((4-methylmorpholin-2-yl)methyl)amino)-3-nitrobenzenesulfonamide

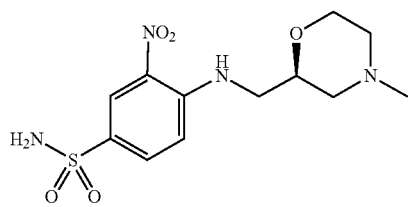 [SMILES: CN1CCO[C@H](CNc2ccc(S(N)(=O)=O)cc2[N+](=O)[O-])C1]

Racemic 4-((4-Methylmorpholin-2-yl)methylamino)-3-nitrobenzenesulfonamide (400 mg) was subjected to chiral SFC separation (Chiralpak AD-H (250×30 mm), 5μ, 30% MeOH) to afford 4-((4-Methylmorpholin-2-yl)methylamino)-3-nitrobenzenesulfonamide (160 mg) as the first eluted peak (RT=3.06 min) with 99.6% ee. LC/MS (ESI) m/z 331.2 [M+H]$^+$. The absolute stereochemistry was arbitrarily assigned for Intermediate 17A.

Intermediate 17B (S)-4-(((4-methylmorpholin-2-yl)methyl)amino)-3-nitrobenzenesulfonamide

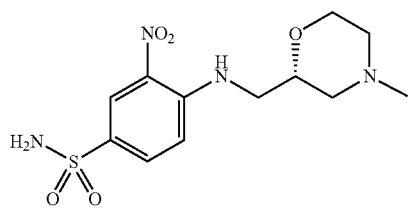 [SMILES: CN1CCO[C@@H](CNc2ccc(S(N)(=O)=O)cc2[N+](=O)[O-])C1]

Racemic 4-((4-Methylmorpholin-2-yl)methylamino)-3-nitrobenzenesulfonamide (400 mg) was subjected to chiral SFC separation (Chiralpak AD-H (250×30 mm), 5μ, 30% MeOH) to afford 4-((4-Methylmorpholin-2-yl)methylamino)-3-nitrobenzenesulfonamide (150 mg) as the second eluted peak (RT=3.64 min) with 99.8% ee. LC/MS (ESI) m/z 331.2 [M+H]$^+$. The absolute stereochemistry was arbitrarily assigned for Intermediate 17B.

Intermediate 18

4-(((((1r,4r)-4-hydroxy-4-methylcyclohexyl)methyl)amino)-3-nitrobenzenesulfonamide

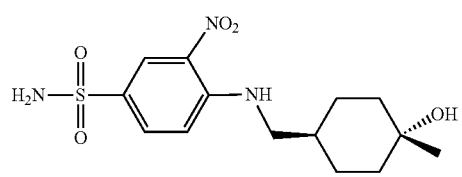 [SMILES: C[C@]1(O)CC[C@H](CNc2ccc(S(N)(=O)=O)cc2[N+](=O)[O-])CC1]

Intermediate 18 was prepared following a procedure described in WO2014/165044A1. LC/MS (ESI) m/z 344.1 [M+H]⁺.

Intermediate 19

2-(Diethoxymethyl)-5,5-dimethylcyclohexan-1-one

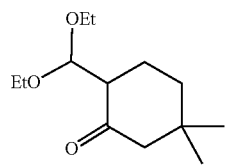 [SMILES: CCOC(OCC)C1CCC(C)(C)CC1=O]

To a solution of triethyl orthoformate (1.32 L, 7.923 mol) in DCM (8.0 L) at −30° C. was added BF₃·OEt₂ (1.244 L, 9.9 mmol) dropwise over 30 min. The reaction mixture was warmed to 0° C. and stirred for 30 min. The reaction mixture was then cooled to −78° C. and 3,3-dimethylcyclohexanone (500 g, 3.96 mol) and N,N-diisopropylethylamine (2.08 L, 11.9 mol) were added dropwise and the reaction was stirred for 2 h at the same temperature. The reaction was then carefully poured into a mixture of sat. aq. NaHCO₃ (25 L) and DCM (10 L). The resulting mixture was stirred for 15 min at rt and the organic layer was separated. The aqueous layer was extracted with DCM (2×10 L) and the combined organic layers were washed with 10% NaCl(aq.) (5 L), dried over Na₂SO₄, filtered and concentrated. The crude product was purified by column chromatography (SiO₂, EtOAc/pet. ether) to afford Intermediate 19 (750 g, 83% yield) as a pale yellow oil. ¹H NMR (400 MHz, CDCl₃) δ 4.83 (d, J=6.0 Hz, 1H), 3.73-3.57 (m, 4H), 2.56-2.53 (m, 1H), 2.20-2.14 (m, 2H), 2.11-2.10 (m, 1H), 1.81 (m, 1H), 1.62-1.56 (m, 2H), 1.21-1.17 (m, 6H), 1.01 (s, 3H), 0.91 (s, 3H).

Intermediate 20

Benzyl 2-bromo-4,4-dimethylcyclohex-1-ene-1-carboxylate

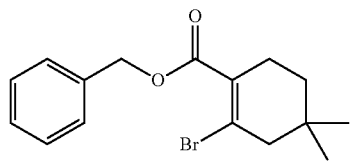 [SMILES: CC1(C)CCC(C(=O)OCc2ccccc2)=C(Br)C1]

Step 1: A solution of NaClO₂ (11.08 g, 122.5 mmol) in water (100 mL) was added drop wise to a stirring mixture of 2-bromo-4,4-dimethylcyclohex-1-ene-1-carbaldehyde (19 g, 87.5 mmol), CH₃CN (100 mL), NaH2PO₄ (2.72 g, 22.75 mmol), water (40 mL) and 30% H₂O₂(aq.) (15 mL) at 10° C. Upon completion, the reaction, was poured into sat. aq. Na₂CO₃ (200 mL) and washed with Et₂O (200 mL). The aqueous phase was poured into 1N HCl solution (500 mL) and extracted with Et₂O (3×200 mL). The combined organic layers were dried over Na₂SO₄, filtered and concentrated. The crude compound was further washed with water and dried to obtain 2-bromo-4,4-dimethylcyclohex-1-ene-1-carboxylic acid (Intermediate 20-1) (15 g, 73% yield) as a white solid. LC/MS (ESI) m/z 231.0 [M−H]⁻.

Step 2: To a stirred solution of Intermediate 20-1 (10 g, 42.9 mmol) in DMF (100 mL) was added K₂CO₃ (17.79 g, 128.7 mmol) followed by benzyl bromide (14.67 g, 85.8 mmol) at 0° C. and the reaction was warmed to rt. After 16 h, water (200 mL) was added and the reaction was extracted with EtOAc (3×200 mL). The combined organic layers were washed with water (3×200 mL), dried over Na₂SO₄, filtered and concentrated. The crude product was purified by column chromatography (SiO₂, EtOAc/pet. ether) to afford Intermediate 20 (11 g, 79% yield) as a colorless oil. ¹H NMR (400 MHz, CDCl₃) δ 7.43-7.32 (m, 5H), 5.22 (s, 2H), 2.45-2.38 (m, 4H), 1.44 (t, J=5.6 Hz, 2H), 0.97 (s, 6H); GC/MS m/z 322.1 [M]⁺.

Intermediate 21

3-(difluoromethyl)-N-methoxy-N-methylbicyclo[1.1.1]pentane-1-carboxamide

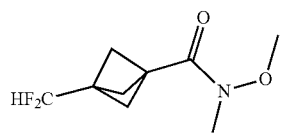

Step 1: A stirring solution of methyl 3-formylbicyclo[1.1.1]pentane-1-carboxylate (7.5 g, 48.7 mmol) in DCM (100 mL) was cooled to −78° C., and treated with DAST (19.3 mL, 146.1 mmol) drop wise and warmed to rt. After 6 h, the reaction mixture was cooled to −78° C. and quenched with sat. aq. NaHCO₃ (100 mL) and extracted with DCM (3×100 mL). The combined organic layers were dried over Na₂SO₄, filtered and concentrated to afford methyl 3-(difluoromethyl) bicyclo[1.1.1] pentane-1-carboxylate (Intermediate 21-1) (7 g) as a viscous oil. This was used in the next step without further purification. ¹H NMR (300 MHz, CDCl₃) δ 5.71 (t, J=56.1 Hz, 1H), 3.70 (s, 3H), 2.15 (s, 6H).

Step 2: To a stirred solution of Intermediate 21-1 (7 g, 39.74 mmol) in anhydrous THF (70 mL) was added N,O-dimethylhydroxylamine hydrochloride (3.89 g, 39.74 mmol) at −78° C., followed by i-PrMgCl (2M in THF, 79.5 mL, 159 mmol). The reaction was warmed to −50° C. and stirred for 2 h. The reaction mixture was then quenched with sat. aq. NH₄Cl solution (100 mL) and extracted with EtOAc (3×100 mL). The combined organic layers were dried over Na₂SO₄, filtered and concentrated. The crude product was purified by column chromatography (SiO₂, EtOAc/pet. ether) to afford Intermediate 21 (4 g, 40% yield over two steps). ¹H NMR (400 MHz, CDCl₃) δ 5.72 (t, J=56.4 Hz, 1H), 3.68 (s, 3H), 3.19 (s, 3H), 2.20 (s, 6H); LC/MS (ESI) m/z 206.1 [M+H]⁺.

Intermediate 22

4,4-dimethyl-2-(3-methylbicyclo[1.1.1]pentan-1-yl)cyclohex-1-ene-1-carbaldehyde

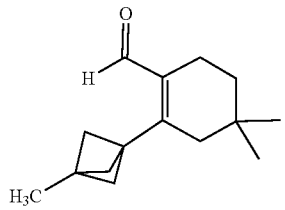

Step 1: A solution of 1-iodo-3-methylbicyclo[1.1.1]pentane (30 g, 144.20 mmol) in THF (225 mL) was cooled to −78° C. and sec-butyllithium (1.4M in cyclohexane, 154.50 mL, 216.30 mmol) was added drop wise over 1 h. The resulting pale yellow suspension was stirred at −78° C. for 10 min and then warmed to 0° C. and stirred for 80 min. The reaction mixture was then cooled to −78° C., and a solution of Intermediate 19 (24.67 g, 108.15 mmol) in THF (75 mL) was added drop wise over 20 min. After 10 min, the reaction was warmed to 0° C. for 1 h. The reaction mixture was then quenched with sat. aq. NH$_4$Cl (300 mL) and extracted with Et$_2$O (2×450 mL). The combined organic layers were dried over Na$_2$SO$_4$, filtered and concentrated to afford 2-(diethoxymethyl)-5,5-dimethyl-1-(3-methylbicyclo[1.1.1]pentan-1-yl)cyclohexan-1-ol (Intermediate 22-1) (31 g, crude) as a pale yellow oil. This was used in the next step without further purification.

Step 2: A solution of Intermediate 22-1 (62 g, 199.69 mmol) in 1,4-dioxane (1.24 L), was treated with 2N HCl (aq.) (299.5 mL, 599.2 mmol) at rt and then warmed to 70° C. After 16 h, the reaction was cooled to rt, poured into water (1.24 L) and extracted with Et$_2$O (2×750 mL). The combined organic layers were dried over Na$_2$SO$_4$, filtered and concentrated. The crude product was purified by column chromatography (SiO$_2$, EtOAc/pet. ether) to provide Intermediate 22 (23 g, 36% yield over 2 steps) as a yellow oil. $^1$H NMR (400 MHz, CDCl$_3$): δ 10.28 (s, 1H), 2.25-2.22 (m, 2H), 1.94 (s, 6H), 1.92 (br s, 2H), 1.35-1.32 (m, 2H), 1.19 (s, 3H), 0.90 (s, 6H).

Intermediate 23

2-(3-ethylbicyclo[1.1.1]pentan-1-yl)-4,4-dimethylcyclohex-1-ene-1-carbaldehyde

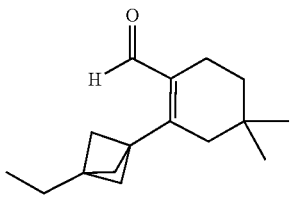 [SMILES: CCC12CC(C3=C(C=O)CCC(C)(C)C3)(C1)C2]

Step 1: To a stirred solution of [1.1.1]propellane (0.19M in Et$_2$O/pentane), 128.6 mmol) at −78° C. was added EtI (18.7 g, 257.38 mmol). The reaction was warmed to rt and stirred for 3 days in the dark. The reaction was then concentrated at 0° C. to afford 1-ethyl-3-iodobicyclo[1.1.1]pentane (Intermediate 23-1) (21.2 g, 74% yield) as yellow oil. $^1$H NMR (400 MHz, CDCl$_3$) δ 2.17 (s, 6H), 1.52 (q, J=8.0 Hz, 2H), 0.84 (t, J=7.2 Hz, 3H).

Step 2: To a stirred solution of Intermediate 23-1 (10.90 g, 49.1 mmol) in Et$_2$O (75 mL) at −78° C. was added sec-BuLi (1.4 M in cyclohexane, 50 mL, 70.0 mmol). After 10 min, the reaction was warmed to rt and stirred for 1 h. The reaction mixture was then cooled to −78° C. and treated with a solution of 2-(diethoxymethyl)-5,5-dimethylcyclohexan-1-one (8 g, 35.0 mmol) in Et$_2$O (25 mL). After 1 h, the reaction was warmed to 0° C. and stirred for 2 h. The reaction was quenched with sat. aq. NH$_4$Cl (20 mL) and extracted with EtOAc (3×70 mL). The combined organic layers were then dried over Na$_2$SO$_4$, filtered and concentrated to provide 8.5 g of crude 2-(diethoxymethyl)-1-(3-ethylbicyclo[1.1.1]pentan-1-yl)-5,5-dimethylcyclohexan-1-ol (Intermediate 23-2). This was used in the next step without further purification.

Step 3: A solution of Intermediate 23-2 (8.5 g, crude) in acetone (80 mL), was treated with 2N HCl(aq.) (20 mL) at rt and then warmed to 75° C. After 24 h, the reaction was concentrated and then diluted with water (50 mL) and extracted with Et$_2$O (3×250 mL). The combined organic layers were washed with sat. aq. NaHCO$_3$, dried over Na$_2$SO$_4$ and concentrated. The crude product was purified by column chromatography (SiO$_2$, Et$_2$O/pet. ether) to provide Intermediate 23 (3.9 g, 48% yield over 2 steps) as a brown oil. $^1$H NMR (400 MHz, CDCl$_3$) δ 10.30 (s, 1H), 2.26-2.22 (m, 2H), 1.93-1.92 (m, 2H), 1.89 (s, 6H), 1.49 (q, J=7.2 Hz, 2H), 1.33 (t, J=6.4 Hz, 2H), 0.89 (s, 6H), 0.87 (t, J=7.6 Hz, 3H).

Intermediate 24

2-(3-(difluoromethyl)bicyclo[1.1.1]pentan-1-yl)-4,4-dimethylcyclohex-1-ene-1-carbaldehyde

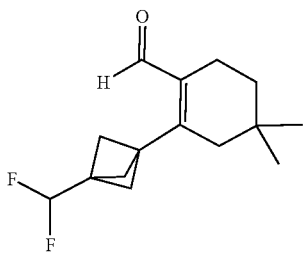 [SMILES: CC1(C)CCC(C=O)=C(C23CC(C(F)F)(C2)C3)C1]

Step 1: Preparation of CF$_2$HI (based on a procedure from Cao, P. et. al. J. Chem. Soc., Chem. Commun. 1994, 737-738): performed in two parallel batches: A mixture of KI (94 g, 568 mol), MeCN (228 ml) and water (18 mL) was heated to 45° C. and treated with, 2,2-difluoro-2-(fluorosulfonyl)acetic acid (50 g, 284 mmol) in MeCN (50 mL) dropwise over 4 h. The reaction mixture was then cooled to 0° C., and diluted with pentane (150 mL) and water (125 mL). The aqueous layer was washed with pentane (150 mL), and the combined organic layers from both reactions were washed with sat. aq. NaHCO$_3$ (200 mL), and dried over Na$_2$SO$_4$ to obtain 500 mL of difluoromethyl iodide solution. The solution was washed with additional water (2×200 mL) to remove residual acetonitrile, and dried over Na$_2$SO$_4$ to obtain difluoroiodomethane (Intermediate 24-1) (0.15 M in pentane, 400 mL, 11% yield). $^1$H NMR (400 MHz, CDCl$_3$) δ 7.67 (t, J=56.0 Hz, 1H).

Step 2: To a stirred solution of [1.1.1]propellane (0.53 M in Et$_2$O, 52 mL, 27.56 mmol) at −40° C. was added Intermediate 24-1 (0.15 M in pentane, 200 mL, 30 mmol). The reaction mixture was warmed to rt, protected from light, and stirred for 2 days. The reaction was then concentrated at 0-10° C. to obtain 1-(difluoromethyl)-3-iodobicyclo[1.1.1]

pentane (Intermediate 24-2) (5 g, 20.5 mmol, 74% yield) as a white solid. $^1$H NMR (400 MHz, CDCl$_3$) δ 5.65 (t, J=56.0 Hz, 1H), 2.40 (s, 6H).

Step 3: A solution of Intermediate 24-2 (30 g, 122.94 mmol) in THF (225 mL) was cooled to −78° C. and sec-butyllithium (1.4M in cyclohexane, 219 mL, 306.7 mmol) was added drop-wise for 1 h. The resulting pale yellow suspension was stirred at −78° C., for 10 min and temperature was raised to 0° C. and stirred for 80 min. The reaction mixture was then cooled to −78° C., and a solution of Intermediate 19 (21 g, 92.20 mmol) in THF (75 mL) was added drop wise to the reaction over 20 min. After 10 min, the reaction was warmed to 0° C. for 1 h. The reaction mixture was quenched with sat. aq. NH$_4$Cl (450 mL) and extracted with Et$_2$O (2×300 mL). The combined organic layers were dried over Na$_2$SO$_4$, filtered and concentrated to afford 2-(diethoxymethyl)-1-(3-(difluoromethyl)bicyclo[1.1.1]pentan-1-yl)-5,5-dimethylcyclohexan-1-ol (Intermediate 24-3) (31 g, crude) as pale yellow oil. The crude product was used in the next step without further purification.

Step 4: Intermediate 24 was prepared following the procedure described in Step 2 for Intermediate 22 using Intermediate 24-3 in place of Intermediate 22-1 (38% over 2 steps). $^1$H NMR (400 MHz, CDCl$_3$): δ 10.26 (s, 1H), 5.73 (t, J=56.0 Hz, 1H), 2.29-2.25 (m, 2H), 2.18 (s, 6H), 1.94-1.93 (m, 2H), 1.37 (t, J=6.8 Hz, 2H), 0.91 (s, 6H).

Intermediate 25

4,4-dimethyl-2-(3-(trifluoromethyl)bicyclo[1.1.1]pentan-1-yl)cyclohex-1-ene-1-carbaldehyde

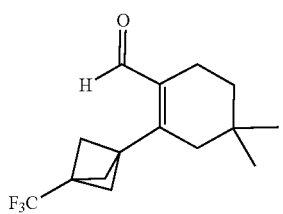 [SMILES: CC1(C)CCC(C=O)=C(C23CC(C(F)(F)F)(C2)C3)C1]

Step 1: To a stirred solution of 1-iodo-3-(trifluoromethyl)bicyclo[1.1.1]pentane (5.00 g, 19.1 mmol) in Et$_2$O (100 mL) at −78° C. was added sec-BuLi (1.4 M in cyclohexane, 13.63 mL, 19.08 mmol. After 10 minutes at −78° C., the reaction was warmed to 0° C. and stirred for 1 h. The reaction mixture was then cooled to −78° C. and then a solution of Intermediate 19 (3.63 g, 15.90 mmol) in Et$_2$O (50 mL) was added. After 1 h, the reaction was warmed to 0° C. and stirred for 2 h and then warmed to rt for 1 h. The reaction mixture was quenched with sat. aq. NH$_4$Cl (100 mL) and extracted with Et$_2$O (3×150 mL). The organic layers were then dried over Na$_2$SO$_4$, filtered and concentrated to provide 2-(diethoxymethyl)-5,5-dimethyl-1-(3-(trifluoromethyl)bicyclo[1.1.1]pentan-1-yl)cyclohexanol (Intermediate 25-1) (7 g, crude) as a brown oil. The crude product was used in the next step without further purification.

Step 2: Intermediate 25 was prepared following the procedure described in Step 3 for Intermediate 23 using Intermediate 25-1 in place of Intermediate 23-2. $^1$H NMR (400 MHz, CDCl$_3$) δ 10.23 (s, 1H), 2.29 (s, 6H), 2.28-2.26 (m, 2H), 1.92 (t, J=2.0 Hz, 2H), 1.36 (t, J=6.8 Hz, 2H), 0.91 (s, 6H).

Intermediate 26

2-((1H-pyrrolo[2,3-b]pyridin-5-yl)oxy)-4-(4-((2-(3-chlorobicyclo[1.1.1]pentan-1-yl)-4,4-dimethylcyclohex-1-en-1-yl)methyl)piperazin-1-yl)benzoic Acid

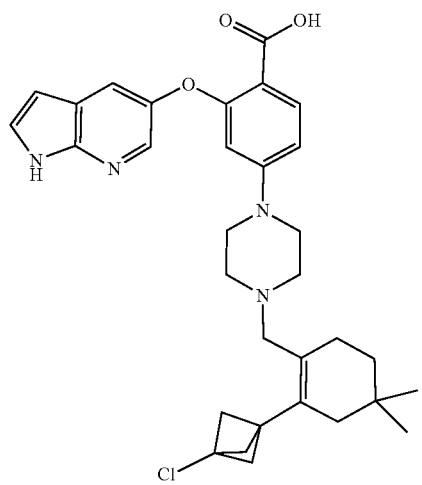 [SMILES: CC1(C)CCC(CN2CCN(c3ccc(C(=O)O)c(Oc4cnc5[nH]ccc5c4)c3)CC2)=C(C23CC(Cl)(C2)C3)C1]

Step 1: A solution of 5-iodo-4,4-dimethylpent-1-ene (9.85 g, 44.0 mmol) in pentane (100 mL) was treated with t-BuLi (64.6 mL, 1.7 M in n-pentane, 109.9 mmol) at −78° C. under inert atmosphere. After 1 h, a solution of Intermediate 1 (5 g, 26.4 mmol) in THF (20 mL) was added and the mixture was stirred at −78° C. for 1 h. The reaction was then warmed to −30° C. over 30 min. and stirred for 1 h. The reaction was quenched with sat. aq. NH$_4$Cl at −30° C., warmed to rt and extracted with EtOAc (3×200 mL). The combined organic layers were washed with water, dried over Na$_2$SO$_4$, filtered and concentrated. The product was purified by column chromatography (SiO$_2$, EtOAc/pet. ether) to provide 1-(3-chlorobicyclo[1.1.1] pentan-1-yl)-3,3-dimethylhex-5-en-1-one (Intermediate 26-1) (7 g, 70%) as an oil. $^1$H NMR (300 MHz, CDCl$_3$) δ 5.83-5.69 (m, 1H), 5.05-4.96 (m, 2H), 2.36 (s, 6H), 2.30 (s, 2H), 2.09 (d, J=7.5 Hz, 2H), 0.98 (s, 6H).

Step 2: A solution of Intermediate 26-1 (3.1 g, 13.7 mmol) and acrylonitrile (2.18 g, 41.0 mmol) in degassed DCM (120 mL) was treated dropwise over 2 h with a solution of Hoveyda-Grubbs Catalyst™ 2$^{nd}$ Generation (343 mg, 0.55 mmol) in DCM (5 mL) at 45° C. The reaction was stirred at 45° C. for 48 h, cooled to rt, concentrated and absorbed onto Celite. The residue was purified by column chromatography (SiO$_2$, EtOAc/pet. ether) to afford 7-(3-Chlorobicyclo[1.1.1] pentan-1-yl)-5,5-dimethyl-7-oxohept-2-enenitrile (Intermediate 26-2) as mixture of E/Z isomers (1.3 g, 38%) as a clear colorless oil. LC/MS (ESI) m/z 252.1 [M+H]$^+$.

Step 3: A solution of Intermediate 26-2 (700 mg, 2.78 mmol) in MeOH (20 mL) was treated with Pd/C (10 wt %, 170 mg) and stirred under an atmosphere of H$_2$ (1 atm) for 2 h. The reaction was purged with N₂ and the reaction mixture was filtered over Celite and concentrated to provide 7-(3-chlorobicyclo[1.1.1]pentan-1-yl)-5,5-dimethyl-7-oxo-heptanenitrile (Intermediate 26-3) (550 mg, 77%) as a clear colorless oil. $^1$H NMR (300 MHz, CDCl$_3$) δ 2.37 (s, 6H), 2.35-2.30 (m, 4H), 1.66-1.55 (m, 2H), 1.52-1.44 (m, 2H), 0.98 (s, 6H).

Step 4: A solution of Intermediate 26-3 (1.1 g, 4.34 mmol, 1 eq) in THF (20 mL) was treated with 4 Å molecular sieves (100 mg) and 15-Crown-5 (956 mg, 4.34 mmol) and was placed in a preheated 70° C. oil bath. After 2 min, the reaction was treated with t-BuONa (2.09 g, 21.7 mmol) in a single portion. After 5 h, the reaction was cooled to rt and poured into a stirring solution of sat. aq. NH$_4$Cl. The aqueous phase was washed with DCM (3×25 mL). The combined organic layers were dried over Na$_2$SO$_4$, filtered and concentrated. The crude product was purified by column chromatography (SiO$_2$, EtOAc/pet. ether) to afford 2-(3-chlorobicyclo[1.1.1]pentan-1-yl)-4,4-dimethylcyclohex-1-enecarbonitrile (Intermediate 26-4) (800 mg, 39%) as a clear colorless oil. LC/MS (ESI) m/z 236.3 [M+H]$^+$.

Step 5: To a stirred solution of Intermediate 26-4 (400 mg, 1.70 mmol) in anhydrous DCM (20 mL) at −78° C. was added DIBAL-H (2.55 mL, 1M in toluene, 2.55 mmol). The reaction was warmed to rt. After 4 h, the reaction was cooled to 0° C., quenched with 2M HCl(aq.) (40 mL) and warmed to rt. The reaction mixture was diluted with water, and extracted with DCM (2×40 mL) and the combined organic layers were dried over Na$_2$SO$_4$, filtered and concentrated to provide 2-(3-chlorobicyclo[1.1.1]pentan-1-yl)-4,4-dimethyl cyclohex-1-enecarbaldehyde (Intermediate 26-5) (400 mg, quantitative). This compound was used directly in the next step without further purification. $^1$H NMR (300 MHz, CDCl$_3$) δ 10.19 (s, 1H), 2.44 (s, 6H), 2.30-2.22 (m, 2H), 1.90 (s, 2H), 1.35 (t, J=6 Hz, 2H), 0.90 (s, 6H).

Step 6: To a stirred solution of Intermediate 26-5 (300 mg, 1.26 mmol) in DCM (10 mL) was added Intermediate 2 (544 mg, 1.38 mmol) and NaBH(OAc)$_3$ (347 mg, 1.64 mmol) at rt. After 16 h, additional NaBH(OAc)$_3$ (347 mg, 1.64 mmol) was added. After 48 h, the reaction was quenched with MeOH (0.2 mL) at 0° C., warmed to rt and concentrated. The residue was diluted with DCM and washed with sat. aq. NaHCO$_3$. The aqueous layer was washed with DCM (3×25 mL) and the combined organic layers were dried over Na$_2$SO$_4$, filtered and concentrated. The residue was purified by column chromatography (SiO$_2$, EtOAc/pet. ether) to afford tert-butyl 2-(1H-pyrrolo[2,3-b]pyridin-5-yl-oxy)-4-(4-((2-(3-chlorobicyclo [1.1.1]pentan-1-yl)-4,4-dimethylcy-clohex-1-en-yl)methyl)piperazin-1-yl)benzoate (Intermediate 26-6) (220 mg, 44.6 mmol; 28%) as a white solid. LC/MS (ESI) m/z 617.3 [M+H]$^+$.

Step 7: To a solution of Intermediate 26-6 (125 mg, 0.20 mmol) in DCM (2 mL) at 0° C. was added TFA (139 mg, 1.22 mmol). The mixture was warmed to rt and stirred for 3 h and concentrated to provide the TFA salt of 2-(1H-pyrrolo[2,3-b]pyridin-5-yl-oxy)-4-(4-((2-(3-chlorobicyclo[1.1.1]pentan-1-yl)-4,4-dimethylcyclohex-1-en-yl)methyl)piper-azin-1-yl)benzoic acid (140 mg, quantitative) as a white solid LC/MS (ESI) m/z 561.3 [C$_{32}$H$_{37}$ClN$_4$O$_3$+H]$^+$.

Intermediate 27

2-((1H-pyrrolo[2,3-b]pyridin-5-yl)oxy)-4-(4-((2-(3-fluorobicyclo[1.1.1]pentan-1-yl)-4,4-dimethylcyclo-hex-1-en-1-yl)methyl)piperazin-1-yl)benzoic Acid

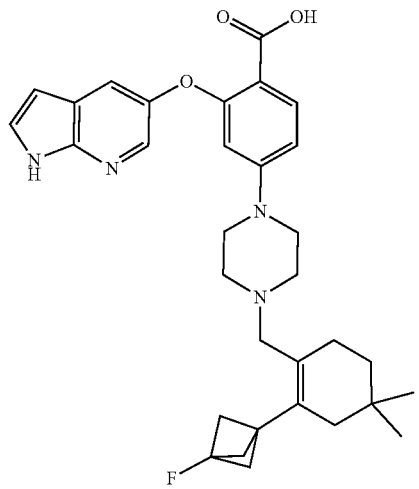 [SMILES: CC1(C)CCC(CN2CCN(c3ccc(C(=O)O)c(Oc4cnc5[nH]ccc5c4)c3)CC2)=C(C23CC(F)(C2)C3)C1]

Step 1: 1-(3-fluorobicyclo[1.1.1]pentan-1-yl)-3,3-dimethylhex-5-en-1-one (Intermediate 27-1) was prepared following the procedure described in Step 1 for Intermediate 26 using Intermediate 11 in place of Intermediate 1. $^1$H NMR (300 MHz, CDCl$_3$) δ 5.84-5.69 (m, 1H), 5.06-4.96 (m, 2H), 2.34 (s, 2H), 2.29 (d, J=2.4 Hz, 6H), 2.10 (d, J=7.2 Hz, 2H), 0.99 (s, 6H).

Step 2: E/Z-7-(3-fluorobicyclo[1.1.1]pentan-1-yl)-5,5-dimethyl-7-oxohept-2-enenitrile (Intermediate 27-2) was prepared following the procedure described in Step 2 for Intermediate 26 using Intermediate 27-1 in place of Intermediate 26-1. LC/MS (ESI) m/z 236.3 [M+H]$^+$.

Step 3: 7-(3-fluorobicyclo[1.1.1]pentan-1-yl)-5,5-dimethyl-7-oxoheptanenitrile (Intermediate 27-3) was prepared following the procedure described in Step 3 for Intermediate 26 using Intermediate 27-2 in place of Intermediate 26-2. $^1$H NMR (400 MHz, CDCl$_3$) δ 2.36 (s, 2H), 2.32 (t, J=6.8 Hz, 2H), 2.31 (d, J=2.8 Hz, 6H), 1.64-1.58 (m, 2H), 1.51-1.47 (m, 2H), 0.99 (s, 6H).

Step 4: 2-(3-fluorobicyclo[1.1.1]pentan-1-yl)-4,4-dimethylcyclohex-1-enecarbonitrile (Intermediate 27-4) was prepared following the procedure described in Step 4 for Intermediate 26 using Intermediate 27-3 in place of Intermediate 26-3. LC/MS (ESI) m/z 220.4 [M+H]$^+$.

Step 5: 2-(3-fluorobicyclo[1.1.1]pentan-1-yl)-4,4-dimethylcyclohex-1-enecarbaldehyde (Intermediate 27-5) was prepared following the procedure described in Step 5 for Intermediate 26 using Intermediate 27-4 in place of Intermediate 26-4. $^1$H NMR (300 MHz, CDCl$_3$) δ 10.19 (s, 1H), 2.37-2.34 (m, 6H), 2.30-2.25 (m, 2H), 1.93 (br s, 2H), 1.40-1.35 (m, 2H), 0.91 (s, 6H).

Step 6: To a stirred solution of Intermediate 27-5 (100 mg, 0.45 mmol) in EtOH (4 mL) was added Intermediate 2 (195 mg, 0.49 mmol) and AcOH (cat.) at rt and stirred for 15 min. The resulting reaction mixture was cooled to 0° C. and NaCNBH$_3$ (42 mg, 0.675 mmol) was added and the reaction was warmed to rt. After 16 h, the reaction was concentrated and the residue was diluted with sat. aq. NaHCO$_3$ (10 ml) and extracted with DCM (3×10 ml). The combined organic layers were dried over Na$_2$SO$_4$ and concentrated. The crude compound was purified by column chromatography (SiO$_2$, EtOAc/pet. ether) to obtain tert-Butyl 2-(1H-pyrrolo[2,3-b]pyridin-5-yl-oxy)-4-(4-((2-(3-fluorobicyclo[1.1.1]pentan-1-yl)-4,4-dimethylcyclohex-1-en-yl)methyl)piperazin-1-yl) benzoate (Intermediate 27-6) as a white solid (40 mg, 15% yield). LC/MS (ESI) m/z 601.7 [M+H]$^+$.

Step 7: 2-(1H-pyrrolo[2,3-b]pyridin-5-yl-oxy)-4-(4-((2-(3-fluorobicyclo[1.1.1]pentan-1-yl)-4,4-dimethylcyclohex-1-en-yl)methyl)piperazin-1-yl)benzoic acid as the TFA salt was prepared following the procedure described in Step 7 for Intermediate 26 by reacting Intermediate 27-6 in place of Intermediate 26-6. LC/MS (ESI) m/z 545.4 [C$_{32}$H$_{37}$FN$_4$O$_3$+H]$^+$.

Intermediate 28

2-((1H-pyrrolo[2,3-b]pyridin-5-yl)oxy)-4-(4-((4,4-dimethyl-2-(3-methylbicyclo[1.1.1]pentan-1 yl)cyclohex-1-en-1-yl)methyl)piperazin-1-yl)benzoic Acid

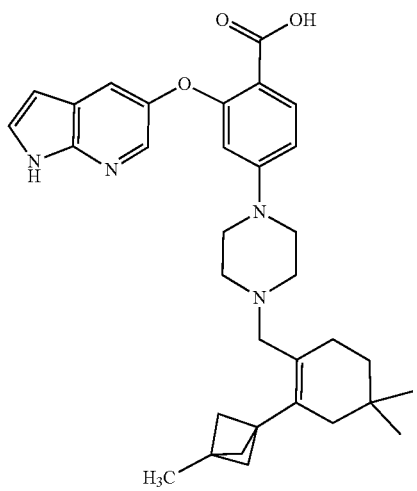 [SMILES: CC1(C)CCC(CN2CCN(c3ccc(C(=O)O)c(Oc4cnc5[nH]ccc5c4)c3)CC2)=C(C23CC(C)(C2)C3)C1]

Route A:

Step 1: 3,3-dimethyl-1-(3-methylbicyclo[1.1.1]pentan-1-yl)hex-5-en-1-one (Intermediate 28-1) was prepared following the procedure described in Step 1 for Intermediate 26 using Intermediate 10 in place of Intermediate 1. $^1$H NMR (300 MHz, CDCl$_3$) δ 5.86-5.71 (m, 1H), 5.04-4.97 (m, 2H), 2.28 (s, 2H), 2.09 (d, J=7.8 Hz, 2H), 1.85 (s, 6H), 1.12 (s, 3H), 0.97 (s, 6H).

Step 2: E/Z-5,5-dimethyl-7-(3-methylbicyclo[1.1.1]pentan-1-yl)-7-oxohept-2-enenitrile (Intermediate 28-2) was prepared following the procedure described in Step 2 for Intermediate 26 using Intermediate 28-1 in place of Intermediate 26-1. LC/MS (ESI) m/z 232.3 [M+H]$^+$.

Step 3: 5,5-dimethyl-7-(3-methylbicyclo[1.1.1]pentan-1-yl)-7-oxoheptanenitrile (Intermediate 28-3) was prepared following the procedure described in Step 3 for Intermediate 26 using Intermediate 28-2 in place of Intermediate 26-2. $^1$H NMR (400 MHz, CDCl$_3$) δ 2.33-2.29 (m, 4H), 1.86 (s, 6H), 1.64-1.56 (m, 2H), 1.50-1.45 (m, 2H), 1.18 (s, 3H), 0.98 (s, 6H).

Step 4: 4,4-dimethyl-2-(3-methylbicyclo[1.1.1]pentan-1-yl)cyclohex-1-enecarbonitrile (Intermediate 28-4) was prepared following the procedure described in Step 4 for Intermediate 26 using Intermediate 28-3 in place of Intermediate 26-3. LC/MS (ESI) m/z 216.4 [M+H]$^+$.

Step 5: Intermediate 22 was prepared following the procedure described in Step 5 for Intermediate 26 using Intermediate 28-4 in place of Intermediate 26-4. LC/MS (ESI) m/z 219.3 [M+H]$^+$.

Step 6: To a stirred solution of Intermediate 22 (70 mg, 0.32 mmol) in EtOH (4 mL) was added Intermediate 2 (190 mg, 0.48 mmol) and AcOH (cat.) at rt. After 15 min, the mixture was cooled to 0° C., NaCNBH$_3$ (31 mg, 0.48 mmol) was added and the reaction was warmed to rt. After 16 h, the reaction was concentrated, and the residue was diluted with sat. aq. NaHCO$_3$ (10 mL) and extracted with DCM (3×10 ml). The combined organic layers were dried over Na$_2$SO$_4$, filtered and concentrated. The crude product was purified by column chromatography (SiO$_2$, EtOAc/pet. ether) to obtain tert-butyl 2-(1H-pyrrolo[2,3-b]pyridin-5-yloxy)-4-(4-((4,4-dimethyl-2-(3-methylbicyclo[1.1.1]pentan-1-yl)cyclohex-1-enyl)methyl)piperazin-1-yl)benzoate (Intermediate 28-5) (80 mg, 42%) as a white solid. LC/MS (ESI) m/z 597.4 [M+H]$^+$.

Step 7: 2-(1H-pyrrolo[2,3-b]pyridin-5-yloxy)-4-(4-((4,4-dimethyl-2-(3-methylbicyclo[1.1.1]pentan-1-yl)cyclohex-1-enyl)methyl)piperazin-1-yl)benzoic acid trifluoroacetate was prepared following the procedure described in Step 7 for Intermediate 26 using Intermediate 28-5 in place of Intermediate 26-6. LC/MS (ESI) m/z 541.4 [C$_{33}$H$_{40}$N$_4$O$_3$+H]$^+$.

Route B:

Step 1: A solution of t-butyl lithium (1.3 M in pentane, 60 mL, 78 mmol) was added dropwise to a solution of 1-iodo-3-methylbicyclo[1.1.1]pentane (6.5 g, 31.2 mmol) in MTBE (60 mL) at −78° C. under N$_2$. The reaction mixture was stirred for 1 h at −78° C. Lithium 2-thienylcyanocuprate (0.25M in THF, 125 mL, 31.2 mmol) was added at −78° C., and the addition was controlled to keep the temperature below −60° C. After the addition, the reaction mixture was warmed to 0° C. and stirred for 30 min. The reaction was then cooled to −78° C. and Intermediate 20 (5 g, 15.5 mmol) in MTBE (5 mL) was added followed by BF$_3$·OEt$_2$ (3.5 mL, 15.5 mmol). The reaction was stirred for 30 min at −78° C. and then warmed to rt. After 16 h, the reaction was cooled to 0° C. and quenched with sat. aq. NH$_4$Cl (50 mL) and H$_2$O (50 mL). MTBE (50 mL) was then added and the reaction mixture was stirred for 20 min at rt. The organic layer was separated, and the aqueous layer was extracted with MTBE (100 mL). The combined organic layers were dried over Na$_2$SO$_4$, filtered, and concentrated. Purification by column chromatography (SiO$_2$, EtOAc/Heptane) followed by column chromatography (C18, CH$_3$CN:H$_2$O) provided benzyl 4,4-dimethyl-2-(3-methylbicyclo[1.1.1]pentan-1-yl)cyclohex-1-ene-1-carboxylate (3.6 g, 70%). $^1$H NMR (400 MHz, DMSO) δ 7.41-7.34 (m, 5H), 5.13 (s, 2H), 2.17-2.12 (m, 2H), 1.72-1.70 (m, 2H), 1.64 (s, 6H), 1.31-1.27 (m, 2H), 1.08 (s, 3H), 0.86 (s, 6H).

Step 2: To a stirred solution of benzyl 4,4-dimethyl-2-(3-methylbicyclo[1.1.1]pentan-1-yl)cyclohex-1-ene-1-carboxylate (1.1 g, 3.39 mmol) in THF (40 mL) at 0° C. was added lithium aluminum hydride (386.6 mg, 10.2 mmol). The reaction was warmed to rt and stirred for 3 h. The reaction was then cooled to 0° C., diluted with Et$_2$O (40 ml)

and treated with H$_2$O (0.386 mL), 0.386 mL of 15% NaOH (aq.) followed by H$_2$O (1.15 mL). The reaction was warmed to rt, stirred for 15 min, and then treated with anhydrous MgSO$_4$. After 15 min, the reaction was filtered, concentrated, and purified by column chromatography (SiO$_2$, EtOAc/pet. ether) to provide (4,4-dimethyl-2-(3-methylbicyclo[1.1.1]pentan-1-yl)cyclohex-1-en-1-yl)methanol (1.1 g, 68% yield) as a colorless oil. $^1$H NMR (400 MHz, CDCl$_3$) δ 4.15 (d, J=5.2 Hz, 2H), 2.16-2.12 (m, 2H), 1.81 (s, 6H), 1.68 (s, 2H), 1.32 (t, J=6.4 Hz, 2H), 1.15 (s, 3H), 0.86 (s, 6H).

Step 3: To a stirred solution of (4,4-dimethyl-2-(3-methylbicyclo[1.1.1]pentan-1-yl)cyclohex-1-en-1-yl)methanol (500 mg, 2.27 mmol) in DCM (20 mL) at 0° C. was added SOCl$_2$ (0.537 mL, 4.54 mmol) drop wise. The reaction mixture was warmed to rt and stirred for 2 h. The reaction was concentrated, diluted with DCM and concentrated once more to obtain 1-(2-(chloromethyl)-5,5-dimethylcyclohex-1-en-1-yl)-3-methylbicyclo[1.1.1]pentane (540 mg, quantitative yield) as a clear oil. This was used for the next step without further purification. $^1$H NMR (400 MHz, CDCl$_3$) δ 4.19 (s, 2H), 2.15-2.11 (m, 2H), 1.85 (s, 6H), 1.70 (s, 2H), 1.34 (t, J=6.4 Hz, 2H), 1.16 (s, 3H), 0.87 (s, 6H).

Step 4: To a stirred solution of 1-(2-(chloromethyl)-5,5-dimethylcyclohex-1-en-1-yl)-3-methylbicyclo[1.1.1]pentane (540 mg, 2.26 mmol) in acetone (20 mL) was added methyl 2-((1H-pyrrolo[2,3-b]pyridin-5-yl)oxy)-4-(piperazin-1-yl)benzoate (798 mg, 2.26 mmol), NaI (33.90 mg, 0.22 mmol) and K$_2$CO$_3$ (938.9 mg, 6.80 mmol) at rt. The reaction was then heated to reflux for 6 h. The reaction was then cooled to rt, diluted with 50 mL of acetone and filtered. The collected solid was washed with acetone (150 mL) and the combined filtrates were concentrated to provide methyl 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)benzoate (1.15 g, 91% yield) as a white solid. LC/MS (ESI) m/z 555.3 [M+H]$^+$.

Step 5: To a stirred solution of methyl 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)benzoate (1.15 g, 2.075 mmol) in MeOH:THF:H$_2$O (1:1:1) (36 mL) was added LiOH·H$_2$O (261.30 mg, 6.23 mmol) at rt. The reaction was heated to 30° C. and stirred for 16 h. The volatile solvents were then removed, and the reaction was neutralized with 1N HCl and extracted with DCM (3×70 mL). The combined organic layers were dried over Na$_2$SO$_4$, filtered and concentrated to provide Intermediate 28 (940 mg, 84% yield) as a white solid. LC/MS (ESI) m/z 541.3 [M+H]$^+$.

Route C:

Step 1: A solution of methyl 2-((1H-pyrrolo[2,3-b]pyridin-5-yl)oxy)-4-(piperazin-1-yl)benzoate (35 g, 99.3 mmol) and Intermediate 22 (26.0 g, 119.2 mmol) in THF (700 mL) was stirred at rt for 20 min. The reaction was then cooled to 0° C. and NaBH(OAc)$_3$ (63.15 g, 297.96 mmol) was added. Following the addition, the reaction was warmed to rt. After 16 h, the reaction was poured into ice cold water (1 L), and extracted with EtOAc (2×500 mL). The combined organic layers were washed with 10% NaHCO$_3$ (aq.) (500 mL), and brine (500 mL). The organic layer was then dried over Na$_2$SO$_4$, filtered and concentrated. The crude product was first purified by column chromatography (SiO$_2$, EtOAc/pet. ether) and then triturated with MeOH and filtered to afford methyl 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)benzoate (38 g, 70%). LC/MS (ESI) m/z 555.1 [M+H]$^+$.

Step 2: Intermediate 28 was prepared following the procedure described in Step 5, Route B for Intermediate 28. LC/MS (ESI) m/z 541.3 [M+H]$^+$.

Intermediate 29

2-((1H-pyrrolo[2,3-b]pyridin-5-yl)oxy)-4-(4-((2-(3-ethylbicyclo[1.1.1]pentan-1-yl)-4,4-dimethylcyclohex-1-en-1-yl)methyl)piperazin-1-yl)benzoic Acid

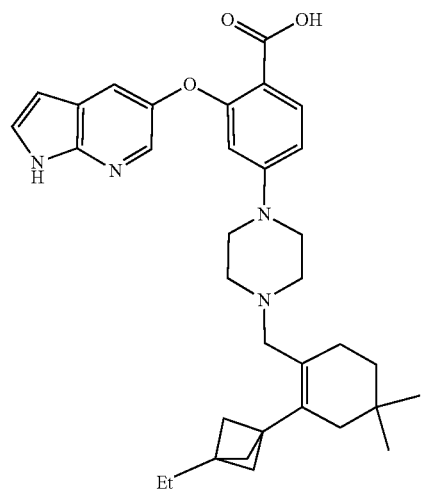 [SMILES: CCC12CC(C3=C(CN4CCN(c5ccc(C(=O)O)c(Oc6cnc7[nH]ccc7c6)c5)CC4)CCC(C)(C)C3)(C1)C2]

Step 1: To a solution of methyl 2-((1H-pyrrolo[2,3-b]pyridin-5-yl)oxy)-4-(piperazin-1-yl)benzoate (1.89 g, 5.38 mmol) in DMSO (25 mL) was added a solution of Intermediate 23 (1.5 g, 6.46 mmol) in THF (25 mL) at rt and the reaction was stirred for 1 h. The reaction was then cooled to 0° C. and treated with Na(OAc)$_3$BH (3.42 g, 16.14 mmol) and warmed to rt. After 24 h, the reaction was diluted with sat. aq. NaHCO$_3$, and extracted with 10% MeOH in DCM (4×50 mL). The combined organic layers were dried over Na$_2$SO$_4$, filtered and concentrated. The crude product was purified by column chromatography (SiO$_2$, Et$_2$O/n-pentane) to afford methyl 2-((1H-pyrrolo[2,3-b]pyridin-5-yl)oxy)-4-(4-((2-(3-ethylbicyclo[1.1.1]pentan-1-yl)-4,4-dimethylcyclohex-1-en-1-yl)methyl)piperazin-1-yl)benzoate (Intermediate 29-1) (1.4 g, 46% yield) as an off white solid. LC/MS (ESI) m/z 569.4 [M+H]$^+$.

Step 2: Intermediate 29 was prepared following the procedure described in Step 5, Route B for Intermediate 28 using Intermediate 29-1 in place of methyl 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)benzoate. LC/MS (ESI) m/z 555.3 [M+H]$^+$.

Intermediate 30

2-((1H-pyrrolo[2,3-b]pyridin-5-yl)oxy)-4-(4-((2-(3-(difluoromethyl)bicyclo[1.1.1]pentan-1-yl)-4,4-dimethylcyclohex-1-en-1-yl)methyl)piperazin-1-yl)benzoic Acid

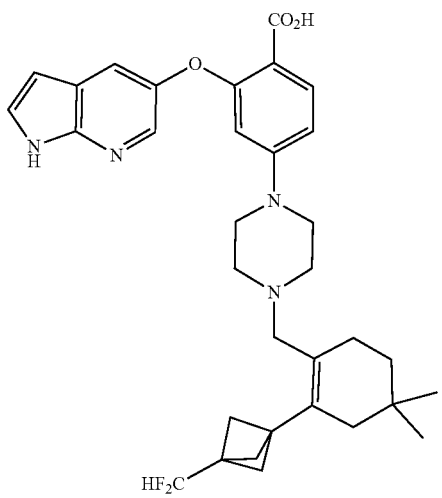

Step 1: Methyl 2-((1H-pyrrolo[2,3-b]pyridin-5-yl)oxy)-4-(4-((2-(3-(difluoromethyl)bicyclo[1.1.1]pentan-1-yl)-4,4-dimethylcyclohex-1-en-1-yl)methyl)piperazin-1-yl)benzoate (Intermediate 30-1) was prepared following the procedure described in Step 1, Route C for Intermediate 28 using Intermediate 24 in place of Intermediate 22. LC/MS (ESI) m/z 591.2 [M+H]+.

Step 2: Intermediate 30 was prepared following the procedure described in Step 5, Route B for Intermediate 26 using Intermediate 30-1 in place of methyl 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)benzoate. LC/MS (ESI) m/z 577.5[M+H]+.

Intermediate 31

2-((1H-pyrrolo[2,3-b]pyridin-5-yl)oxy)-4-(4-((4,4-dimethyl-2-(3-(trifluoromethyl)bicyclo[1.1.1]pentan-1-yl)cyclohex-1-en-1-yl)methyl)piperazin-1-yl)benzoic Acid

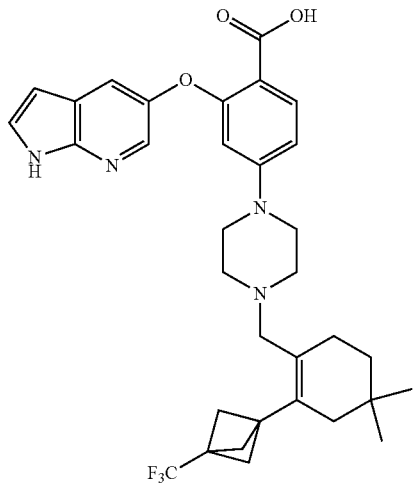 [SMILES: CC1(C)CCC(CN2CCN(c3ccc(C(=O)O)c(Oc4cnc5[nH]ccc5c4)c3)CC2)=C(C23CC(C(F)(F)F)(C2)C3)C1]

Step 1: Representative procedure (reaction was performed in 3 parallel batches): To a stirred solution of methyl 2-((1H-pyrrolo[2,3-b]pyridin-5-yl)oxy)-4-(piperazin-1-yl)benzoate (2 g, 5.68 mmol) in DMSO (0.2 M, 30 mL) was added a solution of Intermediate 25 (1.72 g, 6.22 mmol) in THF (30 mL) at rt. After 1 h, the reaction mixture was cooled to 0° C., and treated with NaBH(OAc)$_3$ (1.70 g, 17.04 mmol). The reaction was warmed to rt and stirred for 24 h. The reaction mixture was diluted with sat. aq. NaHCO$_3$, and extracted with 10% MeOH in DCM (4×150 mL). The combined organic layers were dried over Na$_2$SO$_4$, filtered and concentrated. The crude product was purified by column chromatography (SiO$_2$ EtOAc/pet. ether) to afford methyl 2-(1H-pyrrolo[2,3-b]pyridin-5-yloxy)-4-(4-((4,4-dimethyl-2-(3-(trifluoromethyl)bicyclo[1.1.1]pentan-1-yl)cyclohex-1-enyl)methyl)piperazin-1-yl)benzoate (Intermediate 31-1) (8.7 g, 14.29 mmol, 84% combined for three batches) as a white solid. LC/MS (ESI) m/z 609.3 [M+H]+.

Step 2: To a stirred solution of Intermediate 31-1 (8.3 g, 13.65 mmol) in MeOH:THF:H$_2$O (1:1:1) (100 mL) was added LiOH·H$_2$O (1.7 g, 40.95 mmol) at rt. The reaction mixture was then heated to 35° C. and stirred for 16 h. The reaction mixture was concentrated, diluted with water and neutralized with 1N HCl. The product was then extracted with 10% MeOH-DCM (3×150 mL). The combined organic layers were dried over Na$_2$SO$_4$, filtered and concentrated to provide Intermediate 31 (7.6 g, 90% yield) as a white solid. $^1$H NMR (400 MHz, DMSO-d$_6$) δ 11.91 (br s, 1H), 11.59 (s, 1H), 7.98 (d, J=2.4 Hz, 1H), 7.70 (d, J=8.8 Hz, 1H), 7.43 (t, J=2.8 Hz, 1H), 7.37 (d, J=2.4 Hz, 1H), 6.73-6.71 (m, 1H), 6.36-6.34 (m, 2H), 3.14-3.05 (m, 4H), 2.94 (s, 2H), 2.40-2.28 (m, 4H), 2.12 (s, 6H), 2.09-1.99 (m, 2H), 1.68 (s, 2H), 1.29-1.19 (m, 2H), 0.84 (s, 6H); $^{19}$F NMR (376 MHz, DMSO-d$_6$, unreferenced) 6-71.55; LC/MS (ESI) m/z 595.3 [M+H]+.

Intermediate 32

2-((1H-pyrrolo[2,3-b]pyridin-5-yl)oxy)-4-(4-((2-(3-isopropylbicyclo[1.1.1]pentan-1-yl)-4,4-dimethylcyclohex-1-en-1-yl)methyl)piperazin-1-yl)benzoic Acid

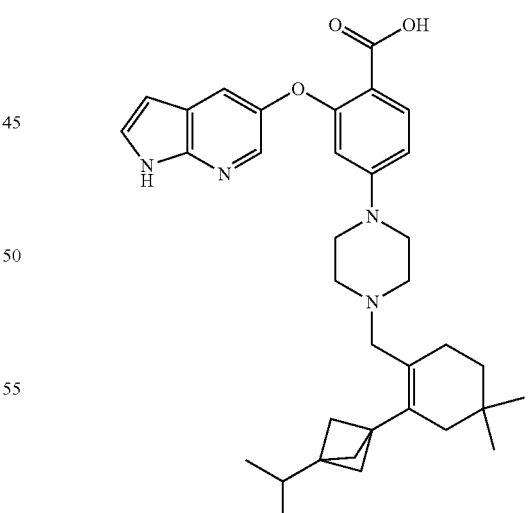

Step 1: 3,3-dimethyl-1-(3-isopropylbicyclo[1.1.1]pentan-1-yl)hex-5-en-1-one (Intermediate 32-1) was prepared following the procedure described in Step 1 from Intermediate 26 using Intermediate 12 in place of Intermediate 1. $^1$H NMR (400 MHz, CDCl$_3$) δ 5.81-5.74 (m, 1H), 5.04-4.97 (m, 2H), 2.31 (s, 2H), 2.10 (d, J=7.6 Hz, 2H), 1.76 (s, 6H), 1.69-1.65 (m, 1H), 0.99 (s, 6H), 0.83 (d, J=6.8 Hz, 6H).

Step 2: E/Z-7-(3-isopropylbicyclo[1.1.1]pentan-1-yl)-5,5-dimethyl-7-oxohept-2-enenitrile (Intermediate 32-2) was prepared following the procedure described in Step 2 from Intermediate 26 using Intermediate 32-1 in place of Intermediate 26-1. LC/MS (ESI) m/z 260.4 [M+H]$^+$.

Step 3: 7-(3-Isopropylbicyclo[1.1.1]pentan-1-yl)-5,5-dimethyl-7-oxoheptanenitrile (Intermediate 32-3) was prepared following the procedure described in Step 3 from Intermediate 26 using Intermediate 32-2 in place of Intermediate 26-2. $^1$HNMR (400 MHz, CDCl$_3$) δ 2.34-2.30 (m, 4H), 1.78 (s, 6H), 1.70-1.57 (m, 4H), 1.51-1.46 (m, 1H), 0.98 (s, 6H), 0.84 (d, J=7.2 Hz, 6H).

Step 4: 2-(3-Isopropylbicyclo[1.1.1]pentan-1-yl)-4,4-dimethylcyclohex-1-enecarbonitrile (Intermediate 32-4) was prepared following the procedure described in Step 4 from Intermediate 26 using Intermediate 32-3 in place of Intermediate 26-3. LC/MS (ESI) m/z 244.4 [M+H]$^+$.

Step 5: 2-(3-Isopropylbicyclo[1.1.1]pentan-1-yl)-4,4-dimethylcyclohex-1-enecarbaldehyde (Intermediate 32-5) was prepared following the procedure described in Step 5 from Intermediate 26 using Intermediate 32-4 in place of Intermediate 26-4. LC/MS (ESI) m/z 247.4 [M+H]$^+$.

Step 6: tert-Butyl 2-(1H-pyrrolo[2,3-b]pyridin-5-yloxy)-4-(4-((2-(3-isopropylbicyclo [1.1.1]pentan-1-yl)-4,4-dimethylcyclohex-1-enyl)methyl)piperazin-1-yl)benzoate (Intermediate 32-6) was prepared following the procedure described in Step 6, Route A for Intermediate 28 using Intermediate 32-5 in place of Intermediate 28-5. LC/MS (ESI) m/z 625.7 [M+H]$^+$.

Step 7: To a solution of Intermediate 32-6 (160 mg, 0.26 mmol) in DCM (5 mL) at 0° C. was added TFA (176 mg, 1.54 mmol). The mixture was warmed to rt and stirred for 3 h. The reaction was then diluted with sat. aq. NaHCO$_3$ (10 mL), and extracted with DCM (3×10 mL). The combined organic layers were dried over Na$_2$SO$_4$, filtered and concentrated to provide Intermediate 32 as an off-white solid. LC/MS (ESI) m/z 569.6 [M+H]$^+$.

Intermediate 33

2-(1H-pyrrolo[2,3-b]pyridin-5-yloxy)-4-(4-((2-(3-(1,1-difluoroethyl)bicyclo[1.1.1]pentan-1-yl)-4,4-dimethylcyclohex-1-enyl)methyl)piperazin-1-yl)benzoic Acid

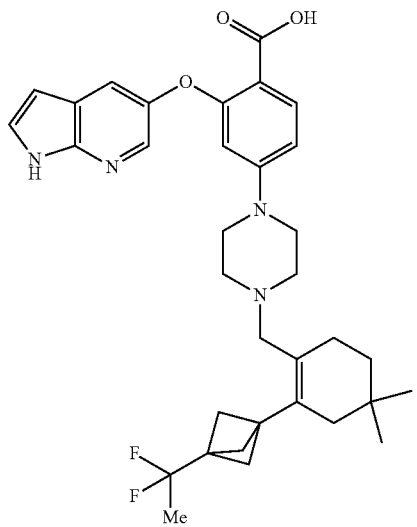 [SMILES: CC1(C)CCC(CN2CCN(c3ccc(C(=O)O)c(Oc4cnc5[nH]ccc5c4)c3)CC2)=C(C23CC(C(C)(F)F)(C2)C3)C1]

Step 1: 1-(3-(1,1-Difluoroethyl)bicyclo[1.1.1]pentan-1-yl)-3,3-dimethylhex-5-en-1-one (Intermediate 33-1) was prepared following the procedure described in Step 1 for Intermediate 26 using Intermediate 13 in place of Intermediate 1. $^1$H NMR (400 MHz, CDCl$_3$) δ 5.85-5.69 (m, 1H), 5.03-4.95 (m, 2H), 2.30 (s, 2H), 2.08 (d, J=8.0 Hz, 2H), 2.03 (s, 6H), 1.53 (t, J=18.0 Hz, 3H), 0.97 (s, 6H).

Step 2: E/Z-7-(3-(1,1-difluoroethyl)bicyclo[1.1.1]pentan-1-yl)-5,5-dimethyl-7-oxohept-2-enenitrile (Intermediate 33-2) was prepared following the procedure described in Step 2 for Intermediate 26 using Intermediate 33-1 in place of Intermediate 26-1. LC/MS (ESI) m/z 282.5 [M+H]$^+$.

Step 3: 7-(3-(1,1-Difluoroethyl)bicyclo[1.1.1]pentan-1-yl)-5,5-dimethyl-7-oxoheptanenitrile (Intermediate 33-3) was prepared following the procedure described in Step 3 for Intermediate 26 using Intermediate 33-2 in place of Intermediate 26-2. $^1$H NMR (400 MHz, CDCl$_3$) δ 2.34-2.31 (m, 4H), 2.06 (s, 6H), 1.66-1.57 (m, 2H), 1.55 (t, J=18.0 Hz, 3H), 1.51-1.46 (m, 2H), 0.99 (s, 6H).

Step 4: 2-(3-(1,1-Difluoroethyl)bicyclo[1.1.1]pentan-1-yl)-4,4-dimethylcyclohex-1-enecarbonitrile (Intermediate 33-4) was prepared following the procedure described in Step 4 for Intermediate 26 using Intermediate 33-3 in place of Intermediate 26-3. LC/MS (ESI) m/z 266.1 [M+H]$^+$.

Step 5: 2-(3-(1,1-difluoroethyl)bicyclo[1.1.1]pentan-1-yl)-4,4-dimethylcyclohex-1-enecarbaldehyde (Intermediate 33-5) was prepared following the procedure described in Step 5 for Intermediate 26 using Intermediate 33-4 in place of Intermediate 26-4. LC/MS (ESI) m/z 269.5 [M+H]$^+$.

Step 6: tert-butyl 2-(1H-pyrrolo[2,3-b]pyridin-5-yloxy)-4-(4-((2-(3-(1,1-difluoroethyl)bicyclo[1.1.1]pentan-1-yl)-4,4-dimethylcyclohex-1-enyl)methyl)piperazin-1-yl)benzoate (Intermediate 33-6) was prepared following the procedure described in Step 6, Route A for Intermediate 28 using Intermediate 33-5 in place of Intermediate 28-5. LC/MS (ESI) m/z 647.3 [M+H]$^+$.

Step 7: Intermediate 33 was prepared following the procedure described in Step 7 for Intermediate 32 using Intermediate 33-6 in place of Intermediate 32-6. LC/MS (ESI) m/z 591.3 [M+H]$^+$.

Intermediate 34

(S)-4-(((1,4-dioxan-2-yl)methyl)amino)-3-nitrobenzenesulfonamide

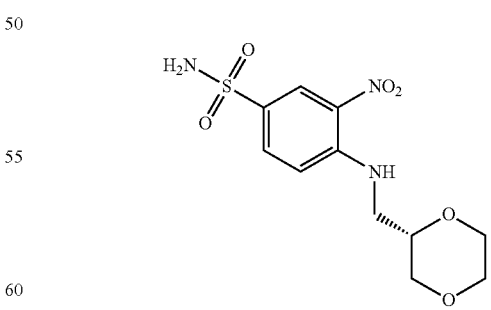

A solution of (S)-(1,4-dioxan-2-yl)methanamine hydrochloride (500 mg, 3.25 mmol) in THF (5 mL) was treated with 4-fluoro-3-nitrobenzenesulfonamide (501 mg, 2.20 mmol) and DIPEA (1.65 g, 13 mmol) and the mixture was heated to 45° C. After 16 h, the reaction was concentrated, triturated with MeOH, and filtered to provide Intermediate 34 (500 mg, 48%) as a yellow solid. LC/MS (ESI) m/z 318.4 [M+H]⁺.

Intermediate 35

(R)-4-((4-((2-((tert-butyldiphenylsilyl)oxy)ethyl)(methyl)amino)-1-(phenylthio)butan-2-yl)amino)-3-((trifluoromethyl)sulfonyl)benzenesulfonamide

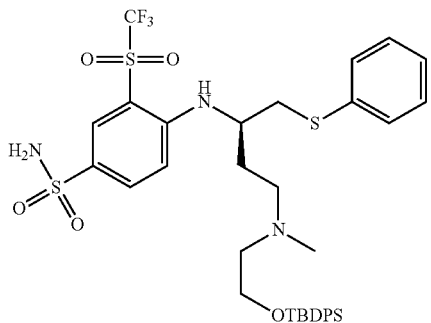

Intermediate 35 was prepared following a procedure described in WO2012/017251A1. LCMS (ESI) m/z 780.6 [M+H]⁺.

Intermediate 36

4-(4-((2-(3-Chlorobicyclo[1.1.1]pentan-1-yl)-5,5-dimethylcyclohex-1-en-1-yl)methyl)piperazin-1-yl) benzoic Acid

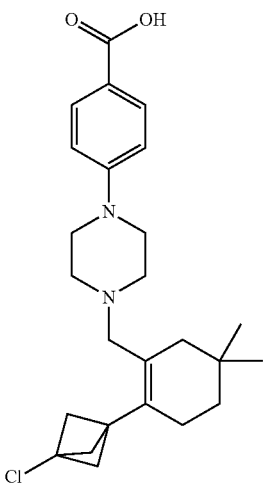 [SMILES: CC1(C)CCC(C23CC(Cl)(C2)C3)=C(CN2CCN(c3ccc(C(=O)O)cc3)CC2)C1]

Step 1: To a stirred solution of 3,3-dimethylpent-4-en-1-ol (18.5 g, 162.01 mmol) in DCM (100 mL), was added MsCl (13.54 mL, 175.0 mmol) followed by NEt₃ (33.87 mL, 243.0 mmol) at 0° C. and the reaction was warmed to rt. After 4 h, sat. aq. NaHCO₃ solution (100 mL) was added and the reaction was extracted with DCM (3×100 mL). The combined organic layers were dried over Na₂SO₄, filtered and concentrated to afford 3,3-dimethylpent-4-enyl methanesulfonate (Intermediate 36-1) (20.0 g, 64% yield) as a clear colorless oil. This was used in the next step without further purification. ¹H NMR (400 MHz, CDCl₃) δ 5.80-5.72 (m, 1H), 5.01-4.94 (m, 2H), 4.22-4.18 (m, 2H), 2.99 (s, 3H), 1.81-1.77 (m, 2H), 1.06 (s, 6H).

Step 2: To a pressure flask was added Intermediate 36-1 (20 g, 104.01 mmol) and NaI (46.77 g, 312.04 mmol) in acetone (100 mL). The flask was sealed and the reaction was stirred at 100° C. for 12 h. The reaction mixture was cooled to rt, diluted with water (250 mL) and extracted with Et₂O (3×200 mL). The combined organic layers were washed with sat. aq. Na₂S2O3, dried over Na₂SO₄, and evaporated to afford 5-iodo-3,3-dimethylpent-1-ene (Intermediate 36-2) (18 g, 77% yield) as a clear colorless oil. ¹H NMR (400 MHz, CDCl₃) δ 5.75-5.68 (m, 1H), 5.01-4.92 (m, 2H), 3.09-3.05 (m, 2H), 1.99-1.95 (m, 2H), 1.01 (s, 6H)

Step 3: 1-(3-Chlorobicyclo[1.1.1]pentan-1-yl)-4,4-dimethylhex-5-en-1-one (Intermediate 36-3) was prepared following the procedure described in Step 1 for Intermediate 26 by reacting 36-2 in place of 5-iodo-4,4-dimethylpent-1-ene. ¹H NMR (400 MHz, CDCl₃) δ 5.71-5.63 (m, 1H), 4.97-4.88 (m, 2H), 2.38 (s, 6H), 2.34-2.30 (m, 2H), 1.57-1.52 (m, 2H), 0.98 (s, 6H).

Step 4: Ozone gas was bubbled into a solution of Intermediate 36-3 (1.5 g, 6.63 mmol) in DCM (40 mL) at −78° C. until the solution turned a blue color (~30 min). Then N₂ gas was bubbled into the reaction mixture until it became colorless. PPh₃ (2.6 g, 9.94 mmol) was added in one portion and the reaction was warmed to rt. After 3 h, the reaction mixture was diluted with DCM (100 mL), washed with water (2×25 mL), and brine (50 mL). The organic layer was dried over Na₂SO₄, filtered and concentrated. The crude product was purified by column chromatography (SiO₂, EtOAc/pet. ether) to afford 5-(3-chlorobicyclo[1.1.1]pentan-1-yl)-2,2-dimethyl-5-oxopentanal (Intermediate 36-4) as a clear colorless oil (800 mg, 53% yield). ¹H NMR (400 MHz, CDCl₃) δ 9.41 (s, 1H), 2.39 (s, 6H), 2.38-2.33 (m, 2H), 1.77-1.72 (m, 2H), 1.05 (s, 6H).

Step 5: To a stirred solution of diethyl cyanomethylphosphonate (619 mg, 3.50 mmol) in toluene (10 mL) at 0° C. was added LiHMDS (1 M in toluene, 3.5 mL, 3.50 mmol). The reaction was then warmed to rt. After 30 min, the solution was added dropwise at −78° C. to a solution of Intermediate 36-4 (800 mg, 3.50 mmol) in toluene (10 mL). The reaction mixture was warmed to rt and stirred for 16 h at which point it was cooled to 0° C. and quenched with sat. aq. NH₄Cl (20 ml). The organic phase was separated and the aqueous phase was further extracted with DCM (3×50 mL). The combined organic layers were dried over Na₂SO₄, filtered and concentrated. The crude product was purified by column chromatography (SiO₂, EtOAc/pet. ether) to obtain (E)-7-(3-chlorobicyclo[1.1.1]pentan-1-yl)-4,4-dimethyl-7-oxohept-2-enenitrile (Intermediate 36-5) as a clear colorless oil (440 mg, 50% yield). LC/MS (ESI) m/z 252.4 [M+H]⁺.

Step 6: A solution of Intermediate 36-5 (440 mg, 1.75 mmol) in MeOH (10 mL) was treated with Pd/C (25 wt %, 110 mg) and stirred under an atmosphere of H₂ (1 atm) for 2 h. The reaction was then purged with N₂, and filtered over Celite. The Celite plug was washed with MeOH (3×25 mL) and the combined organic layers were concentrated to provide 7-(3-chlorobicyclo[1.1.1]pentan-1-yl)-4,4-dimethyl-7-oxoheptanenitrile (Intermediate 36-6) as a clear colorless oil (360 mg, 81% yield). ¹H NMR (400 MHz, CDCl₃) 2.41 (s, 6H), δ 2.40-2.36 (m, 2H), 2.30-2.25 (m, 2H), 1.63-1.56 (m, 2H), 1.50-1.46 (m, 2H), 0.89 (s, 6H).

Step 7: 2-(3-Chlorobicyclo[1.1.1]pentan-1-yl)-5,5-dimethylcyclohex-1-ene-1-carbonitrile (Intermediate 36-7) was prepared following the procedure described in Step 4 for Intermediate 26 by reacting Intermediate 36-6 in place of Intermediate 26-3. LC/MS (ESI) m/z 236.4 [M+H]+.

Step 8: 5,5-Dimethyl-2-(3-methylbicyclo[1.1.1]pentan-1-yl)cyclohex-1-ene-1-carbaldehyde (Intermediate 36-8) was prepared following the procedure described in Step 5 for Intermediate 26 by reacting Intermediate 36-7 in place of Intermediate 26-4. $^1$H NMR (400 MHz, CDCl$_3$) δ 10.17 (s, 1H), 2.46 (s, 6H), 2.44 (s, 2H), 2.03 (t, J=7.6 Hz, 2H), 1.42-1.37 (m, 2H), 0.86 (s, 6H).

Step 9: To a stirred solution of Intermediate 36-8 (85 mg, 0.361 mmol) in EtOH (3 mL) was added tert-Butyl 4-(piperazin-1-yl)benzoate (104 mg, 0.397 mmol) and AcOH (cat.). After 15 min, the reaction was cooled to 0° C., treated with NaCNBH$_3$ (33.6 mg, 0.535 mmol) and warmed to rt. After 16 h, the reaction was diluted with sat. aq. NaHCO$_3$ and extracted with DCM (3×15 mL). The combined organic layers were dried over Na$_2$SO$_4$, filtered and concentrated. The crude product was purified by column chromatography (SiO$_2$, EtOAc/pet. ether) to obtain tert-Butyl 4-(4-((2-(3-chlorobicyclo[1.1.1]pentan-1-yl)-5,5-dimethylcyclohex-1-en-1-yl)methyl)piperazin-1-yl)benzoate (Intermediate 36-9) as a white solid (80 mg, 50% yield). LC/MS (ESI) m/z 485.6 [M+H]+.

Step 10: To a stirred solution of Intermediate 36-9 (80 mg, 0.165 mmol) in DCM (3 mL) at 0° C. was added TFA (113 mg, 0.99 mmol). The reaction was warmed to rt and stirred for 3 h. The reaction was concentrated and then diluted with sat. aq. NaHCO$_3$ and extracted with DCM (3×10 mL). The combined organic layers were dried over Na$_2$SO$_4$, filtered and concentrated to obtain the Intermediate 36 as an off-white solid (60 mg, 85%). LC/MS (ESI) m/z 429.5 [M+H]+.

Intermediate 37

(R)-4-(4-(4-hydroxypiperidin-1-yl)-1-(phenylthio)butan-2-ylamino)-3-(trifluoromethylsulfonyl)benzenesulfonamide

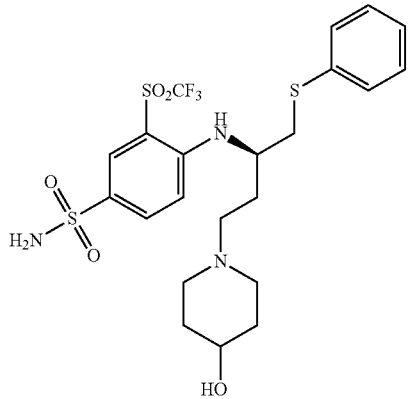

Step 1: To a stirred solution of (R)-3-((((9H-fluoren-9-yl)methoxy)carbonyl)amino)-4-(phenylthio)butanoic acid (6.8 g, 15.7 mmol) in DCM (70 mL) and DMF (10 mL) was added HATU (9.5 g, 25.12 mmol) followed by DIPEA (8.3 mL, 47.1 mmol) at 0° C. After 10 min, 4-hydroxypiperidine (2.4 g, 23.55 mmol) was added and temperature was raised to rt. After 16 h, the reaction was diluted with water and extracted with EtOAc. The combined organic layers were dried over Na$_2$SO$_4$, filtered, and concentrated. The crude product was purified by column chromatography (SiO$_2$ MeOH/DCM) to afford (R)-(9H-fluoren-9-yl)methyl-4-(4-hydroxypiperidin-1-yl)-4-oxo-1-(phenylthio)butan-2-ylcarbamate (Intermediate 37-1) (5.5 g, 68% yield) as a brown oil. LC/MS (ESI) m/z 517.6 [M+H]+.

Step 2: To a stirred solution of Intermediate 37-1 (2.75 g, 5.32 mmol) in CH$_3$CN (20 mL) at rt was added diethylamine (3.3 mL, 31.92 mmol) and stirred at rt. After 16 h, the reaction was concentrated and purified by column chromatography (neutral alumina, MeOH/DCM) to afford (R)-3-amino-1-(4-hydroxypiperidin-1-yl)-4-(phenylthio)butan-1-one (Intermediate 37-2) (900 mg, 57% yield) as a brown liquid. LC/MS (ESI) m/z 295.1 [M+H]+.

Step 3: To a stirred solution of Intermediate 37-2 (0.9 g, 3.06 mmol) in anhydrous THF (12 mL) at 0° C. was added BH$_3$ (1 M in THF, 9.18 mL, 9.18 mmol) and the temperature was raised to 45° C. After 16 h, the reaction was cooled to 0° C. and MeOH (30 ml) was added. After 1 hour, the reaction was concentrated and purified by column chromatography (C18, CH$_3$CN/Water) to afford (R)-1-(3-amino-4-(phenylthio)butyl)piperidin-4-ol (Intermediate 37-3) (305 mg, 36% yield) as an off-white semi solid. LC/MS (ESI) m/z 281.2 [M+H]+.

Step 4: To a stirred solution of Intermediate 37-3 (100 mg, 0.357 mmol) in DMF (1 mL) was added 4-fluoro-3-(trifluoromethylsulfonyl)benzenesulfonamide (99 mg, 0.32 mmol) followed by DIPEA (140 mg, 1.07 mmol) and the resulting reaction mixture was stirred at rt. After 16 h, the reaction was concentrated, diluted with water and extracted with 9:1 DCM:MeOH (2×10 mL). The combined organic layers were dried over Na$_2$SO$_4$, filtered and concentrated. The crude product was purified by trituration with EtOAc/Et$_2$O to afford Intermediate 37 (105 mg, 51% yield) as a white solid. LC/MS (ESI) m/z 568.1 [M+H]+.

Intermediate 38

4-(4-((5,5-dimethyl-2-(3-methylbicyclo[1.1.1]pentan-1-yl)cyclohex-1-en-1-yl)methyl)piperazin-1-yl)benzoic Acid

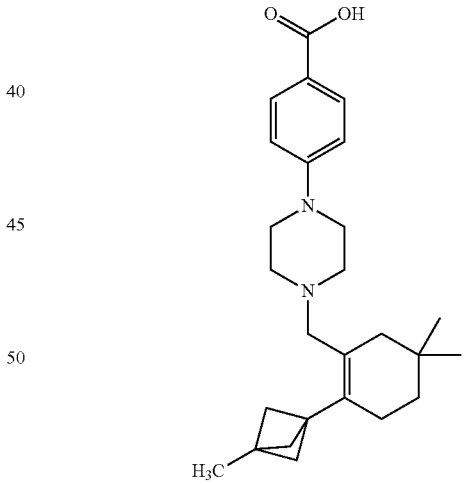

Step 1: 4,4-Dimethyl-1-(3-methylbicyclo[1.1.1]pentan-1-yl)hex-5-en-1-one (Intermediate 38-1) was prepared following the procedure described in Step 1 for Intermediate 26 using Intermediate 10 and Intermediate 36-2 in place of Intermediate 1 and 5-iodo-4,4-dimethylpent-1-ene. $^1$H NMR (400 MHz, CDCl$_3$) δ 5.73-5.66 (m, 1H), 4.95-4.88 (m, 2H), 2.33-2.28 (m, 2H), 1.88 (s, 6H), 1.55-1.51 (m, 2H), 1.21 (s, 3H), 0.99 (s, 6H).

Step 2: 2,2-dimethyl-5-(3-methylbicyclo[1.1.1]pentan-1-yl)-5-oxopentanal (Intermediate 38-2) was prepared following the procedure described in Step 4 for Intermediate 36 using Intermediate 38-1 in place of Intermediate 36-3. 1H NMR (300 MHz, CDCl3) δ 9.41 (s, 1H), 2.36-2.30 (m, 2H), 1.88 (s, 6H), 1.79-1.71 (m, 2H), 1.18 (s, 3H), 1.05 (s, 6H).

Step 3: 4,4-dimethyl-7-(3-methylbicyclo[1.1.1]pentan-1-yl)-7-oxohept-2-enenitrile (Intermediate 38-3) was prepared following the procedure described in Step 5 for Intermediate 36 using Intermediate 38-2 in place of Intermediate 36-4. LC/MS (ESI) m/z 232.5 [M+H]$^+$.

Step 4: 4,4-dimethyl-7-(3-methylbicyclo[1.1.1]pentan-1-yl)-7-oxoheptanenitrile (Intermediate 38-4) was prepared following the procedure described in Step 6 for Intermediate 36 using Intermediate 38-3 in place of Intermediate 36-5. $^1$H NMR (400 MHz, CDCl$_3$) δ 2.38-2.33 (m, 2H), 2.29-2.25 (m, 2H), 1.90 (s, 6H), 1.62-1.58 (m, 2H), 1.48-1.44 (m, 2H), 1.19 (s, 3H), 0.90 (s, 6H).

Step 5: 5,5-dimethyl-2-(3-methylbicyclo[1.1.1]pentan-1-yl)cyclohex-1-ene-1-carbonitrile (Intermediate 38-5) was prepared following the procedure described in Step 4 for Intermediate 26 using Intermediate 38-4 in place of Intermediate 26-3. $^1$H NMR (400 MHz, CDCl$_3$) δ 2.11-2.06 (m, 2H), 2.00-1.98 (m, 2H), 1.93 (s, 6H), 1.35 (t, J=6.4 Hz, 2H), 1.18 (s, 3H), 0.90 (s, 6H).

Step 6: 5,5-dimethyl-2-(3-methylbicyclo[1.1.1]pentan-1-yl)cyclohex-1-ene-1-carbaldehyde (Intermediate 38-6) was prepared following the procedure described in Step 5 for Intermediate 26 using Intermediate 38-5 in place of Intermediate 26-4. $^1$H NMR (400 MHz, CDCl$_3$) δ 10.28 (s, 1H), 2.21-2.17 (m, 2H), 2.14 (br s, 2H), 2.00 (s, 6H), 1.35 (t, J=6.4 Hz, 2H), 1.20 (s, 3H), 0.88 (s, 6H).

Step 7: tert-Butyl 4-(4-((5,5-dimethyl-2-(3-methylbicyclo[1.1.1]pentan-1-yl)cyclohex-1-en-1-yl)methyl)piperazin-1-yl)benzoate (Intermediate 38-7) was prepared following the procedure described in Step 9 from Intermediate 36 using Intermediate 38-6 in place of Intermediate 36-8. LC/MS (ESI) m/z 465.6 [M+H]$^+$.

Step 8: Intermediate 38 was prepared following the procedure described in Step 10 from Intermediate 36 by reacting Intermediate 38-7 in place of Intermediate 36-9. LC/MS (ESI) m/z 409.6 [M+H]$^+$.

Intermediate 39

4-(4-((4,4-Dimethyl-2-(3-methylbicyclo[1.1.1]pentan-1-yl)cyclohex-1-en-1-yl)methyl)piperazin-1-yl)benzoic Acid

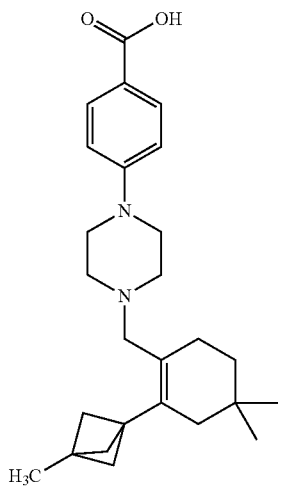

Step 1: To a stirred solution of methyl 4-(piperazin-1-yl)benzoate (1.68 g, 7.6 mmol) and Intermediate 22 (2.0 g, 9.15 mmol) in THF (20 mL) was added Na(OAc)$_3$BH (4.8 g, 22.8 mmol) at rt. After 16 h, the reaction was put in an ice batch and quenched with sat. aq. NaHCO$_3$ (25 mL). The reaction mixture was extracted with EtOAc (3×50 mL), dried over Na$_2$SO$_4$, filtered, and concentrated. The crude product was purified by column chromatography (SiO$_2$, EtOAc/pet. ether) to obtain methyl 4-(4-((4,4-dimethyl-2-(3-methylbicyclo[1.1.1]pentan-1-yl)cyclohex-1-en-1-yl)methyl)piperazin-1-yl)benzoate (Intermediate 39-1) as a white solid (1.5 g, 46% yield). LC/MS (ESI) m/z 423.2[M+H]$^+$.

Step 2: Intermediate 39 was prepared following the procedure described in Step 5, Route B for Intermediate 28 using Intermediate 39-1 in place of methyl 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)benzoate. $^1$H NMR (300 MHz, DMSO-d$_6$) δ 12.25 (br s, 1H), 7.75 (d, J=9.0 Hz, 2H), 6.95 (d, J=9.0 Hz, 2H), 3.32-3.25 (m, 4H), 3.03 (s, 2H), 2.45-2.35 (m, 4H), 2.06-2.04 (m, 2H), 1.79 (s, 6H), 1.68 (s, 2H), 1.26 (t, J=6.3 Hz, 2H), 1.12 (s, 3H), 0.85 (s, 6H); LC/MS (ESI) m/z 409.5 [M+H]$^+$.

Intermediate 40

4-(4-((2-(3-ethylbicyclo[1.1.1]pentan-1-yl)-4,4-dimethylcyclohex-1-en-1-yl)methyl)piperazin-1-yl)benzoic Acid

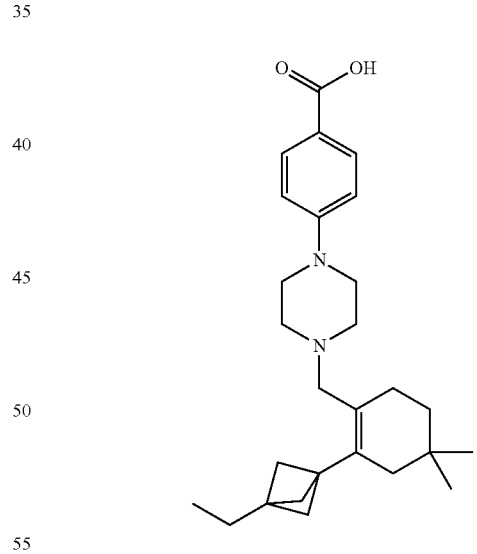

Step 1: Methyl 4-(4-((2-(3-ethylbicyclo[1.1.1]pentan-1-yl)-4,4-dimethylcyclohex-1-en-1-yl)methyl)piperazin-1-yl)benzoate (Intermediate 40-1) was prepared following the procedure described in Step 1 for Intermediate 39 using Intermediate 23 in place of Intermediate 22. LC/MS (ESI) m/z 437.3 [M+H]$^+$.

Step 1: Intermediate 40 was prepared following the procedure described in Step 2 for Intermediate 39 using Intermediate 40-1 in place of Intermediate 39-1. LC/MS (ESI) m/z 423.3 [M+H]$^+$.

Intermediate 41

4-(4-((4,4-dimethyl-2-(3-(trifluoromethyl)bicyclo[1.1.1]pentan-1-yl)cyclohex-1-en-1-yl)methyl)piperazin-1-yl)benzoic Acid

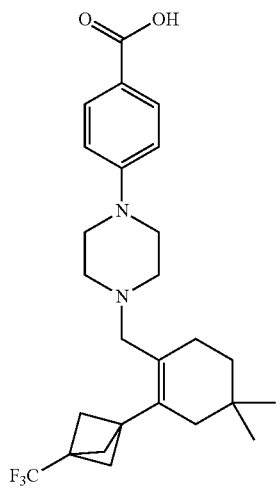 [SMILES: CC1(C)CCC(CN2CCN(c3ccc(C(=O)O)cc3)CC2)=C(C23CC(C(F)(F)F)(C2)C3)C1]

Step 1: To a stirred solution of Intermediate 25 (3.5 g, 12.85 mmol) in toluene was added titanium (IV) ethoxide (3.73 g, 16.36 mmol). After 30 min, a solution of methyl 4-(piperazin-1-yl) benzoate (2.35 g, 10.71 mmol) in toluene (20 mL) was added and the resulting reaction mixture was stirred at rt for 1 h. The reaction mixture was then cooled to 0° C., and Na(OAc)$_3$BH (6.9 g, 32.72 mmol) was added and the reaction was warmed to rt. After 16 h, the reaction was quenched with water (100 mL) at 0° C., and MTBE (200 mL) was added after 30 min. The reaction mixture was filtered over Celite and the collected solid was washed with DCM (2×100 mL). The combined organic layers were washed with sat. aq. NaHCO$_3$, brine, dried over Na$_2$SO$_4$, filtered and concentrated. The crude product was column chromatography (SiO$_2$, EtOAc/pet. ether) to afford methyl 4-(4-((4,4-dimethyl-2-(3-(trifluoromethyl)bicyclo[1.1.1]pentan-1-yl)cyclohex-1-en-1-yl)methyl)piperazin-1-yl)benzoate (Intermediate 41-1) (3.2 g, 63% yield) as a white solid. LC/MS (ESI) m/z 477.3 [M+H]$^+$.

Step 2: Intermediate 41 was prepared following the procedure described in Step 2 for Intermediate 39 by reacting Intermediate 41-1 in place of Intermediate 39-1. LC/MS (ESI) m/z 463.2 [M+H]$^+$.

Intermediate 42

4-(4-((2-(3-(Difluoromethyl)bicyclo[1.1.1]pentan-1-yl)-4,4-dimethylcyclohex-1-en-1-yl)methyl)piperazin-1-yl)benzoic Acid

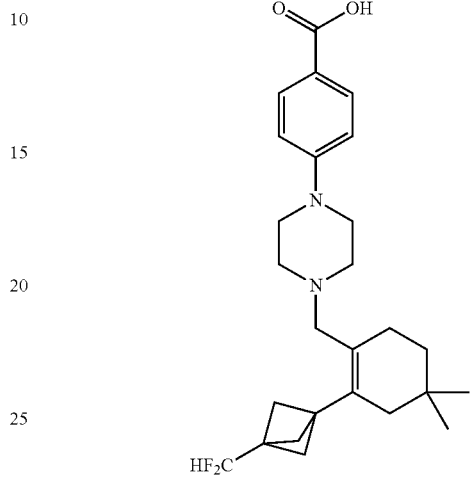

Step 1: Methyl 4-(4-((2-(3-(difluoromethyl)bicyclo[1.1.1]pentan-1-yl)-4,4-dimethylcyclohex-1-en-1-yl)methyl)piperazin-1-yl)benzoate (Intermediate 42-1) was prepared following the procedure described in Step 1 for Intermediate 39 using Intermediate 24 in place of Intermediate 22. $^1$H NMR (400 MHz, DSMO-d$_6$) δ 7.77 (d, J=8.8 Hz, 2H), 6.97 (d, J=8.8 Hz, 2H), 6.01 (t, J=56.4 Hz, 1H), 3.77 (s, 3H), 3.35-3.20 (m, 4H), 3.00 (s, 2H), 2.42 (t, J=4.4 Hz, 4H), 2.10-2.01 (m, 2H), 1.90 (s, 6H), 1.71 (s, 2H), 1.27 (t, J=6.0 Hz, 2H), 0.86 (s, 6H); LC/MS (ESI) m/z 459.6 [M+H]$^+$.

Step 1: Intermediate 42 was prepared following the procedure described in Step 2 for Intermediate 39 using Intermediate 42-1 in place of Intermediate 39-1. LC/MS (ESI) m/z 445.6 [M+H]$^+$.

Intermediate 43

(R)-4-((4-morpholino-1-(phenylthio)butan-2-ylamino)-3-nitrobenzenesulfonamide

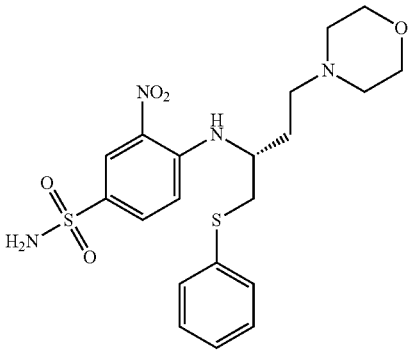 [SMILES: NS(=O)(=O)c1ccc(N[C@H](CCN2CCOCC2)CSc2ccccc2)c([N+](=O)[O-])c1]

To a solution of (R)-4-morpholino-1-(phenylthio)butan-2-amine dihydrochloride (900 mg, 2.6 mmol) in DMF (10 mL) was added 4-fluoro-3-nitrobenzenesulfonamide (56 mg, 2.53 mmol) followed by DIPEA (5.8 mL, 33.8 mmol) at rt. The reaction was then heated to 50° C. for 4 h. The reaction was cooled to rt, quenched with ice cold water (150 mL) and stirred at rt for 15 min. The mixture was then filtered and the collected solid was washed with n-pentane to afford Intermediate 43 (800 mg, 66%) as a yellow solid. LCMS (ESI) m/z 467.1 [M+H]$^+$.

Intermediate 44

(R)-4-((4-(dimethylamino)-1-(phenylthio)butan-2-yl)amino)-3-((trifluoromethyl) sulfonyl)benzenesulfonamide

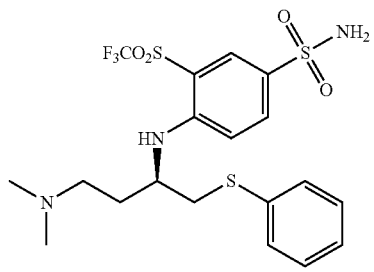

Intermediate 44 was prepared following a procedure described in WO200861208A2. LC/MS (ESI) m/z 512.2 [M+H]$^+$.

Intermediate 45

(R)-4-((4-(4-(dimethylamino)piperidin-1-yl)-1-(phenylthio)butan-2-yl)amino)-3-((trifluoromethyl)sulfonyl)benzenesulfonamide

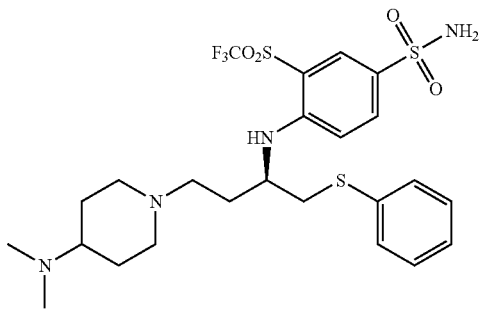

Step 1: To a stirred solution of N,N-dimethylpiperidin-4-amine (462.5 mg, 3.61 mmol), DMAP (367.80 mg, 3.01 mmol), and EDC·HCl (863.75 mg, 4.51 mmol) in DCM (20 mL) was added (R)-4-(phenylthio)-3-((4-sulfamoyl-2-((trifluoromethyl)sulfonyl)phenyl)amino)butanoic acid (prepared following a procedure described in WO2012017251A1) (1.5 g, 3.01 mmol) and Et$_3$N (0.84 mL, 6.02 mmol) at rt. After 15 min, the reaction was heated to 35° C. and stirred for 16 h. The reaction mixture was then cooled to rt, diluted with DCM (100 mL) and MeOH (10 mL) and washed with 10% CH$_3$CO$_2$H (aq.) (2×20 mL). The organic layer was then washed with 5% NaHCO$_3$ (aq.) (20 mL) and 5% NaCl(aq.) (20 mL) and concentrated. The crude product was purified by column chromatography (C$_{18}$, CH$_3$CN/H$_2$O) to provide (R)-4-((4-(4-(dimethylamino)piperidin-1-yl)-4-oxo-1-(phenylthio)butan-2-yl)amino)-3-((trifluoromethyl)sulfonyl)benzenesulfonamide (Intermediate 45-1) (686 mg, 37% yield) LC/MS (ESI) m/z 609.3[M+H]$^+$.

Step 2: To a stirred solution of Intermediate 45-1 (800 mg, 1.31 mmol) in THF (15 mL) was added BH$_3$·THF (1M in THF, 6.57 mL, 6.57 mmol) at rt. The resulting reaction mixture was heated to 55° C. for 24 h in a sealed tube. The reaction was then cooled to rt, and treated with MeOH (8 mL) and conc. HCl (2 mL) and heated to 65° C. After 10 h. the reaction was concentrated, diluted with 2N NaOH solution and extracted with EtOAc. The combined organic layers were dried over Na$_2$SO$_4$, filtered and concentrated. The crude product was purified by column chromatography (C$_{18}$, CH$_3$CN/H$_2$O) to afford Intermediate 45 (490 mg, 62% yield). LC/MS (ESI) m/z 595.3[M+H]$^+$.

Intermediate 46

Tert-butyl (R)-4-(4-(phenylthio)-3-((4-sulfamoyl-2-((trifluoromethyl)sulfonyl)phenyl)amino)butyl)piperazine-1-carboxylate

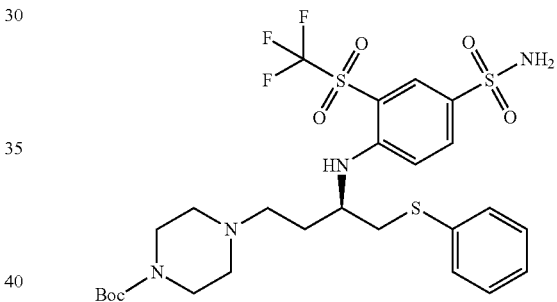

Step 1: (R)-tert-Butyl 4-(4-(phenylthio)-3-((4-sulfamoyl-2-((trifluoromethyl)sulfonyl)phenyl)-amino)butanoyl)piperazine-1-carboxylate (Intermediate 46-1) was prepared following the procedure described in Step 1 for Intermediate 45 using tert-butyl piperazine-1-carboxylate in place of N,N-dimethylpiperidin-4-amine. LC/MS (ESI) m/z 665.4 [M−H]$^-$.

Step 2: Intermediate 46 was prepared following the procedure described in Step 2 for Intermediate 45 using Intermediate 46-1 in place of Intermediate 45-1. LC/MS (ESI) m/z 653.2 [M+H]$^+$.

Intermediate 47

7-(Diethoxymethyl)spiro[3.5]nonan-6-one

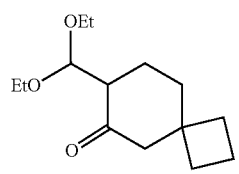 [SMILES: CCOC(OCC)C1CCC2(CCC2)CC1=O]

To a solution of triethyl orthoformate (7.28 ml, 43.79 mmol) in DCM (10 mL) at −30° C. was added BF$_3$·OEt$_2$ (6.75 ml, 54.72 mmol) dropwise over 20 min. The reaction mixture was warmed to 0° C. and stirred for 20 min. The reaction mixture was then cooled to −78° C. and spiro[3.5]nonan-6-one (3.0 g, 21.89 mmol) and N,N-diisopropylethylamine (11.4 ml, 35.7 mmol) were added and stirred for 90 min at the same temperature. The reaction was then carefully poured into a mixture of sat. aq. NaHCO$_3$ (20 mL) and DCM (30 mL). The resulting mixture was stirred for 15 min at rt and the organic layer was separated. The organic layer was washed with cold 1M H$_2$SO$_4$ (2×20 mL) and water. The organic layer was dried over Na$_2$SO$_4$, filtered and concentrated. The crude product was purified by column chromatography (SiO$_2$, Et$_2$O/pet. ether) to afford Intermediate 47 (3.00 g, 57% yield) as a colorless oil. 1H NMR (400 MHz, CDCl$_3$) δ 4.78 (d, J=6.4 Hz, 1H), 3.72-3.56 (m, 4H), 2.48-2.45 (m, 1H), 2.38 (d, J=1.2 Hz, 1H), 2.35 (d, J=0.8 Hz, 1H), 1.90-1.64 (m, 10H), 1.18 (t, J=6.8 Hz, 6H).

Intermediate 48

7-(Diethoxymethyl)-6-(3-(difluoromethyl)bicyclo[1.1.1]pentan-1-yl)spiro[3.5]nonan-6-ol

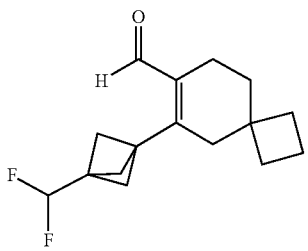 [SMILES: O=CC1=C(C23CC(C(F)F)(C2)C3)CC2(CCC2)CC1]

Step 1: To a stirred solution of Intermediate 24-2 (4.67 g, 19.15 mmol) in Et$_2$O (30 mL) under argon was added sec-BuLi (1.4 M in cyclohexane, 20.8 mL, 29.12 mmol) at −78° C. and the reaction was stirred for 10 minutes at the same temperature. The temperature was then warmed to 0° C. and stirred for 1 h. The reaction was cooled to −78° C. and a solution of Intermediate 47 (2 g, 8.32 mmol) in Et$_2$O (20 mL) was added dropwise for 5 minutes. The reaction was stirred at −78° C. for 1 h, and then warmed to 0° C. and stirred for 1 h. The reaction mixture was quenched with sat. aq. NH$_4$Cl solution (50 mL) at 0° C., and extracted with Et$_2$O (3×150 mL). The combined organic layers were dried over Na$_2$SO$_4$, filtered and concentrated to provide 7-(diethoxymethyl)-6-(3-(difluoromethyl)bicyclo[1.1.1]pentan-1-yl)spiro[3.5]nonan-6-ol (Intermediate 48-1) (1.5 g, crude) as a yellow oil. This was used in the next step without further purification.

Step 2: To a stirred solution of Intermediate 48-1 (1.5 g crude, 4.18 mmol) in 1,4-dioxane (30 mL) was added 2N HCl (aq.) (7 mL) and the resulting reaction mixture was stirred at 65-70° C. for 16 h. The reaction mixture was diluted with ice cold water (15 mL) and extracted with Et$_2$O (3×100 mL). The combined organic layers were dried over Na$_2$SO$_4$, filtered and concentrated. The product was purified by column chromatography (SiO$_2$, Et$_2$O/pet. ether) to afford Intermediate 48 (1 g, 45% yield over 2 steps) as a brown oil. $^1$H NMR (400 MHz, CDCl$_3$) δ 10.21 (s, 1H), 5.74 (t, J=56.4 Hz, 1H), 2.22-2.19 (m, 2H), 2.18 (s, 6H), 1.93-1.86 (m, 4H), 1.83-1.65 (m, 4H), 1.63-1.56 (m, 2H).

Intermediate 49

7-(diethoxymethyl)-6-(3-methylbicyclo[1.1.1]pentan-1-yl)spiro[3.5]nonan-6-ol

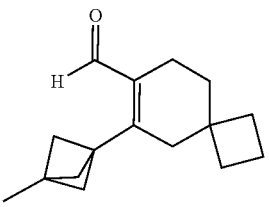 [SMILES: CC12CC(C3=C(C=O)CCC4(CCC4)C3)(C1)C2]

Step 1: 7-(diethoxymethyl)-6-(3-methylbicyclo[1.1.1]pentan-1-yl)spiro[3.5]nonan-6-ol (Intermediate 49-1) was prepared following the procedure described in Step 1 for Intermediate 48 using 1-iodo-3-methylbicyclo[1.1.1]pentane in place of Intermediate 24-2.

Step 2: Intermediate 49 was prepared following the procedure described in Step 2 for Intermediate 49 using Intermediate 49-1 in place of Intermediate 48-1. $^1$H NMR (400 MHz, CDCl$_3$) δ 10.23 (s, 1H), 2.23-2.20 (m, 2H), 1.96 (s, 6H), 1.89-1.71 (m, 8H), 1.58-1.55 (m, 2H), 1.16 (s, 3H).

Intermediate 50

2-((1H-pyrrolo[2,3-b]pyridin-5-yl)oxy)-4-(4-((6-(3-(difluoromethyl)bicyclo[1.1.1]pentan-1-yl)spiro[3.5]non-6-en-7-yl)methyl)piperazin-1-yl)benzoic Acid

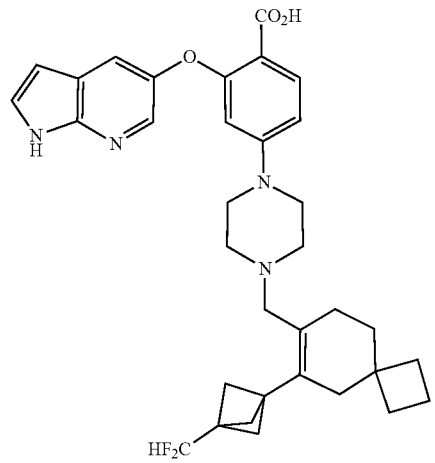

Step 1: Methyl 2-((1H-pyrrolo[2,3-b]pyridin-5-yl)oxy)-4-(4-((6-(3-(difluoromethyl)bicyclo[1.1.1]pentan-1-yl)spiro[3.5]non-6-en-7-yl)methyl)piperazin-1-yl)benzoate (Intermediate 50-1) was prepared following the procedure described in Step 1, Route C for Intermediate 28 using Intermediate 48 in place of Intermediate 22. LC/MS (ESI) m/z 603.5 [M+H]$^+$.

Step 2: Intermediate 50 was prepared following the procedure described in Step 5, Route B for Intermediate 28 using Intermediate 50-1 in place of methyl 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)benzoate. LC/MS (ESI) m/z 589.3.

Intermediate 51

2-((1H-pyrrolo[2,3-b]pyridin-5-yl)oxy)-4-(4-((6-(3-methylbicyclo[1.1.1]pentan-1-yl)spiro[3.5]non-6-en-7-yl)methyl)piperazin-1-yl)benzoic Acid

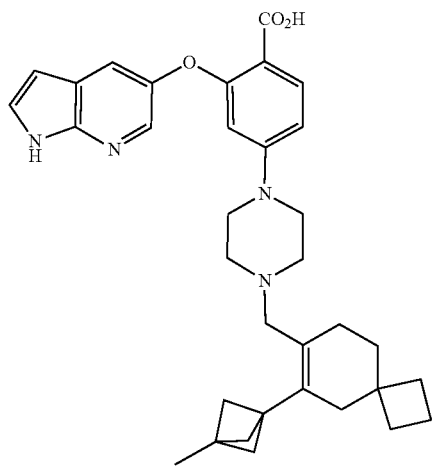 [SMILES: CC12CC(C3=C(CN4CCN(c5ccc(C(=O)O)c(Oc6cnc7[nH]ccc7c6)c5)CC4)CCC4(CCC4)C3)(C1)C2]

Step 1: Methyl 2-((1H-pyrrolo[2,3-b]pyridin-5-yl)oxy)-4-(4-((6-(3-methylbicyclo[1.1.1]pentan-1-yl)spiro[3.5]non-6-en-7-yl)methyl)piperazin-1-yl)benzoate: (Intermediate 51-1) was prepared following the procedure described in Step 1, Route C for Intermediate 28 using Intermediate 49 in place of Intermediate 22. LC/MS (ESI) m/z 567.3 [M+H]⁺.

Step 2: Intermediate 50 was prepared following the procedure described in Step 5, Route B for Intermediate 28 using Intermediate 51-1 in place of methyl 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)benzoate. LC/MS (ESI) m/z 553.3.

Intermediate 52

4-(((4-fluorotetrahydro-2H-pyran-4-yl)methyl)amino)-3-nitrobenzenesulfonamide

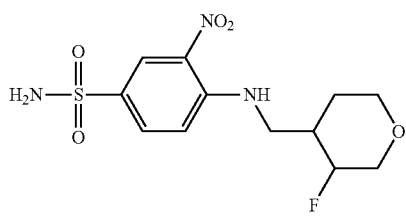 [SMILES: NS(=O)(=O)c1ccc(NCC2CCOCC2F)c([N+](=O)[O-])c1]

To a stirred solution of (4-fluorotetrahydro-2H-pyran-4-yl)methanamine (450 mg, 3.38 mmol) in THF (25 mL) was added 4-fluoro-3-nitrobenzenesulfonamide (669 mg, 3.04 mmol) followed by triethylamine (1.37 g, 13.52 mmol) at rt. After 16 h, the reaction was concentrated and triturated with EtOAc and Et₂O. The crude product was purified by column chromatography (C18, 0.1 µM NH₄CO₃H(aq.):CH₃CN) to provide Intermediate 52 (220 mg, 21% yield) as a yellow solid. LC/MS (ESI) m/z 334.3[M+H]⁺.

Intermediate 53

4-((4-fluorotetrahydro-2H-pyran-4-yl)methoxy)-3-nitrobenzenesulfonamide

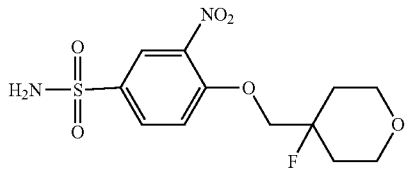 [SMILES: NS(=O)(=O)c1ccc(OCC2(F)CCOCC2)c([N+](=O)[O-])c1]

Intermediate 53 was prepared following the procedure described in Step 3 for Intermediate 7 by using (4-fluorotetrahydro-2H-pyran-4-yl)methanol in place of Intermediate 7-2. LC/MS (ESI) m/z 333.5 [M−H]⁻.

Intermediate 54

4-((2-morpholinoethyl)amino)-3-nitrobenzenesulfonamide

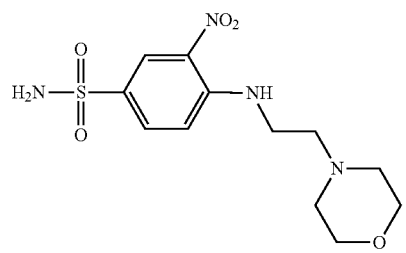 [SMILES: NS(=O)(=O)c1ccc(NCCN2CCOCC2)c([N+](=O)[O-])c1]

Intermediate 54 was prepared following a procedure described in a WO2010/065824. LC/MS (ESI) m/z 331.2 [M+H]⁺.

Intermediate 55

3-nitro-4-((tetrahydro-2H-pyran-4-yl)methoxy)benzenesulfonamide

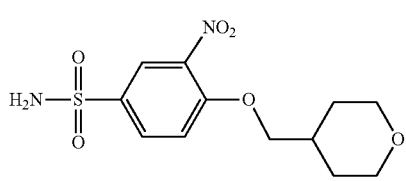 [SMILES: NS(=O)(=O)c1ccc(OCC2CCOCC2)c([N+](=O)[O-])c1]

Intermediate 55 was prepared following the procedure described in Step 3 for Intermediate 7 by using (tetrahydro-2H-pyran-4-yl)methanol in place of Intermediate 7-2. LC/MS (ESI) m/z 315.1 [M−H]⁻.

109

Intermediate 56

4-(4-((2-(3-(difluoromethyl)bicyclo[1.1.1]pentan-1-yl)-5,5-dimethylcyclohex-1-en-1-yl)methyl)piperazin-1-yl)benzoic Acid

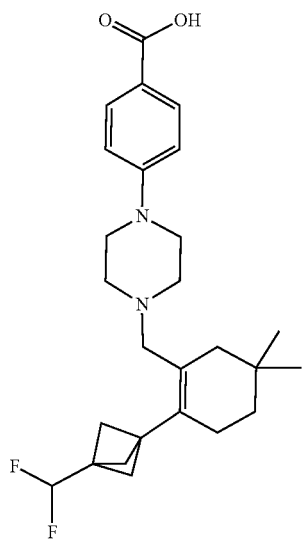 [SMILES: CC1(C)CCC(C23CC(C(F)F)(C2)C3)=C(CN2CCN(c3ccc(C(=O)O)cc3)CC2)C1]

Step 1: 2-(diethoxymethyl)-1-(3-(difluoromethyl)bicyclo[1.1.1]pentan-1-yl)-4,4-dimethylcyclohexanol (Intermediate 56-1) was prepared following the procedure described in Step 1, for Intermediate 25 using Intermediate 24-2 in place of i-iodo-3(trifluoromethyl)bicyclo[1.1.1]pentane and 2-(diethoxymethyl)-4,4-dimethylcyclohexanone in place of Intermediate 19. The crude product was used in the next step without purification.

Step 2: 2-(3-(difluoromethyl)bicyclo[1.1.1]pentan-1-yl)-5,5-dimethylcyclohex-1-enecarbaldehyde (Intermediate 56-2) was prepared following the procedure described in Step 2 for Intermediate 22, using Intermediate 56-1 in place of Intermediate 22-1. $^1$H NMR (400 MHz, CDCl$_3$) δ 10.25 (br s, 1H), 5.74 (t, J=56.0 Hz, 1H), 2.23-2.21 (m, 2H), 2.20 (s, 6H), 2.03 (br s, 2H), 1.38 (t, J=6.4 Hz, 2H), 0.89 (s, 6H).

Step 3: To a stirred solution of methyl 4-(piperazin-1-yl)benzoate (389 mg, 1.77 mmol) in THF (10 mL) was added a solution of Intermediate 56-2 (450 mg, 1.77 mmol) in THF (5 mL) at rt. The reaction was stirred for 1 h, treated with Na(OAc)$_3$BH (1.12 g, 5.31 mmol) at 0° C., and then warmed to rt. After 16 h, MeOH (10 mL) was added and the reaction was stirred for 30 minutes. The reaction mixture was concentrated under reduced pressure, dissolved in DCM (20 mL) and washed with sat. aq. NaHCO$_3$ (3×10 mL). The organic layer was dried over Na$_2$SO$_4$, filtered, and concentrated. The crude product was purified by column chromatography (SiO$_2$, EtOAc/pet. ether) to afford methyl 4-(4-((2-(3-(difluoromethyl)bicyclo[1.1.1]pentan-1-yl)-5,5-dimethylcyclohex-1-en-1-yl)methyl)piperazin-1-yl)benzoate (Intermediate 56-3) (400 mg, 49% yield) as an off-white solid. LC/MS (ESI) m/z 459.2 [M+H]$^+$.

Step 4: Intermediate 56 was prepared following the procedure described in Step 5, Route B for Intermediate 28 using Intermediate 56-3 in place of methyl 2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)benzoate. LC/MS (ESI) m/z 445.4 [M+H]$^+$.

Intermediate 57

(R)-4-((4-(3-hydroxyazetidin-1-yl)-1-(phenylthio)butan-2-yl)amino)-3-((trifluoromethyl)sulfonyl)benzenesulfonamide

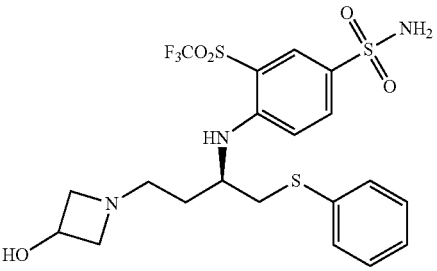

Step 1: To a solution of (R)-4-(phenylthio)-3-((4-sulfamoyl-2-((trifluoromethyl)sulfonyl)phenyl)amino)butanoic acid (1.5 g, 3.01 mmol) and 0-(Benzotriazol-1-yl)-N,N,N',N'-tetramethyluronium tetrafluoroborate (TBTU) (1.09 g, 3.41 mmol) in DCM (3 mL) at 0° C. was added N-methylmorpholine (1.3 mL, 9.3 mmol) and DMF (1.5 mL). The reaction was warmed to rt and stirred for 0.5 h. The reaction mixture was then cooled to 0° C., and azetidin-3-ol (264 mg, 3.61 mmol) was added and the reaction was warmed to rt. After 16 h, the reaction was quenched with sat. aq. NaHCO$_3$ (50 mL) and extracted with EtOAc (3×100 mL). The combined organic layers were dried over Na$_2$SO$_4$, filtered and concentrated. The crude product was purified by column chromatography (SiO$_2$, MeOH/DCM) to afford (R)-4-((4-(3-hydroxyazetidin-1-yl)-4-oxo-1-(phenylthio)butan-2-yl)amino)-3-((trifluoro-methyl)sulfonyl)benzenesulfonamide (Intermediate 57-1) (1.00 g, 60% yield) as an off-white solid. LC/MS (ESI) m/z 554.1.

Step 2: To a stirred solution of Intermediate 57-1 (1.0 g, 1.80 mmol) in THF (20 mL) at 0° C. was added BH$_3$·THF (1 M in THF, 5.0 mL, 5 mmol) and the reaction was warmed to rt. After 1 h, the reaction mixture was heated to 55° C. and stirred for 16 h in a sealed tube. The reaction mixture was then cooled to 0° C., quenched with NH$_3$ (7.0 M in MeOH, 5 mL) at 0° C. and warmed to rt. After 16 h. the reaction was concentrated and purified by column chromatography (SiO$_2$, MeOH/DCM) to afford Intermediate 57 (500 mg, 51% yield) as an off-white solid. LC/MS (ESI) m/z 540.3 [M+H]$^+$.

Intermediate 58

4-(4-((6-(3-(difluoromethyl)bicyclo[1.1.1]pentan-1-yl)spiro[3.5]non-6-en-7-yl)methyl)piperazin-1-yl)benzoic Acid

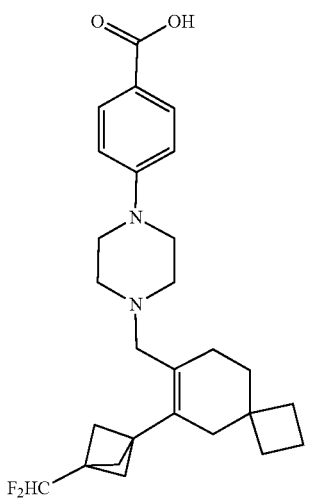 [SMILES: O=C(O)c1ccc(N2CCN(CC3=C(C45CC(C(F)F)(C4)C5)CC4(CCC4)CC3)CC2)cc1]

Step 1: Methyl 4-(4-((6-(3-(difluoromethyl)bicyclo[1.1.1]pentan-1-yl)spiro[3.5]non-6-en-7-yl)methyl)piperazin-1-yl)benzoate (Intermediate 58-1) was prepared following the procedure described in Step 3, for Intermediate 56 using Intermediate 48 in place of Intermediate 56-2. LC/MS (ESI) m/z 471.3 [M+H]⁺.

Step 2: Intermediate 58 was prepared following the procedure described in Step 5, Route B for Intermediate 28 using Intermediate 58-1 in place of methyl 2-((1H-pyrrolo[2,3-b]pyridin-5-yl)oxy)-4-(4-((4,4-dimethyl-2-(3-methyl-bicyclo[1.1.1]pentan-1-yl)cyclohex-1-en-1-yl)methyl)piperazin-1-yl)benzoate. LC/MS (ESI) m/z 457.5 [M+H]⁺.

Intermediate 59

(R)-4-((4-(4-(2-((tert-butyldiphenylsilyl)oxy)ethyl)piperazin-1-yl)-1-(phenylthio)butan-2-yl)amino)-3-((trifluoromethyl)sulfonyl)benzenesulfonamide

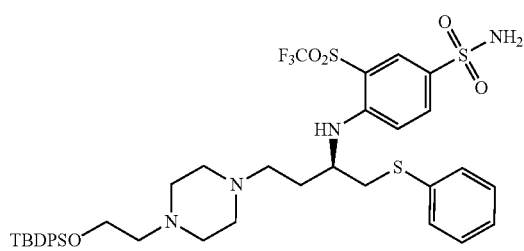

Step 1: (R)-4-((4-(4-(2-((tert-butyldiphenylsilyl)oxy)ethyl)piperazin-1-yl)-4-oxo-1-(phenylthio)butan-2-yl)amino)-3-((trifluoromethyl)sulfonyl)benzenesulfonamide (Intermediate 59-1) was prepared following the procedure described in Step 1 for Intermediate 45 using 1-(2-((tert-butyldiphenylsilyl)oxy)ethyl)piperazine in place of N,N-dimethylpiperidin-4-amine. LC/MS (ESI) m/z 849.3 [M+H]⁺.

Step 2: Intermediate 59 was prepared following the procedure described in Step 2, for Intermediate 57 using Intermediate 59-1 in place of Intermediate 57-1. LC/MS (ESI) m/z 835.0 [M+H]⁺.

Intermediate 60

(R)-4-((4-((2-((tert-butyldiphenylsilyl)oxy)ethyl)(ethyl)amino)-1-(phenylthio)butan-2-yl)amino)-3-((trifluoromethyl)sulfonyl)benzenesulfonamide

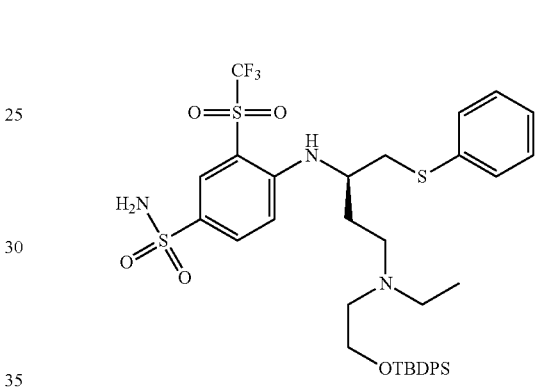

Step 1: 2-((tert-butyldiphenylsilyl)oxy)-N-ethylethanamine (Intermediate 60-1) was prepared following a procedure described in WO2012/017251A1. LC/MS (ESI) m/z 328.4 [M+H]⁺.

Step 2: To a stirred solution of (R)-4-(phenylthio)-3-((4-sulfamoyl-2-((trifluoromethyl)sulfonyl)phenyl)amino)butanoic acid (500 mg, 1.0 mmol) in CH₃CN (10 mL) at 0° C. was added Intermediate 60-1 (328 mg, 1.01 mmol) in CH₃CN (2 mL), followed by N-methyl imidazole (250 mg, 3.1 mmol) and N,N,N',N'-tetramethylchloroformamidinium hexafluorophosphate (TCFH) (308 mg, 1.1 mmol). The reaction was warmed to rt and stirred for 16 h. The reaction was then diluted with water and extracted with EtOAc (3×100 mL). The combined organic layers were washed with sat. aq. NaHCO₃ (2×20 mL), water (2×10 mL) and then brine (2×20 mL). The organic layer was dried over Na₂SO₄, filtered and concentrated. The crude product was purified by column chromatography (SiO₂, EtOAc/pet. ether) to afford (R)—N-(2-((tert-butyldiphenylsilyl)oxy)ethyl)-N-ethyl-4-(phenylthio)-3-((4-sulfamoyl-2-((trifluoromethyl)sulfonyl)phenyl)amino)butanamide (Intermediate 60-2) (500 mg, 65% yield) as a yellow oil. LC/MS (ESI) m/z 808.4 [M+H]⁺.

Step 2: Intermediate 60 was prepared following the procedure described in Step 2, for Intermediate 57 using Intermediate 60-2 in place of Intermediate 57-1. LC/MS (ESI) m/z 794.8 [M+H]⁺.

Intermediate 61

4-(((2R)-4-(3-Hydroxypyrrolidin-1-yl)-1-(phenyl-thio)butan-2-yl)amino)-3-((trifluoromethyl)sulfonyl)benzenesulfonamide

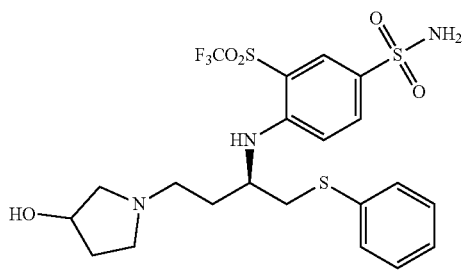

Step 1: 4-(((2R)-4-(3-Hydroxypyrrolidin-1-yl)-4-oxo-1-(phenylthio)butan-2-yl)amino)-3-((trifluoromethyl)sulfonyl)benzenesulfonamide (Intermediate 61-1) was prepared following the procedure described in Step 1, for Intermediate 45 using pyrrolidin-3-ol in place of N,N-dimethylpiperidin-4-amine. LC/MS (ESI) m/z 568.1 [M+H]$^+$.

Step 2: Intermediate 61 was prepared following the procedure described in Step 2, for Intermediate 57 using Intermediate 61-1 in place of Intermediate 57-1. LC/MS (ESI) m/z 554.4 [M+H]$^+$.

Intermediate 62

2-((1H-pyrrolo[2,3-b]pyridin-5-yl)oxy)-4-(4-((2-(3-chlorobicyclo[1.1.1]pentan-1-yl)cyclohex-1-en-1-yl)methyl)piperazin-1-yl)benzoic Acid

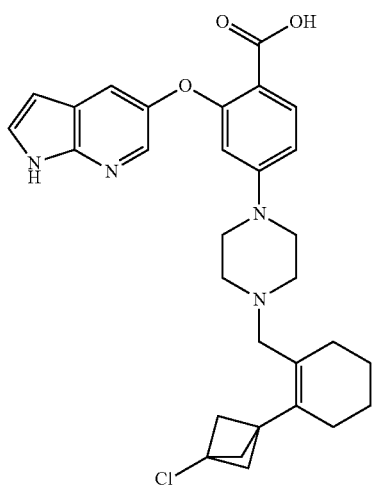 [SMILES: O=C(O)c1ccc(N2CCN(CC3=C(C45CC(Cl)(C4)C5)CCCC3)CC2)cc1Oc1cnc2[nH]ccc2c1]

Step 1: 1-(3-Chlorobicyclo[1.1.1]pentan-1-yl)hex-5-en-1-one (Intermediate 62-1) was prepared following the procedure described in Step 1 for Intermediate 26 using 5-bromopent-1-ene in place of 5-iodo-3,3-dimethylpent-1-ene. $^1$H NMR (300 MHz, CDCl$_3$) δ 5.84-5.66 (m, 1H), 5.03-4.97 (m, 2H), 2.48 (s, 6H), 2.44 (t, J=7.2 Hz, 2H), 2.08-2.01 (m, 2H), 1.71-1.61 (m, 2H).

Step 2: E/Z-7-(3-chlorobicyclo[1.1.1]pentan-1-yl)-7-oxo-hept-2-enenitrile (Intermediate 62-2) was prepared following the procedure described in Step 2 for Intermediate 26 using Intermediate 62-1 in place of Intermediate 26-1. LC/MS (ESI) m/z 236.3 [M+H]$^+$.

Step 3: 7-(3-Chlorobicyclo[1.1.1]pentan-1-yl)-7-oxoheptanenitrile (Intermediate 62-3) was prepared following the procedure described in Step 3 for Intermediate 26 using Intermediate 62-2 in place of Intermediate 26-2. $^1$H NMR (400 MHz, CDCl$_3$) δ 2.47 (t, J=7.2 Hz, 2H), 2.40 (s, 6H), 2.35 (t, J=6.8 Hz, 2H), 1.70-1.62 (m, 2H), 1.61-1.55 (m, 2H), 1.48-1.41 (m, 2H).

Step 4: 2-(3-chlorobicyclo[1.1.1]pentan-1-yl)cyclohex-1-enecarbonitrile (Intermediate 62-4) was prepared following the procedure described in Step 4 for Intermediate 26 using Intermediate 62-3 in place of Intermediate 26-3. LC/MS (ESI) m/z 208.1 [M+H]$^+$.

Step 5: 2-(3-chlorobicyclo[1.1.1]pentan-1-yl)cyclohex-1-enecarbaldehyde (Intermediate 62-5) was prepared following the procedure described in Step 5 for Intermediate 26 using Intermediate 62-4 in place of Intermediate 26-4. $^1$H NMR (300 MHz, CDCl$_3$) δ 10.16 (s, 1H), 2.46 (s, 6H), 2.23-2.21 (m, 2H), 2.15-2.13 (m, 2H), 1.64-1.54 (m, 4H).

Step 6: tert-butyl 2-(1H-pyrrolo[2,3-b]pyridin-5-yloxy)-4-(4-((2-(3-chlorobicyclo[1.1.1]pentan-1-yl)cyclohex-1-enyl)methyl)piperazin-1-yl)benzoate (Intermediate 62-6) was prepared following the procedure described in Step 6, Route A for Intermediate 28 using Intermediate 62-5 in place of Intermediate 22. LC/MS (ESI) m/z 589.3 [M+H]$^+$.

Step 7: Intermediate 62 was prepared following the procedure described in Step 7, for Intermediate 32, using Intermediate 62-6 in place of Intermediate 32-6. LC/MS (ESI) m/z 533.3 [M+H]$^+$.

General Procedure A: Acyl Sulfonamide Formation

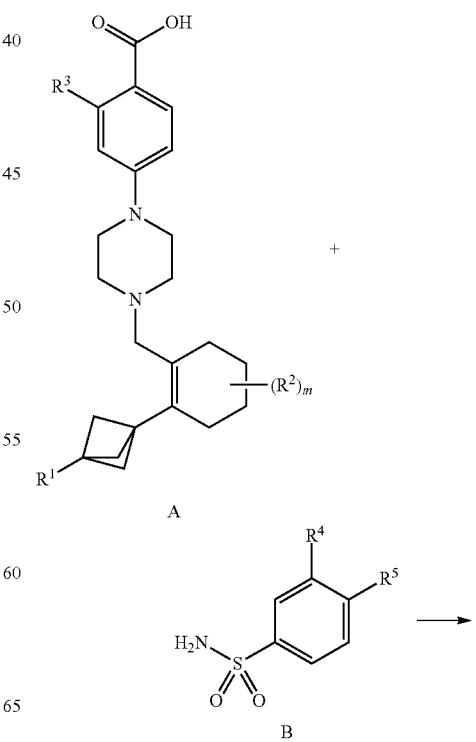

-continued

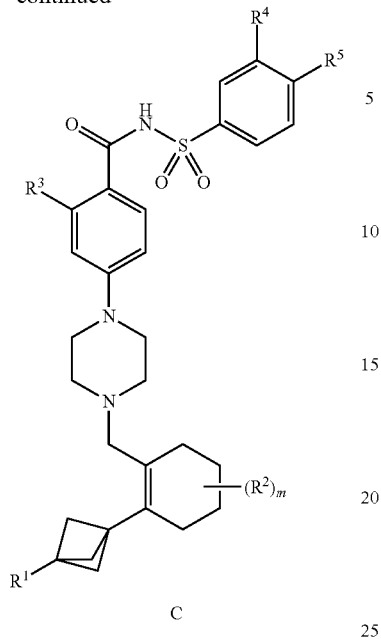

C

To a solution of corresponding sulfonamide B or acid A (1.0-1.2 equiv. Note #1) in DCM (0.01-0.1 M) at 0° C. was added EDC·HCl (1-2.5 equiv.) followed by DMAP (1-2 equiv.). After 10 min, the appropriate acid A or sulfonamide B (1-1.5 equiv. Note #1) and N-methylmorpholine (2-4 equiv. Note #2) were added at 0° C. and the reaction was warmed to rt or to 35° C. Upon completion as determined by LCMS (or TLC), water was added and the reaction was extracted with DCM. The combined organic layers were dried over $Na_2SO_4$ and concentrated. The crude product C was either purified by 1) column chromatography ($SiO_2$), 2) HPLC (10 mM $NH_4CO_3H$(aq): $CH_3CN$ or MeOH) or 3) trituration with an organic solvent.

Note #1: In some instances, the TFA salt of acid A was used.

Note #2: In some instances, N-methylmorpholine was not added.

General Procedure B: Acyl Sulfonamide Formation

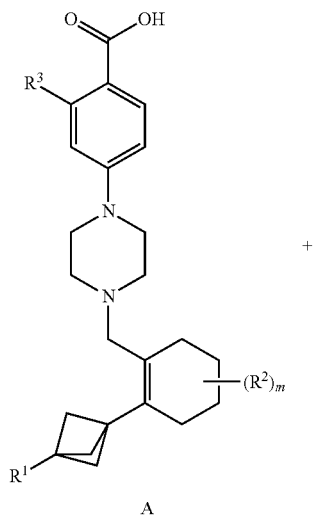

A

-continued

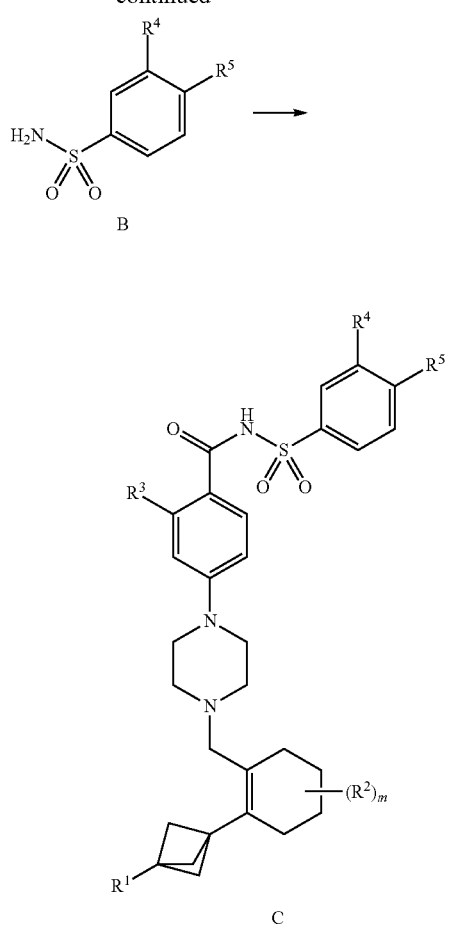

To a solution of corresponding sulfonamide B (1.0 equiv) in DCM (0.01-0.1 M) at rt was added EDC·HCl (1.5-1.75 equiv.) and DMAP (1-2.5 equiv.). In a separate flask, the appropriate acid A (1-1.1 equiv.) was dissolved in DCM (0.02-0.1M) was treated with $Et_3N$ (2 equiv). Note #1). After 15 min, the acid solution was added to the sulfonamide suspension and either stirred at rt or heated to 35° C. Upon completion as determined by LCMS, N,N-dimethylethylenediamine (2-2.5 equiv., Note #2) was added to the reaction mixture and the reaction was stirred for 90 min. The reaction mixture was then washed with 10% aq. AcOH (Note #3), 5% $NaHCO_3$(aq.) and then with 5% NaCl (aq.). The organic layer was concentrated, and crude product C was either purified by 1) column chromatography ($SiO_2$), 2) HPLC (10 mM $NH_4CO_3H$(aq): $CH_3CN$ or MeOH), or 3) trituration with an organic solvent.

Note #1: In some instances, $Et_3N$ was added to the flask containing sulfonamide B Note #2: In some instances, N,N-dimethylethylenediamine was not added during the workup.

Note #3: In some instances, the organic layer was diluted with DCM and MeOH to solubilize the crude product.

Example 1

2-(1H-Pyrrolo[2,3-b]pyridin-5-yl-oxy)-4-(4-((2-(3-chlorobicyclo[1.1.1]pentan-1-yl)-4,4-dimethylcyclohex-1-en-yl)methyl)piperazin-1-yl)-N-(3-nitro-4-(((tetrahydro-2H-pyran-4-yl)methylamino)phenylsulfonyl)benzamide

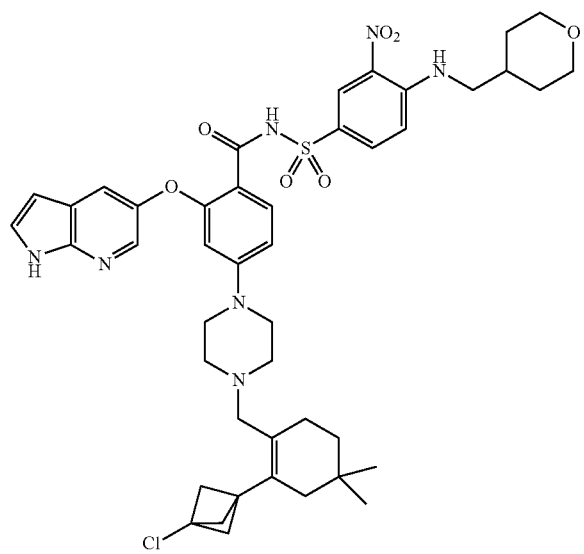 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(C23CC(Cl)(C2)C3)C1]

Representative example of General Procedure A: To a solution of 3-nitro-4-(((tetrahydro-2H-pyran-4-yl)methyl)amino)benzenesulfonamide (63 mg, 0.20 mmol) in DCM (20 mL) was added EDC·HCl (58 mg, 0.30 mmol) followed by DMAP (49 mg, 0.40 mmol) at 0° C. After 10 min, Intermediate 26 (140 mg, 0.20 mmol) and N-methylmorpholine (0.07 mL, 0.60 mmol) were added and the reaction was warmed to rt. After 16 h, water was added, and the mixture was extracted with DCM. The combined organic layers were dried over $Na_2SO_4$, filtered and concentrated. The crude product was purified by HPLC (10:90 to 99:1 10 mM $NH_4CO_3H$(aq.)/$CH_3CN$) to afford Example 1 (69 mg, 39%) as a yellow solid. $^1$H NMR (300 MHz, DMSO-$d_6$) δ 11.68 (br s, 1H), 11.42 (br s, 1H), 8.58 (br s, 1H), 8.53 (s, 1H), 8.03 (d, J=2.1 Hz, 1H), 7.77 (d, J=8.4 Hz, 1H), 7.54-7.46 (m, 3H), 7.10-7.02 (m, 1H), 6.74-6.68 (m, 1H), 6.38 (s, 1H), 6.25 (s, 1H), 3.89-3.82 (m, 2H), 3.33-3.22 (m, 4H), 3.19-3.05 (m, 4H), 2.90 (s, 2H), 2.33 (br s, 4H), 2.29 (s, 6H), 2.05-1.95 (m, 2H), 1.95-1.82 (m, 1H), 1.69-1.57 (m, 4H), 1.32-1.18 (m, 4H), 0.82 (s, 6H). LC/MS (ESI) m/z 858.4 [M+H]$^+$.

Example 2

2-(1H-pyrrolo[2,3-b]pyridin-5-yl-oxy)-N-(4-(2-oxaspiro[3.3]heptan-6-yl-methylamino)-3-nitrophenylsulfonyl)-4-(4-((2-(3-chlorobicyclo[1.1.1]pentan-1-yl)-4,4-dimethylcyclohex-1en-yl)methyl)piperazin-1-yl)benzamide

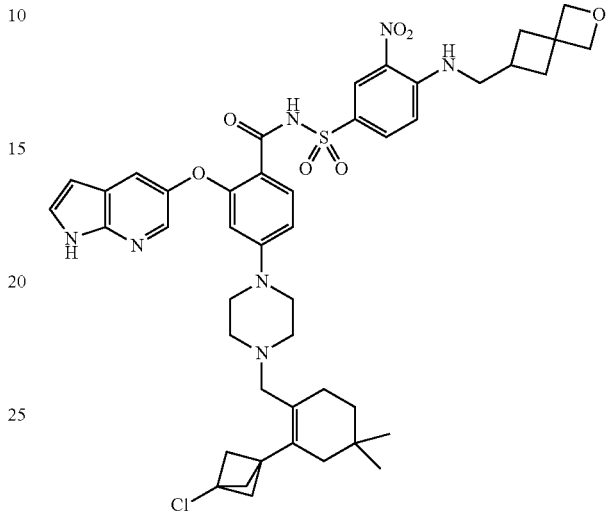

Example 2 was prepared following General Procedure A using Intermediate 26 and Intermediate 3. $^1$H NMR (400 MHz, CDCl$_3$) δ 10.13 (br s, 1H), 8.89 (d, J=2 Hz, 1H), 8.82 (br s, 1H), 8.33 (t, J=5.2 Hz, 1H), 8.22 (d, J=2.8 Hz, 1H), 8.17 (dd, J=9.4, 1.6 Hz, 1H), 7.98 (d, J=9.6 Hz, 1H), 7.72 (d, J=2.4 Hz, 1H), 7.44 (br s, 1H), 6.88 (d, J=9.2 Hz, 1H), 6.59-6.56 (m, 2H), 6.02 (s, 1H), 4.74 (s, 2H), 4.63 (s, 2H), 3.32 (t, J=5.2 Hz, 2H), 3.15-3.05 (m, 4H), 2.89 (s, 2H), 2.55-2.45 (m, 2H), 2.38-2.28 (m, 4H), 2.25 (s, 6H), 2.08-1.95 (br s, 4H), 1.64 (s, 2H), 1.33-1.25 (m, 2H), 0.84 (s, 6H); LC/MS (ESI) m/z 870.6 [M+H]$^+$.

Example 3

2-((1H-pyrrolo[2,3-b]pyridin-5-yl)oxy)-N-((4-((2-(2-oxa-8-azaspiro[4.5]decan-8-yl)ethyl)amino)-3-nitrophenyl)sulfonyl)-4-(4-((2-(3-chlorobicyclo[1.1.1]pentan-1-yl)-4,4-dimethylcyclohex-1-en-1-yl)methyl)piperazin-1-yl)benzamide

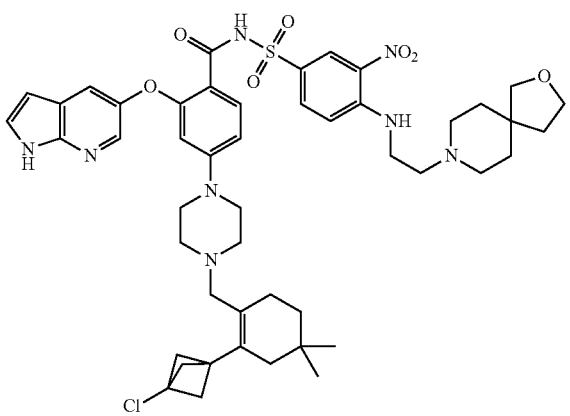 [SMILES: CC1(C)CCC(CN2CCN(c3ccc(C(=O)NS(=O)(=O)c4ccc(NCCN5CCC6(CCOC6)CC5)c([N+](=O)[O-])c4)c(Oc4cnc5[nH]ccc5c4)c3)CC2)=C(C23CC(Cl)(C2)C3)C1]

Example 3 was prepared following General Procedure A using Intermediate 26 and Intermediate 4. $^1$H NMR (300 MHz, CDCl$_3$) δ 10.18 (br s, 1H), 9.21 (br s, 1H), 8.99 (br s, 1H), 8.88 (d, J=2.1 Hz, 1H), 8.21 (d, J=2.1 Hz, 1H), 8.16 (dd, J=9.0, 1.8 Hz, 1H), 7.97 (d, J=8.7 Hz, 1H), 7.71 (d, J=2.1 Hz, 1H), 7.45 (t, J=3.0 Hz, 1H), 6.86 (d, J=9.0 Hz, 1H), 6.60-6.54 (m, 2H), 6.03 (d, J=1.8 Hz, 1H), 3.85 (t, J=7.2 Hz, 2H), 3.57 (s, 2H), 3.42-3.36 (m, 2H), 3.10 (br s, 4H), 2.89 (s, 2H), 2.71 (t, J=5.7 Hz, 2H), 2.58-2.38 (m, 4H), 2.38-2.29 (m, 4H), 2.24 (s, 6H), 2.06-1.95 (m, 2H), 1.77-1.63 (m, 8H), 1.27-1.23 (m, 2H), 0.83 (s, 6H); LC/MS (ESI) m/z 927.6 [M+H]$^+$.

Example 4

2-(1H-pyrrolo[2,3-b]pyridin-5-yloxy)-N-(4-(2-(7-oxa-2-azaspiro[3.5]nonan-2-yl)ethylamino)-3-nitrophenylsulfonyl)-4-(4-((2-(3-chlorobicyclo[1.1.1]pentan-1-yl)-4,4-dimethylcyclohex-1-enyl)methyl)piperazin-1-yl)benzamide

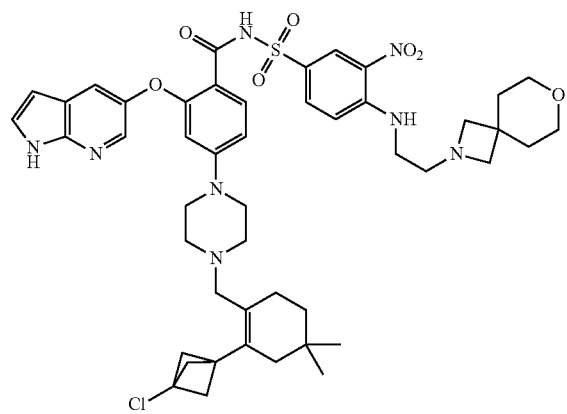 [SMILES: CC1(C)CCC(CN2CCN(c3ccc(C(=O)NS(=O)(=O)c4ccc(NCCN5CC6(CCOCC6)C5)c([N+](=O)[O-])c4)c(Oc4cnc5[nH]ccc5c4)c3)CC2)=C(C23CC(Cl)(C2)C3)C1]

Example 4 was prepared following General Procedure A using Intermediate 26 and Intermediate 5. $^1$H NMR (400 MHz, DMSO-d$_6$) δ 11.60 (s, 1H), 8.50 (br s, 1H), 8.46 (s, 1H), 7.97 (d, J=2.4 Hz, 1H), 7.75 (d, J=8.8 Hz, 1H), 7.57 (d, J=8.8 Hz, 1H), 7.45 (t, J=2.4 Hz, 1H), 7.38 (br s, 1H), 6.93 (d, J=9.2 Hz, 1H), 6.69 (dd, J=9.4, 2.0 Hz, 1H), 6.34 (dd, J=3.2, 2.0 Hz, 1H), 6.28 (d, J=2.0 Hz, 1H), 3.60-3.38 (m, 10H), 3.16-2.95 (m, 6H), 2.89 (s, 2H), 3.38-2.30 (m, 4H), 2.29 (s, 6H), 2.05-1.98 (m, 2H), 1.71-1.66 (m, 6H), 1.23 (t, J=6.4 Hz, 2H), 0.82 (s, 6H), one NH proton not observed; $^1$H NMR (400 MHz, DMSO-d$_6$) LC/MS (ESI) m/z 913.5 [M+H]$^+$.

Example 5

2-((1H-pyrrolo[2,3-b]pyridin-5-yl)oxy)-N-((4-(((7-oxaspiro[3.5]nonan-2-yl)methyl)amino)-3-nitrophenyl)sulfonyl)-4-(4-((2-(3-chlorobicyclo[1.1.1]pentan-1-yl)-4,4-dimethylcyclohex-1-en-1-yl)methyl)piperazin-1-yl)benzamide

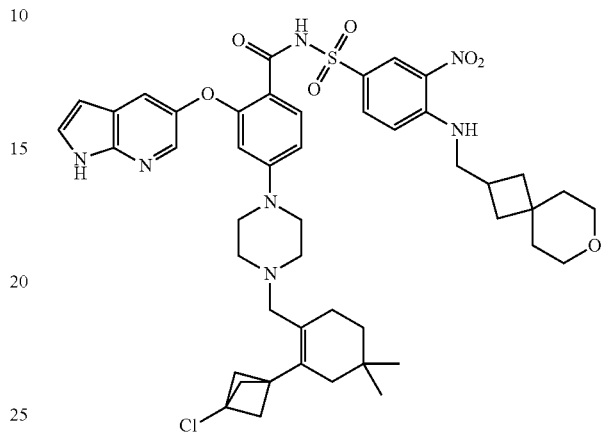

Example 5 was prepared following General Procedure A using Intermediate 26 and Intermediate 6. $^1$H NMR (400 MHz, CDCl$_3$) δ 10.13 (br s, 1H), 8.88 (d, J=2.4 Hz, 1H), 8.81 (br s, 1H), 8.37 (t, J=4.8 Hz, 1H), 8.21 (d, J=2.4 Hz, 1H), 8.17 (dd, J=9.6, 2.4 Hz, 1H), 7.97 (d, J=9.2 Hz, 1H), 7.71 (d, J=2.8 Hz, 1H), 7.44 (t, J=2.8 Hz, 1H), 6.88 (d, J=9.6 Hz, 1H), 6.59-6.54 (m, 2H), 6.01 (d, J=2.0 Hz, 1H), 3.64 (t, J=4.8 Hz, 2H), 3.56 (t, J=5.2 Hz, 2H), 3.39-3.36 (m, 2H), 3.10 (br s, 4H), 2.89 (s, 2H), 2.70-2.65 (m, 1H), 2.32 (br s, 4H), 2.24 (s, 6H), 2.14-2.09 (m, 2H), 2.01 (br s, 2H), 1.68 (t, J=5.2 Hz, 2H), 1.63-1.56 (m, 6H), 1.25 (t, J=6.0 Hz, 2H), 0.83 (s, 6H); LC/MS (ESI) m/z 898.4 [M+H]$^+$.

Example 6

2-((1H-pyrrolo[2,3-b]pyridin-5-yl)oxy)-N-((4-((4-oxaspiro[2.4]heptan-6-yl)oxy)-3-nitrophenyl)sulfonyl)-4-(4-((2-(3-chlorobicyclo[1.1.1]pentan-1-yl)-4,4-dimethylcyclohex-1-en-1-yl)methyl)piperazin-1-yl)benzamide

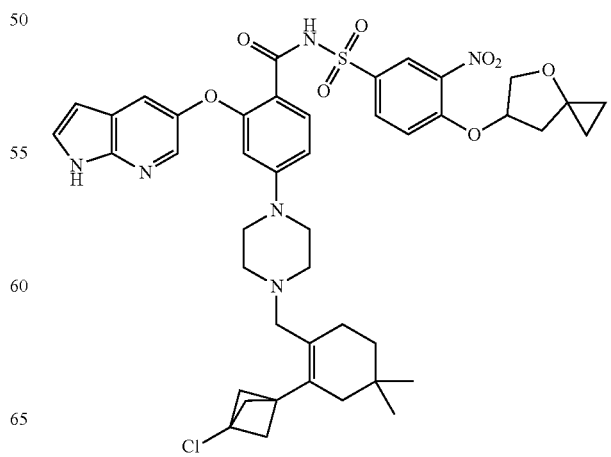

Example 6 was prepared following General Procedure A using Intermediate 26 and Intermediate 7. LC/MS (ESI) m/z 857.4 [M+H]⁺.

Example 7

2-(1H-pyrrolo[2,3-b]pyridin-5-yloxy)-N-(4-(2-(2-oxa-6-azaspiro[3.3]heptan-6-yl)ethoxy)-3-nitrophenylsulfonyl)-4-(4-((2-(3-chlorobicyclo[1.1.1]pentan-1-yl)-4,4-dimethylcyclohex-1-enyl)methyl)piperazin-1-yl)benzamide

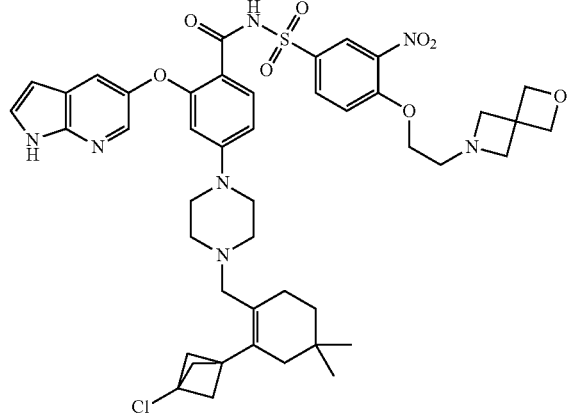 [SMILES: CC1(C)CCC(CN2CCN(c3ccc(C(=O)NS(=O)(=O)c4ccc(OCCN5CC6(COC6)C5)c([N+](=O)[O-])c4)c(Oc4cnc5[nH]ccc5c4)c3)CC2)=C(C23CC(Cl)(C2)C3)C1]

Example 7 was prepared following General Procedure A using Intermediate 26 and Intermediate 8. LC/MS (ESI) m/z 886.5 [M+H]⁺.

Example 8

2-(1H-pyrrolo[2,3-b]pyridin-5-yloxy)-N-(4-(2-oxaspiro[3.3]heptan-6-ylmethoxy)-3-nitrophenylsulfonyl)-4-(4-((2-(3-chlorobicyclo[1.1.1]pentan-1-yl)-4,4-dimethylcyclohex-1-enyl)methyl)piperazin-1-yl)benzamide

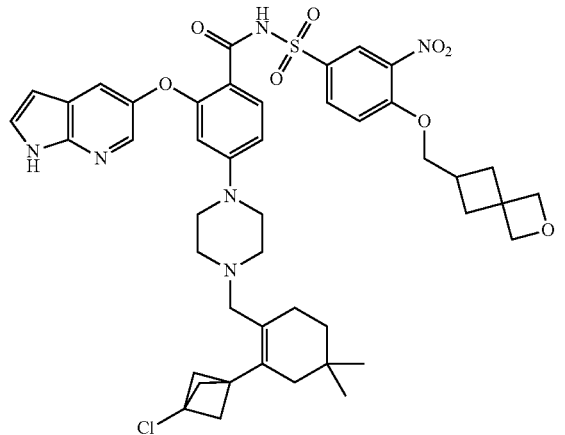 [SMILES: CC1(C)CCC(CN2CCN(c3ccc(C(=O)NS(=O)(=O)c4ccc(OCC5CC6(COC6)C5)c([N+](=O)[O-])c4)c(Oc4cnc5[nH]ccc5c4)c3)CC2)=C(C23CC(Cl)(C2)C3)C1]

Example 8 was prepared following General Procedure A using Intermediate 26 and Intermediate 9. LC/MS (ESI) m/z 871.6 [M+H]⁺.

Example 9

2-(1H-pyrrolo[2,3-b]pyridin-5-yloxy)-4-(4-((4,4-dimethyl-2-(3-methylbicyclo[1.1.1]pentan-1-yl)cyclohex-1-enyl)methyl)piperazin-1-yl)-N-(3-nitro-4-((tetrahydro-2H-pyran-4-yl)methylamino)phenylsulfonyl)benzamide

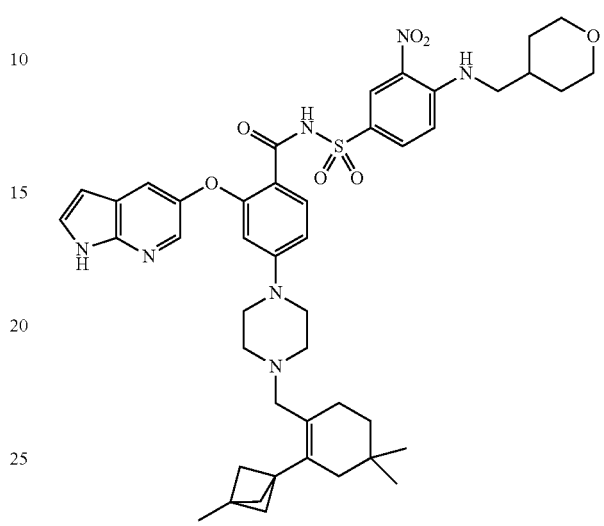

Example 9 was prepared following General Procedure A using Intermediate 28 and 3-nitro-4-(((tetrahydro-2H-pyran-4-yl)methyl)amino)benzenesulfonamide. ¹H NMR (400 MHz, DMSO-d₆) δ 11.68 (s, 1H), 11.42 (br s, 1H), 8.58 (br s, 1H), 8.54 (s, 1H), 8.03 (s, 1H), 7.80-7.76 (m, 1H), 7.53-7.48 (m, 3H), 7.12-7.05 (m, 1H), 6.74-6.70 (m, 1H), 6.38 (s, 1H), 6.25 (s, 1H), 3.85-3.83 (m, 2H), 3.30-3.23 (m, 4H), 3.19-3.05 (m, 4H), 2.99 (br s, 2H), 2.38-2.32 (m, 4H), 2.05-1.95 (m, 2H), 1.93-1.85 (m, 1H), 1.75 (s, 6H), 1.67-1.58 (m, 4H), 1.30-1.20 (m, 4H), 1.10 (s, 3H), 0.81 (s, 6H); LC/MS (ESI) m/z 838.5 [M+H]⁺.

Example 10

2-(1H-pyrrolo[2,3-b]pyridin-5-yloxy)-4-(4-((2-(3-fluorobicyclo[1.1.1]pentan-1-yl)-4,4-dimethylcyclohex-1-enyl)methyl)piperazin-1-yl)-N-(3-nitro-4-((tetrahydro-2H-pyran-4-yl)methylamino)phenylsulfonyl)benzamide

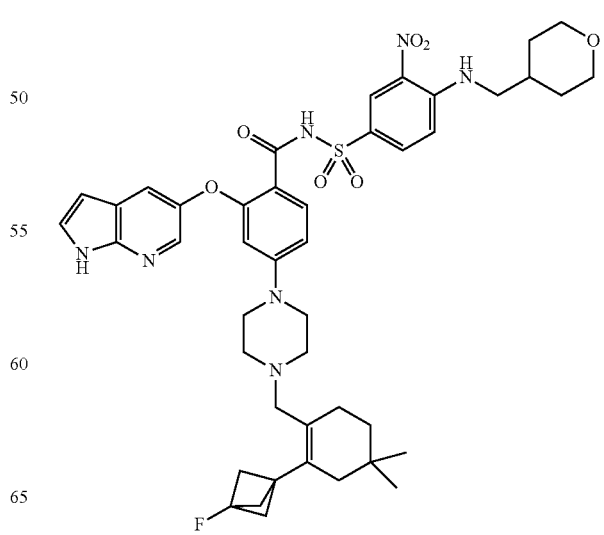

Example 10 was prepared following General Procedure A using Intermediate 27 and 3-nitro-4-((((tetrahydro-2H-pyran-4-yl)methyl)amino)benzenesulfonamide. ¹H NMR (300 MHz, CDCl₃) δ 10.20 (br s, 2H), 9.09 (br s, 1H), 8.90 (d, J=2.4 Hz, 1H), 8.52 (t, J=5.7 Hz, 1H), 8.22-8.15 (m, 2H), 7.98 (d, J=9.3 Hz, 1H), 7.71 (d, J=9.3 Hz, 1H), 7.45 (t, J=3.0 Hz, 1H), 6.92 (d, J=9.3 Hz, 1H), 6.60-6.54 (m, 2H), 6.03-6.01 (m, 1H), 4.03 (dd, J=11.5, 3.9 Hz, 2H), 3.46-3.38 (m, 2H), 3.27 (t, J=6.0 Hz, 2H), 3.12-3.09 (m, 4H), 2.91 (s, 2H), 2.35-2.33 (m, 4H), 2.15 (d, J=2.4 Hz, 6H), 2.09-1.95 (m, 3H), 1.77-1.62 (m, 4H), 1.51-1.38 (m, 2H), 1.27 (t, J=6.3 Hz, 2H), 0.84 (s, 6H); LC/MS (ESI) m/z 842.4 [M+H]⁺.

Example 11

2-((1H-pyrrolo[2,3-b]pyridin-5-yl)oxy)-N-((4-(((7-oxaspiro[3.5]nonan-2-yl)methyl)amino)-3-nitrophenyl)sulfonyl)-4-(4-((4,4-dimethyl-2-(3-methylbicyclo[1.1.1]pentan-1-yl)cyclohex-1-en-1-yl)methyl)piperazin-1-yl)benzamide

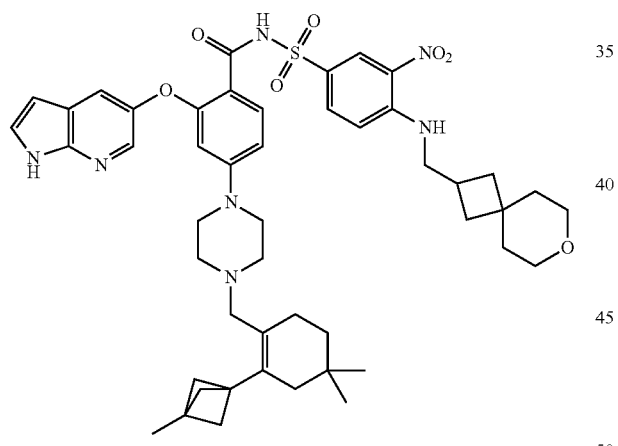

Example 11 was prepared following General Procedure A using Intermediate 28 and Intermediate 6. ¹H NMR (400 MHz, CDCl₃) δ 10.15 (br s, 1H), 9.16 (br s, 1H), 8.88 (d, J=2.0 Hz, 1H), 8.37 (t, J=4.8 Hz, 1H), 8.22 (d, J=2.4 Hz, 1H), 8.17 (dd, J=9.0, 2.0 Hz, 1H), 7.97 (d, J=9.2 Hz, 1H), 7.71 (d, J=2.0 Hz, 1H), 7.45 (t, J=2.8 Hz, 1H), 6.89 (d, J=9.6 Hz, 1H), 6.60-6.54 (m, 2H), 6.02 (d, J=2.0 Hz, 1H), 3.64 (t, J=5.2 Hz, 2H), 3.56 (t, J=5.2 Hz, 2H), 3.38 (dd, J=7.0, 5.2 Hz, 2H), 3.10 (t, J=4.8 Hz, 4H), 3.00 (s, 2H), 2.71-2.64 (m, 1H), 2.35 (t, J=4.8 Hz, 4H), 2.15-2.09 (m, 2H), 2.01-1.98 (m, 2H), 1.73 (s, 6H), 1.68 (t, J=5.2 Hz, 2H), 1.66-1.56 (m, 6H), 1.24 (t, J=6.4 Hz, 2H), 1.10 (s, 3H), 0.82 (s, 6H); LC/MS (ESI) m/z 878.6 [M+H]⁺

Example 12

2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-(((1-methylpiperidin-4-yl)methyl)amino)-3-nitrophenyl)sulfonyl)benzamide

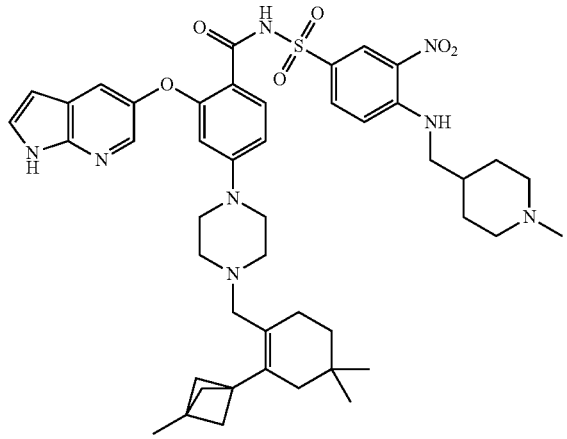 [SMILES: CN1CCC(CNc2ccc(S(=O)(=O)NC(=O)c3ccc(N4CCN(CC5=C(C67CC(C)(C6)C7)CC(C)(C)CC5)CC4)cc3Oc3cnc4[nH]ccc4c3)cc2[N+](=O)[O-])CC1]

To a stirred solution of Intermediate 28 (150 mg, 0.277 mmol) in DMF (1 mL) at 0° C. was added EDC·HCl (106.2 mg, 0.554 mmol) and 1-hydroxy-7-azabenzotriazole (75.4 mg, 0.554 mmol). After 10 min, Intermediate 14 (92 mg, 0.277 mmol) and DIPEA (108 mg, 0.83 mmol) were added and the reaction was warmed to rt. After 48 h, water (10 mL) was added and the reaction was extracted with DCM (3×10 mL). The combined organic layers were dried over anhydrous Na₂SO₄, filtered and concentrated. The crude product was purified by HPLC (30:70 to 1:99, 10 mM NH₄CO₃H (aq.):CH₃CN) to afford Example 12 as a yellow solid (6 mg, 3% yield). LC/MS (ESI) m/z 851.4 [M+H]⁺

Example 13

2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-(((4-fluoro-1-methylpiperidin-4-yl)methyl)amino)-3-nitrophenyl)sulfonyl)benzamide

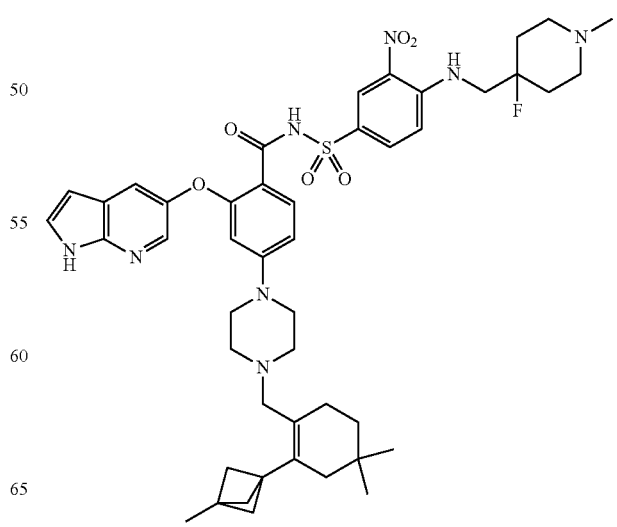

Example 13 was prepared following General Procedure A using Intermediate 28 and Intermediate 15. $^1$H NMR (400 MHz, CDCl$_3$) δ 9.07 (br s, 1H), 8.90 (d, J=2.4 Hz, 1H), 8.66 (t, J=5.2, 1H), 8.17 (d, J=2.4 Hz, 1H), 8.10 (dd, J=9.2, 1.6 Hz, 1H), 7.96 (d, J=9.2 Hz, 1H), 7.69 (d, J=2.4 Hz, 1H), 7.44 (d, J=3.2 Hz, 1H), 6.92 (d, J=9.2 Hz, 1H), 6.59 (dd, J=9.2, 2.4 Hz, 1H), 6.54 (dd, J=3.6, 2.0 Hz, 1H), 6.04 (d, J=2.4 Hz, 1H), 3.52 (dd, J=19.6, 6.0 Hz, 2H), 3.11 (t, J=4.8 Hz, 4H), 2.99 (s, 2H), 2.82-2.75 (m, 2H), 2.41-2.31 (m, 8H), 2.06-1.97 (m, 4H), 1.74 (s, 6H), 1.65 (s, 2H), 1.33-1.22 (s, 5H), 1.10 (s, 3H), 0.82 (s, 6H). One NH proton not observed; LC/MS (ESI) m/z 869.5 [M+H]$^+$.

Example 14

2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-(((1r,4r)-4-(dimethylamino)cyclohexyl)amino)-3-nitrophenyl)sulfonyl)benzamide

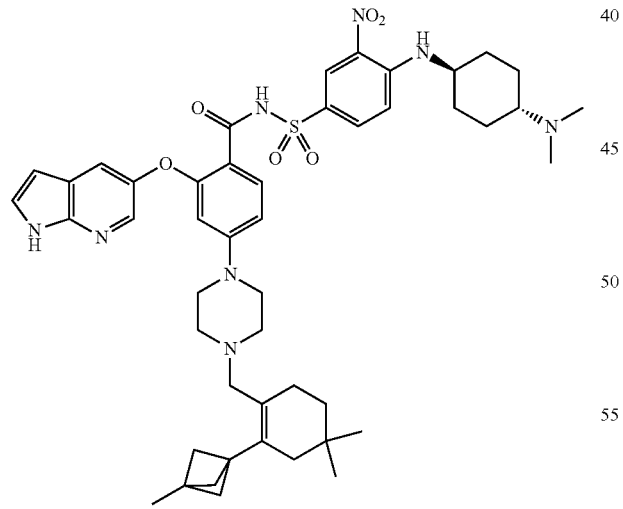

Example 14 was prepared following General Procedure A using Intermediate 28 and Intermediate 16. LC/MS (ESI) m/z 865.5 [M+H]$^+$.

Example 15

2-(1H-pyrrolo[2,3-b]pyridin-5-yloxy)-4-(4-((4,4-dimethyl-2-(3-methylbicyclo[1.1.1]pentan-1-yl)cyclohex-1-enyl)methyl)piperazin-1-yl)-N-(4-((4-fluorotetrahydro-2H-pyran-4-yl)methylamino)-3-nitrophenylsulfonyl)benzamide

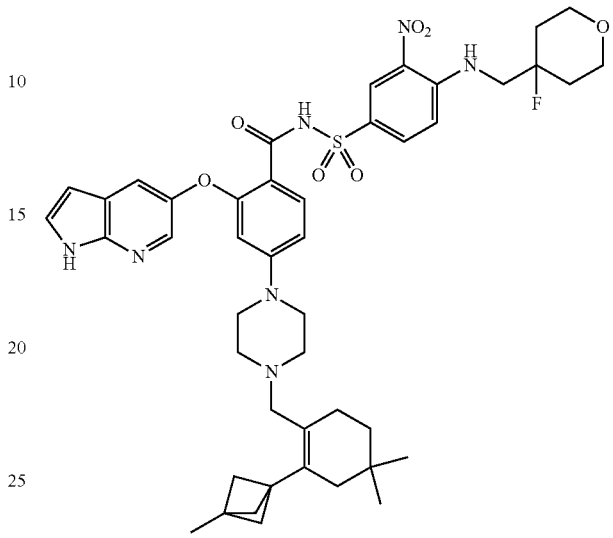

Example 15 was prepared following General Procedure A using Intermediate 28 and Intermediate 52. $^1$H NMR (400 MHz, CDCl$_3$) δ 10.16 (br s, 1H), 8.97 (br s, 1H), 8.91 (d, J=2.0 Hz, 1H), 8.67 (t, J=5.6 Hz, 1H), 8.22 (d, J=2.4 Hz, 1H), 8.19 (dd, J=9.0, 2.4 Hz, 1H), 7.97 (d, J=8.8 Hz, 1H), 7.71 (d, J=2.4 Hz, 1H), 7.45 (t, J=2.8 Hz, 1H), 6.98 (d, J=9.2 Hz, 1H), 6.59 (dd, J=9.0, 2.4 Hz, 1H), 6.55 (dd, J=3.2, 2.0 Hz, 1H), 6.02 (d, J=2.4 Hz, 1H), 3.89 (dd, J=11.8, 4.0 Hz, 2H), 3.79-3.72 (m, 2H), 3.55 (dd, J=19.6, 6.0 Hz, 2H), 3.11-3.09 (m, 4H), 3.00 (s, 2H), 2.36-2.33 (m, 4H), 2.05-1.95 (m, 2H), 1.94-1.75 (m, 4H), 1.74 (s, 6H), 1.64 (s, 2H), 1.24 (t, J=6.4 Hz, 2H), 1.10 (s, 3H), 0.82 (s, 6H); LC/MS (ESI) m/z 856.5 [M+H]$^+$.

Example 16

2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-((4-fluorotetrahydro-2H-pyran-4-yl)methoxy)-3-nitrophenyl)sulfonyl)benzamide

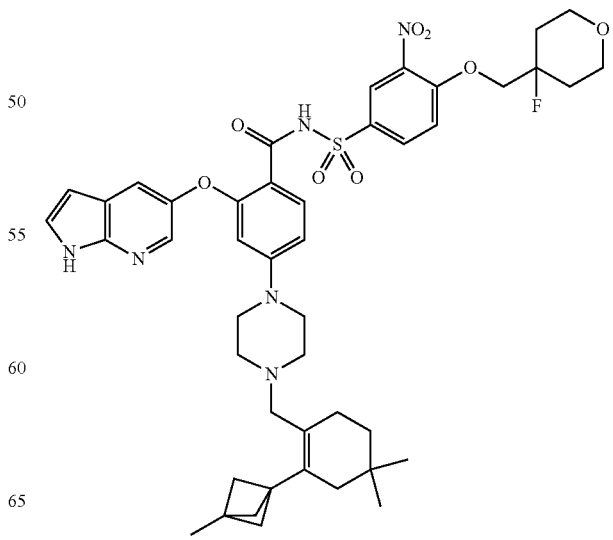

Example 16 was prepared following General Procedure A using Intermediate 28 and Intermediate 53. ¹H NMR (400 MHz, CDCl₃) δ 10.16 (br s, 1H), 8.85 (br s, 1H), 8.58 (d, J=2.4 Hz, 1H), 8.38 (dd, J=9.2, 2.4 Hz, 1H), 8.22 (d, J=2.8 Hz, 1H), 7.95 (d, J=9.2 Hz, 1H), 7.70 (d, J=2.8 Hz, 1H), 7.45 (t, J=2.8 Hz, 1H), 7.18 (d, J=8.8 Hz, 1H), 6.60-6.54 (m, 2H), 6.01 (d, J=2.0 Hz, 1H), 4.18 (d, J=18.0 Hz, 2H), 3.91-3.87 (m, 2H), 3.81-3.74 (m, 2H), 3.12-3.10 (m, 4H), 2.99 (s, 2H), 2.36-2.34 (m, 4H), 2.01-1.83 (m, 6H), 1.74 (s, 6H), 1.65 (s, 2H), 1.24 (t, J=6.0 Hz, 2H), 1.10 (s, 3H), 0.82 (s, 6H); LC/MS (ESI) m/z 857.5 [M+H]⁺.

Example 17

2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-(((4-methylmorpholin-2-yl)methyl)amino)-3-nitrophenyl)sulfonyl)benzamide

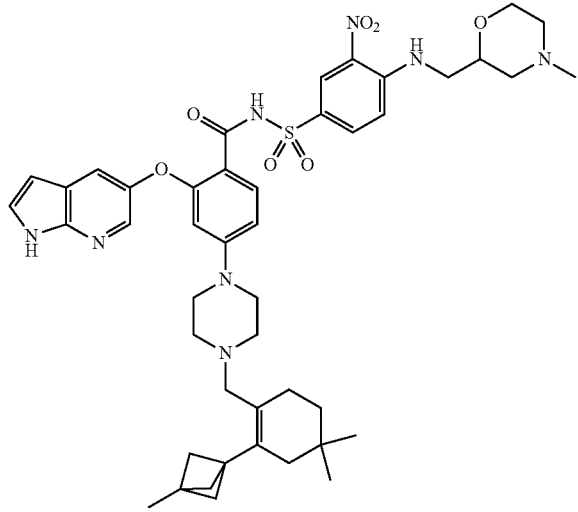 [SMILES: CN1CCOC(CNc2ccc(S(=O)(=O)NC(=O)c3ccc(N4CCN(CC5=C(C67CC(C)(C6)C7)CC(C)(C)CC5)CC4)cc3Oc3cnc4[nH]ccc4c3)cc2[N+](=O)[O-])C1]

Example 17 was prepared following General Procedure A using Intermediate 28 and Intermediate 17. ¹H NMR (400 MHz, CDCl₃) δ 10.16 (br s, 1H), 8.97 (br s, 1H), 8.88 (d, J=2.0 Hz, 1H), 8.65 (t, J=5.6 Hz, 1H), 8.18 (d, J=2.4 Hz, 1H), 8.13 (dd, J=9.0, 2.4 Hz, 1H), 7.96 (d, J=9.2 Hz, 1H), 7.70 (d, J=2.4 Hz, 1H), 7.43 (t, J=2.8 Hz, 1H), 6.88 (d, J=9.2 Hz, 1H), 6.58 (dd, J=9.2, 2.0 Hz, 1H), 6.55 (dd, J=3.6, 2.0 Hz, 1H), 6.03 (d, J=2.0 Hz, 1H), 3.95 (d, J=10.4 Hz, 1H), 3.90-3.84 (m, 1H), 3.73 (dt, J=11.4, 2.4 Hz, 1H), 3.49-3.36 (m, 2H), 3.12-3.09 (m, 4H), 2.99 (s, 2H), 2.77 (d, J=11.2 Hz, 1H), 2.67 (d, J=11.6 Hz, 1H), 2.36-2.33 (m, 4H), 2.32 (s, 3H), 2.19 (dt, J=11.4, 3.2 Hz, 1H), 2.03-1.98 (m, 3H), 1.74 (s, 6H), 1.65 (s, 2H), 1.24 (t, J=6.4 Hz, 2H), 1.10 (s, 3H), 0.82 (s, 6H); LC/MS (ESI) m/z 853.5[M+H]⁺.

Example 18

(R)-2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-(((4-methylmorpholin-2-yl)methyl)amino)-3-nitrophenyl)sulfonyl)benzamide

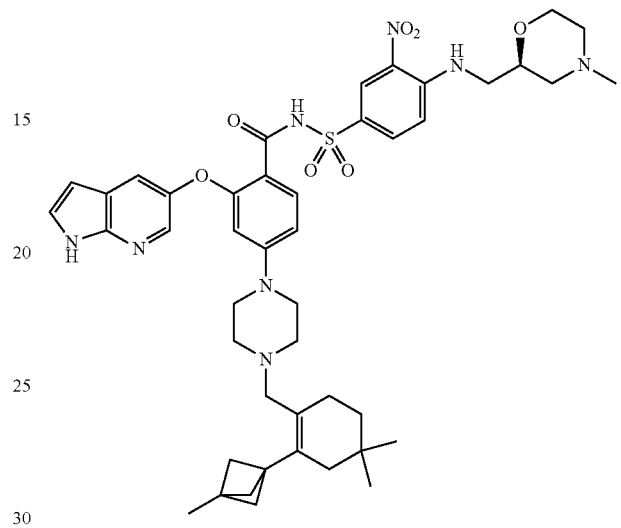

Example 18 was prepared following General Procedure A using Intermediate 28 and Intermediate 17A. LC/MS (ESI) m/z 853.5[M+H]⁺. The absolute stereochemistry was arbitrarily assigned.

Example 19

(S)-2-((1H-pyrrolo[2,3-b]pyridin-5-yl)oxy)-4-(4-((4,4-dimethyl-2-(3-methylbicyclo[1.1.1]pentan-1-yl)cyclohex-1-en-1-yl)methyl)piperazin-1-yl)-N-((4-(((4-methylmorpholin-2-yl)methyl)amino)-3-nitrophenyl) sulfonyl)benzamide

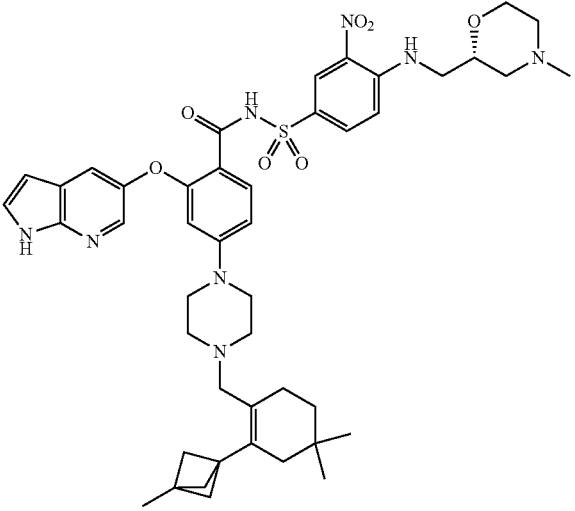 [SMILES: CN1CCO[C@@H](CNc2ccc(S(=O)(=O)NC(=O)c3ccc(N4CCN(CC5=C(C67CC(C)(C6)C7)CC(C)(C)CC5)CC4)cc3Oc3cnc4[nH]ccc4c3)cc2[N+](=O)[O-])C1]

Example 19 was prepared following General Procedure A using Intermediate 28 and Intermediate 17B. LC/MS (ESI) m/z 853.6[M+H]⁺. The absolute stereochemistry was arbitrarily assigned.

Example 20

2-(1H-pyrrolo[2,3-b]pyridin-5-yloxy)-4-(4-((4,4-dimethyl-2-(3-methylbicyclo[1.1.1] pentan-1-yl) cyclohex-1-enyl)methyl)piperazin-1-yl)-N-(4-(((1r,4r)-4-hydroxy-4-methylcyclohexyl)methylamino)-3-nitrophenylsulfonyl)benzamide

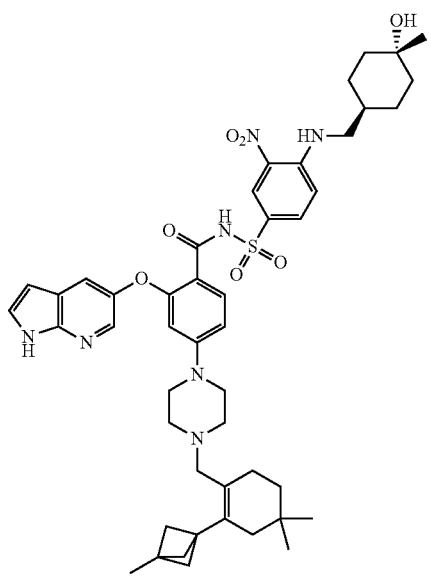 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(C23CC(C)(C2)C3)C1]

Example 19 was prepared following General Procedure A using Intermediate 28 and Intermediate 18. LC/MS (ESI) m/z 866.5 [M+H]⁺

Example 21

2-(1H-pyrrolo[2,3-b]pyridin-5-yloxy)-4-(4-((4,4-dimethyl-2-(3-methylbicyclo[1.1.1]pentan-1-yl)cyclohex-1-enyl)methyl)piperazin-1-yl)-N-(4-(2-morpholinoethylamino)-3-nitrophenylsulfonyl)benzamide

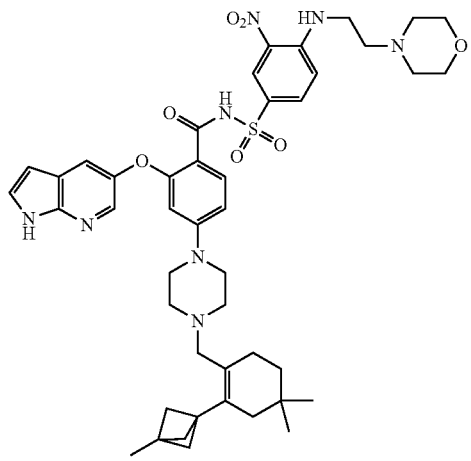 [SMILES: CC1(C)CCC(CN2CCN(c3ccc(C(=O)NS(=O)(=O)c4ccc(NCCN5CCOCC5)c([N+](=O)[O-])c4)c(Oc4cnc5[nH]ccc5c4)c3)CC2)=C(C23CC(C)(C2)C3)C1]

Example 21 was prepared following General Procedure A using Intermediate 28 and Intermediate 54. LC/MS (ESI) m/z 853.6 [M+H]⁺.

Example 22

2-(1H-pyrrolo[2,3-b]pyridin-5-yloxy)-4-(4-((4,4-dimethyl-2-(3-methylbicyclo[1.1.1]pentan-1-yl)cyclohex-1-enyl)methyl)piperazin-1-yl)-N-(3-nitro-4-((tetrahydro-2H-pyran-4-yl)methoxy)phenylsulfonyl)benzamide Representative example of General Procedure B: To a stirred solution of Intermediate 55 (70.03 mg, 0.22 mmol) in DCM (5 mL) was added DMAP (54.02 mg, 0.44 mmol), and EDC·HCl (63.15 mg, 0.33 mmol) and DCM (5 mL). In a separate flask, Intermediate 28 (120 mg, 0.222 mmol), Et₃N (0.046 mL, 0.44 mmol) and DCM (3 mL) were combined and stirred for 15 minutes. The solution containing the acid was then slowly added to the suspension of the sulfonamide and the reaction mixture was stirred at rt. After 20 hours, N,N-dimethylethylenediamine (0.055 mL) was charged to the reaction mixture, and stirring was continued for 90 min. The reaction mixture was then washed with 10% acetic acid solution (2×10 mL). Note: The organic layer was diluted with DCM (10 mL) and MeOH (3 mL), before final separation of the aqueous layer. The organic layer was washed with 5% NaHCO₃(aq.) (10 mL), 5% NaCl(aq.) (10 mL) and the organic layer was concentrated. The crude product was purified by HPLC (30:70 to 1:99 10 mM NH₄CO₃H(aq): CH₃CN) to provide Example 22 (55 mg, 30% yield) as a white solid. LC/MS (ESI) m/z 839.6 [M+H]⁺

Example 23

2-(1H-pyrrolo[2,3-b]pyridin-5-yloxy)-4-(4-((2-(3-ethylbicyclo[1.1.1]pentan-1-yl)-4,4-dimethylcyclohex-1-enyl)methyl)piperazin-1-yl)-N-(3-nitro-4-(((tetrahydro-2H-pyran-4-yl)methylamino)phenylsulfonyl)benzamide

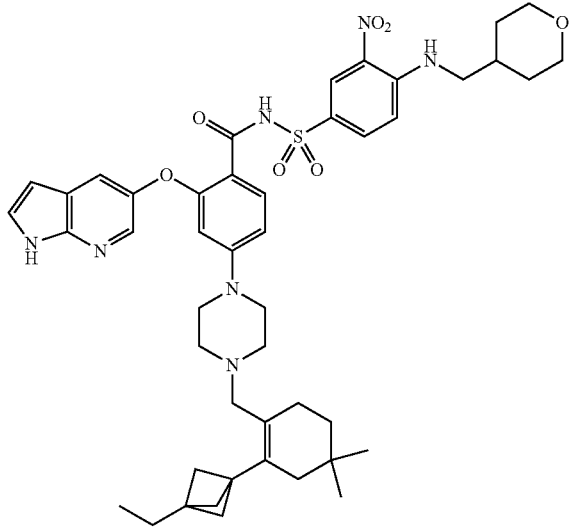 [SMILES: CCC12CC(C3=C(CN4CCN(c5ccc(C(=O)NS(=O)(=O)c6ccc(NCC7CCOCC7)c([N+](=O)[O-])c6)c(Oc6cnc7[nH]ccc7c6)c5)CC4)CCC(C)(C)C3)(C1)C2]

Example 23 was prepared following General Procedure B using Intermediate 29 and 3-nitro-4-((((tetrahydro-2H-pyran-4-yl)methyl)amino)benzenesulfonamide. $^1$H NMR (400 MHz, DMSO-$d_6$) δ 11.69 (s, 1H), 11.40 (br s, 1H), 8.59 (br s, 1H), 8.54 (s, 1H), 8.03 (s, 1H), 7.77 (d, J=9.6 Hz, 1H), 7.56-7.48 (m, 3H), 7.07 (d, J=8.8 Hz, 1H), 6.72 (d, J=8.8 Hz, 1H), 6.37 (s, 1H), 6.26 (s, 1H), 3.85 (d, J=11.2 Hz, 2H), 3.33-3.23 (m, 4H), 3.20-3.05 (m, 4H), 3.05-2.94 (m, 2H), 2.41-2.28 (m, 4H), 2.05-1.95 (m, 2H), 1.94-1.81 (m, 1H), 1.70 (s, 6H), 1.66-1.59 (m, 4H), 1.38 (q, J=7.6 Hz, 2H), 1.31-1.19 (m, 4H), 0.82 (s, 6H), 0.78 (t, J=8.0 Hz, 3H); LC/MS (ESI) m/z 852.5 [M+H]$^+$.

Example 24

2-(1H-pyrrolo[2,3-b]pyridin-5-yloxy)-4-(4-((2-(3-ethylbicyclo[1.1.1]pentan-1-yl)-4,4-dimethylcyclohex-1-enyl)methyl)piperazin-1-yl)-N-(4-(((4-fluoro-1-methylpiperidin-4-yl)methylamino)-3-nitrophenylsulfonyl)benzamide

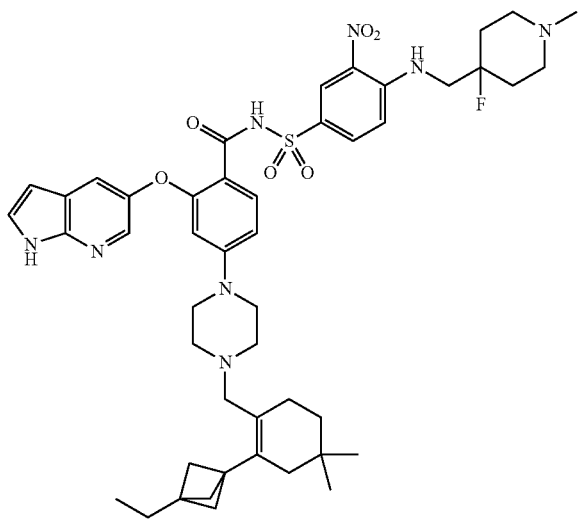 [SMILES: CCC12CC(C3=C(CN4CCN(c5ccc(C(=O)NS(=O)(=O)c6ccc(NCC7(F)CCN(C)CC7)c([N+](=O)[O-])c6)c(Oc6cnc7[nH]ccc7c6)c5)CC4)CCC(C)(C)C3)(C1)C2]

Example 24 was prepared following General Procedure B using Intermediate 29 and Intermediate 15. LC/MS (ESI) m/z 883.9 [M+H]$^+$.

Example 25

2-((1H-pyrrolo[2,3-b]pyridin-5-yl)oxy)-4-(4-((2-(3-ethylbicyclo[1.1.1]pentan-1-yl)-4,4-dimethylcyclohex-1-en-1-yl)methyl)piperazin-1-yl)-N-((4-(((4-fluorotetrahydro-2H-pyran-4-yl)methyl)amino)-3-nitrophenyl)sulfonyl)benzamide

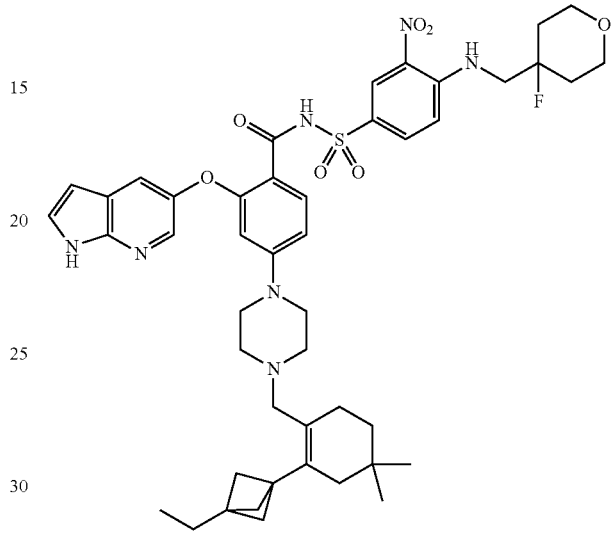

Example 25 was prepared following General Procedure B using Intermediate 29 and Intermediate 52. LC/MS (ESI) m/z 870.8 [M+H]$^+$.

Example 26

2-((1H-pyrrolo[2,3-b]pyridin-5-yl)oxy)-4-(4-((2-(3-ethylbicyclo[1.1.1]pentan-1-yl)-4,4-dimethylcyclohex-1-en-1-yl)methyl)piperazin-1-yl)-N-((4-((4-fluorotetrahydro-2H-pyran-4-yl)methoxy)-3-nitrophenyl)sulfonyl)benzamide

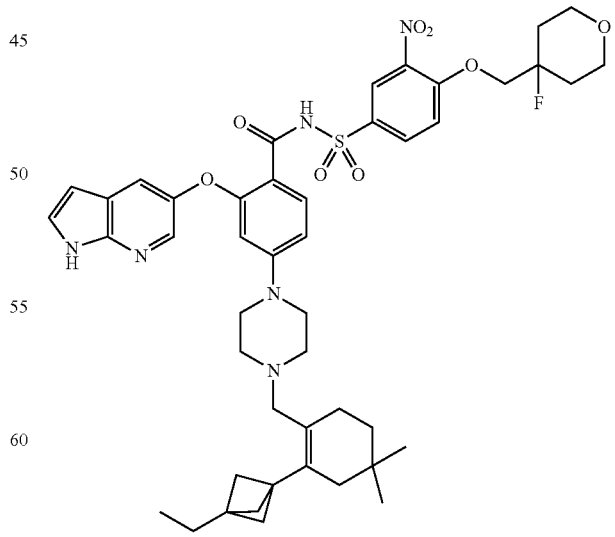

Example 26 was prepared following General Procedure B using Intermediate 29 and Intermediate 53. LC/MS (ESI) m/z 871.7 [M+H]$^+$.

Example 27

2-((1H-pyrrolo[2,3-b]pyridin-5-yl)oxy)-4-(4-((2-(3-ethylbicyclo[1.1.1]pentan-1-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

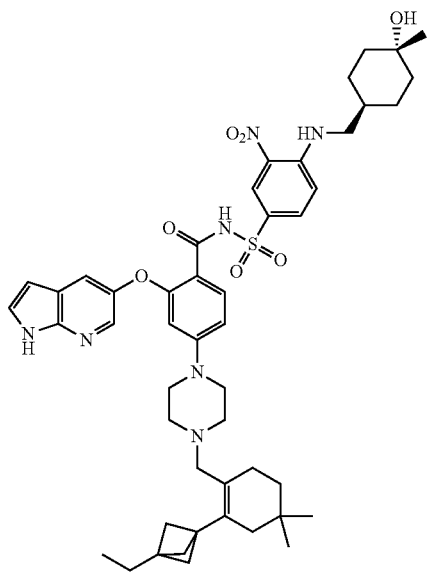 [SMILES: CCC12CC(C3=C(CN4CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)CCC(C)(C)C3)(C1)C2]

Example 27 was prepared following General Procedure B using Intermediate 29 and Intermediate 18. LC/MS (ESI) m/z 880.6 [M+H]$^+$.

Example 28

2-((1H-pyrrolo[2,3-b]pyridin-5-yl)oxy)-4-(4-((4,4-dimethyl-2-(3-(trifluoromethyl)bicyclo[1.1.1]pentan-1-yl)cyclohex-1-en-1-yl)methyl)piperazin-1-yl)-N-((3-nitro-4-(((tetrahydro-2H-pyran-4-yl)methyl)amino)phenyl)sulfonyl)benzamide

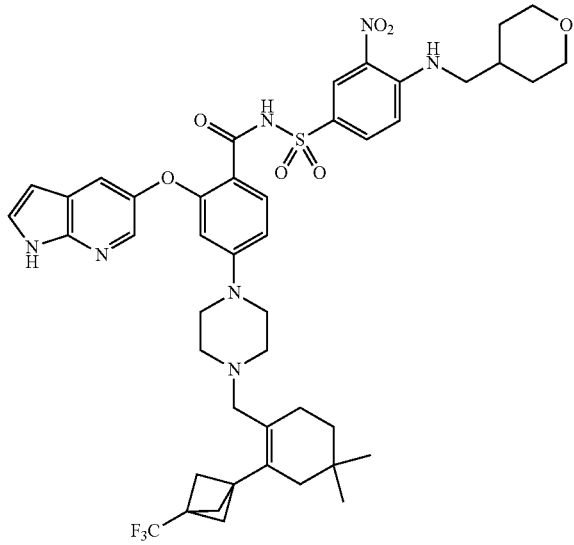 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(C23CC(C(F)(F)F)(C2)C3)C1]

Example 28 was prepared following General Procedure A using Intermediate 31 and 3-nitro-4-(((tetrahydro-2H-pyran-4-yl)methyl)amino)benzenesulfonamide. $^1$H NMR (400 MHz, DMSO-d$_6$) δ 11.68 (s, 1H), 11.50 (br s, 1H), 8.60 (br s, 1H), 8.55 (s, 1H), 8.42 (d, J=2.4 Hz, 1H), 7.82-7.77 (m, 1H), 7.53-7.49 (m, 3H), 7.12-7.08 (m, 1H), 6.73-6.70 (m, 1H), 6.39-6.38 (m, 1H), 6.25-6.23 (m, 1H), 3.87-3.83 (m, 2H), 3.38-3.24 (m, 4H), 3.14-3.09 (m, 4H), 2.94 (br s, 2H), 2.39-2.31 (m, 4H), 2.11 (s, 6H), 2.04-1.98 (m, 2H), 1.90-1.85 (m, 1H), 1.68 (s, 2H), 1.64-1.59 (m, 2H), 1.31-1.22 (m, 4H), 0.83 (s, 6H); $^{19}$F NMR (376 MHz, DMSO-d$_6$, unreferenced) 6-71.53; LC/MS (ESI) m/z 892.6 [M+H]$^+$.

Example 29

2-((1H-pyrrolo[2,3-b]pyridin-5-yl)oxy)-4-(4-((4,4-dimethyl-2-(3-(trifluoromethyl)bicyclo[1.1.1]pentan-1-yl)cyclohex-1-en-1-yl)methyl)piperazin-1-yl)-N-((4-(((4-fluoro-1-methylpiperidin-4-yl)methyl)amino)-3-nitrophenyl)sulfonyl)benzamide

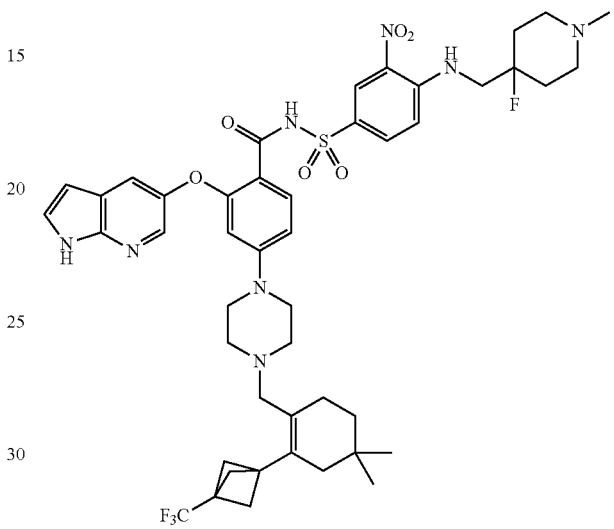

Example 29 was prepared following General Procedure B using Intermediate 31 and Intermediate 15. LC/MS (ESI) m/z 923.9 [M+H]$^+$.

Example 30

2-((1H-pyrrolo[2,3-b]pyridin-5-yl)oxy)-4-(4-((4,4-dimethyl-2-(3-(trifluoromethyl)bicyclo[1.1.1]pentan-1-yl)cyclohex-1-en-1-yl)methyl)piperazin-1-yl)-N-((4-(((4-fluorotetrahydro-2H-pyran-4-yl)methyl)amino)-3-nitrophenyl)sulfonyl)benzamide

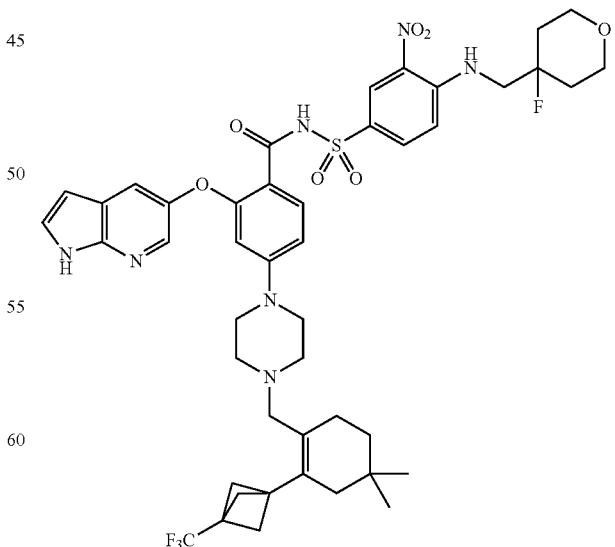

Example 30 was prepared following General Procedure B using Intermediate 31 and Intermediate 52. LC/MS (ESI) m/z 910.6 [M+H]$^+$.

Example 31

2-((1H-pyrrolo[2,3-b]pyridin-5-yl)oxy)-4-(4-((4,4-dimethyl-2-(3-(trifluoromethyl)bicyclo[1.1.1]pentan-1-yl)cyclohex-1-en-1-yl)methyl)piperazin-1-yl)-N-((4-(4-fluorotetrahydro-2H-pyran-4yl)methoxy)-3-nitrophenyl)sulfonyl)benzamide

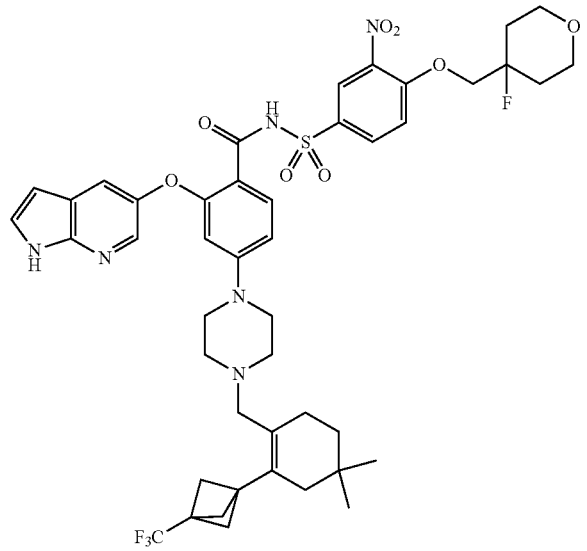 [SMILES: CC1(C)CCC(CN2CCN(c3ccc(C(=O)NS(=O)(=O)c4ccc(OCC5(F)CCOCC5)c([N+](=O)[O-])c4)c(Oc4cnc5[nH]ccc5c4)c3)CC2)=C(C23CC(C(F)(F)F)(C2)C3)C1]

Example 31 was prepared following General Procedure B using Intermediate 31 and Intermediate 53. LC/MS (ESI) m/z 911.6 [M+H]⁺.

Example 32

2-((1H-pyrrolo[2,3-b]pyridin-5-yl)oxy)-4-(4-((4,4-dimethyl-2-(3-(trifluoromethyl)bicyclo[1.1.1]pentan-1-yl)cyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

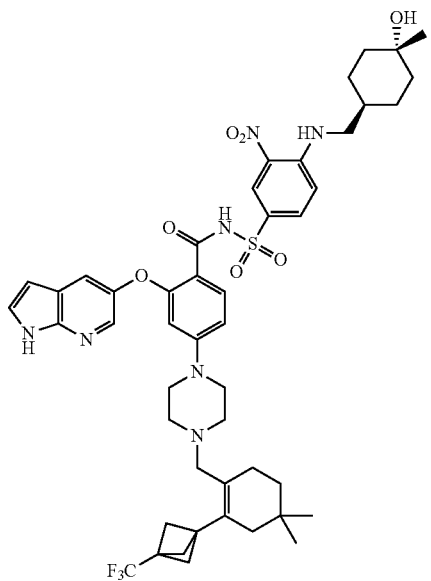 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(C23CC(C(F)(F)F)(C2)C3)C1]

Example 32 was prepared following General Procedure B using Intermediate 31 and Intermediate 18. LC/MS (ESI) m/z 920.7 [M+H]⁺.

Example 33

2-((1H-pyrrolo[2,3-b]pyridin-5-yl)oxy)-4-(4-((2-(3-(difluoromethyl)bicyclo[1.1.1]pentan-1-yl)-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide

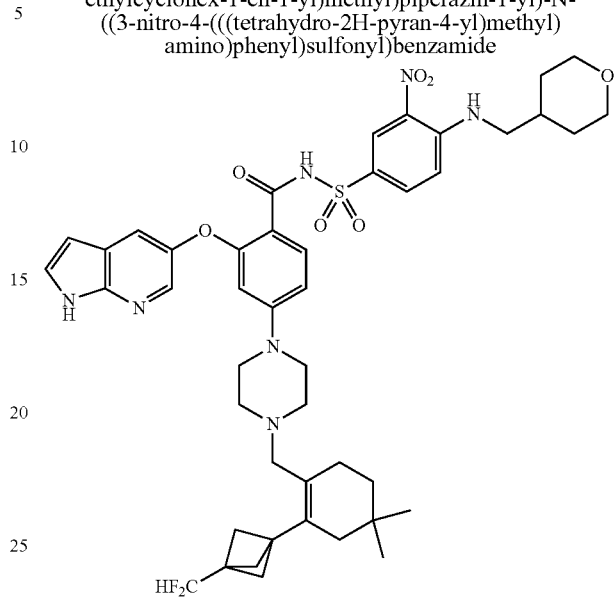

Example 33 was prepared following General Procedure A using Intermediate 30 and 3-nitro-4-(((tetrahydro-2H-pyran-4-yl)methyl)amino)benzenesulfonamide. ¹H NMR (400 MHz, CDCl₃) δ 10.06 (br s, 1H), 8.94 (br s, 1H), 8.90 (d, J=2.0 Hz, 1H), 8.53 (t, J=5.6 Hz, 1H), 8.22 (d, J=2.4 Hz, 1H), 8.18 (dd, J=9.6, 2.0 Hz, 1H), 7.98 (d, J=9.2 Hz, 1H), 7.71 (d, J=2.0 Hz, 1H), 7.45 (t, J=3.2 Hz, 1H), 6.92 (d, J=9.6 Hz, 1H), 6.60-6.55 (m, 2H), 6.02 (d, J=2.0 Hz, 1H), 5.65 (t, J=56.8 Hz, 1H), 4.03 (dd, J=11.2, 3.2 Hz, 2H), 3.46-3.39 (m, 2H), 3.27 (t, J=6.4 Hz, 2H), 3.12-3.09 (m, 4H), 2.96 (s, 2H), 2.35-2.32 (m, 4H), 2.05-1.98 (m, 3H), 1.96 (s, 6H), 1.76-1.72 (m, 2H), 1.66 (s, 2H), 1.49-1.38 (m, 2H), 1.26 (t, J=6.4 Hz, 2H), 0.84 (s, 6H); LC/MS (ESI) m/z 874.4 [M+H]⁺.

Example 34

2-((1H-pyrrolo[2,3-b]pyridin-5-yl)oxy)-4-(4-((2-(3-(difluoromethyl)bicyclo[1.1.1]pentan-1-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl) sulfonyl)benzamide

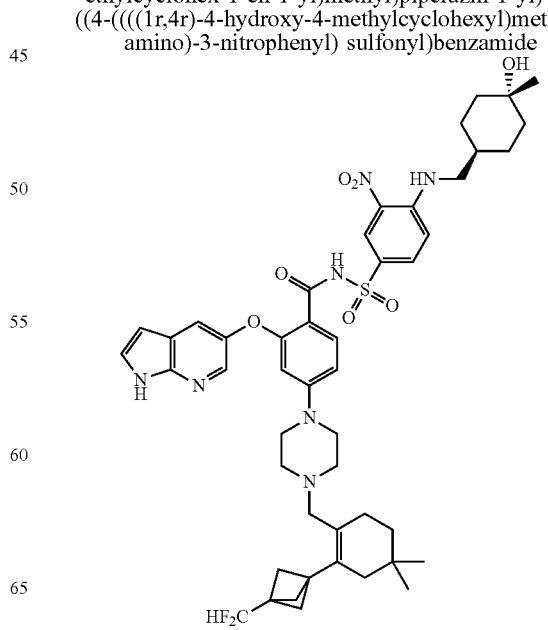

Example 34 was prepared following General Procedure A using Intermediate 30 and Intermediate 18. $^1$H NMR (400 MHz, DMSO-d$_6$) δ 11.70 (s, 1H), 11.40 (br s, 1H), 8.59-8.49 (m, 2H), 8.04 (d, J=2.0 Hz, 1H), 7.78 (d, J=8.8 Hz, 1H), 7.53-7.48 (m, 3H), 7.06 (d, J=9.2 Hz, 1H), 6.72 (d, J=7.2 Hz, 1H), 6.38 (s, 1H), 6.25 (s, 1H), 5.99 (t, J=56.8 Hz, 1H), 4.25 (s, 1H), 3.33-3.25 (m, 2H), 3.18-3.05 (m, 4H), 2.97 (s, 2H), 2.40-2.28 (m, 4H), 2.05-1.95 (m, 2H), 1.94 (s, 6H), 1.71-1.59 (m, 5H), 1.58-1.49 (m, 2H), 1.39-1.28 (m, 2H), 1.27-1.20 (m, 2H), 1.18-1.09 (m, 2H), 1.10 (s, 3H), 0.83 (s, 6H); LC/MS (ESI) m/z 902.6 [M+H]$^+$.

Example 35

2-((1H-pyrrolo[2,3-b]pyridin-5-yl)oxy)-4-(4-((2-(3-(difluoromethyl)bicyclo[1.1.1]pentan-1-yl)-4,4-dimethylcyclohex-1-en-1-yl)methyl)piperazin-1-yl)-N-((4-(((4-fluorotetrahydro-2H-pyran-4-yl)methyl)amino)-3-nitrophenyl)sulfonyl)benzamide

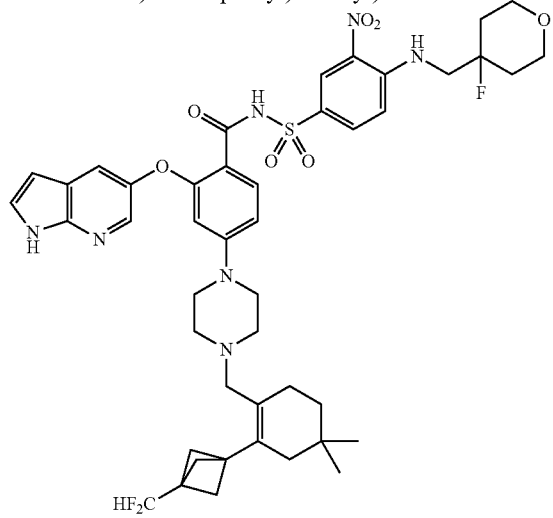

Example 35 was prepared following General Procedure A using Intermediate 30 and Intermediate 52. LC/MS (ESI) m/z 892.5 [M+H]$^+$.

Example 36

2-((1H-pyrrolo[2,3-b]pyridin-5-yl)oxy)-4-(4-((2-(3-(difluoromethyl)bicyclo[1.1.1]pentan-1-yl)-4,4-dimethylcyclohex-1-en-1-yl)methyl)piperazin-1-yl)-N-((4-((4-fluorotetrahydro-2H-pyran-4-yl)methoxy)-3-nitrophenyl)sulfonyl)benzamide

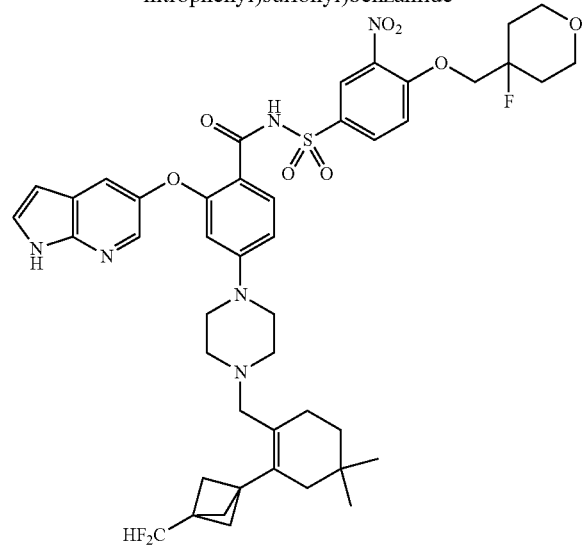

Example 36 was prepared following General Procedure A using Intermediate 30 and Intermediate 53. LC/MS (ESI) m/z 893.5 [M+H]$^+$.

Example 37

2-((1H-pyrrolo[2,3-b]pyridin-5-yl)oxy)-N-((4-(((7-oxaspiro[3.5]nonan-2-yl)methyl)amino)-3-nitrophenyl)sulfonyl)-4-(4-((2-(3-(difluoromethyl)bicyclo[1.1.1]pentan-1-yl)-4,4-dimethylcyclohex-1-en-1-yl)methyl)piperazin-1-yl)benzamide

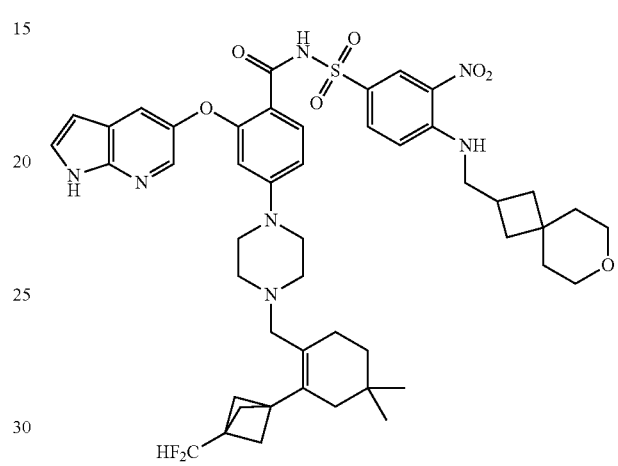

Example 37 was prepared following General Procedure A using Intermediate 30 and Intermediate 6. LC/MS (ESI) m/z 914.5 [M+H]$^+$.

Example 38

2-((1H-pyrrolo[2,3-b]pyridin-5-yl)oxy)-4-(4-((2-(3-(difluoromethyl)bicyclo[1.1.1]pentan-1-yl)-4,4-dimethylcyclohex-1-en-1-yl)methyl)piperazin-1-yl)-N-((4-(((4-fluoro-1-methylpiperidin-4-yl)methyl)amino)-3-nitrophenyl)sulfonyl)benzamide

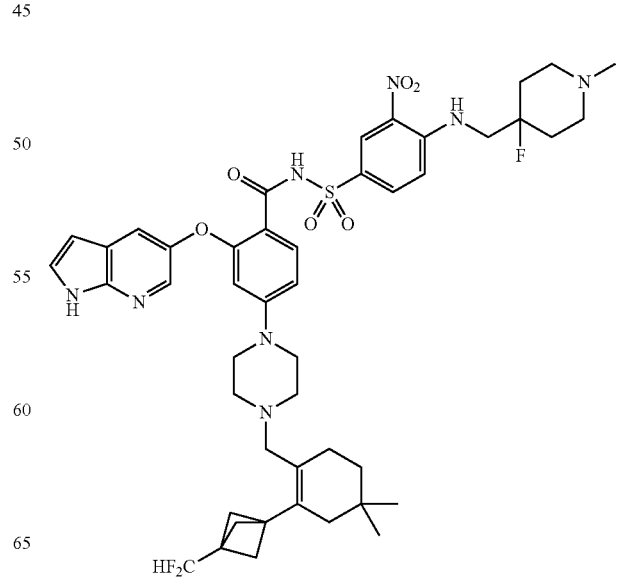

Example 38 was prepared following General Procedure A using Intermediate 30 and Intermediate 15. LC/MS (ESI) m/z 905.5 [M+H]⁺.

Example 39

2-((1H-pyrrolo[2,3-b]pyridin-5-yl)oxy)-4-(4-((2-(3-isopropylbicyclo[1.1.1]pentan-1-yl)-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide

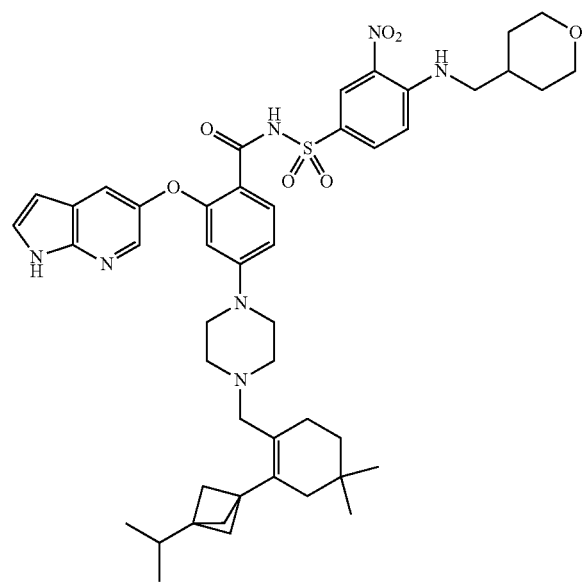 [SMILES: CC(C)C12CC(C3=C(CN4CCN(c5ccc(C(=O)NS(=O)(=O)c6ccc(NCC7CCOCC7)c([N+](=O)[O-])c6)c(Oc6cnc7[nH]ccc7c6)c5)CC4)CCC(C)(C)C3)(C1)C2]

Example 39 was prepared following General Procedure A using Intermediate 32 and 3-nitro-4-((((tetrahydro-2H-pyran-4-yl)methyl)amino)benzenesulfonamide. ¹H NMR (400 MHz, CDCl₃) δ 10.18 (br s, 1H), 8.92 (br s, 1H), 8.90 (d, J=1.6 Hz, 1H), 8.53 (t, J=5.6 Hz, 1H), 8.23 (d, J=2.8 Hz, 1H), 8.18 (dd, J=9.0, 2.4 Hz, 1H), 7.97 (d, J=9.2 Hz, 1H), 7.71 (d, J=2.4 Hz, 1H), 7.44 (t, J=2.8 Hz, 1H), 6.91 (d, J=9.6 Hz, 1H), 6.59 (dd, J=9.2, 2.4 Hz, 1H), 6.56 (dd, J=3.4, 2.4 Hz, 1H), 6.02 (d, J=2.0 Hz, 1H), 4.03 (dd, J=11.2, 4.0 Hz, 2H), 3.46-3.39 (m, 2H), 3.27 (t, J=6.4 Hz, 2H), 3.12-3.09 (m, 4H), 3.02 (s, 2H), 2.37-2.34 (m, 4H), 2.05-1.95 (m, 3H), 1.78-1.71 (m, 2H), 1.66 (s, 2H), 1.65 (s, 6H), 1.62-1.56 (m, 1H), 1.49-1.39 (m, 2H), 1.25 (t, J=6.4 Hz, 2H), 0.83 (s, 6H), 0.78 (d, J=6.8 Hz, 6H); LC/MS (ESI) m/z 866.4 [M+H]⁺.

Example 40

2-(1H-pyrrolo[2,3-b]pyridin-5-yloxy)-4-(4-((2-(3-(1,1-difluoroethyl)bicyclo[1.1.1]pentan-1-yl)-4,4-dimethylcyclohex-1-enyl)methyl)piperazin-1-yl)-N-(3-nitro-4-(((tetrahydro-2H-pyran-4-yl)methylamino)phenylsulfonyl)benzamide

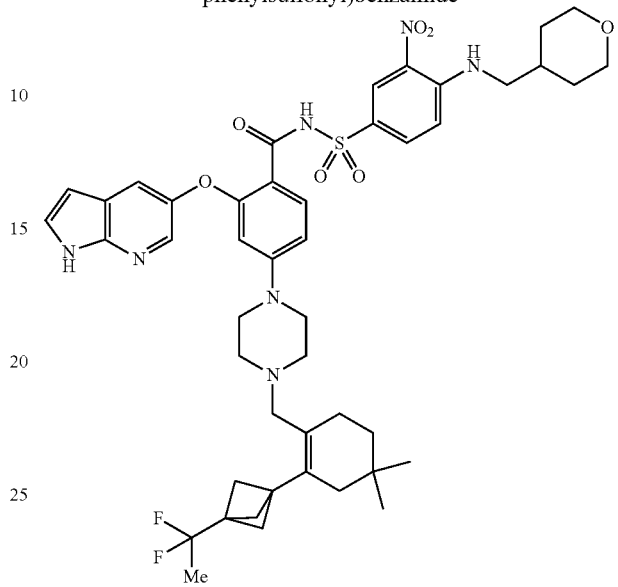

Example 40 was prepared following General Procedure B using Intermediate 33 and 3-nitro-4-((((tetrahydro-2H-pyran-4-yl)methyl)amino)benzenesulfonamide. ¹H NMR (400 MHz, DMSO-d₆) δ 11.70 (s, 1H), 11.50 (br s, 1H), 8.61-8.49 (m, 2H), 8.03 (s, 1H), 7.80-7.70 (m, 1H), 7.54-7.45 (m, 3H), 7.04 (br s, 1H), 6.71 (d, J=8.8 Hz, 1H), 6.37 (s, 1H), 6.25 (s, 1H), 3.87-3.83 (m, 2H), 3.33-3.21 (m, 4H), 3.15-3.05 (m, 4H), 2.97 (s, 2H), 2.40-2.25 (m, 4H), 2.04-1.97 (m, 2H), 1.94 (s, 6H), 1.93-1.82 (m, 1H), 1.67-1.57 (m, 4H), 1.53 (t, J=18.8 Hz, 3H), 1.30-1.15 (m, 4H), 0.83 (s, 6H); LC/MS (ESI) m/z 888.7 [M+H]⁺.

Example 41

(S)—N-((4-((((1,4-dioxan-2-yl)methyl)amino)-3-nitrophenyl)sulfonyl)-2-((1H-pyrrolo[2,3-b]pyridin-5-yl)oxy)-4-(4-((2-(3-(difluoromethyl)bicyclo[1.1.1]pentan-1-yl)-4,4-dimethylcyclohex-1-en-1-yl)methyl)piperazin-1-yl)benzamide

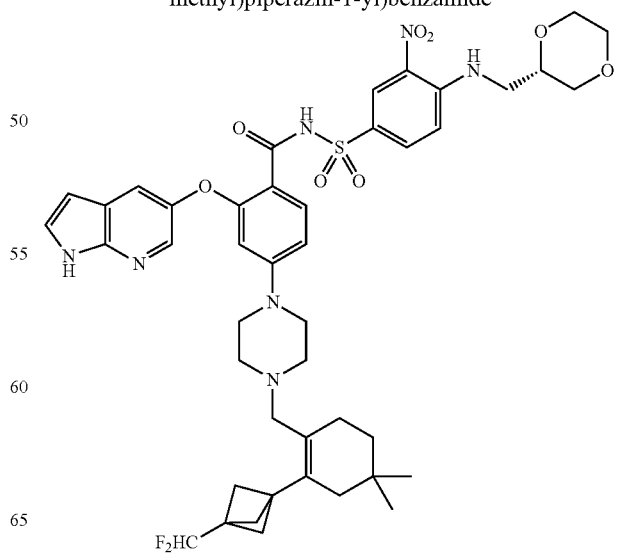

141

Example 41 was prepared following General Procedure B using Intermediate 30 and Intermediate 34. LC/MS (ESI) m/z 876.5 [M+H]⁺.

Example 42

2-((1H-pyrrolo[2,3-b]pyridin-5-yl)oxy)-4-(4-((6-(3-(difluoromethyl)bicyclo[1.1.1]pentan-1-yl)spiro[3.5]non-6-en-7-yl)methyl)piperazin-1-yl)-N-((3-nitro-4-((((tetrahydro-2H-pyran-4-yl)methyl)amino)phenyl)sulfonyl)benzamide

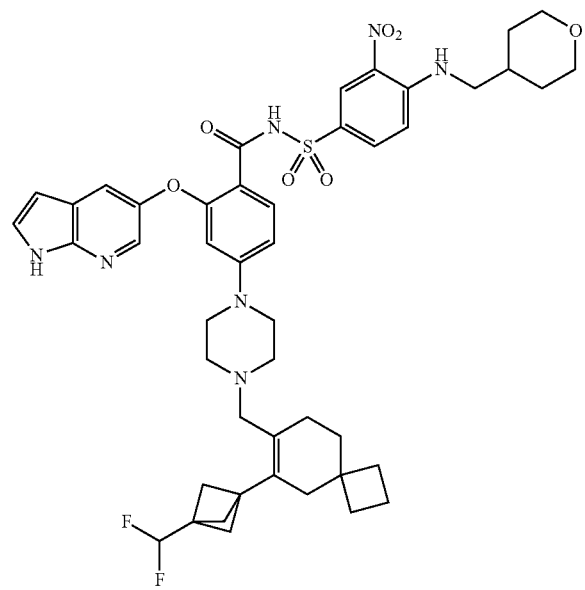 [SMILES: O=C(NS(=O)(=O)c1ccc(NCC2CCOCC2)c([N+](=O)[O-])c1)c1ccc(N2CCN(CC3=C(C45CC(C(F)F)(C4)C5)CC4(CCC4)CC3)CC2)cc1Oc1cnc2[nH]ccc2c1]

Example 42 was prepared following General Procedure B using Intermediate 50 and 3-nitro-4-((((tetrahydro-2H-pyran-4-yl)methyl)amino)benzenesulfonamide. ¹H NMR (400 MHz, DMSO-d₆) δ 11.63 (s, 1H), 11.38 (br s, 1H), 8.61-8.54 (m, 2H), 8.04 (d, J=2.8 Hz, 1H), 7.78 (dd, J=9.6, 1.6 Hz, 1H), 7.53-7.50 (m, 3H), 7.10 (d, J=9.2 Hz, 1H), 6.71 (dd, J=9.2, 1.6 Hz, 1H), 6.39-6.38 (m, 1H), 6.25-6.24 (m, 1H), 5.99 (t, J=56.4 Hz, 1H), 3.84 (dd, J=11.2, 3.2 Hz, 2H), 3.32-3.23 (m, 4H), 3.11 (br s, 4H), 2.94 (s, 2H), 2.33 (br s, 4H), 2.09-1.73 (m, 13H), 1.71-1.60 (m, 6H), 1.46 (t, J=5.6 Hz, 2H), 1.30-1.20 (m, 2H); LC/MS (ESI) m/z 886.3 [M+H]⁺.

142

Example 43

2-((1H-pyrrolo[2,3-b]pyridin-5-yl)oxy)-N-((4-(((4-fluorotetrahydro-2H-pyran-4-yl)methyl)amino)-3-nitrophenyl)sulfonyl)-4-(4-((6-(3-methylbicyclo[1.1.1]pentan-1-yl)spiro[3.5]non-6-en-7-yl)methyl)piperazin-1-yl)benzamide

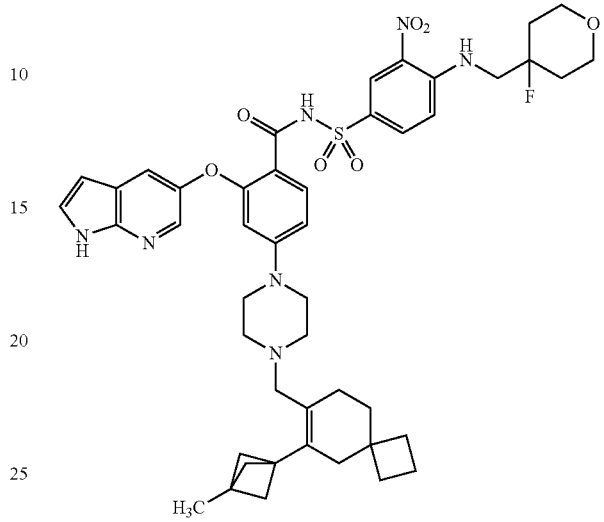

Example 43 was prepared following General Procedure B using Intermediate 51 and Intermediate 52. ¹H NMR (400 MHz, DMSO-d₆) δ 11.64 (s, 1H), 11.40 (br s, 1H), 8.57-8.53 (m, 2H), 8.01 (d, J=2.4 Hz, 1H), 7.78 (d, J=8 Hz, 1H), 7.53-7.48 (m, 3H), 7.19-7.17 (m, 1H), 6.70 (dd, J=8.8, 1.6 Hz, 1H), 6.36 (br s, 1H), 6.26-6.25 (m, 1H), 3.76-3.68 (m, 4H), 3.55-3.50 (m, 2H), 3.09 (br s, 4H), 2.95 (br s, 2H), 2.32-2.32 (br s, 4H), 1.98-1.92 (m, 4H), 1.83-1.58 (m, 16H), 1.45 (t, J=5.6 Hz, 2H), 1.10 (s, 3H); LC/MS (ESI) m/z 868.4 [M+H]⁺.

Example 44

2-((1H-pyrrolo[2,3-b]pyridin-5-yl)oxy)-4-(4-((6-(3-(difluoromethyl)bicyclo[1.1.1]pentan-1-yl)spiro[3.5]non-6-en-7-yl)methyl)piperazin-1-yl)-N-((4-((((1r,4r)-4-hydroxy-4-methylcyclohexyl)methyl)amino)-3-nitrophenyl)sulfonyl)benzamide

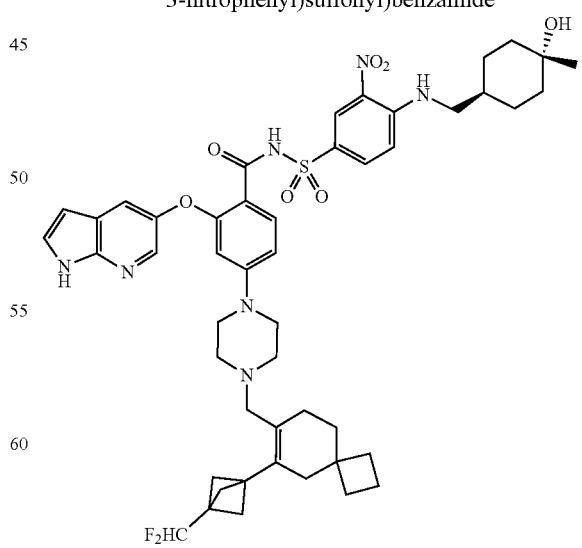

Example 44 was prepared following General Procedure B using Intermediate 50 and Intermediate 18. LC/MS (ESI) m/z 914.5 [M+H]⁺.

Example 45

(R)-4-(4-((2-(3-Chlorobicyclo[1.1.1]pentan-1-yl)-5,5-dimethylcyclohex-1-en-1-yl)methyl)piperazin-1-yl)-N-((4-((4-morpholino-1-(phenylthio)butan-2-yl)amino)-3-((trifluoromethyl)sulfonyl)phenyl)sulfonyl)benzamide

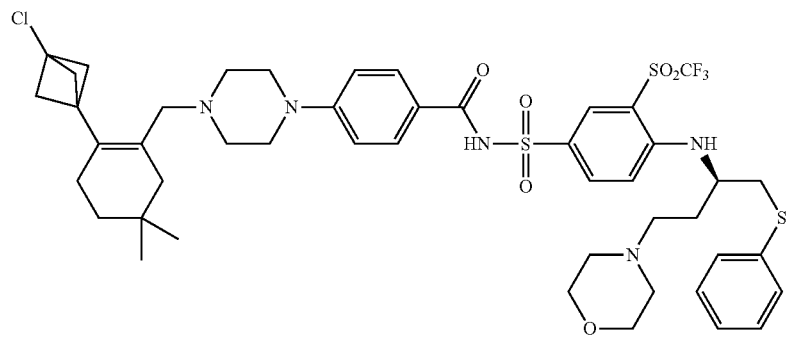

To a stirred solution of Intermediate 36 (45 mg, 0.105 mmol) in DCM (5 mL) was added EDC·HCl (21 mg, 0.0252 mmol) followed by DMAP (26 mg, 0.21 mmol) at 0° C. After 10 min, (R)-4-((4-morpholino-1-(phenylthio)butan-2-yl)amino)-3-((trifluoromethyl)sulfonyl)benzenesulfonamide (70 mg, 0.126 mmol) was added and the reaction was warmed to rt. After 48 h, water (10 mL) was added and the reaction mixture was extracted with DCM (3×20 mL). The combined organic layers were dried over $Na_2SO_4$, filtered and concentrated. The product was purified by HPLC (45:55 to 1:99 10 mM $NH_4CO_3H$(aq.)/$CH_3CN$) to afford Example 45 (4 mg, 4% yield) as a white solid. LC/MS (ESI) m/z 964.4 $[M+H]^+$.

Example 46

(R)-4-(4-((2-(3-chlorobicyclo[1.1.1]pentan-1-yl)-5,5-dimethylcyclohex-1-enyl)methyl)piperazin-1-yl)-N-(4-(4-(4-hydroxypiperidin-1-yl)-1-(phenylthio)butan-2-ylamino)-3-(trifluoromethylsulfonyl)phenylsulfonyl)benzamide

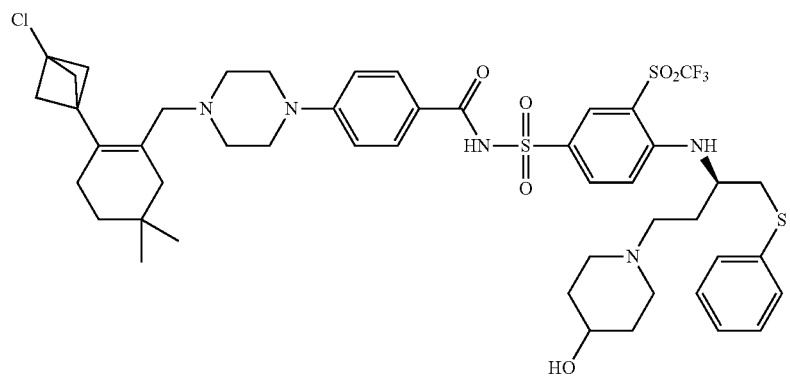

Example 46 was prepared following the procedure described for Example 45 by using Intermediate 37 in place of (R)-4-((4-morpholino-1-(phenylthio)butan-2-yl)amino)-3-((trifluoromethyl)sulfonyl)benzenesulfonamide. LC/MS (ESI) m/z 978.4 $[M+H]^+$

Example 47

(R)-4-(4-((5,5-Dimethyl-2-(3-methylbicyclo[1.1.1]
pentan-1-yl)cyclohex-1-enyl)methyl)piperazin-1-yl)-
N-(4-(4-morpholino-1-(phenylthio)butan-2-
ylamino)-3-(trifluoromethylsulfonyl)phenylsulfonyl)
benzamide

Example 47 was prepared following the procedure described for Example 45 by using Intermediate 38 in place of Intermediate 36. $^1$H NMR (400 MHz, CDCl$_3$) δ 8.36 (d, J=2.4 Hz, 1H), 8.11 (dd, J=9.4, 1.6 Hz, 1H), 7.67 (d, J=8.8 Hz, 2H), 7.38 (d, J=6.8 Hz, 2H), 7.33-7.26 (m, 3H), 7.05 (d, J=8.4 Hz, 1H), 6.81 (d, J=8.8 Hz, 2H), 6.59 (d, J=10.0 Hz, 1H), 3.95-3.85 (m, 1H), 3.71-3.60 (m, 4H), 3.36-3.24 (m, 4H), 3.14 (s, 2H), 3.13-2.98 (m, 2H), 2.61-2.50 (m, 4H), 2.49-2.28 (m, 6H), 2.19-2.08 (m, 1H), 1.99-1.92 (m, 2H), 1.86 (s, 2H), 1.81 (s, 6H), 1.71-1.61 (m, 1H), 1.30 (t, J=6.4 Hz, 2H), 1.13 (s, 3H), 0.86 (s, 6H). One —NH proton was not observed; LC/MS (ESI) m/z 944.6 [M+H]$^+$.

Example 48

(R)-4-(4-((5,5-dimethyl-2-(3-methylbicyclo[1.1.1]
pentan-1-yl)cyclohex-1-enyl)methyl)piperazin-1-yl)-
N-(4-(4-(4-hydroxypiperidin-1-yl)-1-(phenylthio)
butan-2-ylamino)-3-(trifluoromethylsulfonyl)
phenylsulfonyl)benzamide

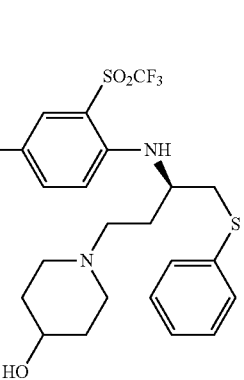

Example 48 was prepared following the procedure described Example 46 by using Intermediate 38 in place of Intermediate 36. LC/MS (ESI) m/z 958.3 [M+H]$^+$.

Example 49

(R)-4-(4-((4,4-dimethyl-2-(3-methylbicyclo[1.1.1]
pentan-1-yl)cyclohex-1-en-1-yl)methyl)piperazin-1-
yl)-N-((4-((4-((2-hydroxyethyl)(methyl)amino)-1-
(phenylthio)butan-2-yl)amino)-3-((trifluoromethyl)
sulfonyl)phenyl)sulfonyl)benzamide

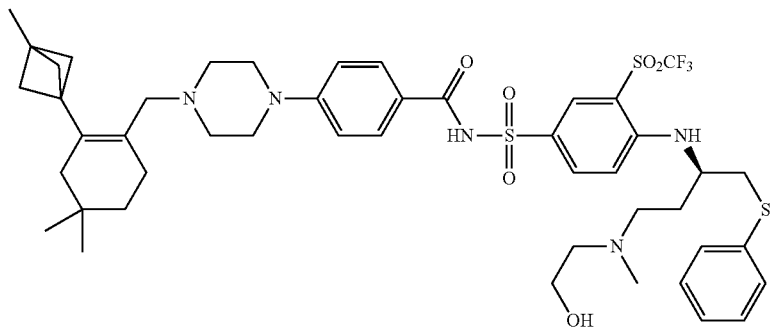

Step 1: (R)—N-((4-((4-((2-((tert-butyldiphenylsilyl)oxy)ethyl)(methyl)amino)-1-(phenylthio)butan-2-yl)amino)-3-((trifluoromethyl)sulfonyl)phenyl)sulfonyl)-4-(4-((4,4-dimethyl-2-(3-methylbicyclo[11.1.1]pentan-1-yl)cyclohex-1-en-1-yl)methyl)piperazin-1-yl)benzamide (Example 49-1) was prepared following General Procedure B using Intermediate 39 and Intermediate 35. LC/MS (ESI) m/z 1170.9 [M+H]$^+$.

Step 2: To a stirred solution of Example 49-1 (375 mg, 0.32 mmol) in THF (15 mL) at 0° C. was added TBAF (1M in THF, 0.48 mL). After 5 min the reaction was warmed to rt. After 2 h, the reaction was quenched with water (25 mL) and extracted with 9:1 DCM/MeOH (3×35 mL), and concentrated. The crude compound was purified by HPLC (50:50 to 0:100 10 mM NH$_4$CO$_3$H(aq.)/CH$_3$CN) to obtain Example 49 as a white solid. LC/MS (ESI) m/z 932.6 [M+H]$^+$

Example 50

(R)-4-(4-((2-(3-Ethylbicyclo[1.1.1]pentan-1-yl)-4,4-
dimethylcyclohex-1-en-1-yl)methyl)piperazin-1-yl)-
N-((4-((4-((2-hydroxyethyl)(methyl)amino)-1-(phe-
nylthio)butan-2-yl)amino)-3-((trifluoromethyl)
sulfonyl)phenyl)sulfonyl)benzamide

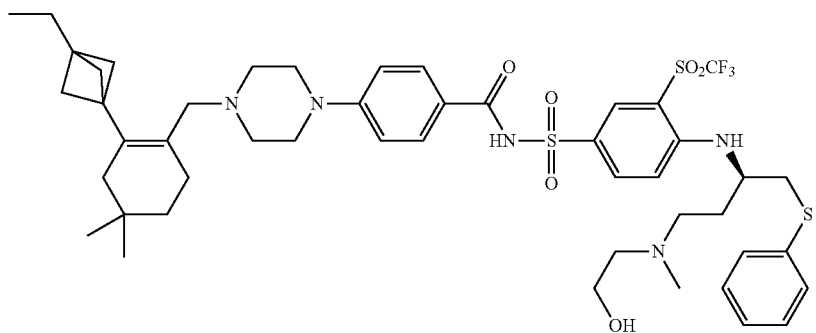

Step 1: (R)—N-((4-((4-((2-((tert-Butyldiphenylsilyl)oxy)ethyl)(methyl)amino)-1-(phenylthio)butan-2-yl)amino)-3-((trifluoromethyl)sulfonyl)phenyl)sulfonyl)-4-(4-((2-(3-ethylbicyclo[1.1.1]pentan-1-yl)-4,4-dimethylcyclohex-1-en-1-yl)methyl)piperazin-1-yl)benzamide (Example 50-1) was prepared following General Procedure B using Intermediate 40 and Intermediate 35. LC/MS (ESI) m/z 1186.0 [M+H]+

Step 2: Example 50 was prepared following the procedure described in Step 2 for Example 49 by using Example 50-1 in place of Example 49-1. LC/MS (ESI) m/z 946.7 [M+H]+

Example 51

(R)-4-(4-((4,4-dimethyl-2-(3-(trifluoromethyl)bicyclo[1.1.1]pentan-1-yl)cyclohex-1-en-1-yl)methyl)piperazin-1-yl)-N-((4-((4-((2-hydroxyethyl)(methyl)amino)-1-(phenylthio)butan-2-yl)amino)-3-((trifluoromethyl)sulfonyl)phenyl)sulfonyl)benzamide

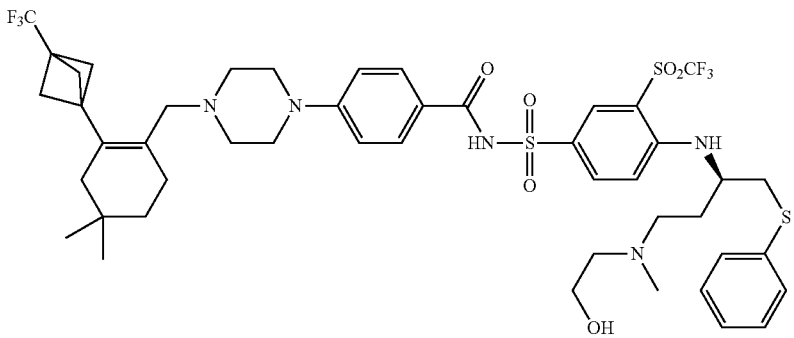

Step 1: (R)—N-((4-((4-((2-((tert-Butyldiphenylsilyl)oxy)ethyl)(methyl)amino)-1-(phenylthio)butan-2-yl)amino)-3-((trifluoromethyl)sulfonyl)phenyl)sulfonyl)-4-(4-((2-(3-ethylbicyclo[1.1.1]pentan-1-yl)-4,4-dimethylcyclohex-1-en-1-yl)methyl)piperazin-1-yl)benzamide (Example 51-1) was prepared following General Procedure B using Intermediate 41 and Intermediate 35. LC/MS (ESI m/z 1225.9 [M+2H]+

Step 2: To a stirred solution of Example 51-1 (500 mg, 0.4 mmol) in THF at 0° C. was added TBAF (1M in THF, 0.49 mL). After 5 min the reaction was warmed to rt. After 5 h, the reaction was quenched with water (25 mL) and with 9:1 DCM/MeOH (3×50 mL). The combined organic layers were washed with brine (2×15 mL), dried over Na2SO4, filtered and concentrated. The crude compound was purified by column chromatography (SiO2, 7-10% MeOH in DCM) to obtain Example 51 (101 mg, 20%, over 2 steps) as a white solid. LC/MS (ESI) m/z 986.7 [M+H]+

Example 52

(R)-4-(4-((4,4-Dimethyl-2-(3-methylbicyclo[1.1.1]pentan-1-yl)cyclohex-1-en-1-yl)methyl)piperazin-1-yl)-N-((4-((4-morpholino-1-(phenylthio)butan-2-yl)amino)-3-((trifluoromethyl)sulfonyl)phenyl)sulfonyl)benzamide

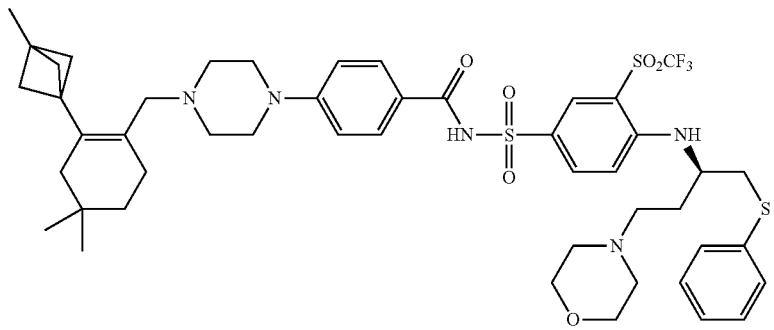

Example 52 was prepared following General Procedure B using Intermediate 39 and (R)-4-((4-morpholino-1-(phenylthio)butan-2-yl)amino)-3-((trifluoromethyl)sulfonyl)benzenesulfonamide. LC/MS (ESI) m/z 944.9 [M+H]+.

Example 53

(R)-4-(4-((2-(3-Ethylbicyclo[1.1.1]pentan-1-yl)-4,4-dimethylcyclohex-1-en-1-yl)methyl)piperazin-1-yl)-N-((4-((4-morpholino-1-(phenylthio)butan-2-yl)amino)-3-((trifluoromethyl)sulfonyl)phenyl)sulfonyl)benzamide

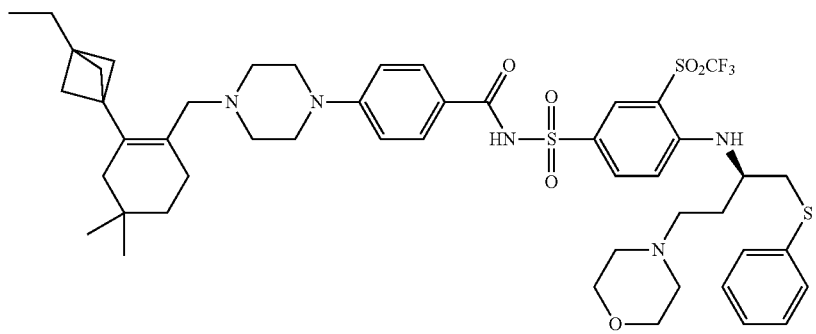

Example 53 was prepared following General Procedure B using Intermediate 40 and (R)-4-((4-morpholino-1-(phenylthio)butan-2-yl)amino)-3-((trifluoromethyl)sulfonyl)benzenesulfonamide. LC/MS (ESI) m/z 958.8 [M+H]+.

Example 54

(R)-4-(4-((4,4-dimethyl-2-(3-(trifluoromethyl)bicyclo[1.1.1]pentan-1-yl)cyclohex-1-en-1-yl)methyl)piperazin-1-yl)-N-((4-((4-morpholino-1-(phenylthio)butan-2-yl)amino)-3-((trifluoromethyl)sulfonyl)phenyl)sulfonyl)benzamide

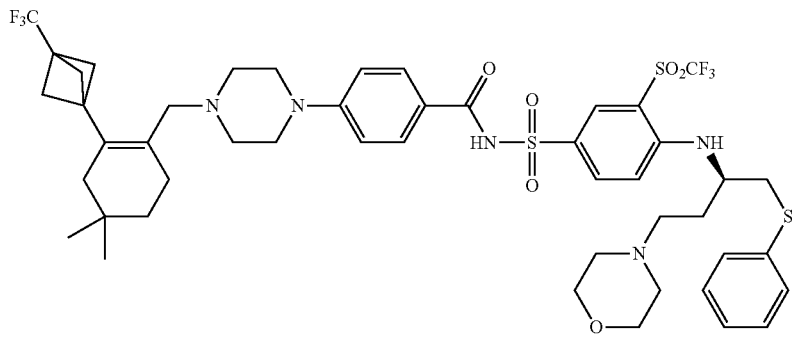

Example 54 was prepared following General Procedure B using Intermediate 41 and (R)-4-((4-morpholino-1-(phenylthio)butan-2-yl)amino)-3-((trifluoromethyl)sulfonyl)benzenesulfonamide. LC/MS (ESI) m/z 998.9 [M+H]+.

Example 55

(R)-4-(4-((2-(3-(difluoromethyl)bicyclo[1.1.1]pentan-1-yl)-4,4-dimethylcyclohex-1-en-1-yl)methyl)piperazin-1-yl)-N-((4-((4-morpholino-1-(phenylthio)butan-2-yl)amino)-3-((trifluoromethyl)sulfonyl)phenyl)sulfonyl)benzamide

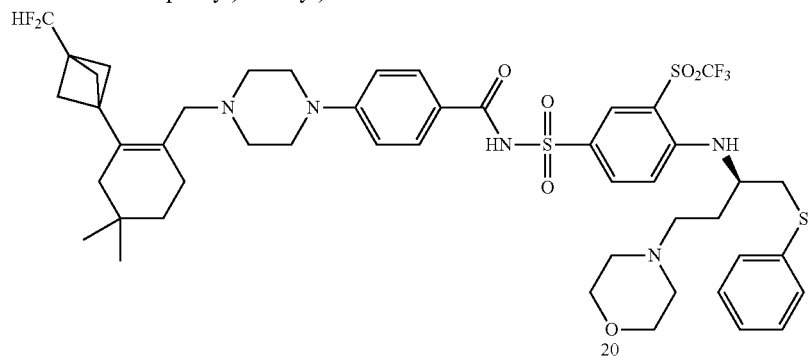

Example 55 was prepared following General Procedure B using Intermediate 42 and (R)-4-((4-morpholino-1-(phenylthio)butan-2-yl)amino)-3-((trifluoromethyl)sulfonyl)benzenesulfonamide. LC/MS (ESI) m/z 980.9 [M+H]$^+$.

Example 56

(R)-4-(4-((4,4-dimethyl-2-(3-methylbicyclo[1.1.1]pentan-1-yl)cyclohex-1-en-1-yl)methyl)piperazin-1-yl)-N-((4-((4-morpholino-1-(phenylthio)butan-2-yl)amino)-3-nitrophenyl)sulfonyl)benzamide

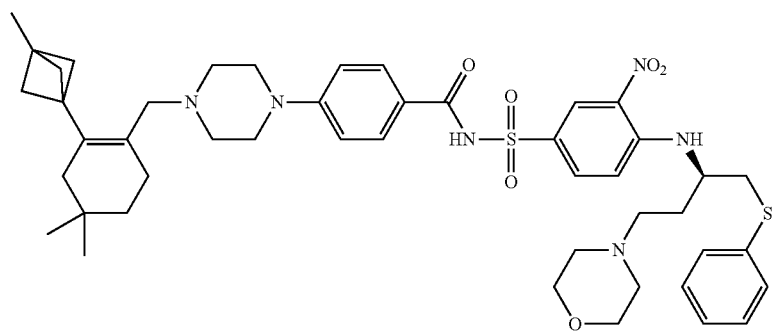 [SMILES: CC1(C)CCC(CN2CCN(c3ccc(C(=O)NS(=O)(=O)c4ccc(N[C@H](CCN5CCOCC5)CSc5ccccc5)c([N+](=O)[O-])c4)cc3)CC2)=C(C23CC(C)(C2)C3)C1]

Example 56 was prepared following General Procedure B using Intermediate 39 and Intermediate 43. LC/MS (ESI) m/z 857.8 [M+H]$^+$.

Example 57

(R)-4-(4-((2-(3-ethylbicyclo[1.1.1]pentan-1-yl)-4,4-dimethylcyclohex-1-en-1-yl)methyl)piperazin-1-yl)-N-((4-((4-morpholino-1-(phenylthio)butan-2-yl)amino)-3-nitrophenyl)sulfonyl)benzamide

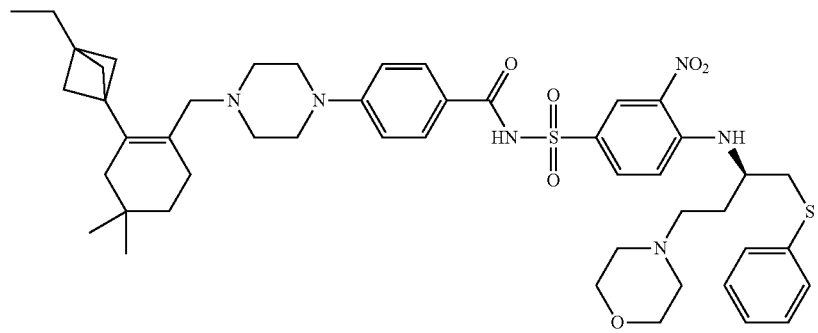

Example 57 was prepared following General Procedure B using Intermediate 40 and Intermediate 43. LC/MS (ESI) m/z 871.8 [M+H]+.

Example 58

(R)-4-(4-((2-(3-(difluoromethyl)bicyclo[1.1.1]pentan-1-yl)-4,4-dimethylcyclohex-1-en-1-yl)methyl)piperazin-1-yl)-N-((4-((4-morpholino-1-(phenylthio)butan-2-yl)amino)-3-nitrophenyl)sulfonyl)benzamide

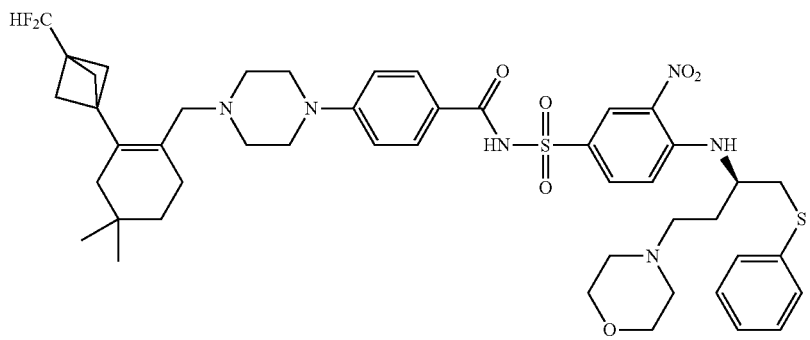

Example 58 was prepared following General Procedure B using Intermediate 42 and Intermediate 43. $^1$H NMR (400 MHz, DMSO-d$_6$) δ 8.48 (s, 1H), 8.40-8.30 (m, 1H), 7.78 (d, J=9.2 Hz, 1H), 7.73 (d, J=8.8 Hz, 2H), 7.31-7.28 (m, 2H), 7.25-7.20 (m, 2H), 7.17-7.13 (m, 1H), 7.05-6.95 (m, 1H), 6.87 (d, J=8.8 Hz, 2H), 6.01 (t, J=56.0 Hz, 1H), 4.19-4.09 (m, 1H), 3.60-3.45 (m, 4H), 3.30-3.15 (m, 6H), 3.10-2.90 (m, 2H), 2.55-2.10 (m, 10H), 2.10-2.01 (m, 3H), 1.99 (s, 6H), 1.90-1.80 (m, 1H), 1.71 (s, 2H), 1.30-1.21 (m, 2H), 0.86 (s, 6H). One —NH proton was not observed; LC/MS (ESI) m/z 893.6 [M+H]+.

Example 59

(R)-4-(4-((4,4-dimethyl-2-(3-methylbicyclo[1.1.1]pentan-1-yl)cyclohex-1-en-1-yl)methyl)piperazin-1-yl)-N-((4-((4-(dimethylamino)-1-(phenylthio)butan-2-yl)amino)-3-((trifluoromethyl)sulfonyl)phenyl)sulfonyl)benzamide

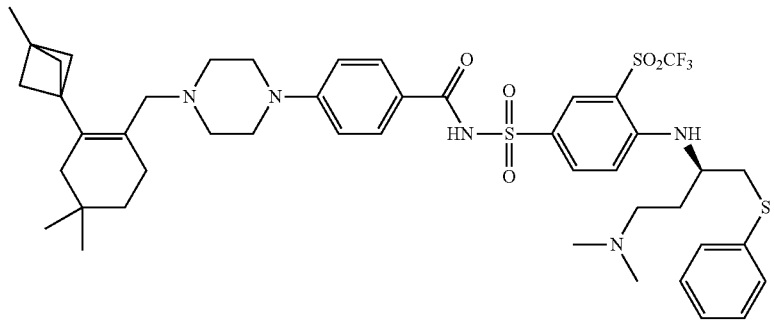

Example 59 was prepared following General Procedure B using Intermediate 39 and Intermediate 44. LC/MS (ESI) m/z 902.6 [M+H]+.

Example 60

(R)-4-(4-((2-(3-(difluoromethyl)bicyclo[1.1.1]pen-tan-1-yl)-4,4-dimethylcyclohex-1-en-1-yl)methyl)piperazin-1-yl)-N-((4-((4-((2-hydroxyethyl)(methyl)amino)-1-(phenylthio)butan-2-yl)amino)-3-((trifluoromethyl)sulfonyl)phenyl)sulfonyl)benzamide

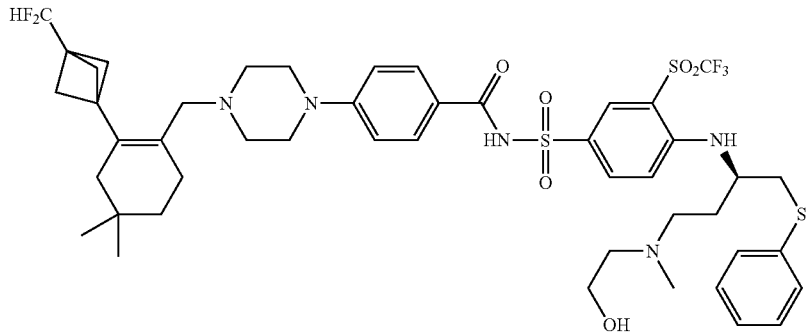

Step 1: (R)—N-((4-((4-((2-((tert-butyldiphenylsilyl)oxy)ethyl)(methyl)amino)-1-(phenylthio)butan-2-yl)amino)-3-((trifluoromethyl)sulfonyl)phenyl)sulfonyl)-4-(4-((2-(3-(di-fluoromethyl)bicyclo[1.1.1]pentan-1-yl)-4,4-dimethylcyclohex-1-en-1-yl)methyl)piperazin-1-yl)benzamide (Example 60-1) was prepared following General Procedure B using Intermediate 42 and Intermediate 35. LC/MS (ESI) m/z 1206.5 [M+H]$^+$ Step 2: To a stirred solution of Example 60-1 (130 mg, 0.10 mmol) in 1,4-dioxane (5 mL) was added HCl (4M in 1,4 dioxane, 1 mL) followed by 3 drops of water at 0° C. The reaction was warmed to rt, stirred for 16 h, and then concentrated. The crude reaction mixture was diluted with sat. aq. NaHCO$_3$ and extracted with EtOAc (3×25 mL). The combined organic layers were dried over Na$_2$SO$_4$, filtered and concentrated. The crude product was purified by column chromatography (SiO$_2$, MeOH/DCM) to afford Example 60 (30 mg, 29% yield) as an off-white colored solid. LC/MS (ESI) m/z 968.2 [M+H]$^+$.

Example 61

(R)-4-(4-((2-(3-(Difluoromethyl)bicyclo[1.1.1]pen-tan-1-yl)-4,4-dimethylcyclohex-1-en-1-yl)methyl)piperazin-1-yl)-N-((4-((4-(4-hydroxypiperidin-1-yl)-1-(phenylthio)butan-2-yl)amino)-3-((trifluoromethyl)sulfonyl)phenyl)sulfonyl)benzamide

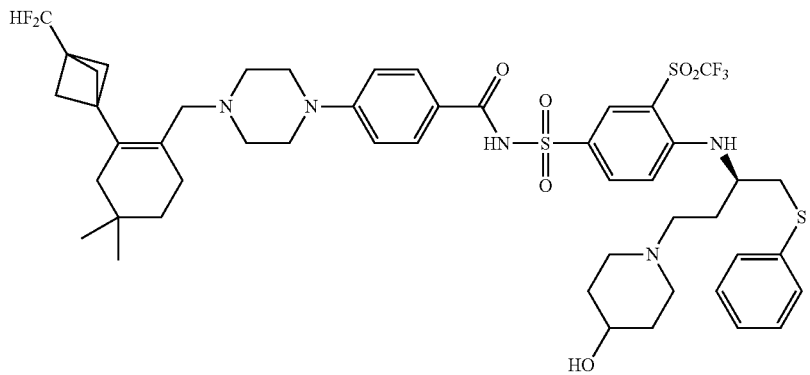

Example 61 was prepared following General Procedure B using Intermediate 42 and Intermediate 37. LC/MS (ESI) m/z 994.6 M+H]+.

Example 62

(R)-4-(4-((2-(3-(Difluoromethyl)bicyclo[1.1.1]pentan-1-yl)-4,4-dimethylcyclohex-1-en-1-yl)methyl)piperazin-1-yl)-N-((4-((4-(4-(dimethylamino)piperidin-1-yl)-1-(phenylthio) butan-2-yl)amino-3-((trifluoromethyl)sulfonyl)phenyl)sulfonyl)benzamide

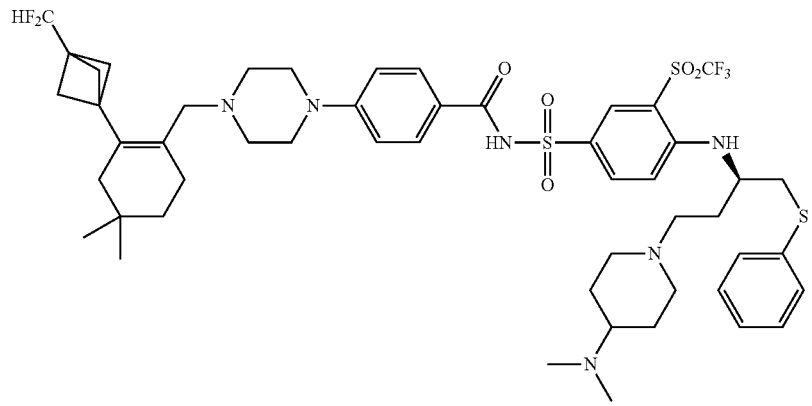

Example 62 was prepared following General Procedure B using Intermediate 42 and Intermediate 45. LC/MS (ESI) m/z 1021.2 [M+H]+.

Example 63

(R)-4-(4-((2-(3-(Difluoromethyl)bicyclo[1.1.1]pentan-1-yl)-4,4-dimethylcyclohex-1-en-1-yl)methyl)piperazin-1-yl)-N-((4-((4-(dimethylamino)-1-(phenylthio)butan-2-yl)amino)-3-((trifluoromethyl)sulfonyl)phenyl)sulfonyl)benzamide

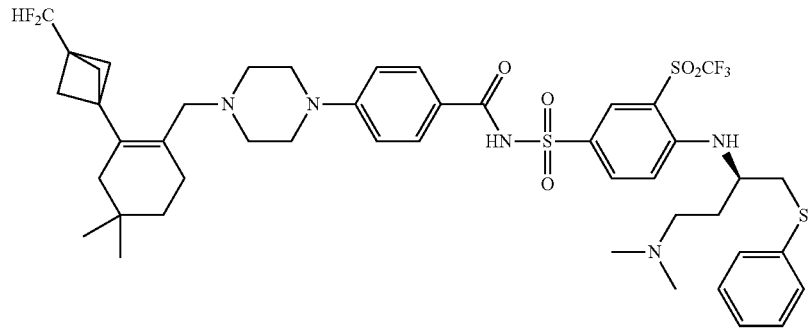

Example 63 was prepared following General Procedure B using Intermediate 42 and Intermediate 44. LC/MS (ESI) m/z 938.4 [M+H]+.

Example 64

(R)-4-(4-((2-(3-(difluoromethyl)bicyclo[1.1.1]pentan-1-yl)-4,4-dimethylcyclohex-1-en-1-yl)methyl)piperazin-1-yl)-N-((4-(((1-(phenylthio)-4-(piperazin-1-yl)butan-2-yl)amino)-3-((trifluoromethyl)sulfonyl)phenyl)sulfonyl)benzamide

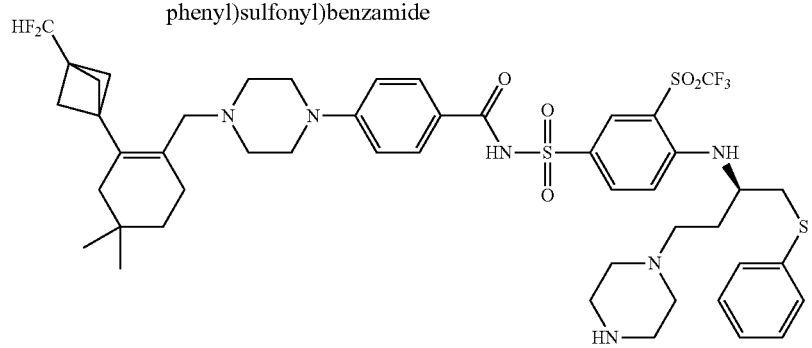

Step 1: (R)-tert-Butyl 4-(3-((4-(N-(4-(4-((2-(3-(difluoromethyl)bicyclo[1.1.1]pentan-1-yl)-4,4-dimethylcyclohex-1-en-1-yl)methyl)piperazin-1-yl)benzoyl)sulfamoyl)-2-((trifluoro-methyl)sulfonyl)phenyl)amino)-4-(phenylthio)butyl)piperazine-1-carboxylate (Example 64-1) was prepared following General Procedure B using Intermediate 42 and Intermediate 46. LC/MS (ESI) m/z 1079.3 [M+H]$^+$ Step 2: To a stirred solution of Example 64-1 (350 mg, 0.32 mmol) in Et$_2$O (5 mL) at 0° C., was added HCl (2M in Et$_2$O, 2.0 mL). The reaction was warmed to rt and stirred for 16 h. The reaction was concentrated, diluted with ice cold water, basified with sat. aq. NaHCO$_3$ (10 mL) and extracted with 10% MeOH in DCM (3×30 mL). The combined organic layers were dried over anhydrous Na$_2$SO$_4$, filtered and concentrated. The crude product was purified by HPLC (30:70 to 1:99 10 mM NH$_4$CO$_3$H(aq.)/CH$_3$CN) to provide Example 64 (14 mg, 4% yield) as an off-white solid. $^1$H NMR (400 MHz, DMSO-d$_6$) δ 8.32 (br s, 2H), 8.02 (s, 1H), 7.91 (d, J=8.8 Hz, 1H), 7.68 (d, J=8.8 Hz, 2H), 7.34-7.23 (m, 4H), 7.19-7.15 (m, 1H), 6.83-6.75 (m, 3H), 6.66 (d, J=8.8 Hz, 1H), 5.97 (t, J=56.8 Hz, 1H), 3.97 (br s, 1H), 3.26-3.23 (m, 2H), 3.15-3.10 (m, 4H), 3.02-2.90 (m, 6H), 2.52-2.50 (m, 2H), 2.40-2.23 (m, 8H), 2.10-1.83 (m, 9H), 1.67 (s, 3H), 1.23 (t, J=6.4 Hz, 2H), 0.82 (s, 6H); LC/MS (ESI) m/z 979.4 [M+H]$^+$.

Example 65

(R)-4-(4-((2-(3-(difluoromethyl)bicyclo[1.1.1]pentan-1-yl)-5,5-dimethylcyclohex-1-en-1-yl)methyl)piperazin-1-yl)-N-((4-(((4-(4-hydroxypiperidin-1-yl)-1-(phenylthio)butan-2-yl)amino)-3-((trifluoromethyl)sulfonyl)phenyl)sulfonyl)benzamide

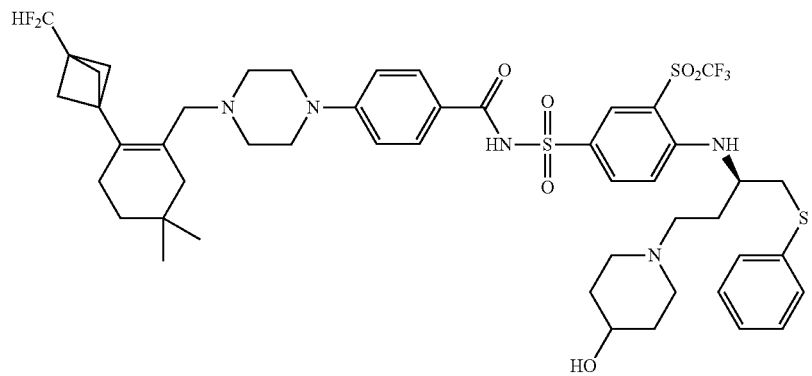

Example 65 was prepared following General Procedure B using Intermediate 56 and Intermediate 37. LC/MS (ESI) m/z 994.4 [M+H]⁺.

Example 66

(R)-4-(4-((2-(3-(difluoromethyl)bicyclo[1.1.1]pentan-1-yl)-4,4-dimethylcyclohex-1-en-1-yl)methyl)piperazin-1-yl)-N-((4-((4-(3-hydroxyazetidin-1-yl)-1-(phenylthio)butan-2-yl)amino)-3-(trifluoromethyl)sulfonyl)phenyl)sulfonyl)benzamide

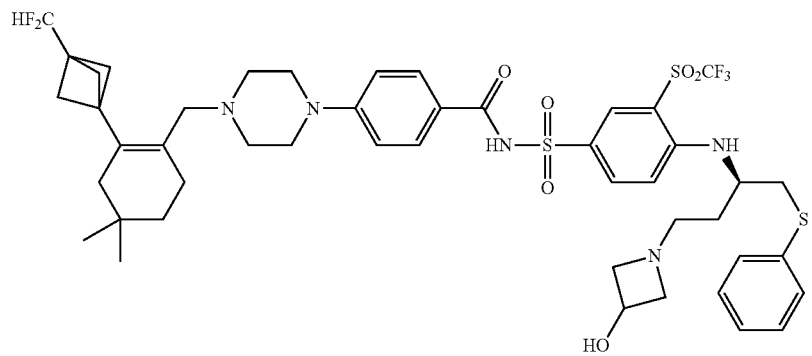

Example 66 was prepared following General Procedure B using Intermediate 42 and Intermediate 57. LC/MS (ESI) m/z 966.5 [M+H]⁺.

Example 67

(R)-4-(4-((6-(3-(difluoromethyl)bicyclo[1.1.1]pentan-1-yl)spiro[3.5]non-6-en-7-yl)methyl)piperazin-1-yl)-N-((4-((4-(4-hydroxypiperidin-1-yl)-1-(phenylthio)butan-2-yl)amino)-3-((trifluoromethyl)sulfonyl)phenyl)sulfonyl)benzamide

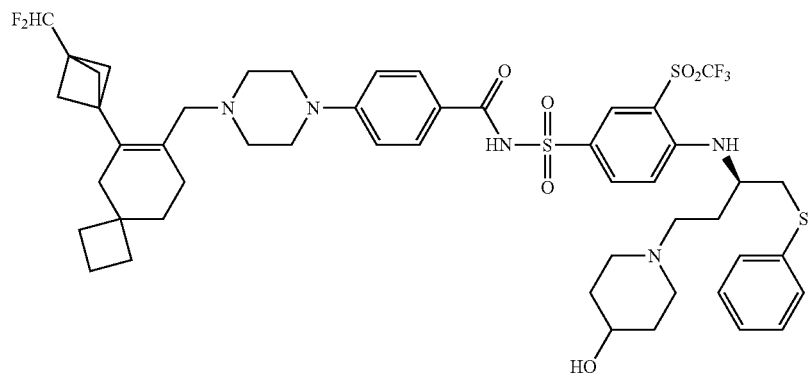

Example 67 was prepared following General Procedure B using Intermediate 58 and Intermediate 37. LC/MS (ESI) m/z 1006.5 [M+H]⁺.

Example 68

(R)-4-(4-((4,4-dimethyl-2-(3-methylbicyclo[1.1.1]pentan-1-yl)cyclohex-1-en-1-yl)methyl)piperazin-1-yl)-N-((4-((4-(4-hydroxypiperidin-1-yl)-1-(phenylthio)butan-2-yl)amino)-3-((trifluoromethyl)sulfonyl)phenyl)sulfonyl)benzamide

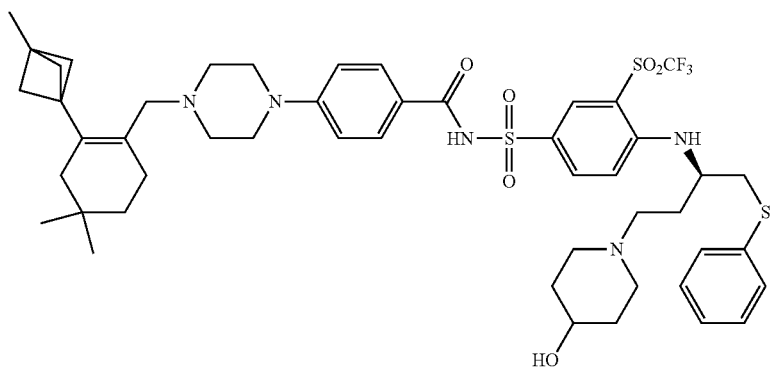

Example 68 was prepared following General Procedure B using Intermediate 37 and Intermediate 39. LC/MS (ESI) m/z 958.2 [M+H]$^+$.

Example 69

(R)-4-(4-((2-(3-(difluoromethyl)bicyclo[1.1.1]pentan-1-yl)-4,4-dimethylcyclohex-1-en-1-yl)methyl)piperazin-1-yl)-N-((4-((4-(4-(2-hydroxyethyl)piperazin-1-yl)-1-(phenylthio)butan-2-yl)amino)-3-(trifluoromethyl)sulfonoyl)phenyl)sulfonyl)benzamide

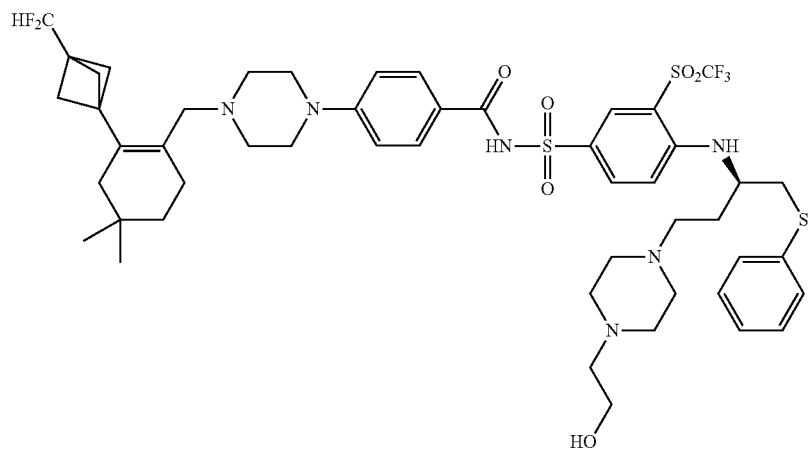

Step 1: (R)—N-((4-((4-(4-(2-((tert-butyldiphenylsilyl)oxy)ethyl)piperazin-1-yl)-1-(phenylthio)butan-2-yl)amino)-3-((trifluoromethyl)sulfonyl)phenyl)sulfonyl)-4-(4-((2-(3-(difluoromethyl)bicyclo[1.1.1]pentan-1-yl)-4,4-dimethylcyclohex-1-en-1-yl)methyl)piperazin-1-yl)benzamide (Example 69-1) was prepared following General Procedure B using Intermediate 42 and Intermediate 59. LC/MS (ESI) m/z 631.6 [M+2H]$^+$ Step 2: To a stirred solution of Example 69-1 (250 mg, 0.198 mmol) in 1,4-dioxane was added HCl (4M in 1,4 dioxane, 1.5 mL) followed by 3 drops of water at 0° C. The reaction was warmed to rt, stirred for 16 h, and then concentrated. The crude reaction mixture was diluted with sat. aq. NaHCO$_3$ and extracted with 9:1 DCM:MeOH (3×30 mL). The combined organic layers were dried over Na$_2$SO$_4$, filtered and concentrated. The crude product was purified by HPLC (10 mM NH$_4$OAc(aq):CH$_3$CN) to afford the title compound (22 mg, 11% yield) as an off-white solid. LC/MS (ESI) m/z 1023.3 [M+H]$^+$.

Example 70

(R)-4-(4-((2-(3-(difluoromethyl)bicyclo[1.1.1]pentan-1-yl)-4,4-dimethylcyclohex-1-en-1-yl)methyl)piperazin-1-yl)-N-((4-((4-(ethyl(2-hydroxyethyl)amino)-1-(phenylthio)butan-2-yl)amino)-3-((trifluoromethyl)sulfonyl)phenyl)sulfonyl)benzamide

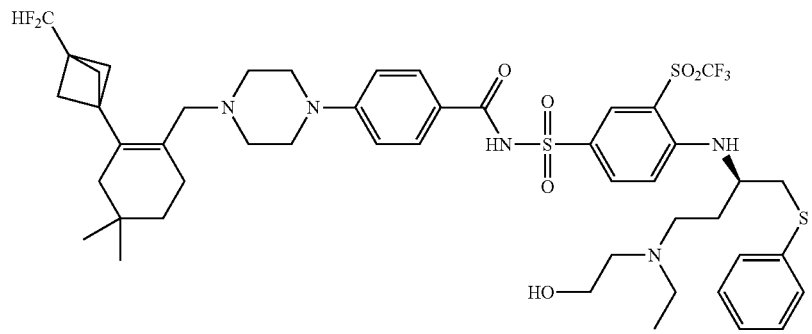

Step 1: (R)—N-((4-((4-((2-((tert-butyldiphenylsilyl)oxy)ethyl)(ethyl)amino)-1-(phenylthio)butan-2-yl)amino)-3-((trifluoromethyl)sulfonyl)phenyl)sulfonyl)-4-(4-((2-(3-(difluoromethyl)bicyclo[1.1.1]pentan-1-yl)-4,4-dimethylcyclohex-1-en-1-yl)methyl)piperazin-1-yl)benzamide (Example 70-1) was prepared following General Procedure B using Intermediate 42 and Intermediate 60. LC/MS (ESI) m/z 611.3 [M+2H]$^+$ Step 2: Example 70 was prepared following the procedure described in Example 69 using Example 70-1 in place of Example 69-1. LC/MS (ESI) m/z 982.5 [M+H]$^+$.

Example 71

(R)—N-((4-((4-((2-((tert-butyldiphenylsilyl)oxy)ethyl)(ethyl)amino)-1-(phenylthio)butan-2-yl)amino)-3-((trifluoromethyl)sulfonyl)phenyl)sulfonyl)-4-(4-((2-(3-(difluoromethyl)bicyclo[1.1.1]pentan-1-yl)-4,4-dimethylcyclohex-1-en-1-yl)methyl)piperazin-1-yl)benzamide

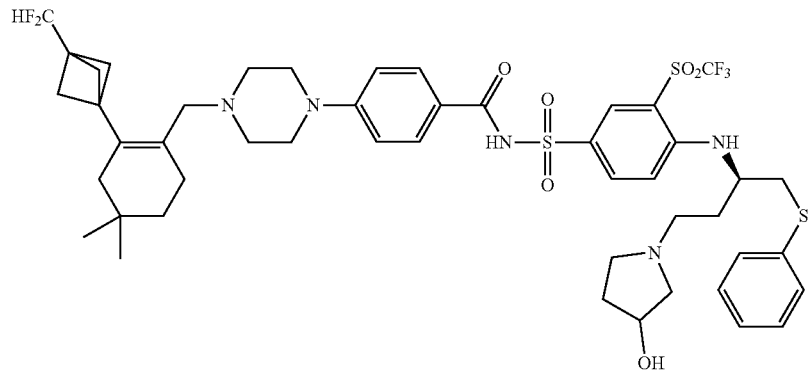

Example 71 was prepared following General Procedure B using Intermediate 42 and Intermediate 61. LC/MS (ESI) m/z 980.4 [M+H]$^+$.

169

Example 72

2-((1H-pyrrolo[2,3-b]pyridin-5-yl)oxy)-4-(4-((2-(3-chlorobicyclo[1.1.1]pentan-1-yl)cyclohex-1-en-1-yl)methyl)piperazin-1-yl)-N-((3-nitro-4-(((tetrahydro-2H-pyran-4-yl)methyl)amino)phenyl)sulfonyl)benzamide

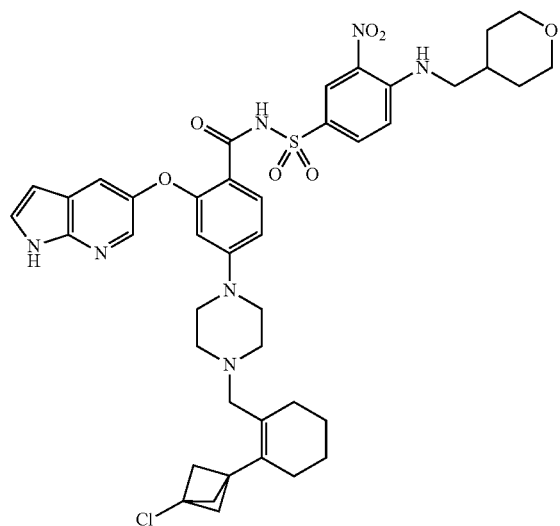 [SMILES: O=C(NS(=O)(=O)c1ccc(NCC2CCOCC2)c([N+](=O)[O-])c1)c1ccc(N2CCN(CC3=C(C45CC(Cl)(C4)C5)CCCC3)CC2)cc1Oc1cnc2[nH]ccc2c1]

Example 72 was prepared following General Procedure A using Intermediate 62 and 3-nitro-4-(((tetrahydro-2H-pyran-4-yl)methyl)amino)benzenesulfonamide. LC/MS (ESI) m/z 830.8 [M+H]$^+$.

Example 73

(R)-2-((1H-pyrrolo[2,3-b]pyridin-5-yl)oxy)-4-(4-((2-(3-(difluoromethyl)bicyclo[1.1.1]pentan-1-yl)-4,4-dimethylcyclohex-1-en-1-yl)methyl)piperazin-1-yl)-N-((4-(((4-methylmorpholin-2-yl)methyl)amino)-3-nitrophenyl)sulfonyl)benzamide

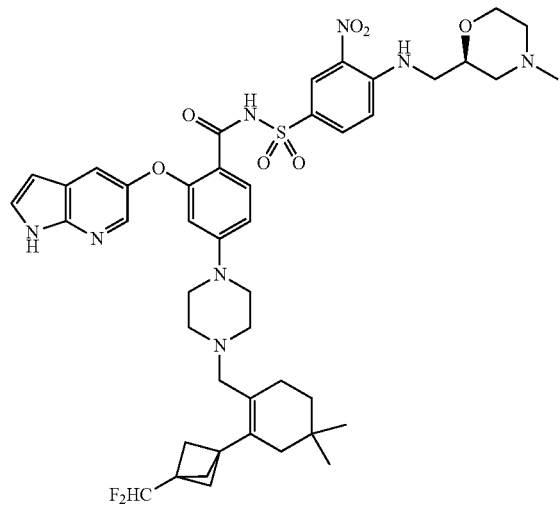 [SMILES: CN1CCO[C@H](CNc2ccc(S(=O)(=O)NC(=O)c3ccc(N4CCN(CC5=C(C67CC(C(F)F)(C6)C7)CC(C)(C)CC5)CC4)cc3Oc3cnc4[nH]ccc4c3)cc2[N+](=O)[O-])C1]

Example 73 was prepared following General Procedure B using Intermediate 30 and Intermediate 17A. The absolute stereochemistry was arbitrarily assigned. LC/MS (ESI) m/z 445.5 [M+2H]$^+$.

170

Examples 74-97

Examples 74-97, having the chemical names and structures shown in FIGS. 3, 4A and 4B, are prepared in accordance with the methods described herein. Similar results are obtained.

Example A

Bcl-2 Protein Family Binding Assay

Binding to Bcl-2 proteins Bcl-2, and Bcl-X$_L$ was assessed using the Bcl2scan™ platform: T7 phage strains displaying BCL2 proteins were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (5,000×g) and filtered (0.2 m) to remove cell debris. Streptavidin-coated magnetic beads were treated with biotinylated BIM peptide ligand for 30 minutes at room temperature to generate affinity resins for BCL2 assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining BCL2 proteins, liganded affinity beads, and test compounds in 1× binding buffer (20% SeaBlock, 0.17×PBS, 0.05% Tween 20, 6 mM DTT). Test compounds were prepared as 100× stocks in 100% DMSO. Kds were determined using an 11-point 3-fold compound dilution series with one DMSO control point. All compounds for Kd measurements were distributed by acoustic transfer in 100% DMSO. The compounds were then diluted directly into the assays such that the final concentration of DMSO was 0.9%. All reactions performed in polypropylene 384-well plates. Each was a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 2 μM non-biotinylated affinity ligand) and incubated at room temperature with shaking for 30 minutes. The BCL2 concentration in the eluates was measured by qPCR. Binding constants (Kds) were calculated with a standard dose-response curve using the Hill equation:

$$\text{Response} = \text{Background} + \frac{\text{Signal} - \text{Background}}{1 + (Kd^{Hill\ Slope} / Dose^{Hill\ Slope})}.$$

The Hill Slope was set to −1.
Curves were fitted using a non-linear least square fit with the Levenberg-Marquardt algorithm. The results are shown in Table 1.

TABLE 1

| Example | Bcl-2 Kd (nm) | Bcl-X$_L$ Kd (nm) |
| --- | --- | --- |
| 1 | A | C |
| 9 | A | C |
| 10 | A | C |
| 11 | A | C |
| 13 | A | C |
| 15 | A | C |

TABLE 1-continued

| Example | Bcl-2 Kd (nm) | Bcl-$X_L$ Kd (nm) |
|---|---|---|
| 16 | A | C |
| 17 | A | B |
| 20 | A | C |
| 23 | A | C |
| 25 | A | C |
| 26 | A | C |
| 27 | A | C |
| 28 | A | C |
| 30 | A | C |
| 31 | A | C |
| 32 | A | C |
| 33 | A | C |
| 34 | A | C |
| 35 | A | C |
| 36 | A | B |
| 38 | A | B |
| 39 | B | C |
| 40 | A | C |
| 47 | C | B |
| 48 | B | B |
| ABT-199 | A | B |
| ABT-263 | B | B |

Bcl-2 Binding Assay (Kd):
A = a single Kd ≤10 nM;
B = a single Kd >10 nM and <100 nM;
C = a single Kd ≥100 nM Example B Bcl-2/Bcl-$X_L$ Homogeneous Time Resolved Fluorescence (HTRF) Assay Binding to Bcl-2 proteins Bcl-2, and Bcl-$X_L$ was also assessed using an HTRF assay. Background: FAM-Bak/Bad binds to surface pocket of the Bcl-2 protein family. This binding can be monitored by HTRF signals between anti-GST-Tb and FAM-peptide using GST-tagged Bcl proteins. Assay conditions: Bcl-2: 4 nM Bcl-2, 100 nM FAM-Bak peptide, Bcl-$X_L$: 3 nM Bcl-$X_L$, 40 nM FAM-Bad peptide in 20 mM K Phosphate, pH 7.5, 50 mM NaCl, 1 mM EDTA, 0.005% Triton X-100 and 1% DMSO (final). Assay procedure: Compounds were tested in 10-dose $IC_{50}$ mode, in singlicate, with 3-fold serial dilution starting at 10 μM or 1 μM. Compound stock solutions were added to protein solution using Acoustic technology. The compounds were then incubated with protein for 10 min at room temperature. The respective FAM labeled peptide was added and incubated for another 10 min and then anti-GST-Tb was added. After 60 min at rt, the HTRF fluorescence signal ratio was measured. Curve fits were performed in GraphPad Prism 4 with "sigmoidal dose-response (variable slope)"; 4 parameters with Hill Slope. The results are shown in Table 2.

TABLE 2

| Example | Bcl-2 $IC_{50}$ (nM) | Bcl-$X_L$ $IC_{50}$ (nM) |
|---|---|---|
| 15 | A | C |
| 20 | A | C |
| 34 | A | B |
| 46 | A | A |
| 48 | A | A |
| 49 | A | A |
| 50 | A | A |
| 55 | A | A |
| 58 | A | A |
| 59 | A | A |
| 60 | A | A |

TABLE 2-continued

| Example | Bcl-2 $IC_{50}$ (nM) | Bcl-$X_L$ $IC_{50}$ (nM) |
|---|---|---|
| 61 | A | A |
| 62 | A | A |
| 63 | A | A |
| 64 | A | A |
| 67 | A | A |
| 69 | A | A |
| 70 | A | A |
| ABT-199 | A | B |
| ABT-263 | A | A |

Bcl-2 Binding Assay ($IC_{50}$):
A = a single $IC_{50}$ ≤10 nM;
B = a single $IC_{50}$ >10 nM and <100 nM;
C = a single $IC_{50}$ ≥100 nM.

Example C

RS4;11 and NCI-H1963 Cell Proliferation Assay

Cell proliferation was measured using the CellTiter-Glo® Luminescent Cell Viability Assay. The assay involved the addition of a single reagent (CellTiter-Glo® Reagent) directly to cells cultured in serum-supplemented medium. RS4;11 (ATC, CRL-1873) cells were cultured according to ATCC recommendations and were seeded at 50,000 cells per well. NCI-H1963 cells (ATCC CRL-5982) were cultured according to ATCC recommendations and seeded at 12,000 cells per well.

Each compound evaluated was prepared as a DMSO stock solution (10 mM). Compounds were tested in duplicate on each plate, with a 10-point serial dilution curve (1:3 dilution). Compound treatment (1.0 μL) was added from the compound dilution plate to the cell plate. The highest compound concentration was 10 μM (final), with a 0.1% final DMSO concentration. Plates were then incubated at 37° C., 5% $CO_2$. After 48 h of compound treatment for RS4;11 or 72 h for NCI-H1963, cell plates were equilibrated at rt for approximately 30 mins. An equi-volume amount of CellTiter-Glo® Reagent (40 μL) was added to each well. Plates were mixed for 2 mins on an orbital shaker to induce cell lysis and then incubated at RT for 10 mins to stabilize the luminescent signal. Luminescence was recorded using a Envision plate reader according to CellTiter-Glo protocol. $IC_{50}$ of each compound was calculated using GraphPad Prism by nonlinear regression analysis. $IC_{50}$ values are provided in Table 3.

TABLE 3

| Example # | RS4;11 (nM) | H1963 (nM) |
|---|---|---|
| 1 | A | |
| 2 | A | |
| 3 | B | |
| 4 | B | |
| 5 | B | |
| 6 | C | |
| 7 | C | |
| 8 | B | |
| 9 | A | |
| 10 | A | |
| 11 | A | |
| 12 | A | |
| 13 | A | |
| 14 | A | |
| 15 | A | |

TABLE 3-continued

| Example # | RS4;11 (nM) | H1963 (nM) |
|---|---|---|
| 16 | A | |
| 17 | A | |
| 18 | A | |
| 19 | A | |
| 20 | A | |
| 21 | B | |
| 22 | A | |
| 23 | A | |
| 24 | A | |
| 25 | A | |
| 26 | A | |
| 27 | A | |
| 28 | A | |
| 29 | A | |
| 30 | A | |
| 31 | A | |
| 32 | A | |
| 33 | A | |
| 34 | A | |
| 35 | A | |
| 36 | A | |
| 37 | A | |
| 38 | A | |
| 39 | A | |
| 40 | A | |
| 41 | | |
| 42 | A | |
| 43 | B | |
| 44 | | |
| 45 | C | |
| 46 | B | |
| 47 | C | |
| 48 | B | |
| 49 | B | |
| 50 | B | |
| 51 | B | |
| 52 | B | |
| 53 | C | |
| 54 | C | |
| 55 | B | |
| 56 | C | B |
| 57 | C | C |
| 58 | B | |
| 59 | B | B |
| 60 | A | B |
| 61 | A | A |
| 62 | B | A |
| 63 | A | A |
| 64 | B | C |
| 65 | | B |
| 66 | | |
| 67 | B | |
| 68 | B | A |
| 69 | | B |
| 70 | B | C |
| 71 | | B |
| 72 | C | |
| 73 | | |
| ABT-199 | A | C |
| ABT-263 | A | A |

For RS4;11 CTG $IC_{50}$:
A = a single $IC_{50}$ ≤100 nM;
B = a single $IC_{50}$ >100 nM and <1000 nM;
C = a single $IC_{50}$ ≥1000 nM.
For H1963 CTG $IC_{50}$:
A = a single $IC_{50}$ ≤500 nM;
B = a single $IC_{50}$ >500 nM and <1000 nM;
C = a single $IC_{50}$ ≥1000 nM.

Example D

Figure 5:
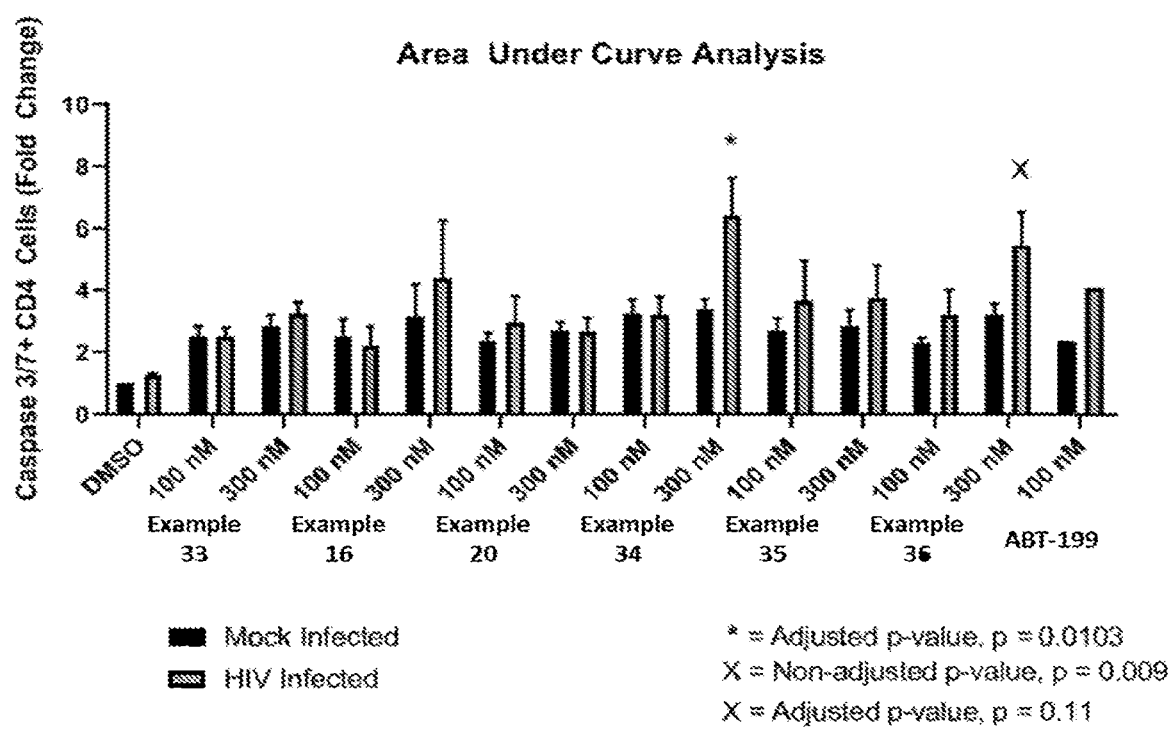
FIG. 5 shows a plot illustrating HIV assay data for examples of compounds of the Formula (I).

Measurement of Caspase Release in Mock and HIV-1 (IIIB Strain) Inflected CD4 Cells Primary CD4 T cells were purified by negative selection, using RosetteSep human CD4+ T cell enrichment cocktail (Stemcell Technologies) or an EasySep human CD4+ T cell isolation kit (Stemcell Technologies) as per the manufacturer's protocol. Primary CD4 T cells were isolated and activated with IL-2 50 IU/mL and phytohaemagglutinin (PHA) 1 µg/mL for 48 hours. Then cells were infected with HIV-$1_{IIIb}$ (NIH AIDS Reagent Program) viral stock for 3-6 hours with 6 ug/mL Polybrene (Sigma-Aldrich), washed, and resuspended with complete RPMI and IL-2 for 48 hours. The cells were treated with compounds as 100 µM and 300 µM DMSO stock solutions or DMSO. Cell death was measured using an IncuCyte system (Essen BioScience) and IncuCyte Caspase 3/7 Green Apoptosis Assay Reagent (catalog number 4440, Essen BioScience). Analysis of the data was done using IncuCyte Zoom software (2018A). Statistical analysis was performed using GraphPad Prism. Results are depicted as standard error (SE). The fold changes for area under the curve analysis were compared by multiple t-tests. P values of less than 0.05 were considered statistically significant. The results of this assay are summarized in FIG. 5 and indicate that Examples 34 and 36 exhibit selectivity in killing HIV vs. mock infected cells.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method for treating a cancer or a tumor comprising administering an effective amount of a compound of Formula (I), or a pharmaceutically acceptable salt thereof, or a pharmaceutical composition comprising an effective amount of the compound, or a pharmaceutically acceptable salt thereof, and a pharmaceutically acceptable carrier, diluent, excipient or combination thereof, to a subject having the cancer or the tumor, wherein the cancer or the tumor is selected from a bladder cancer, a brain cancer, a breast cancer, a bone marrow cancer, a cervical cancer, a colorectal cancer, an esophageal cancer, a hepatocellular cancer, a lymphoblastic leukemia, a follicular lymphoma, a lymphoid malignancy of T-cell or B-cell origin, a melanoma, a myelogenous leukemia, a Hodgkin's lymphoma, a Non-Hodgkin's lymphoma, a head and neck cancer (including oral cancer), an ovarian cancer, a non-small cell lung cancer, a chronic lymphocytic leukemia, a myeloma, a prostate cancer, a small cell lung cancer, a spleen cancer, a polycythemia vera, a thyroid cancer, an endometrial cancer, a stomach cancer, a gallbladder cancer, a bile duct cancer, a testicular cancer, a neuroblastoma, an osteosarcoma, an Ewings's tumor and a Wilm's tumor, Formula (I) having the structure:

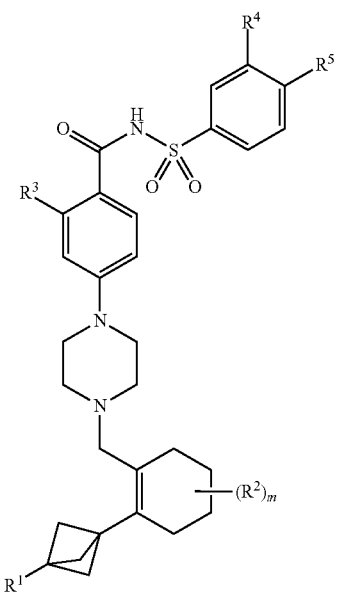

(I)

wherein:
R¹ is selected from the group consisting of hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine;

each R² is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl; or when m is 2 or 3, each R² is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl, or two R² groups taken together with the atom(s) to which they are attached form a substituted or unsubstituted $C_3$-$C_6$ cycloalkyl or a substituted or unsubstituted 3 to 6 membered heterocyclyl;

R³ is selected from the group consisting of X—$R^{3A}$,

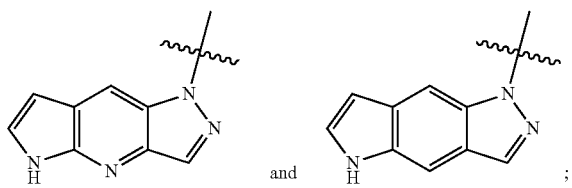 [SMILES: *n1ncc2nc3[nH]ccc3cc21 ; *n1ncc2cc3[nH]ccc3cc21]

$R^{3A}$ is a substituted or unsubstituted 5 to 10 membered heteroaryl;

R⁴ is selected from the group consisting of $NO_2$, $S(O)R^6$, $SO_2R^6$, halogen, cyano and an unsubstituted $C_1$-$C_6$ haloalkyl;

R⁵ is selected from the group consisting of —$X^1$-(Alk¹)$_n$-R⁷ and —$X^2$(CHR⁸)-(Alk²)$_p$-$X^3$—R⁹;

Alk¹ and Alk² are independently selected from an unsubstituted $C_1$-$C_4$ alkylene and a $C_1$-$C_4$ alkylene substituted with 1, 2 or 3 substituents independently selected from fluoro, chloro, an unsubstituted $C_1$-$C_3$ alkyl and an unsubstituted $C_1$-$C_3$ haloalkyl;

R⁶ is selected from the group consisting of a substituted or unsubstituted $C_1$-$C_6$ alkyl, a substituted or unsubstituted $C_1$-$C_6$ haloalkyl and a substituted or unsubstituted $C_3$-$C_6$ cycloalkyl;

R⁷ is selected from a substituted or unsubstituted $C_1$-$C_6$ alkoxy, a substituted or unsubstituted $C_3$-$C_{10}$ cycloalkyl, a substituted or unsubstituted 3 to 10 membered heterocyclyl, hydroxy, amino, a substituted or unsubstituted mono-substituted amine group, a substituted or unsubstituted di-substituted amine group, a substituted or unsubstituted N-carbamyl, a substituted or unsubstituted C-amido and a substituted or unsubstituted N-amido;

R⁸ is selected from a substituted or unsubstituted 3 to 10 membered heterocyclyl($C_1$-$C_6$ alkyl), a substituted or unsubstituted di-$C_1$-$C_6$ alkylamine($C_1$-$C_6$ alkyl) and a substituted or unsubstituted mono-$C_1$-$C_6$ alkylamine($C_1$-$C_6$ alkyl);

R⁹ is selected from a substituted or unsubstituted 5 to 10 membered heteroaryl and a substituted or unsubstituted $C_6$-$C_{10}$ aryl;

m is 0, 1, 2 or 3;

n and p are independently selected from 0 and 1;

$X^1$ and $X^2$ are —NH—; and

X and $X^3$ are independently selected from the group consisting of —O—, —S— and —NH—.

2. A method for inhibiting replication of a malignant growth or a tumor comprising contacting the growth or the tumor with an effective amount of a compound of Formula (I), or a pharmaceutically acceptable salt thereof, or a pharmaceutical composition comprising an effective amount of the compound, or a pharmaceutically acceptable salt thereof, and a pharmaceutically acceptable carrier, diluent, excipient or combination thereof, wherein the malignant growth or tumor selected from an Ewings's tumor and a Wilm's tumor, or the malignant growth of tumor is due to a cancer selected from a bladder cancer, a brain cancer, a breast cancer, a bone marrow cancer, a cervical cancer, a colorectal cancer, an esophageal cancer, a hepatocellular cancer, a lymphoblastic leukemia, a follicular lymphoma, a lymphoid malignancy of T-cell or B-cell origin, a melanoma, a myelogenous leukemia, a Hodgkin's lymphoma, a Non-Hodgkin's lymphoma, a head and neck cancer (including oral cancer), an ovarian cancer, a non-small cell lung cancer, a chronic lymphocytic leukemia, a myeloma, a prostate cancer, a small cell lung cancer, a spleen cancer, a polycythemia vera, a thyroid cancer, an endometrial cancer, a stomach cancer, a gallbladder cancer, a bile duct cancer, a testicular cancer, a neuroblastoma, an osteosarcoma, Formula (I) having the structure:

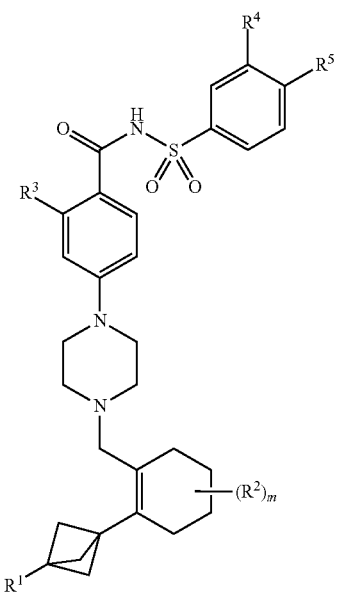

wherein:
R¹ is selected from the group consisting of hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine;

each R² is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl; or when m is 2 or 3, each R² is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl, or two R² groups taken together with the atom(s) to which they are attached form a substituted or unsubstituted $C_3$-$C_6$ cycloalkyl or a substituted or unsubstituted 3 to 6 membered heterocyclyl;

R³ is selected from the group consisting of X—$R^{3A}$,

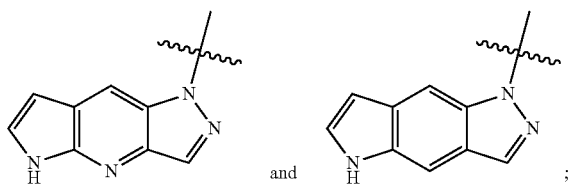 [SMILES: *n1ncc2nc3[nH]ccc3cc21 ; *n1ncc2cc3[nH]ccc3cc21]

$R^{3A}$ is a substituted or unsubstituted 5 to 10 membered heteroaryl;

R⁴ is selected from the group consisting of $NO_2$, $S(O)R^6$, $SO_2R^6$, halogen, cyano and an unsubstituted $C_1$-$C_6$ haloalkyl;

R⁵ is selected from the group consisting of —$X^1$-$(Alk^1)_n$-$R^7$ and —$X^2(CHR^8)$-$(Alk^2)_p$-$X^3$—$R^9$;

$Alk^1$ and $Alk^2$ are independently selected from an unsubstituted $C_1$-$C_4$ alkylene and a $C_1$-$C_4$ alkylene substituted with 1, 2 or 3 substituents independently selected from fluoro, chloro, an unsubstituted $C_1$-$C_3$ alkyl and an unsubstituted $C_1$-$C_3$ haloalkyl;

R⁶ is selected from the group consisting of a substituted or unsubstituted $C_1$-$C_6$ alkyl, a substituted or unsubstituted $C_1$-$C_6$ haloalkyl and a substituted or unsubstituted $C_3$-$C_6$ cycloalkyl;

R⁷ is selected from a substituted or unsubstituted $C_1$-$C_6$ alkoxy, a substituted or unsubstituted $C_3$-$C_{10}$ cycloalkyl, a substituted or unsubstituted 3 to 10 membered heterocyclyl, hydroxy, amino, a substituted or unsubstituted mono-substituted amine group, a substituted or unsubstituted di-substituted amine group, a substituted or unsubstituted N-carbamyl, a substituted or unsubstituted C-amido and a substituted or unsubstituted N-amido;

R⁸ is selected from a substituted or unsubstituted 3 to 10 membered heterocyclyl($C_1$-$C_6$ alkyl), a substituted or unsubstituted di-$C_1$-$C_6$ alkylamine($C_1$-$C_6$ alkyl) and a substituted or unsubstituted mono-$C_1$-$C_6$ alkylamine($C_1$-$C_6$ alkyl);

R⁹ is selected from a substituted or unsubstituted 5 to 10 membered heteroaryl and a substituted or unsubstituted $C_6$-$C_{10}$ aryl;

m is 0, 1, 2 or 3;

n and p are independently selected from 0 and 1;

$X^1$ and $X^2$ are —NH—; and

X and $X^3$ are independently selected from the group consisting of —O—, —S— and —NH—.

3. A method for treating a cancer comprising contacting a malignant growth or a tumor with an effective amount of a compound of Formula (I), or a pharmaceutically acceptable salt thereof, or a pharmaceutical composition comprising an effective amount of the compound, or a pharmaceutically acceptable salt thereof, and a pharmaceutically acceptable carrier, diluent, excipient or combination thereof, wherein the malignant growth or tumor selected from an Ewings's tumor and a Wilm's tumor, or the malignant growth of tumor is due to a cancer selected from a bladder cancer, a brain cancer, a breast cancer, a bone marrow cancer, a cervical cancer, a colorectal cancer, an esophageal cancer, a hepatocellular cancer, a lymphoblastic leukemia, a follicular lymphoma, a lymphoid malignancy of T-cell or B-cell origin, a melanoma, a myelogenous leukemia, a Hodgkin's lymphoma, a Non-Hodgkin's lymphoma, a head and neck cancer (including oral cancer), an ovarian cancer, a non-small cell lung cancer, a chronic lymphocytic leukemia, a myeloma, a prostate cancer, a small cell lung cancer, a spleen cancer, a polycythemia vera, a thyroid cancer, an endometrial cancer, a stomach cancer, a gallbladder cancer, a bile duct cancer, a testicular cancer, a neuroblastoma or an osteosarcoma, Formula (I) having the structure:

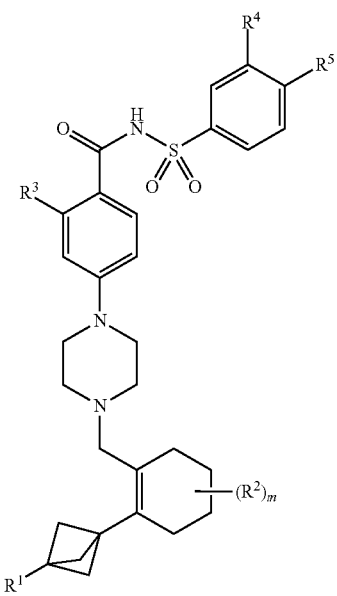

wherein:
- $R^1$ is selected from the group consisting of hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine;
- each $R^2$ is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl; or
- when m is 2 or 3, each $R^2$ is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl, or two $R^2$ groups taken together with the atom(s) to which they are attached form a substituted or unsubstituted $C_3$-$C_6$ cycloalkyl or a substituted or unsubstituted 3 to 6 membered heterocyclyl;
- $R^3$ is selected from the group consisting of X—$R^{3A}$,

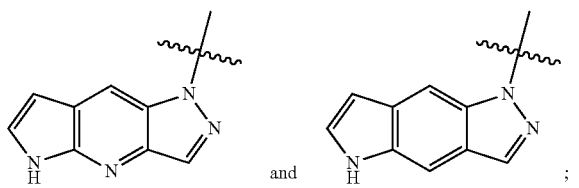 [SMILES: *n1ncc2nc3[nH]ccc3cc21 ; *n1ncc2cc3[nH]ccc3cc21]

- $R^{3A}$ is a substituted or unsubstituted 5 to 10 membered heteroaryl;
- $R^4$ is selected from the group consisting of $NO_2$, $S(O)R^6$, $SO_2R^6$, halogen, cyano and an unsubstituted $C_1$-$C_6$ haloalkyl;
- $R^5$ is selected from the group consisting of —$X^1$-$(Alk^1)_n$-$R^7$ and —$X^2(CHR^8)$-$(Alk^2)_p$-$X^3$—$R^9$;
- $Alk^1$ and $Alk^2$ are independently selected from an unsubstituted $C_1$-$C_4$ alkylene and a $C_1$-$C_4$ alkylene substituted with 1, 2 or 3 substituents independently selected from fluoro, chloro, an unsubstituted $C_1$-$C_3$ alkyl and an unsubstituted $C_1$-$C_3$ haloalkyl;
- $R^6$ is selected from the group consisting of a substituted or unsubstituted $C_1$-$C_6$ alkyl, a substituted or unsubstituted $C_1$-$C_6$ haloalkyl and a substituted or unsubstituted $C_3$-$C_6$ cycloalkyl;
- $R^7$ is selected from a substituted or unsubstituted $C_1$-$C_6$ alkoxy, a substituted or unsubstituted $C_3$-$C_{10}$ cycloalkyl, a substituted or unsubstituted 3 to 10 membered heterocyclyl, hydroxy, amino, a substituted or unsubstituted mono-substituted amine group, a substituted or unsubstituted di-substituted amine group, a substituted or unsubstituted N-carbamyl, a substituted or unsubstituted C-amido and a substituted or unsubstituted N-amido;
- $R^8$ is selected from a substituted or unsubstituted 3 to 10 membered heterocyclyl($C_1$-$C_6$ alkyl), a substituted or unsubstituted di-$C_1$-$C_6$ alkylamine($C_1$-$C_6$ alkyl) and a substituted or unsubstituted mono-$C_1$-$C_6$ alkylamine($C_1$-$C_6$ alkyl);
- $R^9$ is selected from a substituted or unsubstituted 5 to 10 membered heteroaryl and a substituted or unsubstituted $C_6$-$C_{10}$ aryl;
- m is 0, 1, 2 or 3;
- n and p are independently selected from 0 and 1;
- $X^1$ and $X^2$ are —NH—; and
- X and $X^3$ are independently selected from the group consisting of —O—, —S— and —NH—.

4. A method for inhibiting the activity of Bcl-2 comprising providing an effective amount of a compound of Formula (I), or a pharmaceutically acceptable salt thereof, or a pharmaceutical composition comprising an effective amount of the compound, or a pharmaceutically acceptable salt thereof, and a pharmaceutically acceptable carrier, diluent, excipient or combination thereof, to a cancer cell or a tumor, wherein the cancer cell or the tumor is from a cancer selected from a bladder cancer, a brain cancer, a breast cancer, a bone marrow cancer, a cervical cancer, a colorectal cancer, an esophageal cancer, a hepatocellular cancer, a lymphoblastic leukemia, a follicular lymphoma, a lymphoid malignancy of T-cell or B-cell origin, a melanoma, a myelogenous leukemia, a Hodgkin's lymphoma, a Non-Hodgkin's lymphoma, a head and neck cancer (including oral cancer), an ovarian cancer, a non-small cell lung cancer, a chronic lymphocytic leukemia, a myeloma, a prostate cancer, a small cell lung cancer, a spleen cancer, a polycythemia vera, a thyroid cancer, an endometrial cancer, a stomach cancer, a gallbladder cancer, a bile duct cancer, a testicular cancer, a neuroblastoma, an osteosarcoma, an Ewings's tumor and a Wilm's tumor, Formula (I) having the structure:

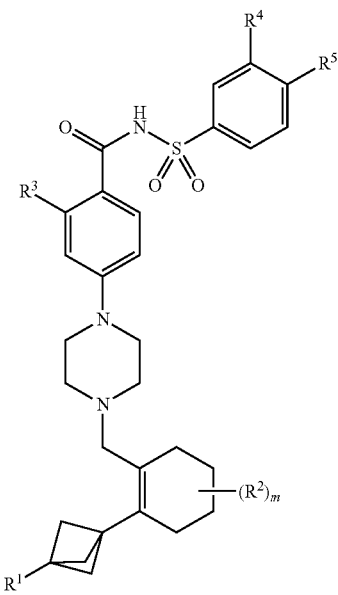

(I)

wherein:
R¹ is selected from the group consisting of hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine;

each R² is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl; or when m is 2 or 3, each R² is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl, or two R² groups taken together with the atom(s) to which they are attached form a substituted or unsubstituted $C_3$-$C_6$ cycloalkyl or a substituted or unsubstituted 3 to 6 membered heterocyclyl;

R³ is selected from the group consisting of X—$R^{3A}$,

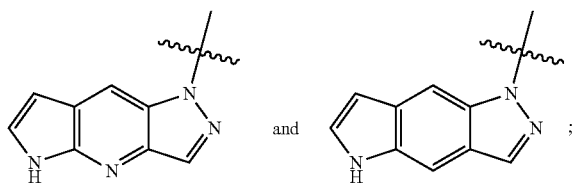 [SMILES: *n1ncc2nc3[nH]ccc3cc21 ; "and" ; *n1ncc2cc3[nH]ccc3cc21 ; ";"]

$R^{3A}$ is a substituted or unsubstituted 5 to 10 membered heteroaryl;

R⁴ is selected from the group consisting of $NO_2$, $S(O)R^6$, $SO_2R^6$, halogen, cyano and an unsubstituted $C_1$-$C_6$ haloalkyl;

R⁵ is selected from the group consisting of —$X^1$-$(Alk^1)_n$-$R^7$ and —$X^2(CHR^8)$-$(Alk^2)_p$-$X^3$—$R^9$;

$Alk^1$ and $Alk^2$ are independently selected from an unsubstituted $C_1$-$C_4$ alkylene and a $C_1$-$C_4$ alkylene substituted with 1, 2 or 3 substituents independently selected from fluoro, chloro, an unsubstituted $C_1$-$C_3$ alkyl and an unsubstituted $C_1$-$C_3$ haloalkyl;

R⁶ is selected from the group consisting of a substituted or unsubstituted $C_1$-$C_6$ alkyl, a substituted or unsubstituted $C_1$-$C_6$ haloalkyl and a substituted or unsubstituted $C_3$-$C_6$ cycloalkyl;

R⁷ is selected from a substituted or unsubstituted $C_1$-$C_6$ alkoxy, a substituted or unsubstituted $C_3$-$C_{10}$ cycloalkyl, a substituted or unsubstituted 3 to 10 membered heterocyclyl, hydroxy, amino, a substituted or unsubstituted mono-substituted amine group, a substituted or unsubstituted di-substituted amine group, a substituted or unsubstituted N-carbamyl, a substituted or unsubstituted C-amido and a substituted or unsubstituted N-amido;

R⁸ is selected from a substituted or unsubstituted 3 to 10 membered heterocyclyl($C_1$-$C_6$ alkyl), a substituted or unsubstituted di-$C_1$-$C_6$ alkylamine($C_1$-$C_6$ alkyl) and a substituted or unsubstituted mono-$C_1$-$C_6$ alkylamine($C_1$-$C_6$ alkyl);

R⁹ is selected from a substituted or unsubstituted 5 to 10 membered heteroaryl and a substituted or unsubstituted $C_6$-$C_{10}$ aryl;

m is 0, 1, 2 or 3;

n and p are independently selected from 0 and 1;

$X^1$ and $X^2$ are —NH—; and

X and $X^3$ are independently selected from the group consisting of —O—, —S— and —NH—.

5. A method for inhibiting the activity of Bcl-2 in a subject comprising providing an effective amount of a compound of Formula (I), or a pharmaceutically acceptable salt thereof, or a pharmaceutical composition comprising an effective amount of the compound, or a pharmaceutically acceptable salt thereof, and a pharmaceutically acceptable carrier, diluent, excipient or combination thereof, to the subject having a cancer or a tumor, wherein the cancer or the tumor is selected from a bladder cancer, a brain cancer, a breast cancer, a bone marrow cancer, a cervical cancer, a colorectal cancer, an esophageal cancer, a hepatocellular cancer, a lymphoblastic leukemia, a follicular lymphoma, a lymphoid malignancy of T-cell or B-cell origin, a melanoma, a myelogenous leukemia, a Hodgkin's lymphoma, a Non-Hodgkin's lymphoma, a head and neck cancer (including oral cancer), an ovarian cancer, a non-small cell lung cancer, a chronic lymphocytic leukemia, a myeloma, a prostate cancer, a small cell lung cancer, a spleen cancer, a polycythemia vera, a thyroid cancer, an endometrial cancer, a stomach cancer, a gallbladder cancer, a bile duct cancer, a testicular cancer, a neuroblastoma, an osteosarcoma, an Ewings's tumor and a Wilm's tumor, Formula (I) having the structure:

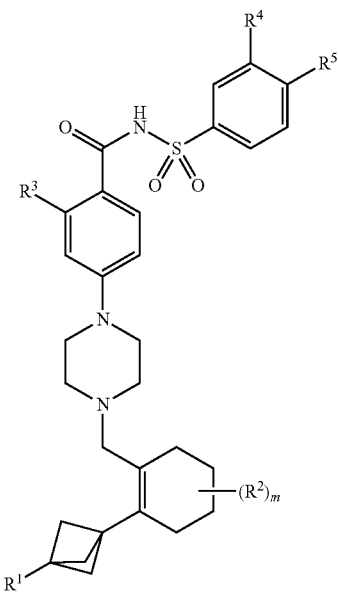

(I)

wherein:
  $R^1$ is selected from the group consisting of hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine;
  each $R^2$ is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl; or
  when m is 2 or 3, each $R^2$ is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl, or two $R^2$ groups taken together with the atom(s) to which they are attached form a substituted or unsubstituted $C_3$-$C_6$ cycloalkyl or a substituted or unsubstituted 3 to 6 membered heterocyclyl;
  $R^3$ is selected from the group consisting of X—$R^{3A}$,

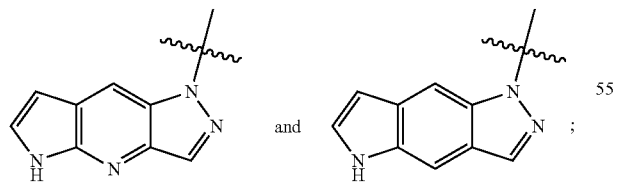

and ;

$R^{3A}$ is a substituted or unsubstituted 5 to 10 membered heteroaryl;
  $R^4$ is selected from the group consisting of $NO_2$, $S(O)R^6$, $SO_2R^6$, halogen, cyano and an unsubstituted $C_1$-$C_6$ haloalkyl;
  $R^5$ is selected from the group consisting of —$X^1$-$(Alk^1)_n$-$R^7$ and —$X^2(CHR^8)$-$(Alk^2)_p$-$X^3$—$R^9$;
  $Alk^1$ and $Alk^2$ are independently selected from an unsubstituted $C_1$-$C_4$ alkylene and a $C_1$-$C_4$ alkylene substituted with 1, 2 or 3 substituents independently selected from fluoro, chloro, an unsubstituted $C_1$-$C_3$ alkyl and an unsubstituted $C_1$-$C_3$ haloalkyl;
  $R^6$ is selected from the group consisting of a substituted or unsubstituted $C_1$-$C_6$ alkyl, a substituted or unsubstituted $C_1$-$C_6$ haloalkyl and a substituted or unsubstituted $C_3$-$C_6$ cycloalkyl;
  $R^7$ is selected from a substituted or unsubstituted $C_1$-$C_6$ alkoxy, a substituted or unsubstituted $C_3$-$C_{10}$ cycloalkyl, a substituted or unsubstituted 3 to 10 membered heterocyclyl, hydroxy, amino, a substituted or unsubstituted mono-substituted amine group, a substituted or unsubstituted di-substituted amine group, a substituted or unsubstituted N-carbamyl, a substituted or unsubstituted C-amido and a substituted or unsubstituted N-amido;
  $R^8$ is selected from a substituted or unsubstituted 3 to 10 membered heterocyclyl($C_1$-$C_6$ alkyl), a substituted or unsubstituted di-$C_1$-$C_6$ alkylamine($C_1$-$C_6$ alkyl) and a substituted or unsubstituted mono-$C_1$-$C_6$ alkylamine($C_1$-$C_6$ alkyl);
  $R^9$ is selected from a substituted or unsubstituted 5 to 10 membered heteroaryl and a substituted or unsubstituted $C_6$-$C_{10}$ aryl;
  m is 0, 1, 2 or 3;
  n and p are independently selected from 0 and 1;
  $X^1$ and $X^2$ are —NH—; and
  X and $X^3$ are independently selected from the group consisting of —O—, —S— and —NH—.

6. A method of ameliorating or treating a HIV infection, comprising administering to a subject suffering from the HIV infection an effective amount of a compound of Formula (I), or a pharmaceutically acceptable salt thereof, or a pharmaceutical composition comprising an effective amount of the compound, or a pharmaceutically acceptable salt thereof, and a pharmaceutically acceptable carrier, diluent, excipient or combination thereof, and an effective amount of a HIV latency reversing agent, or a pharmaceutically acceptable salt thereof, Formula (I) having the structure:

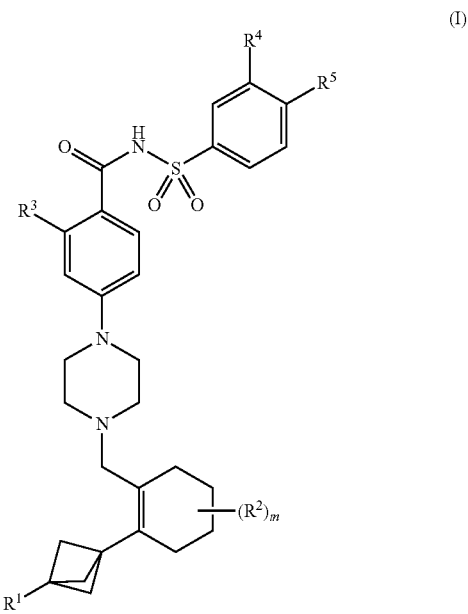

(I)

wherein:
R¹ is selected from the group consisting of hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine;

each R² is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl; or when m is 2 or 3, each R² is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl, or two R² groups taken together with the atom(s) to which they are attached form a substituted or unsubstituted $C_3$-$C_6$ cycloalkyl or a substituted or unsubstituted 3 to 6 membered heterocyclyl;

R³ is selected from the group consisting of X—$R^{3,4}$,

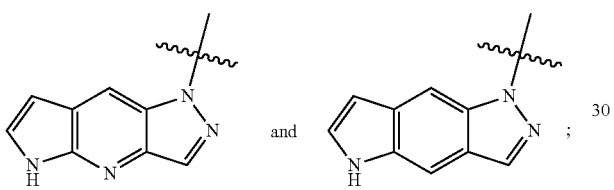

and $R^{3,4}$ is a substituted or unsubstituted 5 to 10 membered heteroaryl;

R⁴ is selected from the group consisting of $NO_2$, $S(O)R^6$, $SO_2R^6$, halogen, cyano and an unsubstituted $C_1$-$C_6$ haloalkyl;

R⁵ is selected from the group consisting of —$X^1$-$(Alk^1)_n$-$R^7$ and —$X^2(CHR^8)$-$(Alk^2)_p$-$X^3$—$R^9$;

$Alk^1$ and $Alk^2$ are independently selected from an unsubstituted $C_1$-$C_4$ alkylene and a $C_1$-$C_4$ alkylene substituted with 1, 2 or 3 substituents independently selected from fluoro, chloro, an unsubstituted $C_1$-$C_3$ alkyl and an unsubstituted $C_1$-$C_3$ haloalkyl;

R⁶ is selected from the group consisting of a substituted or unsubstituted $C_1$-$C_6$ alkyl, a substituted or unsubstituted $C_1$-$C_6$ haloalkyl and a substituted or unsubstituted $C_3$-$C_6$ cycloalkyl;

R⁷ is selected from a substituted or unsubstituted $C_1$-$C_6$ alkoxy, a substituted or unsubstituted $C_3$-$C_{10}$ cycloalkyl, a substituted or unsubstituted 3 to 10 membered heterocyclyl, hydroxy, amino, a substituted or unsubstituted mono-substituted amine group, a substituted or unsubstituted di-substituted amine group, a substituted or unsubstituted N-carbamyl, a substituted or unsubstituted C-amido and a substituted or unsubstituted N-amido;

R⁸ is selected from a substituted or unsubstituted 3 to 10 membered heterocyclyl($C_1$-$C_6$ alkyl), a substituted or unsubstituted di-$C_1$-$C_6$ alkylamine($C_1$-$C_6$ alkyl) and a substituted or unsubstituted mono-$C_1$-$C_6$ alkylamine($C_1$-$C_6$ alkyl);

R⁹ is selected from a substituted or unsubstituted 5 to 10 membered heteroaryl and a substituted or unsubstituted $C_6$-$C_{10}$ aryl;

m is 0, 1, 2 or 3;

n and p are independently selected from 0 and 1;

$X^1$ and $X^2$ are —NH—; and

X and $X^3$ are independently selected from the group consisting of —O—, —S— and —NH—.

7. A method of reducing the population of HIV infected cells, comprising administering to a subject suffering from the HIV infection an effective amount of a compound of Formula (I), or a pharmaceutically acceptable salt thereof, or a pharmaceutical composition comprising an effective amount of the compound, or a pharmaceutically acceptable salt thereof, and a pharmaceutically acceptable carrier, diluent, excipient or combination thereof, and an effective amount of a HIV latency reversing agent, or a pharmaceutically acceptable salt thereof, Formula (I) having the structure:

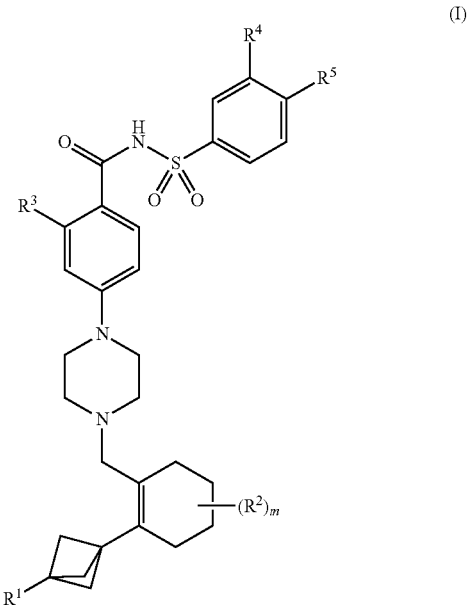

(I)

wherein:
R¹ is selected from the group consisting of hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine;

each R² is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl; or when m is 2 or 3, each R² is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl, or two R² groups taken together with the atom(s) to which they are attached form a substituted or unsubstituted $C_3$-$C_6$ cycloalkyl or a substituted or unsubstituted 3 to 6 membered heterocyclyl;

R³ is selected from the group consisting of X—R³ᴬ,

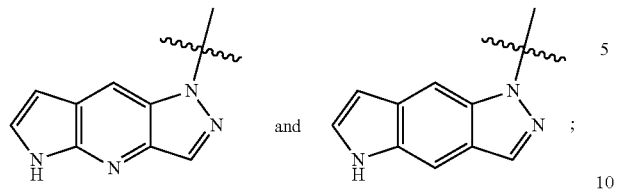
and

R³ᴬ is a substituted or unsubstituted 5 to 10 membered heteroaryl;
R⁴ is selected from the group consisting of NO₂, S(O)R⁶, SO₂R⁶, halogen, cyano and an unsubstituted $C_1$-$C_6$ haloalkyl;
R⁵ is selected from the group consisting of —X¹-(Alk¹)$_n$-R⁷ and —X²(CHR⁸)-(Alk²)$_p$-X³—R⁹;
Alk¹ and Alk² are independently selected from an unsubstituted $C_1$-$C_4$ alkylene and a $C_1$-$C_4$ alkylene substituted with 1, 2 or 3 substituents independently selected from fluoro, chloro, an unsubstituted $C_1$-$C_3$ alkyl and an unsubstituted $C_1$-$C_3$ haloalkyl;
R⁶ is selected from the group consisting of a substituted or unsubstituted $C_1$-$C_6$ alkyl, a substituted or unsubstituted $C_1$-$C_6$ haloalkyl and a substituted or unsubstituted $C_3$-$C_6$ cycloalkyl;
R⁷ is selected from a substituted or unsubstituted $C_1$-$C_6$ alkoxy, a substituted or unsubstituted $C_3$-$C_{10}$ cycloalkyl, a substituted or unsubstituted 3 to 10 membered heterocyclyl, hydroxy, amino, a substituted or unsubstituted mono-substituted amine group, a substituted or unsubstituted di-substituted amine group, a substituted or unsubstituted N-carbamyl, a substituted or unsubstituted C-amido and a substituted or unsubstituted N-amido;
R⁸ is selected from a substituted or unsubstituted 3 to 10 membered heterocyclyl($C_1$-$C_6$ alkyl), a substituted or unsubstituted di-$C_1$-$C_6$ alkylamine($C_1$-$C_6$ alkyl) and a substituted or unsubstituted mono-$C_1$-$C_6$ alkylamine($C_1$-$C_6$ alkyl);
R⁹ is selected from a substituted or unsubstituted 5 to 10 membered heteroaryl and a substituted or unsubstituted $C_6$-$C_{10}$ aryl;
m is 0, 1, 2 or 3;
n and p are independently selected from 0 and 1;
X¹ and X² are —NH—; and
X and X³ are independently selected from the group consisting of —O—, —S— and —NH—.

8. A method of ameliorating or treating a HIV infection, comprising contacting a cell infected with HIV with a compound of Formula (I), or a pharmaceutically acceptable salt thereof, or a pharmaceutical composition comprising an effective amount of the compound, or a pharmaceutically acceptable salt thereof, and a pharmaceutically acceptable carrier, diluent, excipient or combination thereof and an effective amount of a HIV latency reversing agent, or a pharmaceutically acceptable salt thereof, Formula (I) having the structure:

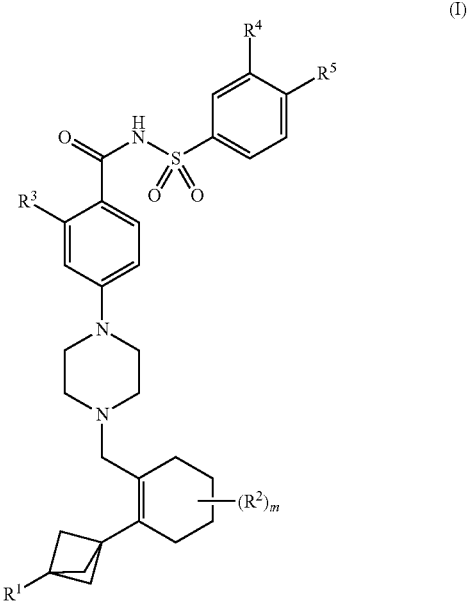
(I)

wherein:
R¹ is selected from the group consisting of hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine;
each R² is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl; or
when m is 2 or 3, each R² is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl, or two R² groups taken together with the atom(s) to which they are attached form a substituted or unsubstituted $C_3$-$C_6$ cycloalkyl or a substituted or unsubstituted 3 to 6 membered heterocyclyl;
R³ is selected from the group consisting of X—R³ᴬ,

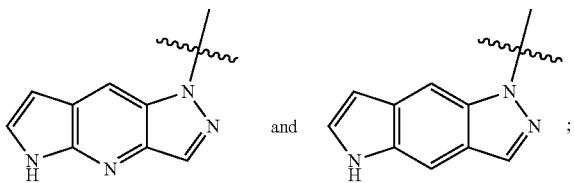 [SMILES: *n1ncc2nc3[nH]ccc3cc21 ; "and" ; *n1ncc2cc3[nH]ccc3cc21 ; ";"]
and

R³ᴬ is a substituted or unsubstituted 5 to 10 membered heteroaryl;
R⁴ is selected from the group consisting of NO₂, S(O)R⁶, SO₂R⁶, halogen, cyano and an unsubstituted $C_1$-$C_6$ haloalkyl;
R⁵ is selected from the group consisting of —X¹-(Alk¹)$_n$-R⁷ and —X²(CHR⁸)-(Alk²)$_p$-X³—R⁹;

Alk¹ and Alk² are independently selected from an unsubstituted $C_1$-$C_4$ alkylene and a $C_1$-$C_4$ alkylene substituted with 1, 2 or 3 substituents independently selected from fluoro, chloro, an unsubstituted $C_1$-$C_3$ alkyl and an unsubstituted $C_1$-$C_3$ haloalkyl;

$R^6$ is selected from the group consisting of a substituted or unsubstituted $C_1$-$C_6$ alkyl, a substituted or unsubstituted $C_1$-$C_6$ haloalkyl and a substituted or unsubstituted $C_3$-$C_6$ cycloalkyl;

$R^7$ is selected from a substituted or unsubstituted $C_1$-$C_6$ alkoxy, a substituted or unsubstituted $C_3$-$C_{10}$ cycloalkyl, a substituted or unsubstituted 3 to 10 membered heterocyclyl, hydroxy, amino, a substituted or unsubstituted mono-substituted amine group, a substituted or unsubstituted di-substituted amine group, a substituted or unsubstituted N-carbamyl, a substituted or unsubstituted C-amido and a substituted or unsubstituted N-amido;

$R^8$ is selected from a substituted or unsubstituted 3 to 10 membered heterocyclyl($C_1$-$C_6$ alkyl), a substituted or unsubstituted di-$C_1$-$C_6$ alkylamine($C_1$-$C_6$ alkyl) and a substituted or unsubstituted mono-$C_1$-$C_6$ alkylamine($C_1$-$C_6$ alkyl);

$R^9$ is selected from a substituted or unsubstituted 5 to 10 membered heteroaryl and a substituted or unsubstituted $C_6$-$C_{10}$ aryl;

m is 0, 1, 2 or 3;

n and p are independently selected from 0 and 1;

$X^1$ and $X^2$ are —NH—; and

X and $X^3$ are independently selected from the group consisting of —O—, —S— and —NH—.

9. A method of reducing the reoccurrence of a HIV infection, comprising contacting a cell infected with HIV with a compound of Formula (I), or a pharmaceutically acceptable salt thereof, or a pharmaceutical composition comprising an effective amount of the compound, or a pharmaceutically acceptable salt thereof, and a pharmaceutically acceptable carrier, diluent, excipient or combination thereof, and an effective amount of a HIV latency reversing agent, or a pharmaceutically acceptable salt thereof, Formula (I) having the structure:

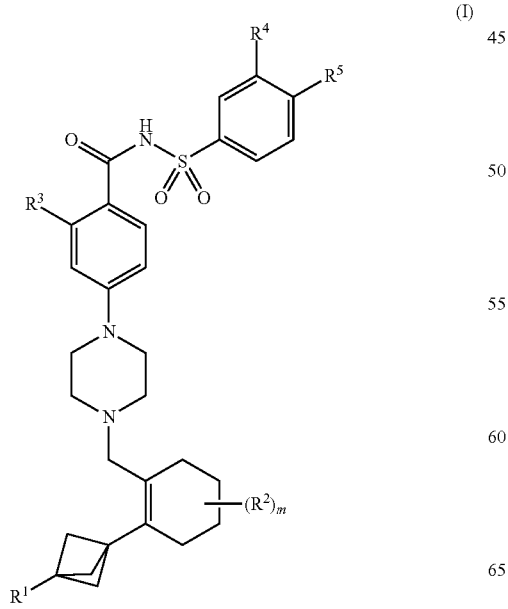

wherein:

$R^1$ is selected from the group consisting of hydrogen, halogen, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted $C_1$-$C_6$ alkoxy, an unsubstituted mono-$C_1$-$C_6$ alkylamine and an unsubstituted di-$C_1$-$C_6$ alkylamine;

each $R^2$ is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl; or when m is 2 or 3, each $R^2$ is independently selected from the group consisting of halogen, a substituted or unsubstituted $C_1$-$C_6$ alkyl, a substituted or unsubstituted $C_1$-$C_6$ haloalkyl and a substituted or unsubstituted $C_3$-$C_6$ cycloalkyl, or two $R^2$ groups taken together with the atom(s) to which they are attached form a substituted or unsubstituted $C_3$-$C_6$ cycloalkyl or a substituted or unsubstituted 3 to 6 membered heterocyclyl;

$R^3$ is selected from the group consisting of X—$R^{3A}$,

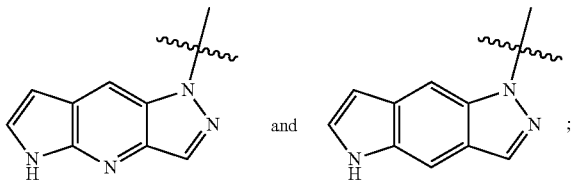 [SMILES: *n1ncc2nc3[nH]ccc3cc21 ; "and" ; *n1ncc2cc3[nH]ccc3cc21 ; ";"]

$R^{3A}$ is a substituted or unsubstituted 5 to 10 membered heteroaryl;

$R^4$ is selected from the group consisting of $NO_2$, $S(O)R^6$, $SO_2R^6$, halogen, cyano and an unsubstituted $C_1$-$C_6$ haloalkyl;

$R^5$ is selected from the group consisting of —$X^1$-(Alk¹)$_n$-$R^7$ and —$X^2$(CHR⁸)-(Alk²)$_p$-$X^3$—$R^9$;

Alk¹ and Alk² are independently selected from an unsubstituted $C_1$-$C_4$ alkylene and a $C_1$-$C_4$ alkylene substituted with 1, 2 or 3 substituents independently selected from fluoro, chloro, an unsubstituted $C_1$-$C_3$ alkyl and an unsubstituted $C_1$-$C_3$ haloalkyl;

$R^6$ is selected from the group consisting of a substituted or unsubstituted $C_1$-$C_6$ alkyl, a substituted or unsubstituted $C_1$-$C_6$ haloalkyl and a substituted or unsubstituted $C_3$-$C_6$ cycloalkyl;

$R^7$ is selected from a substituted or unsubstituted $C_1$-$C_6$ alkoxy, a substituted or unsubstituted $C_3$-$C_{10}$ cycloalkyl, a substituted or unsubstituted 3 to 10 membered heterocyclyl, hydroxy, amino, a substituted or unsubstituted mono-substituted amine group, a substituted or unsubstituted di-substituted amine group, a substituted or unsubstituted N-carbamyl, a substituted or unsubstituted C-amido and a substituted or unsubstituted N-amido;

$R^8$ is selected from a substituted or unsubstituted 3 to 10 membered heterocyclyl($C_1$-$C_6$ alkyl), a substituted or unsubstituted di-$C_1$-$C_6$ alkylamine($C_1$-$C_6$ alkyl) and a substituted or unsubstituted mono-$C_1$-$C_6$ alkylamine($C_1$-$C_6$ alkyl);

$R^9$ is selected from a substituted or unsubstituted 5 to 10 membered heteroaryl and a substituted or unsubstituted $C_6$-$C_{10}$ aryl;

m is 0, 1, 2 or 3;

n and p are independently selected from 0 and 1;

$X^1$ and $X^2$ are —NH—; and

X and $X^3$ are independently selected from the group consisting of —O—, —S— and —NH—.

10. A method of ameliorating or treating a HIV infection, comprising administering to a subject suffering from the HIV infection an effective amount of a Bcl protein inhibitor, or a pharmaceutically acceptable salt thereof, and an effective amount of a HIV latency reversing agent, or a pharmaceutically acceptable salt thereof.

11. A method of reducing the population of HIV infected cells, comprising administering to a subject suffering from the HIV infection an effective amount of a Bcl protein inhibitor, or a pharmaceutically acceptable salt thereof, and an effective amount of a HIV latency reversing agent, or a pharmaceutically acceptable salt thereof.

12. A method of ameliorating or treating a HIV infection, comprising contacting a cell infected with HIV with an effective amount of a Bcl protein inhibitor, or a pharmaceutically acceptable salt thereof, and an effective amount of a HIV latency reversing agent, or a pharmaceutically acceptable salt thereof.

13. A method of reducing the reoccurrence of a HIV infection, comprising contacting a cell infected with HIV with an effective amount of a Bcl protein inhibitor, or a pharmaceutically acceptable salt thereof, and an effective amount of a HIV latency reversing agent, or a pharmaceutically acceptable salt thereof.

14. The method of claim 8, wherein the cells are CD4+ T cells.

15. The method of claim 6, wherein the HIV latency reversing agent is selected from: a protein kinase C agonist, a PD-1 inhibitor, a PD-L1 inhibitor, an HDAC inhibitor, a phorbol ester and a bromodomain inhibitor.

16. The method of claim 15, wherein the HIV latency reversing agent is selected from: ingenol, rostatin, nivolumab, pembrolizumab, pidilizumab, AMP-224, AMP-514, PDR001, REGN2810, MEDIO680, durvalumab, atezolizumab, avelumab, BMS-936559, BGB-A317, vorinostat, panobinostat, valproic acid, romidepsin, prostratin, phorbol 12-myristate-13-acetate, bryostatin-1, (S)-tert-butyl 2-(4-(4-chlorophenyl)-2,3,9-trimethyl-6H-thieno[3,2-f][1,2,4]triazolo[4,3-a][1,4]diazepin-6-yl)acetate, JQ1, I-BET762, OTX015, I-BET151, CPI203, PFI-1, MS436, CPI-0610, RVX2135, FT-1101, BAY1238097, INCB054329, TEN-010, GSK2820151, ZENO03694, BAY-299, BMS-986158, ABBV-075 and GS-5829.

17. The method of claim 6, further comprising the use of one or more agents selected from the group consisting of a non-nucleoside reverse transcriptase inhibitor (NNRTI), a nucleoside reverse transcriptase inhibitor (NRTI), a protease inhibitor (PI), a fusion/entry inhibitor, an integrase strand transfer inhibitor (INSTI), a HIV vaccine, a HIV other antiretroviral therapy compound and combinations thereof, or a pharmaceutically acceptable salt of any of the aforementioned.

* * * * *

UNITED STATES PATENT AND TRADEMARK OFFICE
CERTIFICATE OF CORRECTION

PATENT NO. : 11,813,259 B2
APPLICATION NO. : 17/656726
DATED : November 14, 2023
INVENTOR(S) : Joseph Robert Pinchman et al.

It is certified that error appears in the above-identified patent and that said Letters Patent is hereby corrected as shown below:

In the Claims

In Column 187, Claim 7, Line 1, delete "$R^A$," and insert --$R^{3A}$,--.

In Column 187, Claim 8, Line 63, delete "thereof" and insert --thereof,--.

In Column 192, Claim 16, Line 10, delete "MEDIO680," and insert --MEDI0680,--.

In Column 192, Claim 16, Line 18, delete "ZENO03694," and insert --ZEN003694,--.

Signed and Sealed this
Twentieth Day of February, 2024

Katherine Kelly Vidal
*Director of the United States Patent and Trademark Office*